US006077866A

United States Patent [19]

Kitagawa et al.

[11] Patent Number: 6,077,866

[45] Date of Patent: Jun. 20, 2000

[54] BENZOPHENONE HYDRAZONE DERIVATIVES AS INSECTICIDES

[75] Inventors: Yoshinori Kitagawa; Katsuaki Wada; Yoshiko Kyo; Yuichi Otsu, all of Tochigi; Yumi Hattori, Ibaraki; Toru Obinata; Takahisa Abe, both of Tochigi; Katsuhiko Shibuya, Minamikawachi-machi, all of Japan; Wolfram Andersch, Bergisch Gladbach, Germany

[73] Assignee: Nihon Bayer Agrochem K.K., Tokyo, Japan

[21] Appl. No.: 08/644,139

[22] Filed: May 10, 1996

[30] Foreign Application Priority Data

| | | | |
|---|---|---|---|
| May 12, 1995 | [JP] | Japan | 7-137482 |
| Feb. 15, 1996 | [JP] | Japan | 8-050744 |

[51] Int. Cl.$^7$ .......................... A01N 47/12; C07C 323/48

[52] U.S. Cl. ............................ 514/482; 514/63; 514/487; 514/512; 514/513; 514/514; 514/521; 514/523; 514/590; 514/615; 514/639; 556/413; 556/420; 558/15; 558/247; 558/257; 558/391; 558/396; 558/397; 560/9; 560/13

[58] Field of Search .................................... 556/413, 420; 558/15, 247, 257, 391, 396, 397; 560/9, 13; 564/19, 20, 36, 148, 149, 150, 151, 251; 514/63, 482, 487, 512, 513, 514, 521, 523, 590, 614, 615, 639

[56] References Cited

U.S. PATENT DOCUMENTS

| | | | |
|---|---|---|---|
| 4,331,680 | 5/1982 | Giles et al. | 424/300 |
| 4,344,893 | 8/1982 | Copping et al. | 558/53 |
| 4,394,387 | 7/1983 | Copping et al. | 424/300 |
| 4,432,994 | 2/1984 | Giles et al. | 424/300 |
| 4,980,373 | 12/1990 | Kisida et al. | 514/517 |
| 5,728,699 | 3/1998 | Toriyabe et al. | 514/247 |

FOREIGN PATENT DOCUMENTS

| | | |
|---|---|---|
| 3913 | 9/1979 | European Pat. Off. . |
| 355832 | 2/1990 | European Pat. Off. . |
| 566534 | 10/1993 | European Pat. Off. . |
| 581725 | 2/1994 | European Pat. Off. . |
| WO 96/33168 | 10/1996 | WIPO . |

OTHER PUBLICATIONS

Abstract of JP 03074356 A; "New hydrazone compounds . . . "; Sumitomo Chem.Ind.KK; Aug. 10, 1989.

Abstract of JP 04001173 A; "Agent for exterminating . . . "; Chugai Pharmaceutical KK; Apr. 17, 1990.

Abstract of AU 9510291 A; "Benzophenone acyl;hydrozone(s) . . . "; Sumitomo Chem.Co.Ltd.; Jan. 24, 1994.

*Primary Examiner*—Richard L. Raymond
*Attorney, Agent, or Firm*—Norris, McLaughlin & Marcus, P.A.

[57] ABSTRACT

Novel benzophenonehydrazone derivatives represented by the formula (I):

(I)

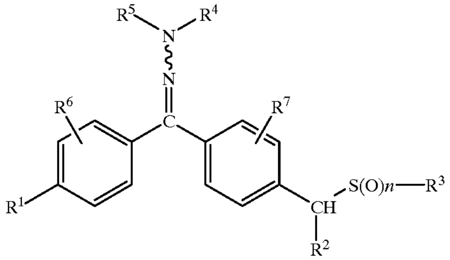

wherein, $R^1$ is halogen; $R^2$ is hydrogen or $C_{1-4}$ alkyl; $R^3$ is cyano, optically substituted $C_{1-4}$ alkyl, $C_{2-4}$ alkenyl, $C_{3-4}$ alkynyl, $C_{1-4}$ alkyl-carbonyl or $C_{1-4}$ alkoxy-thiocarbonyl; $R^4$ is hydrogen, phenyl, optionally substituted $C_{1-6}$ alkyl, optionally substituted $C_{2-8}$ alkenyl, —CO—$R^8$, —CO—O—$R^9$ or

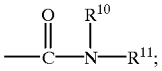

;

$R^5$ is hydrogen, formyl, phenyl, optionally substituted $C_{1-8}$ alkyl, optionally substituted $C_{2-8}$ alkenyl, optionally substituted $C_{3-8}$ alkynyl, optionally substituted $C_{1-8}$ alkyl-arbonyl, optionally substituted $C_{1-6}$ alkyl-oxalyl, optionally substituted $C_{1-8}$ alkoxy-carbonyl, optionally substituted $C_{1-8}$ alkoxy-oxalyl, optionally substituted $C_{3-8}$ cycloalkyl-carbonyl, optionally substituted $C_{2-8}$ alkenyl-carbonyl or optionally substituted benzoyl; $R^6$ is hydrogen or halogen; $R^7$ is hydrogen, halogen or $C_{1-2}$ alkyl, $C_{1-4}$ alkyl-carbonyl or $C_{1-4}$ alkoxy-thiocarbonyl; n is 0, 1 or 2, provided that n is 0 when $R^3$ is cyano, $C_{1-4}$ alkyl-carbonyl or $C_{1-4}$ alkoxy-thiocarbonyl, 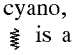 is a single bond of Anti form or of Syn form.

The benzophenonehydrazone derivatives of the formula (I) have excellent insecticidal activities.

3 Claims, No Drawings

BENZOPHENONE HYDRAZONE DERIVATIVES AS INSECTICIDES

The present invention relates to novel benzophenone hydrazone derivatives, to processes for the preparation thereof and to their use as insecticides, as well as to novel intermediates for their preparation and to processes for their preparation.

It has been already known that certain 4-substituted-4'-alkysufonyloxybenzophenone hydrazone derivatives have insecticidal activities (see British Crop Protection Conference Pests and Diseases 1984, Vol.2, 405–412, Japanese Patent Kokai Publications Sho 54-122261 (=EP-3913-A, U.S. Pat. No. 4,394,387), Sho 56-45452 (=EP-26040-A, U.S. Pat. Nos. 4,331,680, 4,432,994), Hei 2-138246 (=EP-355832-A, U.S. Pat. No. 4,980,373), Hei 3-74356 (DERWENT AN-91-136915), Hei 4-1173 (DERWENT AN-92-053936), Hei 6-25134(=CA2094010), Hei 6-184079 (=U.S. Pat. Nos. 5,340,837, 5,405,871), Hei 7-149708(=EP-647622), Hei 7-242618(=CA2139465) and Hei 7-247261 (=DERWENT AN=95-363559)).

However, the level and/or duration of activity of these known compounds are not entirely satisfactory in all fields of application, in particular against certain organisms or when low concentrations are applied.

There have now been found novel benzophenone hydrazone derivatives of the formula (I).

(I)

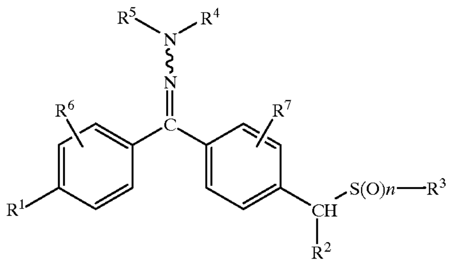

wherein $R^1$ is halogen, $R^2$ is hydrogen or $C_{1-4}$ alkyl, $R^3$ is cyano, optionally substituted $C_{1-4}$ alkyl, $C_{2-4}$ alkenyl or $C_{3-4}$ alkynyl, $C_{1-4}$ alkyl-carbonyl or $C_{1-4}$ alkoxy-thiocarbonyl, $R^4$ is hydrogen, phenyl, benzyl, optionally substituted $C_{1-8}$ alkyl, optionally substituted $C_{2-8}$alkenyl, —CO—$R^8$, —CO—O—$R^9$ or

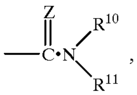 , $R^5$ is hydrogen, formyl, phenyl, optionally substituted $C_{1-8}$ alkyl, optionally substituted $C_{2-8}$ alkenyl, optionally substituted $C_{3-8}$ alkynyl, optionally substituted $C_{1-8}$ alkyl-carbonyl, optionally substituted $C_{1-6}$ alkyl-oxalyl, optionally substituted $C_{1-8}$ alkoxy-carbonyl, optionally substituted $C_{1-8}$ alkoxy-oxalyl, optionally substituted $C_{3-8}$ cycloalkyl-carbonyl, optionally substituted $C_{2-8}$ alkenyl-carbonyl or optionally substituted benzoyl, $R^6$ is hydrogen or halogen, $R^7$ is hydrogen, halogen or $C_{1-2}$ alkyl, n is 0, 1 or 2, provided that n is 0 when $R^3$ is cyano, $C_{1-4}$ alkyl-carbonyl or $C_{1-4}$ alkoxy-thiocarbonyl, is a single bond of Anti form or of Syn form, $R^8$ is optionally substituted $C_{1-8}$ alkyl, optionally substituted $C_{2-8}$ alkenyl, optionally substituted phenyl, optionally substituted $C_{3-8}$ cycloalkyl, optionally substituted $C_{1-8}$ alkyl-carbonyl or optionally substituted $C_{1-8}$ alkoxy-carbonyl, or hydrogen, $R^9$ is optionally substituted $C_{1-8}$ alkyl, optionally substituted $C_{3-8}$ cycloalkyl, optionally substituted $C_{2-8}$ alkenyl or optionally substituted $C_{3-8}$ alkynyl, $R^{10}$ is hydrogen or $C_{1-4}$ alkyl, $R^{11}$ is hydrogen, optionally substituted $C_{1-4}$ alkyl or optionally substituted phenyl and, Z is oxygen or sulfur.

The compounds of the formula (I), according to the invention, are obtained when (a) in the case where $R^5$ is hydrogen:

compounds of the formula (II)

(II)

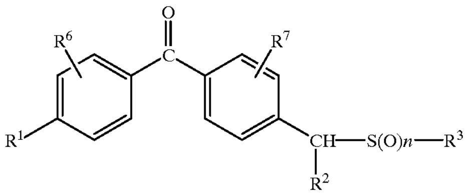

wherein $R^1$, $R^2$, $R^3$, $R^6$, $R^7$ and n are defined as above, are reacted with compounds of the formula (III)

(III)

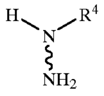

wherein $R^4$ is defined as above;

in the presence of an inert solvent, and, if appropriate, in the presence of an acid catalyst, or (b) in the case where $R^5$ is hydrogen and $R^4$ is

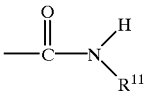

and $R^{11}$ is not hydrogen, then $R^{11}$ is replaced by $R^{12}$, then $R^{12}$ is optionally substituted $C_{1-4}$ alkyl or optionally substituted phenyl:

compounds of the formula (IV)

(IV)

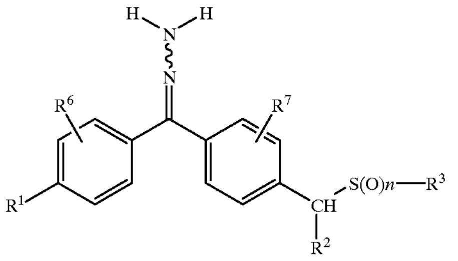

wherein $R^1$, $R^2$, $R^3$, $R^6$, $R^7$ and n are defined as above, are reacted with compound of the formula (V)

$OCN—R^{12}$ (V)

wherein $R^{12}$ is optionally substituted $C_{1-4}$ alkyl or optionally substituted phenyl, in the presence of an inert solvent, or (c) in the case where $R^4$ is —CO—$R^8$ or —CO—O—$R^9$, provided that $R^8$ is not hydrogen, then $R^8$ or —O—$R^9$ is replaced by $R^{13}$, the aforementioned compounds of the formula (IV) are reacted with compounds of the formula (VI)

(VI)

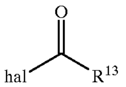

wherein hal is chlorine or bromine and $R^{13}$ is $R^8$ or —O—$R^9$, in the presence of an inert solvent, and if appropriate in the presence of an acid binder, or (d) in the case where $R^5$ is not hydrogen, then $R^5$ is replaced by $R^{14}$:

compounds of the formula (VII)

(VII)

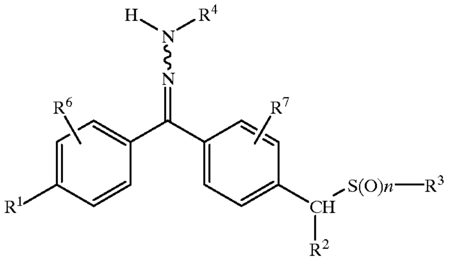

wherein $R^1$, $R^2$, $R^3$, $R^4$, $R^6$, $R^7$ and n have the same meaning as mentioned above, are reacted with compounds of the formula (VIII)

$hal—R^{14}$ (VIII)

wherein hal and $R^{14}$ have the same meaning as mentioned above, in the presence of an inert solvent, and if appropriate in the presence of an acid binder, or (e) in the case where n is 1:

compounds the formula (IX)

(IX)

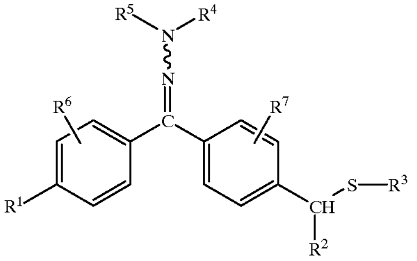

wherein $R^1$, $R^2$, $R^3$, $R^4$, $R^5$, $R^6$ and $R^7$ have the same meaning as mentioned above, are oxidized in the presence of an inert solvent, or (f): in the case where n is 2:

compounds of the formula (X)

(X)

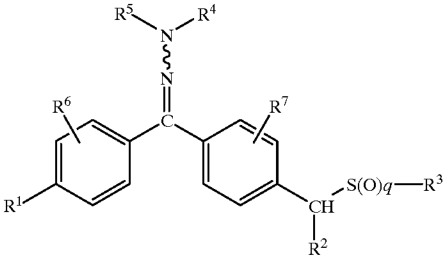

wherein $R^1$, $R^2$, $R^3$, $R^4$, $R^5$, $R^6$ and $R^7$ have the same meanings as mentioned above and q is 0 or 1, are oxidized in the presence of an inert solvent.

The benzophenone hydrazone derivatives of the formula (I) according to the invention exhibit powerful insecticidal action, especially against lepidoptera, coleoptera and soil insects.

According to the invention, unexpectedly, the benzophenone hydrazone derivatives of the formula (I) exhibit substantially, superior insecticidal action as compared with those of the compounds described in the above references which are similar to the compounds of the invention.

In the compounds of the formula (I) according to the invention, and the respective formulae representing their intermediates employed for the preparation of the compounds of formula (I), each of the halogen as well as the halogen parts of the haloalkyl, haloalkenyl and haloalkoxy represent fluorine, chlorine, bromine and iodine, preferably fluorine, chlorine or bromine.

Alkyl represents, for example, methyl, ethyl, propyl, isopropyl, n-(iso-, sec- or tert-)butyl, n-(iso-, sec-, tert- or neo-)pentyl and n-(iso-, sec-, tert- or neo-)hexyl, preferably, methyl, ethyl, propyl, isopropyl and n-(iso-, sec- or tert-)butyl.

Alkenyl represents, for example, vinyl, allyl, isopropenyl, 1-methyl-2-propenyl, 2-methyl-2-propenyl, 2- (or 3-)butenyl, 2-(3- or 4-)pentenyl, Alkynyl represents, for example, propargyl.

Phenyl and the phenoxy may optionally be substituted by one or more than one substituent. The substituent(s) of those are selected from the group consisting of halogen(fluorine, chlorine, bromine), cyano, nitro, alkyl (methyl, ethyl, propyl or isopropyl), haloalkyl(trifluoromethyl), alkoxy(methoxy, ethoxy), haloalkoxy (trifluoromethoxy) and alkylthio (methylthio).

Cycloalkyl represents, for example, cyclopropyl, cyclobutyl, cyclopentyl, cyclohexyl, cycloheptyl and cyclooctyl. The cycloalkyl may optionally be substituted by $C_{1-4}$ alkyl(methyl, ethyl, propyl, isopropyl and butyl).

Alkoxy represents, for example, methoxy, ethoxy, propoxy, isopropoxy, n-(iso-, sec- or tert-)butoxy, n-(iso-, sec-, tert- or neo-)pentoxy, n-(iso-, sec-, tert- or neo-)hexoxy.

Haloalkoxy represents the above mentioned alkoxy groups which are substituted with the same or different halogen atom(s) and is, for example, trifluoromethoxy.

Alkylthio represents, for example, methylthio, ethylthio, propylthio, isopropylthio, n-(iso-, sec- or tert-)butylthio, n-(iso-, sec-, tert- or neo-)pentylthio, n-(iso-, sec-, tert- or neo-)hexylthio.

Among the benzophenone hydrazone derivatives according to the invention, of the formula (I), preferred compounds are those in which $R^1$ is halogen, $R^2$ is hydrogen or $C_{1-3}$ alkyl, $R^3$ is cyano, $C_{1-4}$ alkyl which may be substituted by one or more than one substituent selected from the group consisting of halogen, cyano, methoxy, ethoxy and trimethylsilyl or is $C_{2-3}$ alkenyl, propargyl, methyl-carbonyl, methoxy-thiocarbonyl or ethoxy-thiocarbonyl, $R^4$ is hydrogen, $C_{1-4}$ alkyl, $C_{2-4}$ alkenyl, phenyl, or is benzyl, —CO—$R^8$, —CO—O—$R^9$ or

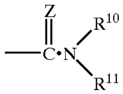, $R^5$ is hydrogen, formyl, phenyl, $C_{1-6}$ alkyl which may be substituted by one or more than one substituent selected from the group consisting of halogen, cyano, $C_{1-4}$ alkoxy, $C_{1-4}$ alkylthio, hydroxycarbonyl, $C_{1-4}$ alkoxy-carbonyl, phenyl, phenyl which is substituted by halogen and methoxyphenyl or is $C_{2-6}$ alkenyl, $C_{3-6}$ alkynyl, $C_{1-6}$ alkyl-carbonyl, $C_{1-6}$ halogenalkyl-carbonyl, $C_{1-4}$ alkoxy-$C_{1-6}$ alkyl-carbonyl, $C_{1-6}$ alkyl-oxalyl, $C_{1-6}$ alkoxy-carbonyl which may be substituted by one or more than one substituent selected from the group consisting of $C_{3-6}$ cycloalkyl and $C_{1-4}$ alkoxy or is $C_{1-6}$ alkoxy-oxalyl, $C_{3-6}$ cycloalkyl-carbonyl which may be substituted by $C_{1-4}$ alkyl, $C_{2-6}$ alkenyl-carbonyl which may be substituted by phenyl or is benzoyl which may be substituted by one or more than one substituent selected from the group consisting of halogen, nitro, cyano, $C_{1-4}$ alkoxy and $C_{1-4}$ alkylthio, $R^6$ is hydrogen or halogen, $R^7$ is hydrogen or halogen or $C_{1-2}$ alkyl, n is 0, 1 or 2, provided that n is 0 when $R^3$ is cyano, methyl-carbonyl, methoxy-thiocarbonyl or ethoxy-thiocarbonyl, ⌇ is a single bond of Anti form or of Syn form, $R^8$ is $C_{1-6}$ alkyl which may be substituted by one or more than one substituent selected from the group consisting of halogen, cyano, $C_{1-4}$ alkoxy, $C_{14}$ alkoxy-carbonyl and phenoxy or is $C_{2-6}$ alkenyl which may be substituted by one or more than one substituent selected from the group consisting of halogen and phenyl, or is phenyl which may be substituted by one or more than one substituent selected from the group consisting of halogen, nitro, cyano, $C_{1-4}$ alkyl, $C_{1-4}$ alkoxy and $C_{1-4}$ alkythio, or is $C_{3-6}$ cycloalkyl which may be substituted by $C_{1-4}$ alkyl, or is $C_{1-6}$ alkyl-carbonyl or $C_{1-6}$ alkoxy-carbonyl, or hydrogen, $R^9$ is $C_{1-6}$ alkyl which may be substituted by one or more than one substituent selected from the group consisting of halogen, phenyl, 4-nitrophenyl, trimethylsilyl and $C_{3-6}$ cycloalkyl, or is $C_{3-6}$ cycloalkyl, or $C_{2-6}$ alkenyl which may be substituted by phenyl or is $C_{3-6}$ alkynyl, $R^{10}$ is hydrogen or $C_{1-4}$ alkyl, $R^{11}$ is hydrogen, $C_{1-4}$ alkyl which may be substituted by halogen or is phenyl which may be substituted by one or more than one substituent selected from the group consisting of halogen, $C_{1-4}$ alkoxy or $C_{1-4}$ haloalkoxy and Z is oxygen or sulfur.

Particularly preferred benzophenone hydrazone derivatives of the formula (I) are those in which $R^1$ is fluorine, chlorine, bromine or iodine, $R^2$ is hydrogen, methyl, ethyl or n-propyl, $R^3$ is cyano, methyl, ethyl, propyl, isopropyl, n-butyl, sec-butyl, cyanomethyl, fluoromethyl, chloromethyl, difluoromethyl, trifluoromethyl, 2-fluroroethyl, 2-chloroethyl, 2,2-difluoroethyl, 2,2,2-trifluoroethyl, 3-fluoropropyl, 3-chloropropyl, 2,2,3,3-tetrafluoropropyl, methoxymethyl, ethoxymethyl, trimethylsilylmethyl, vinyl, allyl, propargyl, methyl-carbonyl or ethoxythiocarbonyl, $R^4$ is hydrogen, methyl, ethyl, propyl, isopropyl, n-butyl, tert-butyl, allyl, phenyl, benzyl, —CO—$R^8$, —CO—O—$R^9$ or

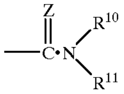, $R^5$ is hydrogen, methyl, ethyl, propyl, isopropyl, n-butyl, tert-butyl, n-pentyl, n-hexyl, methoxymethyl, ethoxymethyl, methylthiomethyl, methylthioethyl, methoxycarbonylmethyl, ethoxycarbonylmethyl, 2-ethoxycarbonylethyl, difluoromethyl, 2-chloroethyl, 2,2-difluoroethyl, 2,2,2-trifluoroethyl, cyanomethyl, cyanoethyl, vinyl, allyl, propargyl, phenyl, benzoyl, cinnamoyl, benzyl, 4-chlorobenzoyl, 4-methoxybenzoyl, formyl,methylcarbonyl, ethylcarbonyl, propylcarbonyl, isopropylcarbonyl, n-butylcarbonyl, 2,2,2-trifluoroethylcarbonyl, 5-bromopentylcarbonyl, methoxymethylcarbonyl, methyloxalyl, ethyloxalyl, propyloxalyl, isopropyloxalyl, n-butyl-oxalyl, methoxycarbonyl, ethoxycarbonyl, propoxycarbonyl, butoxycarbonyl, methoxyoxalyl, ethoxyoxalyl, propoxyoxalyl, butoxyoxalyl, cyclopropylcarbonyl, 1-methylcyclopropylcarbonyl, cyclopropylmethoxy-carbonyl or 2-methoxyethoxycarbonyl, hydroxycarbonylethyl, $R^6$ is hydrogen, fluorine or chlorine, $R^7$ is hydrogen, bromine or methyl, n is 0, 1 or 2, provided that n is 0 when $R^3$ is methyl-carbonyl or ethoxythiocarbonyl, ⌇ is a single bond of Anti form or of Syn form, $R^8$ is methyl, ethyl, propyl, isopropyl, n-butyl, isobutyl, sec-butyl, tert-butyl, n-pentyl, n-hexyl, cyanomethyl, 2-chloroethyl, 3-chloropropyl, 4-chlorobutyl, methoxymethyl, 2-methoxyethyl, phenoxymethyl, ethoxycarbonylmethyl, vinyl, isopropenyl, 1-propenyl, 2,3,3-trifluoro-2-propenyl, phenyl, 4-chlorophenyl, 4-bromophenyl, 4-methylphenyl, 4-methoxyphenyl, styryl, cyclopropyl, cyclopentyl, cyclohexyl, 1-methylcyclopropyl, methylcarbonyl, ethylcarbonyl, propylcarbonyl, methoxycarbonyl, ethoxycarbonyl or propyoxcarbonyl, or hydrogen, $R^9$ is methyl, ethyl, propyl, isopropyl, n-butyl, isobutyl, tert-butyl, sec-butyl, n-pentyl, neo-pentyl, 2-methylbutyl, n-hexyl, trimethylsilylmethyl, allyl, cyclopentyl, cyclohexyl, 2-methyl-2-propenyl, propargyl, 2-chloroethyl, 2,2,2-trifluoroethyl, 2,2,3,3-tetrafluoropropyl, cyclopropylmethyl, cyclohexylmethyl, benzyl or 4-nitrobenzyl $R^{10}$ is hydrogen or methyl, $R^{11}$ is hydrogen, methyl, ethyl, 2-chloroethyl, phenyl, 2-chlorophenyl, 2-methoxyphenyl or 4-trifluoromethoxyphenyl, and Z is oxygen or sulfur.

Specifically mentioned are the following compounds in Table 1 to Table 4.

TABLE 1

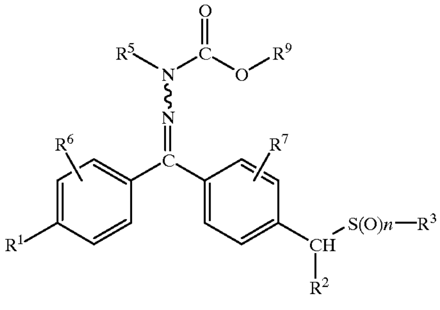

| $R^1$ | $R^2$ | $R^3$ | n | $R^5$ | $R^6$ | $R^7$ | $R^9$ |
|---|---|---|---|---|---|---|---|
| F | H | $CH_3$ | 0 | H | H | H | $CH_3$ |
| F | H | $CH_3$ | 0 | H | H | H | $C_2H_5$ |
| F | H | $CH_3$ | 0 | H | 3-F | H | $CH_3$ |
| F | H | $CH_3$ | 0 | H | 3-F | H | $C_2H_5$ |
| F | H | $CH_3$ | 1 | H | H | H | $CH_3$ |
| F | H | $CH_3$ | 1 | H | H | H | $C_2H_5$ |
| F | H | $CH_3$ | 1 | H | H | H | n-$C_3H_7$ |
| F | H | $CH_3$ | 1 | H | H | H | iso-$C_3H_7$ |
| F | H | $CH_3$ | 1 | H | H | H | iso-$C_4H_9$ |
| F | H | $CH_3$ | 1 | H | H | H | $CH_2CF_3$ |
| F | H | $CH_3$ | 2 | H | H | H | $C_2H_5$ |
| F | H | $CH_3$ | 2 | H | H | H | n-$C_3H_7$ |
| F | H | $CH_3$ | 2 | H | H | H | iso-$C_3H_7$ |
| F | H | $CH_3$ | 2 | H | H | H | iso-$C_4H_9$ |
| F | H | $CH_3$ | 2 | H | H | H | $CH_2CF_3$ |
| F | H | $C_2H_5$ | 0 | H | H | H | $C_2H_5$ |
| F | H | $C_2H_5$ | 0 | H | 3-F | H | $C_2H_5$ |
| F | H | $C_2H_5$ | 1 | H | H | H | $CH_3$ |
| F | H | $C_2H_5$ | 1 | H | H | H | $C_2H_5$ |
| F | H | $C_2H_5$ | 1 | H | H | H | $CH_2CF_3$ |
| F | H | $C_2H_5$ | 1 | H | H | H | iso-$C_3H_7$ |
| F | H | $C_2H_5$ | 2 | H | H | H | $CH_3$ |
| F | H | $C_2H_5$ | 2 | H | H | H | $C_2H_5$ |
| F | H | $C_2H_5$ | 2 | H | H | H | n-$C_3H_7$ |
| F | H | $C_2H_5$ | 2 | H | H | H | iso-$C_4H_9$ |
| F | H | $C_2H_5$ | 2 | H | H | H | $CH_2CF_3$ |
| F | H | $C_2H_5$ | 2 | H | 3-F | H | $C_2H_5$ |
| F | H | $CH_2CH_2F$ | 0 | H | H | H | $CH_3$ |
| F | H | $CH_2CF_3$ | 0 | H | H | H | $CH_3$ |
| F | H | $CH_2CF_3$ | 0 | H | 3-F | H | $CH_3$ |
| Cl | H | $CH_3$ | 0 | H | H | H | $CH_3$ |
| Cl | H | $CH_3$ | 0 | H | H | H | $C_2H_5$ |
| Cl | H | $CH_3$ | 0 | H | H | H | n-$C_3H_7$ |
| Cl | H | $CH_3$ | 0 | H | H | H | iso-$C_3H_7$ |
| Cl | H | $CH_3$ | 0 | H | H | H | sec-$C_4H_9$ |
| Cl | H | $CH_3$ | 0 | H | H | H | tert-$C_4H_9$ |
| Cl | H | $CH_3$ | 0 | H | H | H | n-$C_4H_9$ |
| Cl | H | $CH_3$ | 0 | H | H | H | iso-$C_4H_9$— |
| Cl | H | $CH_3$ | 0 | H | H | H | n-$C_5H_{11}$ |
| Cl | H | $CH_3$ | 0 | H | H | H | neo-$C_5H_{11}$ |
| Cl | H | $CH_3$ | 0 | H | H | H | $CH_2CH(CH_3)C_2H_5$ |
| Cl | H | $CH_3$ | 0 | H | H | H | n-$C_6H_{13}$ |
| Cl | H | $CH_3$ | 0 | H | H | H | n-$C_7H_{15}$ |
| Cl | H | $CH_3$ | 0 | H | H | H | n-$C_8H_{17}$ |
| Cl | H | $CH_3$ | 0 | H | H | H | $CH_2CH{=}CH_2$ |
| Cl | H | $CH_3$ | 0 | H | H | H | $CH_2C(CH_3){=}CH_2$ |
| Cl | H | $CH_3$ | 0 | H | H | H | $CH_2C{\equiv}CH$ |

TABLE 1-continued

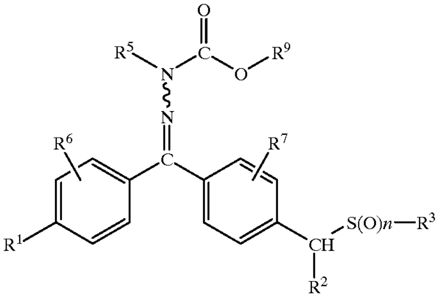

| $R^1$ | $R^2$ | $R^3$ | n | $R^5$ | $R^6$ | $R^7$ | $R^9$ |
|---|---|---|---|---|---|---|---|
| Cl | H | $CH_3$ | 0 | H | H | H | $CH_2C_6H_5$ |
| Cl | H | $CH_3$ | 0 | H | H | H | $CH_2CF_3$ |
| Cl | H | $CH_3$ | 0 | H | H | H | $CH_2CH_2Cl$ |
| Cl | H | $CH_3$ | 0 | H | H | H | $CH_2CH_2OCH_3$ |
| Cl | H | $CH_3$ | 0 | H | H | H | $CH_2Si(CH_3)_3$ |
| Cl | H | $CH_3$ | 0 | H | H | H | 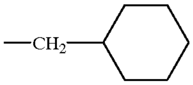 |
| Cl | H | $CH_3$ | 0 | H | H | H | 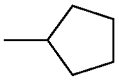 |
| Cl | H | $CH_3$ | 0 | H | H | H | 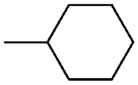 |
| Cl | H | $CH_3$ | 0 | H | H | 2-F | $C_2H_5$ |
| Cl | H | $CH_3$ | 0 | H | H | 3-F | $C_2H_5$ |
| Cl | H | $CH_3$ | 0 | H | H | 3-Cl | $C_2H_5$ |
| Cl | H | $CH_3$ | 0 | H | H | 3-Br | $C_2H_5$ |
| Cl | H | $CH_3$ | 0 | H | H | 3-$CH_3$ | $C_2H_5$ |
| Cl | H | $CH_3$ | 0 | H | 2-F | H | $CH_3$ |
| Cl | H | $CH_3$ | 0 | H | 2-F | H | $C_2H_5$ |
| Cl | H | $CH_3$ | 0 | H | 2-Cl | H | $CH_3$ |
| Cl | H | $CH_3$ | 0 | H | 2-Cl | H | $C_2H_5$ |
| Cl | H | $CH_3$ | 0 | H | 3-F | H | $CH_3$ |
| Cl | H | $CH_3$ | 0 | H | 3-F | H | $C_2H_5$ |
| Cl | H | $CH_3$ | 0 | H | 3-Cl | H | $CH_3$ |
| Cl | H | $CH_3$ | 0 | H | 3-Cl | H | $C_2H_5$ |
| Cl | H | $CH_3$ | 0 | $CH_3$ | H | H | $CH_3$ |
| Cl | H | $CH_3$ | 0 | $CH_3$ | H | H | $C_2H_5$ |
| Cl | H | $CH_3$ | 0 | $CH_3$ | H | H | n-$C_3H_7$ |
| Cl | H | $CH_3$ | 0 | $CH_3$ | H | H | iso-$C_3H_7$ |
| Cl | H | $CH_3$ | 0 | $CH_3$ | H | H | $CH_2CF_3$ |
| Cl | H | $CH_3$ | 0 | $C_2H_5$ | H | H | $CH_3$ |
| Cl | H | $CH_3$ | 0 | $C_2H_5$ | H | H | $C_2H_5$ |
| Cl | H | $CH_3$ | 0 | $C_2H_5$ | H | H | n-$C_3H_7$ |
| Cl | H | $CH_3$ | 0 | $C_2H_5$ | H | H | iso-$C_3H_7$ |
| Cl | H | $CH_3$ | 0 | $C_2H_5$ | H | H | n-$C_4H_9$ |
| Cl | H | $CH_3$ | 0 | $C_2H_5$ | H | H | iso-$C_4H_9$ |
| Cl | H | $CH_3$ | 0 | $C_2H_5$ | H | H | sec-$C_4H_9$ |
| Cl | H | $CH_3$ | 0 | $C_2H_5$ | H | H | $CH_2CF_3$ |
| Cl | H | $CH_3$ | 0 | n-$C_3H_7$ | H | H | $CH_3$ |
| Cl | H | $CH_3$ | 0 | n-$C_3H_7$ | H | H | $C_2H_5$ |
| Cl | H | $CH_3$ | 0 | n-$C_3H_7$ | H | H | n-$C_3H_7$ |
| Cl | H | $CH_3$ | 0 | n-$C_3H_7$ | H | H | iso-$C_3H_7$ |
| Cl | H | $CH_3$ | 0 | n-$C_3H_7$ | H | H | $CH_2CF_3$ |
| Cl | H | $CH_3$ | 0 | iso-$C_3H_7$ | H | H | $CH_3$ |
| Cl | H | $CH_3$ | 0 | iso-$C_3H_7$ | H | H | $C_2H_5$ |
| Cl | H | $CH_3$ | 0 | iso-$C_3H_7$ | H | H | n-$C_3H_7$ |
| Cl | H | $CH_3$ | 0 | iso-$C_3H_7$ | H | H | iso-$C_3H_7$ |
| Cl | H | $CH_3$ | 0 | iso-$C_3H_7$ | H | H | n-$C_4H_9$ |
| Cl | H | $CH_3$ | 0 | iso-$C_3H_7$ | H | H | iso-$C_4H_9$ |
| Cl | H | $CH_3$ | 0 | iso-$C_3H_7$ | H | H | sec-$C_4H_9$ |
| Cl | H | $CH_3$ | 0 | iso-$C_3H_7$ | H | H | $CH_2CF_3$ |

TABLE 1-continued

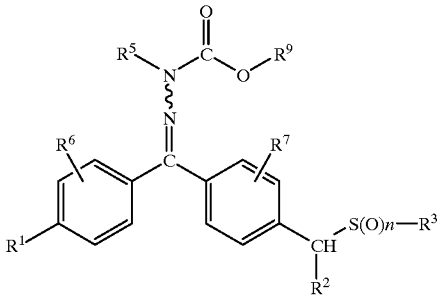

| $R^1$ | $R^2$ | $R^3$ | n | $R^5$ | $R^6$ | $R^7$ | $R^9$ |
|---|---|---|---|---|---|---|---|
| Cl | H | $CH_3$ | 0 | n-$C_4H_9$ | H | H | $CH_3$ |
| Cl | H | $CH_3$ | 0 | n-$C_4H_9$ | H | H | $C_2H_5$ |
| Cl | H | $CH_3$ | 0 | n-$C_4H_9$ | H | H | n-$C_3H_7$ |
| Cl | H | $CH_3$ | 0 | n-$C_4H_9$ | H | H | iso-$C_3H_7$ |
| Cl | H | $CH_3$ | 0 | $CHF_2$ | H | H | $C_2H_5$ |
| Cl | H | $CH_3$ | 0 | $CH_2OCH_3$ | H | H | $CH_3$ |
| Cl | H | $CH_3$ | 0 | $CH_2OCH_3$ | H | H | $C_2H_5$ |
| Cl | H | $CH_3$ | 0 | $CH_2OCH_3$ | H | H | n-$C_3H_7$ |
| Cl | H | $CH_3$ | 0 | $CH_2OCH_3$ | H | H | iso-$C_3H_7$ |
| Cl | H | $CH_3$ | 0 | $CH_2OCH_3$ | H | H | $CH_2CF_3$ |
| Cl | H | $CH_3$ | 0 | $CH_2OC_2H_5$ | H | H | $CH_3$ |
| Cl | H | $CH_3$ | 0 | $CH_2OC_2H_5$ | H | H | $C_2H_5$ |
| Cl | H | $CH_3$ | 0 | $CH_2OC_2H_5$ | H | H | n-$C_3H_7$ |
| Cl | H | $CH_3$ | 0 | $CH_2OC_2H_5$ | H | H | iso-$C_3H_7$ |
| Cl | H | $CH_3$ | 0 | $CH_2OC_2H_5$ | H | H | $CH_2CF_3$ |
| Cl | H | $CH_3$ | 0 | $CH_2SCH_3$ | H | H | $CH_3$ |
| Cl | H | $CH_3$ | 0 | $CH_2SCH_3$ | H | H | $C_2H_5$ |
| Cl | H | $CH_3$ | 0 | $CH_2SCH_3$ | H | H | n-$C_3H_7$ |
| Cl | H | $CH_3$ | 0 | $CH_2SCH_3$ | H | H | iso-$C_3H_7$ |
| Cl | H | $CH_3$ | 0 | $CH_2SCH_3$ | H | H | $CH_2CF_3$ |
| Cl | H | $CH_3$ | 0 | $CH_2C_6H_5$ | H | H | $C_2H_5$ |
| Cl | H | $CH_3$ | 0 | $CH_2CO_2C_2H_5$ | H | H | $C_2H_5$ |
| Cl | H | $CH_3$ | 0 | $CH_2CH_2CO_2C_2H_5$ | H | H | $C_2H_5$ |
| Cl | H | $CH_3$ | 0 | CHO | H | H | $CH_3$ |
| Cl | H | $CH_3$ | 0 | CHO | H | H | $C_2H_5$ |
| Cl | H | $CH_3$ | 0 | $COCH_3$ | H | H | $CH_3$ |
| Cl | H | $CH_3$ | 0 | $COCH_3$ | H | H | $C_2H_5$ |
| Cl | H | $CH_3$ | 0 | $COCH_3$ | H | H | n-$C_3H_7$ |
| Cl | H | $CH_3$ | 0 | $COCH_3$ | H | H | iso-$C_3H_7$ |
| Cl | H | $CH_3$ | 0 | $COC_2H_5$ | H | H | $CH_3$ |
| Cl | H | $CH_3$ | 0 | $COC_2H_5$ | H | H | $C_2H_5$ |
| Cl | H | $CH_3$ | 0 | $COC_2H_5$ | H | H | n-$C_3H_7$ |
| Cl | H | $CH_3$ | 0 | $COC_2H_5$ | H | H | iso-$C_3H_7$ |
| Cl | H | $CH_3$ | 0 | $COC_2H_5$ | H | H | $CH_2CF_3$ |
| Cl | H | $CH_3$ | 0 | $COC_3H_7$-n | H | H | $CH_3$ |
| Cl | H | $CH_3$ | 0 | $COC_3H_7$-n | H | H | $C_2H_5$ |
| Cl | H | $CH_3$ | 0 | $COC_3H_7$-n | H | H | n-$C_3H_7$ |
| Cl | H | $CH_3$ | 0 | $COC_3H_7$-n | H | H | iso-$C_3H_7$ |
| Cl | H | $CH_3$ | 0 | $COC_3H_7$-n | H | H | n-$C_4H_9$ |
| Cl | H | $CH_3$ | 0 | $COC_3H_7$-n | H | H | sec-$C_4H_9$ |
| Cl | H | $CH_3$ | 0 | $COC_3H_7$-n | H | H | iso-$C_4H_9$ |
| Cl | H | $CH_3$ | 0 | $COC_3H_7$-n | H | H | $CH_2CF_3$ |
| Cl | H | $CH_3$ | 0 | $COC_3H_7$-iso | H | H | $CH_3$ |
| Cl | H | $CH_3$ | 0 | $COC_3H_7$-iso | H | H | $C_2H_5$ |
| Cl | H | $CH_3$ | 0 | $COC_3H_7$-iso | H | H | n-$C_3H_7$ |
| Cl | H | $CH_3$ | 0 | $COC_4H_9$-n | H | H | $CH_3$ |
| Cl | H | $CH_3$ | 0 | $COC_4H_9$-n | H | H | $C_2H_5$ |
| Cl | H | $CH_3$ | 0 | $COC_4H_9$-n | H | H | n-$C_3H_7$ |
| Cl | H | $CH_3$ | 0 | $COC_4H_9$-n | H | H | iso-$C_3H_7$ |
| Cl | H | $CH_3$ | 0 | 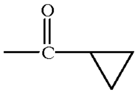 | H | H | $CH_3$ |
| Cl | H | $CH_3$ | 0 | 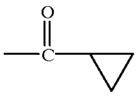 | H | H | $C_2H_5$ |

TABLE 1-continued

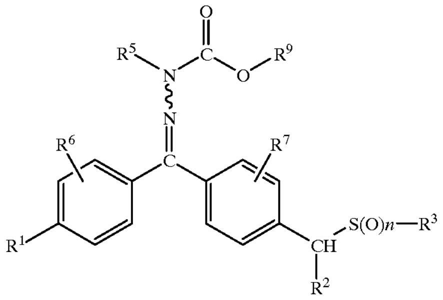

| $R^1$ | $R^2$ | $R^3$ | n | $R^5$ | $R^6$ | $R^7$ | $R^9$ |
|---|---|---|---|---|---|---|---|
| Cl | H | $CH_3$ | 0 | 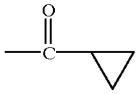 | H | H | n-$C_3H_7$ |
| Cl | H | $CH_3$ | 0 | 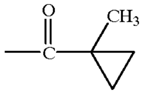 | H | H | $C_2H_5$ |
| Cl | H | $CH_3$ | 0 | $COC_6H_5$ | H | H | $CH_3$ |
| Cl | H | $CH_3$ | 0 | $COC_6H_5$ | H | H | $C_2H_5$ |
| Cl | H | $CH_3$ | 0 | $COC_6H_5$ | H | H | n-$C_3H_7$ |
| Cl | H | $CH_3$ | 0 | $COC_6H_5$ | H | H | iso-$C_3H_7$ |
| Cl | H | $CH_3$ | 0 | $COC_6H_5$ | H | H | $CH_2CF_3$ |
| Cl | H | $CH_3$ | 0 | 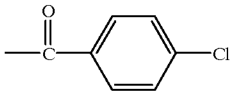 | H | H | $C_2H_5$ |
| Cl | H | $CH_3$ | 0 | 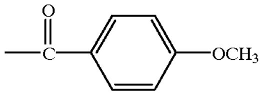 | H | H | $C_2H_5$ |
| Cl | H | $CH_3$ | 0 | $COCH{=}CHC_6H_5$ | H | H | $C_2H_5$ |
| Cl | H | $CH_3$ | 0 | $COCH_2OCH_3$ | H | H | $CH_3$ |
| Cl | H | $CH_3$ | 0 | $COCH_2OCH_3$ | H | H | $C_2H_5$ |
| Cl | H | $CH_3$ | 0 | $COCH_2OCH_3$ | H | H | n-$C_3H_7$ |
| Cl | H | $CH_3$ | 1 | H | H | H | $CH_3$ |
| Cl | H | $CH_3$ | 1 | H | H | H | $C_2H_5$ |
| Cl | H | $CH_3$ | 1 | H | H | H | n-$C_3H_7$ |
| Cl | H | $CH_3$ | 1 | H | H | H | iso-$C_3H_7$ |
| Cl | H | $CH_3$ | 1 | H | H | H | $CH_2CF_3$ |
| Cl | H | $CH_3$ | 1 | H | H | H | iso-$C_4H_9$ |
| Cl | H | $CH_3$ | 1 | H | H | H | tert-$C_4H_9$ |
| Cl | H | $CH_3$ | 1 | H | 2-Cl | H | $C_2H_5$ |
| Cl | H | $CH_3$ | 1 | H | 2-F | H | $C_2H_5$ |
| Cl | H | $CH_3$ | 1 | H | 3-F | H | $C_2H_5$ |
| Cl | H | $CH_3$ | 1 | H | 3-Cl | H | $C_2H_5$ |
| Cl | H | $CH_3$ | 1 | $CH_3$ | H | H | $C_2H_5$ |
| Cl | H | $CH_3$ | 1 | $C_2H_5$ | H | H | $C_2H_5$ |
| Cl | H | $CH_3$ | 1 | $C_2H_5$ | H | H | $CH_2CF_3$ |
| Cl | H | $CH_3$ | 1 | $C_2H_5$ | H | H | n-$C_3H_7$ |
| Cl | H | $CH_3$ | 1 | $C_2H_5$ | H | H | n-$C_4H_9$ |
| Cl | H | $CH_3$ | 1 | $C_2H_5$ | H | H | sec-$C_4H_9$ |
| Cl | H | $CH_3$ | 1 | $C_2H_5$ | H | H | iso-$C_4H_9$ |
| Cl | H | $CH_3$ | 1 | $C_2H_5$ | H | H | $CH_3$ |
| Cl | H | $CH_3$ | 1 | $C_2H_5$ | H | H | iso-$C_3H_7$ |
| Cl | H | $CH_3$ | 1 | iso-$C_3H_7$ | H | H | $CH_3$ |
| Cl | H | $CH_3$ | 1 | iso-$C_3H_7$ | H | H | $C_2H_5$ |
| Cl | H | $CH_3$ | 1 | iso-$C_3H_7$ | H | H | n-$C_3H_7$ |
| Cl | H | $CH_3$ | 1 | iso-$C_3H_7$ | H | H | iso-$C_3H_7$ |
| Cl | H | $CH_3$ | 1 | $CH_2OCH_3$ | H | H | $CH_3$ |
| Cl | H | $CH_3$ | 1 | $CH_2OCH_3$ | H | H | $C_2H_5$ |
| Cl | H | $CH_3$ | 1 | $CH_2OC_2H_5$ | H | H | $CH_3$ |

TABLE 1-continued

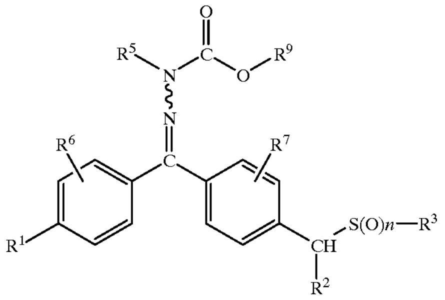

| $R^1$ | $R^2$ | $R^3$ | n | $R^5$ | $R^6$ | $R^7$ | $R^9$ |
|---|---|---|---|---|---|---|---|
| Cl | H | $CH_3$ | 1 | $CH_2OC_2H_5$ | H | H | $C_2H_5$ |
| Cl | H | $CH_3$ | 1 | $CH_2SCH_3$ | H | H | $CH_3$ |
| Cl | H | $CH_3$ | 1 | $CH_2SCH_3$ | H | H | $C_2H_5$ |
| Cl | H | $CH_3$ | 1 | $COCH_3$ | H | H | $C_2H_5$ |
| Cl | H | $CH_3$ | 1 | $COC_2H_5$ | H | H | $CH_3$ |
| Cl | H | $CH_3$ | 1 | $COC_2H_5$ | H | H | $C_2H_5$ |
| Cl | H | $CH_3$ | 1 | $COC_2H_5$ | H | H | n-$C_3H_7$ |
| Cl | H | $CH_3$ | 1 | $COC_2H_5$ | H | H | iso-$C_3H_7$ |
| Cl | H | $CH_3$ | 1 | $COC_3H_7$-n | H | H | $CH_3$ |
| Cl | H | $CH_3$ | 1 | $COC_3H_7$-n | H | H | $C_2H_5$ |
| Cl | H | $CH_3$ | 1 | $COC_3H_7$-n | H | H | n-$C_3H_7$ |
| Cl | H | $CH_3$ | 1 | $COC_3H_7$-n | H | H | iso-$C_3H_7$ |
| Cl | H | $CH_3$ | 1 | $COC_3H_7$-iso | H | H | $CH_3$ |
| Cl | H | $CH_3$ | 1 | $COC_3H_7$-iso | H | H | $C_2H_5$ |
| Cl | H | $CH_3$ | 1 | $COC_3H_7$-iso | H | H | n-$C_3H_7$ |
| Cl | H | $CH_3$ | 1 | $COC_3H_7$-iso | H | H | iso-$C_3H_7$ |
| Cl | H | $CH_3$ | 1 | 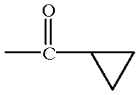 | H | H | $CH_3$ |
| Cl | H | $CH_3$ | 1 | 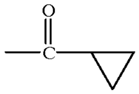 | H | H | n-$C_3H_7$ |
| Cl | H | $CH_3$ | 1 | 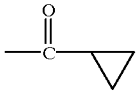 | H | H | iso-$C_3H_7$ |
| Cl | H | $CH_3$ | 1 | 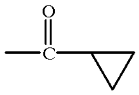 | H | H | $C_2H_5$ |
| Cl | H | $CH_3$ | 1 | $COC_6H_5$ | H | H | $CH_3$ |
| Cl | H | $CH_3$ | 1 | $COC_6H_5$ | H | H | $C_2H_5$ |
| Cl | H | $CH_3$ | 1 | $COC_6H_5$ | H | H | n-$C_3H_7$ |
| Cl | H | $CH_3$ | 1 | $COC_6H_5$ | H | H | iso-$C_3H_7$ |
| Cl | H | $CH_3$ | 1 | $COCH_2OCH_3$ | H | H | $CH_3$ |
| Cl | H | $CH_3$ | 1 | $COCH_2OCH_3$ | H | H | $C_2H_5$ |
| Cl | H | $CH_3$ | 1 | $COCH_2OCH_3$ | H | H | n-$C_3H_7$ |
| Cl | H | $CH_3$ | 2 | H | H | H | $CH_3$ |
| Cl | H | $CH_3$ | 2 | H | H | H | $C_2H_5$ |
| Cl | H | $CH_3$ | 2 | H | H | H | $CH_2CF_3$ |
| Cl | H | $CH_3$ | 2 | H | H | H | n-$C_3H_7$ |
| Cl | H | $CH_3$ | 2 | H | H | H | iso-$C_3H_7$ |
| Cl | H | $CH_3$ | 2 | H | H | H | iso-$C_4H_9$ |
| Cl | H | $CH_3$ | 2 | H | H | H | sec-$C_4H_9$ |
| Cl | H | $CH_3$ | 2 | H | H | H | tert-$C_4H_9$ |
| Cl | H | $CH_3$ | 2 | $CH_3$ | H | H | $C_2H_5$ |
| Cl | H | $CH_3$ | 2 | $C_2H_5$ | H | H | $CH_3$ |
| Cl | H | $CH_3$ | 2 | $C_2H_5$ | H | H | $C_2H_5$ |
| Cl | H | $CH_3$ | 2 | $C_2H_5$ | H | H | n-$C_3H_7$ |
| Cl | H | $CH_3$ | 2 | $C_2H_5$ | H | H | iso-$C_3H_7$ |
| Cl | H | $CH_3$ | 2 | $C_2H_5$ | H | H | n-$C_4H_9$ |

TABLE 1-continued

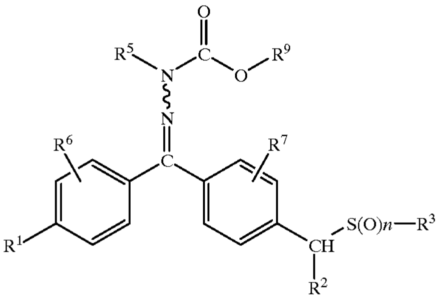

| $R^1$ | $R^2$ | $R^3$ | n | $R^5$ | $R^6$ | $R^7$ | $R^9$ |
|---|---|---|---|---|---|---|---|
| Cl | H | $CH_3$ | 2 | $C_2H_5$ | H | H | iso-$C_4H_9$ |
| Cl | H | $CH_3$ | 2 | $C_2H_5$ | H | H | sec-$C_4H_9$ |
| Cl | H | $CH_3$ | 2 | $C_2H_5$ | H | H | $CH_2CF_3$ |
| Cl | H | $CH_3$ | 2 | iso-$C_3H_7$ | H | H | $CH_3$ |
| Cl | H | $CH_3$ | 2 | iso-$C_3H_7$ | H | H | $C_2H_5$ |
| Cl | H | $CH_3$ | 2 | iso-$C_3H_7$ | H | H | n-$C_3H_7$ |
| Cl | H | $CH_3$ | 2 | iso-$C_3H_7$ | H | H | iso-$C_3H_7$ |
| Cl | H | $CH_3$ | 2 | $CH_2OCH_3$ | H | H | $CH_3$ |
| Cl | H | $CH_3$ | 2 | $CH_2OCH_3$ | H | H | $C_2H_5$ |
| Cl | H | $CH_3$ | 2 | $CH_2OC_2H_5$ | H | H | $CH_3$ |
| Cl | H | $CH_3$ | 2 | $CH_2OC_2H_5$ | H | H | $C_2H_5$ |
| Cl | H | $CH_3$ | 2 | $CH_2SCH_3$ | H | H | $CH_3$ |
| Cl | H | $CH_3$ | 2 | $CH_2SCH_3$ | H | H | $C_2H_5$ |
| Cl | H | $CH_3$ | 2 | $COCH_3$ | H | H | $C_2H_5$ |
| Cl | H | $CH_3$ | 2 | $COC_2H_5$ | H | H | $CH_3$ |
| Cl | H | $CH_3$ | 2 | $COC_2H_5$ | H | H | $C_2H_5$ |
| Cl | H | $CH_3$ | 2 | $COC_2H_5$ | H | H | n-$C_3H_7$ |
| Cl | H | $CH_3$ | 2 | $COC_2H_5$ | H | H | iso-$C_3H_7$ |
| Cl | H | $CH_3$ | 2 | $COC_3H_7$-n | H | H | $C_2H_5$ |
| Cl | H | $CH_3$ | 2 | $COC_3H_7$-n | H | H | n-$C_3H_7$ |
| Cl | H | $CH_3$ | 2 | $COC_3H_7$-n | H | H | iso-$C_3H_7$ |
| Cl | H | $CH_3$ | 2 | $COC_3H_7$-n | H | H | $CH_3$ |
| Cl | H | $CH_3$ | 2 | $COC_3H_7$-iso | H | H | $CH_3$ |
| Cl | H | $CH_3$ | 2 | $COC_3H_7$-iso | H | H | $C_2H_5$ |
| Cl | H | $CH_3$ | 2 | $COC_3H_7$-iso | H | H | n-$C_3H_7$ |
| Cl | H | $CH_3$ | 2 | $COC_3H_7$-iso | H | H | iso-$C_3H_7$ |
| Cl | H | $CH_3$ | 2 | 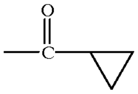 | H | H | $CH_3$ |
| Cl | H | $CH_3$ | 2 | 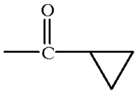 | H | H | $C_2H_5$ |
| Cl | H | $CH_3$ | 2 | 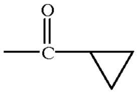 | H | H | n-$C_3H_7$ |
| Cl | H | $CH_3$ | 2 | 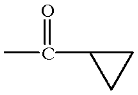 | H | H | iso-$C_3H_7$ |
| Cl | H | $CH_3$ | 2 | $COC_6H_5$ | H | H | $CH_3$ |
| Cl | H | $CH_3$ | 2 | $COC_6H_5$ | H | H | $C_2H_5$ |
| Cl | H | $CH_3$ | 2 | $COC_6H_5$ | H | H | n-$C_3H_7$ |
| Cl | H | $CH_3$ | 2 | $COC_6H_5$ | H | H | iso-$C_3H_7$ |
| Cl | H | $CH_3$ | 2 | $COCH_2OCH_3$ | H | H | $CH_3$ |
| Cl | H | $CH_3$ | 2 | $COCH_2OCH_3$ | H | H | $C_2H_5$ |
| Cl | H | $CH_3$ | 2 | $COCH_2OCH_3$ | H | H | n-$C_3H_7$ |
| Cl | H | $C_2H_5$ | 0 | H | H | H | $CH_3$ |
| Cl | H | $C_2H_5$ | 0 | H | H | H | $C_2H_5$ |
| Cl | H | $C_2H_5$ | 0 | H | H | H | iso-$C_3H_7$ |

TABLE 1-continued

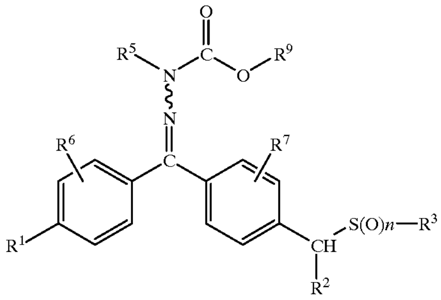

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 0 | H | H | H | iso-$C_4H_9$ |
| Cl | H | $C_2H_5$ | 0 | H | H | H | n-$C_3H_7$ |
| Cl | H | $C_2H_5$ | 0 | H | H | H | n-$C_4H_9$ |
| Cl | H | $C_2H_5$ | 0 | H | H | H | sec-$C_4H_9$ |
| Cl | H | $C_2H_5$ | 0 | H | H | H | n-$C_5H_{11}$ |
| Cl | H | $C_2H_5$ | 0 | H | H | H | $CH_2CF_3$ |
| Cl | H | $C_2H_5$ | 0 | H | H | H | $CH_2Si(CH_3)_3$ |
| Cl | H | $C_2H_5$ | 0 | H | 2-F | H | $C_2H_5$ |
| Cl | H | $C_2H_5$ | 0 | H | 3-F | H | $C_2H_5$ |
| Cl | H | $C_2H_5$ | 0 | H | 2-Cl | H | $C_2H_5$ |
| Cl | H | $C_2H_5$ | 0 | H | 3-Cl | H | $C_2H_5$ |
| Cl | H | $C_2H_5$ | 0 | $CH_3$ | H | H | $CH_3$ |
| Cl | H | $C_2H_5$ | 0 | $CH_3$ | H | H | $C_2H_5$ |
| Cl | H | $C_2H_5$ | 0 | $CH_3$ | H | H | n-$C_3H_7$ |
| Cl | H | $C_2H_5$ | 0 | $CH_3$ | H | H | iso-$C_3H_7$ |
| Cl | H | $C_2H_5$ | 0 | $C_2H_5$ | H | H | $CH_3$ |
| Cl | H | $C_2H_5$ | 0 | $C_2H_5$ | H | H | $C_2H_5$ |
| Cl | H | $C_2H_5$ | 0 | $C_2H_5$ | H | H | n-$C_3H_7$ |
| Cl | H | $C_2H_5$ | 0 | $C_2H_5$ | H | H | iso-$C_3H_7$ |
| Cl | H | $C_2H_5$ | 0 | $C_2H_5$ | H | H | n-$C_4H_9$ |
| Cl | H | $C_2H_5$ | 0 | $C_2H_5$ | H | H | iso-$C_4H_9$ |
| Cl | H | $C_2H_5$ | 0 | $C_2H_5$ | H | H | sec-$C_4H_9$ |
| Cl | H | $C_2H_5$ | 0 | $C_2H_5$ | H | H | $CH_2CF_3$ |
| Cl | H | $C_2H_5$ | 0 | n-$C_3H_7$ | H | H | $CH_3$ |
| Cl | H | $C_2H_5$ | 0 | n-$C_3H_7$ | H | H | $C_2H_5$ |
| Cl | H | $C_2H_5$ | 0 | n-$C_3H_7$ | H | H | n-$C_3H_7$ |
| Cl | H | $C_2H_5$ | 0 | n-$C_3H_7$ | H | H | iso-$C_3H_7$ |
| Cl | H | $C_2H_5$ | 0 | iso-$C_3H_7$ | H | H | $CH_3$ |
| Cl | H | $C_2H_5$ | 0 | iso-$C_3H_7$ | H | H | $C_2H_5$ |
| Cl | H | $C_2H_5$ | 0 | iso-$C_3H_7$ | H | H | n-$C_3H_7$ |
| Cl | H | $C_2H_5$ | 0 | iso-$C_3H_7$ | H | H | iso-$C_3H_7$ |
| Cl | H | $C_2H_5$ | 0 | iso-$C_3H_7$ | H | H | n-$C_4H_9$ |
| Cl | H | $C_2H_5$ | 0 | iso-$C_3H_7$ | H | H | iso-$C_4H_9$ |
| Cl | H | $C_2H_5$ | 0 | iso-$C_3H_7$ | H | H | sec-$C_4H_9$ |
| Cl | H | $C_2H_5$ | 0 | iso-$C_3H_7$ | H | H | $CH_2CF_3$ |
| Cl | H | $C_2H_5$ | 0 | n-$C_4H_9$ | H | H | $CH_3$ |
| Cl | H | $C_2H_5$ | 0 | n-$C_4H_9$ | H | H | $C_2H_5$ |
| Cl | H | $C_2H_5$ | 0 | n-$C_4H_9$ | H | H | n-$C_3H_7$ |
| Cl | H | $C_2H_5$ | 0 | n-$C_4H_9$ | H | H | iso-$C_3H_7$ |
| Cl | H | $C_2H_5$ | 0 | $CH_2OCH_3$ | H | H | $CH_3$ |
| Cl | H | $C_2H_5$ | 0 | $CH_2OCH_3$ | H | H | $C_2H_5$ |
| Cl | H | $C_2H_5$ | 0 | $CH_2OCH_3$ | H | H | n-$C_3H_7$ |
| Cl | H | $C_2H_5$ | 0 | $CH_2OCH_3$ | H | H | iso-$C_3H_7$ |
| Cl | H | $C_2H_5$ | 0 | $CH_2OCH_3$ | H | H | $CH_2CF_3$ |
| Cl | H | $C_2H_5$ | 0 | $CH_2OC_2H_5$ | H | H | $CH_3$ |
| Cl | H | $C_2H_5$ | 0 | $CH_2OC_2H_5$ | H | H | $C_2H_5$ |
| Cl | H | $C_2H_5$ | 0 | $CH_2OC_2H_5$ | H | H | n-$C_3H_7$ |
| Cl | H | $C_2H_5$ | 0 | $CH_2OC_2H_5$ | H | H | iso-$C_3H_7$ |
| Cl | H | $C_2H_5$ | 0 | $CH_2OC_2H_5$ | H | H | $CH_2CF_3$ |
| Cl | H | $C_2H_5$ | 0 | $CH_2SCH_3$ | H | H | $CH_3$ |
| Cl | H | $C_2H_5$ | 0 | $CH_2SCH_3$ | H | H | $C_2H_5$ |
| Cl | H | $C_2H_5$ | 0 | $CH_2SCH_3$ | H | H | n-$C_3H_7$ |
| Cl | H | $C_2H_5$ | 0 | $CH_2SCH_3$ | H | H | iso-$C_3H_7$ |
| Cl | H | $C_2H_5$ | 0 | $CH_2SCH_3$ | H | H | $CH_2CF_3$ |
| Cl | H | $C_2H_5$ | 0 | CHO | H | H | $C_2H_5$ |
| Cl | H | $C_2H_5$ | 0 | $COCH_3$ | H | H | $CH_3$ |
| Cl | H | $C_2H_5$ | 0 | $COCH_3$ | H | H | $C_2H_5$ |
| Cl | H | $C_2H_5$ | 0 | $COCH_3$ | H | H | n-$C_3H_7$ |
| Cl | H | $C_2H_5$ | 0 | $COC_2H_5$ | H | H | $CH_3$ |
| Cl | H | $C_2H_5$ | 0 | $COC_2H_5$ | H | H | $C_2H_5$ |
| Cl | H | $C_2H_5$ | 0 | $COC_2H_5$ | H | H | n-$C_3H_7$ |

TABLE 1-continued

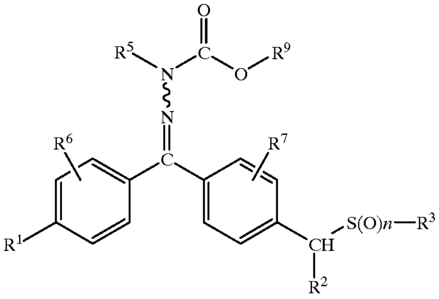

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 0 | $COC_2H_5$ | H | H | iso-$C_3H_7$ |
| Cl | H | $C_2H_5$ | 0 | $COC_2H_5$ | H | H | $CH_2CF_3$ |
| Cl | H | $C_2H_5$ | 0 | $COC_3H_7$-n | H | H | $CH_3$ |
| Cl | H | $C_2H_5$ | 0 | $COC_3H_7$-n | H | H | $C_2H_5$ |
| Cl | H | $C_2H_5$ | 0 | $COC_3H_7$-n | H | H | n-$C_3H_7$ |
| Cl | H | $C_2H_5$ | 0 | $COC_3H_7$-n | H | H | iso-$C_3H_7$ |
| Cl | H | $C_2H_5$ | 0 | $COC_3H_7$-n | H | H | n-$C_4H_9$ |
| Cl | H | $C_2H_5$ | 0 | $COC_3H_7$-n | H | H | iso-$C_4H_9$ |
| Cl | H | $C_2H_5$ | 0 | $COC_3H_7$-n | H | H | sec-$C_4H_9$ |
| Cl | H | $C_2H_5$ | 0 | $COC_3H_7$-n | H | H | $CH_2CF_3$ |
| Cl | H | $C_2H_5$ | 0 | $COC_3H_7$-iso | H | H | $CH_3$ |
| Cl | H | $C_2H_5$ | 0 | $COC_3H_7$-iso | H | H | $C_2H_5$ |
| Cl | H | $C_2H_5$ | 0 | $COC_3H_7$-iso | H | H | n-$C_3H_7$ |
| Cl | H | $C_2H_5$ | 0 | $COC_4H_9$-n | H | H | $CH_3$ |
| Cl | H | $C_2H_5$ | 0 | $COC_4H_9$-n | H | H | $C_2H_5$ |
| Cl | H | $C_2H_5$ | 0 | $COC_4H_9$-n | H | H | n-$C_3H_7$ |
| Cl | H | $C_2H_5$ | 0 | $COC_4H_9$-n | H | H | iso-$C_3H_7$ |
| Cl | H | $C_2H_5$ | 0 | $COCH_2OCH_3$ | H | H | $CH_3$ |
| Cl | H | $C_2H_5$ | 0 | $COCH_2OCH_3$ | H | H | $C_2H_5$ |
| Cl | H | $C_2H_5$ | 0 | $COCH_2OCH_3$ | H | H | n-$C_3H_7$ |
| Cl | H | $C_2H_5$ | 0 | 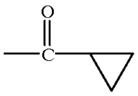 | H | H | $CH_3$ |
| Cl | H | $C_2H_5$ | 0 | 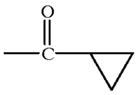 | H | H | $C_2H_5$ |
| Cl | H | $C_2H_5$ | 0 | 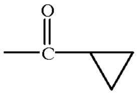 | H | H | n-$C_3H_7$ |
| Cl | H | $C_2H_5$ | 0 | $COC_6H_5$ | H | H | $CH_3$ |
| Cl | H | $C_2H_5$ | 0 | $COC_6H_5$ | H | H | $C_2H_5$ |
| Cl | H | $C_2H_5$ | 0 | $COC_6H_5$ | H | H | n-$C_3H_7$ |
| Cl | H | $C_2H_5$ | 0 | $COC_6H_5$ | H | H | iso-$C_3H_7$ |
| Cl | H | $C_2H_5$ | 0 | $COC_6H_5$ | H | H | $CH_2CF_3$ |
| Cl | H | $C_2H_5$ | 0 | 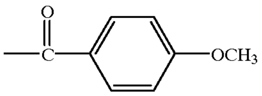 | H | H | $C_2H_5$ |
| Cl | H | $C_2H_5$ | 1 | H | H | H | $CH_3$ |
| Cl | H | $C_2H_5$ | 1 | H | H | H | $C_2H_5$ |
| Cl | H | $C_2H_5$ | 1 | H | H | H | n-$C_3H_7$ |
| Cl | H | $C_2H_5$ | 1 | H | H | H | iso-$C_3H_7$ |
| Cl | H | $C_2H_5$ | 1 | H | H | H | iso-$C_4H_9$ |
| Cl | H | $C_2H_5$ | 1 | H | H | H | $CH_2CF_3$ |
| Cl | H | $C_2H_5$ | 1 | $C_2H_5$ | H | H | $CH_3$ |
| Cl | H | $C_2H_5$ | 1 | $C_2H_5$ | H | H | $C_2H_5$ |
| Cl | H | $C_2H_5$ | 1 | $C_2H_5$ | H | H | n-$C_3H_7$ |
| Cl | H | $C_2H_5$ | 1 | $C_2H_5$ | H | H | iso-$C_3H_7$ |
| Cl | H | $C_2H_5$ | 1 | $C_2H_5$ | H | H | n-$C_4H_9$ |

TABLE 1-continued

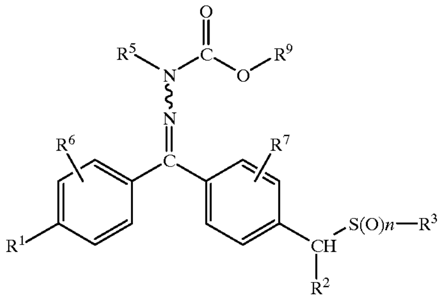

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 1 | $C_2H_5$ | H | H | iso-$C_4H_9$ |
| Cl | H | $C_2H_5$ | 1 | $C_2H_5$ | H | H | sec-$C_4H_9$ |
| Cl | H | $C_2H_5$ | 1 | $C_2H_5$ | H | H | $CH_2CF_3$ |
| Cl | H | $C_2H_5$ | 1 | iso-$C_3H_7$ | H | H | $CH_3$ |
| Cl | H | $C_2H_5$ | 1 | iso-$C_3H_7$ | H | H | $C_2H_5$ |
| Cl | H | $C_2H_5$ | 1 | iso-$C_3H_7$ | H | H | n-$C_3H_7$ |
| Cl | H | $C_2H_5$ | 1 | iso-$C_3H_7$ | H | H | iso-$C_3H_7$ |
| Cl | H | $C_2H_5$ | 1 | $CH_2OCH_3$ | H | H | $CH_3$ |
| Cl | H | $C_2H_5$ | 1 | $CH_2OC_2H_5$ | H | H | $CH_3$ |
| Cl | H | $C_2H_5$ | 1 | $CH_2OC_2H_5$ | H | H | $C_2H_5$ |
| Cl | H | $C_2H_5$ | 1 | $CH_2SCH_3$ | H | H | $CH_3$ |
| Cl | H | $C_2H_5$ | 1 | $CH_2SCH_3$ | H | H | $C_2H_5$ |
| Cl | H | $C_2H_5$ | 1 | $COC_2H_5$ | H | H | $CH_3$ |
| Cl | H | $C_2H_5$ | 1 | $COC_2H_5$ | H | H | $C_2H_5$ |
| Cl | H | $C_2H_5$ | 1 | $COC_2H_5$ | H | H | n-$C_3H_7$ |
| Cl | H | $C_2H_5$ | 1 | $COC_2H_5$ | H | H | iso-$C_3H_7$ |
| Cl | H | $C_2H_5$ | 1 | $COC_3H_7$-n | H | H | $CH_3$ |
| Cl | H | $C_2H_5$ | 1 | $COC_3H_7$-n | H | H | $C_2H_5$ |
| Cl | H | $C_2H_5$ | 1 | $COC_3H_7$-n | H | H | n-$C_3H_7$ |
| Cl | H | $C_2H_5$ | 1 | $COC_3H_7$-n | H | H | iso-$C_3H_7$ |
| Cl | H | $C_2H_5$ | 1 | $COC_3H_7$-iso | H | H | $CH_3$ |
| Cl | H | $C_2H_5$ | 1 | $COC_3H_7$-iso | H | H | $C_2H_5$ |
| Cl | H | $C_2H_5$ | 1 | $COC_3H_7$-iso | H | H | n-$C_3H_7$ |
| Cl | H | $C_2H_5$ | 1 | $COC_3H_7$-iso | H | H | iso-$C_3H_7$ |
| Cl | H | $C_2H_5$ | 1 | 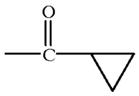 | H | H | $CH_3$ |
| Cl | H | $C_2H_5$ | 1 | 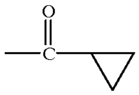 | H | H | $C_2H_5$ |
| Cl | H | $C_2H_5$ | 1 | 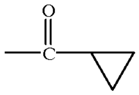 | H | H | n-$C_3H_7$ |
| Cl | H | $C_2H_5$ | 1 | 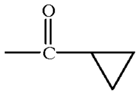 | H | H | iso-$C_3H_7$ |
| Cl | H | $C_2H_5$ | 1 | $COCH_2OCH_3$ | H | H | $CH_3$ |
| Cl | H | $C_2H_5$ | 1 | $COCH_2OCH_3$ | H | H | $C_2H_5$ |
| Cl | H | $C_2H_5$ | 1 | $COCH_2OCH_3$ | H | H | n-$C_3H_7$ |
| Cl | H | $C_2H_5$ | 1 | $COC_6H_5$ | H | H | $CH_3$ |
| Cl | H | $C_2H_5$ | 1 | $COC_6H_5$ | H | H | $C_2H_5$ |
| Cl | H | $C_2H_5$ | 1 | $COC_6H_5$ | H | H | n-$C_3H_7$ |
| Cl | H | $C_2H_5$ | 1 | $COC_6H_5$ | H | H | iso-$C_3H_7$ |
| Cl | H | $C_2H_5$ | 2 | H | H | H | $CH_3$ |
| Cl | H | $C_2H_5$ | 2 | H | H | H | $C_2H_5$ |
| Cl | H | $C_2H_5$ | 2 | H | H | H | n-$C_3H_7$ |
| Cl | H | $C_2H_5$ | 2 | H | H | H | iso-$C_3H_7$ |
| Cl | H | $C_2H_5$ | 2 | H | H | H | iso-$C_4H_9$ |
| Cl | H | $C_2H_5$ | 2 | H | H | H | $CH_2CF_3$ |

TABLE 1-continued

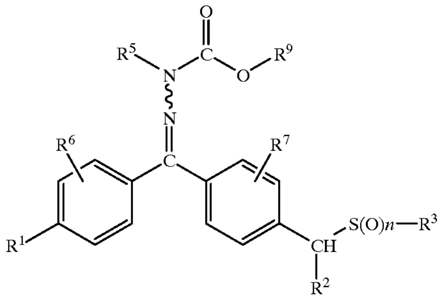

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 2 | H | 2-F | H | $C_2H_5$ |
| Cl | H | $C_2H_5$ | 2 | H | 3-F | H | $C_2H_5$ |
| Cl | H | $C_2H_5$ | 2 | H | 2-Cl | H | $C_2H_5$ |
| Cl | H | $C_2H_5$ | 2 | H | 3-Cl | H | $C_2H_5$ |
| Cl | H | $C_2H_5$ | 2 | $C_2H_5$ | H | H | $CH_3$ |
| Cl | H | $C_2H_5$ | 2 | $C_2H_5$ | H | H | $C_2H_5$ |
| Cl | H | $C_2H_5$ | 2 | $C_2H_5$ | H | H | n-$C_3H_7$ |
| Cl | H | $C_2H_5$ | 2 | $C_2H_5$ | H | H | iso-$C_3H_7$ |
| Cl | H | $C_2H_5$ | 2 | $C_2H_5$ | H | H | n-$C_4H_9$ |
| Cl | H | $C_2H_5$ | 2 | $C_2H_5$ | H | H | sec-$C_4H_9$ |
| Cl | H | $C_2H_5$ | 2 | $C_2H_5$ | H | H | iso-$C_4H_9$ |
| Cl | H | $C_2H_5$ | 2 | $C_2H_5$ | H | H | $CH_2CF_3$ |
| Cl | H | $C_2H_5$ | 2 | iso-$C_3H_7$ | H | H | $CH_3$ |
| Cl | H | $C_2H_5$ | 2 | iso-$C_3H_7$ | H | H | $C_2H_5$ |
| Cl | H | $C_2H_5$ | 2 | iso-$C_3H_7$ | H | H | n-$C_3H_7$ |
| Cl | H | $C_2H_5$ | 2 | iso-$C_3H_7$ | H | H | iso-$C_3H_7$ |
| Cl | H | $C_2H_5$ | 2 | $CH_2OCH_3$ | H | H | $CH_3$ |
| Cl | H | $C_2H_5$ | 2 | $CH_2OCH_3$ | H | H | $C_2H_5$ |
| Cl | H | $C_2H_5$ | 2 | $CH_2OC_2H_5$ | H | H | $CH_3$ |
| Cl | H | $C_2H_5$ | 2 | $CH_2OC_2H_5$ | H | H | $C_2H_5$ |
| Cl | H | $C_2H_5$ | 2 | $CH_2SCH_3$ | H | H | $CH_3$ |
| Cl | H | $C_2H_5$ | 2 | $CH_2SCH_3$ | H | H | $C_2H_5$ |
| Cl | H | $C_2H_5$ | 2 | CHO | H | H | $C_2H_5$ |
| Cl | H | $C_2H_5$ | 2 | $COC_2H_5$ | H | H | $CH_3$ |
| Cl | H | $C_2H_5$ | 2 | $COC_2H_5$ | H | H | $C_2H_5$ |
| Cl | H | $C_2H_5$ | 2 | $COC_2H_5$ | H | H | n-$C_3H_7$ |
| Cl | H | $C_2H_5$ | 2 | $COC_2H_5$ | H | H | iso-$C_3H_7$ |
| Cl | H | $C_2H_5$ | 2 | $COC_3H_7$-n | H | H | $CH_3$ |
| Cl | H | $C_2H_5$ | 2 | $COC_3H_7$-n | H | H | $C_2H_5$ |
| Cl | H | $C_2H_5$ | 2 | $COC_3H_7$-n | H | H | n-$C_3H_7$ |
| Cl | H | $C_2H_5$ | 2 | $COC_3H_7$-n | H | H | iso-$C_3H_7$ |
| Cl | H | $C_2H_5$ | 2 | $COC_3H_7$-iso | H | H | $CH_3$ |
| Cl | H | $C_2H_5$ | 2 | $COC_3H_7$-iso | H | H | $C_2H_5$ |
| Cl | H | $C_2H_5$ | 2 | $COC_3H_7$-iso | H | H | n-$C_3H_7$ |
| Cl | H | $C_2H_5$ | 2 | $COC_3H_7$-iso | H | H | iso-$C_3H_7$ |
| Cl | H | $C_2H_5$ | 2 | 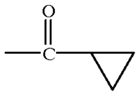 | H | H | $CH_3$ |
| Cl | H | $C_2H_5$ | 2 | 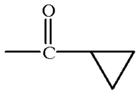 | H | H | $C_2H_5$ |
| Cl | H | $C_2H_5$ | 2 | 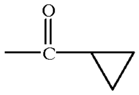 | H | H | n-$C_3H_7$ |
| Cl | H | $C_2H_5$ | 2 | 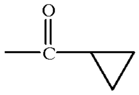 | H | H | iso-$C_3H_7$ |
| Cl | H | $C_2H_5$ | 2 | $COC_6H_5$ | H | H | $CH_3$ |
| Cl | H | $C_2H_5$ | 2 | $COC_6H_5$ | H | H | $C_2H_5$ |

TABLE 1-continued

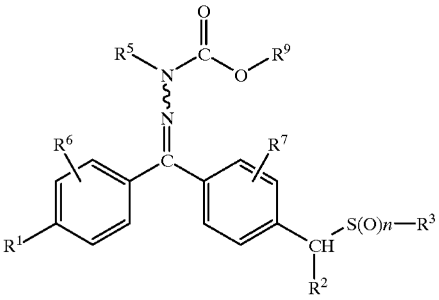

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 2 | $COC_6H_5$ | H | H | n-$C_3H_7$ |
| Cl | H | $C_2H_5$ | 2 | $COCH_2OCH_3$ | H | H | $CH_3$ |
| Cl | H | $C_2H_5$ | 2 | $COCH_2OCH_3$ | H | H | $C_2H_5$ |
| Cl | H | $C_2H_5$ | 2 | $COCH_2OCH_3$ | H | H | n-$C_3H_7$ |
| Cl | H | n-$C_3H_7$ | 0 | H | H | H | $CH_3$ |
| Cl | H | n-$C_3H_7$ | 0 | H | H | H | $C_2H_5$ |
| Cl | H | n-$C_3H_7$ | 0 | H | H | H | n-$C_3H_7$ |
| Cl | H | n-$C_3H_7$ | 0 | H | H | H | iso-$C_4H_9$ |
| Cl | H | n-$C_3H_7$ | 0 | $C_2H_5$ | H | H | $CH_3$ |
| Cl | H | n-$C_3H_7$ | 0 | $C_2H_5$ | H | H | $C_2H_5$ |
| Cl | H | n-$C_3H_7$ | 0 | iso-$C_3H_7$ | H | H | $C_2H_5$ |
| Cl | H | n-$C_3H_7$ | 0 | $COC_3H_7$-n | H | H | $C_2H_5$ |
| Cl | H | n-$C_3H_7$ | 1 | H | H | H | $CH_3$ |
| Cl | H | n-$C_3H_7$ | 1 | H | H | H | $C_2H_5$ |
| Cl | H | n-$C_3H_7$ | 1 | H | H | H | n-$C_3H_7$ |
| Cl | H | n-$C_3H_7$ | 1 | H | H | H | iso-$C_3H_7$ |
| Cl | H | n-$C_3H_7$ | 1 | H | H | H | iso-$C_4H_9$ |
| Cl | H | n-$C_3H_7$ | 1 | H | H | H | $CH_2CF_3$ |
| Cl | H | n-$C_3H_7$ | 2 | H | H | H | $CH_3$ |
| Cl | H | n-$C_3H_7$ | 2 | H | H | H | $C_2H_5$ |
| Cl | H | n-$C_3H_7$ | 2 | H | H | H | $CH_2CF_3$ |
| Cl | H | n-$C_3H_7$ | 2 | H | H | H | n-$C_3H_7$ |
| Cl | H | n-$C_3H_7$ | 2 | H | H | H | iso-$C_3H_7$ |
| Cl | H | n-$C_3H_7$ | 2 | H | H | H | iso-$C_4H_9$ |
| Cl | H | iso-$C_3H_7$ | 0 | H | H | H | $CH_3$ |
| Cl | H | iso-$C_3H_7$ | 0 | H | H | H | $C_2H_5$ |
| Cl | H | iso-$C_3H_7$ | 1 | H | H | H | $CH_3$ |
| Cl | H | iso-$C_3H_7$ | 1 | H | H | H | $C_2H_5$ |
| Cl | H | iso-$C_3H_7$ | 2 | H | H | H | $CH_3$ |
| Cl | H | iso-$C_3H_7$ | 2 | H | H | H | $C_2H_5$ |
| Cl | H | n-$C_4H_9$ | 0 | H | H | H | $C_2H_5$ |
| Cl | H | sec-$C_4H_9$ | 0 | H | H | H | $C_2H_5$ |
| Cl | H | $CH_2OCH_3$ | 0 | H | H | H | $CH_3$ |
| Cl | H | $CH_2OCH_3$ | 0 | H | H | H | $C_2H_5$ |
| Cl | H | $CH_2OC_2H_5$ | 0 | H | H | H | $C_2H_5$ |
| Cl | H | $CH_2Si(CH_3)_3$ | 0 | H | H | H | $C_2H_5$ |
| Cl | H | $CH_2F$ | 0 | H | H | H | $C_2H_5$ |
| Cl | H | $CH_2F$ | 1 | H | H | H | $CH_3$ |
| Cl | H | $CH_2F$ | 1 | H | H | H | $C_2H_5$ |
| Cl | H | $CH_2F$ | 1 | H | H | H | n-$C_3H_7$ |
| Cl | H | $CH_2F$ | 1 | H | H | H | iso-$C_3H_7$ |
| Cl | H | $CH_2F$ | 1 | H | H | H | iso-$C_4H_9$ |
| Cl | H | $CH_2F$ | 1 | H | H | H | $CH_2CF_3$ |
| Cl | H | $CHF_2$ | 0 | H | H | H | $CH_3$ |
| Cl | H | $CHF_2$ | 0 | H | H | H | $C_2H_5$ |
| Cl | H | $CHF_2$ | 0 | H | H | H | iso-$C_3H_7$ |
| Cl | H | $CHF_2$ | 0 | H | H | H | iso-$C_4H_9$ |
| Cl | H | $CHF_2$ | 0 | H | H | H | n-$C_4H_9$ |
| Cl | H | $CHF_2$ | 0 | H | H | H | n-$C_5H_{11}$ |
| Cl | H | $CHF_2$ | 0 | H | H | H | n-$C_6H_{13}$ |
| Cl | H | $CHF_2$ | 0 | H | H | H | $CH_2CF_3$ |
| Cl | H | $CHF_2$ | 0 | $C_2H_5$ | H | H | $CH_3$ |
| Cl | H | $CHF_2$ | 0 | $C_2H_5$ | H | H | $C_2H_5$ |
| Cl | H | $CHF_2$ | 0 | iso-$C_3H_7$ | H | H | $CH_3$ |
| Cl | H | $CHF_2$ | 0 | iso-$C_3H_7$ | H | H | $C_2H_5$ |
| Cl | H | $CHF_2$ | 0 | $COC_3H_7$-n | H | H | $C_2H_5$ |
| Cl | H | $CHF_2$ | 1 | H | H | H | $CH_3$ |
| Cl | H | $CHF_2$ | 1 | H | H | H | $C_2H_5$ |
| Cl | H | $CHF_2$ | 1 | H | H | H | $CH_2CF_3$ |
| Cl | H | $CHF_2$ | 1 | H | H | H | n-$C_3H_7$ |
| Cl | H | $CHF_2$ | 1 | H | H | H | iso-$C_3H_7$ |

TABLE 1-continued

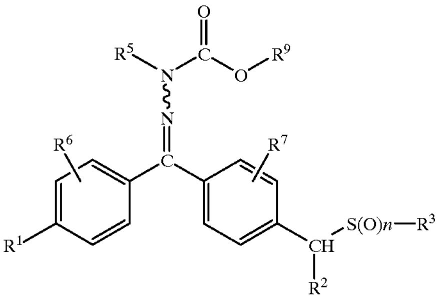

| $R^1$ | $R^2$ | $R^3$ | n | $R^5$ | $R^6$ | $R^7$ | $R^9$ |
|---|---|---|---|---|---|---|---|
| Cl | H | $CHF_2$ | 1 | H | H | H | iso-$C_4H_9$ |
| Cl | H | $CF_3$ | 0 | H | H | H | $CH_3$ |
| Cl | H | $CF_3$ | 0 | H | H | H | $C_2H_5$ |
| Cl | H | $CF_3$ | 0 | H | H | H | $CH_2CF_3$ |
| Cl | H | $CF_3$ | 0 | H | H | H | iso-$C_4H_9$ |
| Cl | H | $CF_3$ | 0 | H | H | H | n-$C_4H_9$ |
| Cl | H | $CF_3$ | 0 | H | H | H | n-$C_5H_{11}$ |
| Cl | H | $CF_3$ | 0 | H | H | H | n-$C_6H_{13}$ |
| Cl | H | $CH_2Cl$ | 0 | H | H | H | $C_2H_5$ |
| Cl | H | $CH_2CH_2F$ | 0 | H | H | H | $C_2H_5$ |
| Cl | H | $CH_2CH_2F$ | 0 | H | H | H | $CH_2CF_3$ |
| Cl | H | $CH_2CH_2F$ | 0 | H | H | H | $CH_3$ |
| Cl | H | $CH_2CH_2F$ | 0 | H | H | H | iso-$C_4H_9$ |
| Cl | H | $CH_2CH_2F$ | 0 | H | H | H | n-$C_3H_7$ |
| Cl | H | $CH_2CH_2F$ | 1 | H | H | H | $CH_3$ |
| Cl | H | $CH_2CH_2F$ | 1 | H | H | H | $C_2H_5$ |
| Cl | H | $CH_2CH_2F$ | 1 | H | H | H | n-$C_3H_7$ |
| Cl | H | $CH_2CH_2F$ | 1 | H | H | H | iso-$C_3H_7$ |
| Cl | H | $CH_2CH_2F$ | 1 | H | H | H | iso-$C_4H_9$ |
| Cl | H | $CH_2CH_2F$ | 1 | H | H | H | $CH_2CF_3$ |
| Cl | H | $CH_2CH_2F$ | 2 | H | H | H | $CH_3$ |
| Cl | H | $CH_2CH_2F$ | 2 | H | H | H | $C_2H_5$ |
| Cl | H | $CH_2CH_2F$ | 2 | H | H | H | $CH_2CF_3$ |
| Cl | H | $CH_2CH_2F$ | 2 | H | H | H | n-$C_3H_7$ |
| Cl | H | $CH_2CH_2F$ | 2 | H | H | H | iso-$C_3H_7$ |
| Cl | H | $CH_2CH_2F$ | 2 | H | H | H | iso-$C_4H_9$ |
| Cl | H | $CH_2CHF_2$ | 0 | H | H | H | $CH_3$ |
| Cl | H | $CH_2CHF_2$ | 0 | H | H | H | $C_2H_5$ |
| Cl | H | $CH_2CHF_2$ | 0 | H | H | H | $CH_2CF_3$ |
| Cl | H | $CH_2CHF_2$ | 0 | H | H | H | iso-$C_4H_9$ |
| Cl | H | $CH_2CHF_2$ | 0 | H | H | H | n-$C_3H_7$ |
| Cl | H | $CH_2CHF_2$ | 1 | H | H | H | $CH_3$ |
| Cl | H | $CH_2CHF_2$ | 1 | H | H | H | $C_2H_5$ |
| Cl | H | $CH_2CHF_2$ | 1 | H | H | H | n-$C_3H_7$ |
| Cl | H | $CH_2CHF_2$ | 1 | H | H | H | iso-$C_3H_7$ |
| Cl | H | $CH_2CHF_2$ | 1 | H | H | H | iso-$C_4H_9$ |
| Cl | H | $CH_2CHF_2$ | 1 | H | H | H | $CH_2CF_3$ |
| Cl | H | $CH_2CHF_2$ | 2 | H | H | H | $CH_3$ |
| Cl | H | $CH_2CHF_2$ | 2 | H | H | H | $C_2H_5$ |
| Cl | H | $CH_2CHF_2$ | 2 | H | H | H | $CH_2CF_3$ |
| Cl | H | $CH_2CHF_2$ | 2 | H | H | H | n-$C_3H_7$ |
| Cl | H | $CH_2CHF_2$ | 2 | H | H | H | iso-$C_3H_7$ |
| Cl | H | $CH_2CHF_2$ | 2 | H | H | H | iso-$C_4H_9$ |
| Cl | H | $CH_2CF_3$ | 0 | $C_2H_5$ | H | H | $C_2H_5$ |
| Cl | H | $CH_2CF_3$ | 0 | $COC_3H_7$-n | H | H | $C_2H_5$ |
| Cl | H | $CH_2CF_3$ | 0 | iso-$C_3H_7$ | H | H | $C_2H_5$ |
| Cl | H | $CH_2CF_3$ | 0 | H | H | H | $CH_3$ |
| Cl | H | $CH_2CF_3$ | 0 | $C_2H_5$ | H | H | $CH_3$ |
| Cl | H | $CH_2CF_3$ | 0 | H | H | H | $C_2H_5$ |
| Cl | H | $CH_2CF_3$ | 0 | H | H | H | n-$C_4H_9$ |
| Cl | H | $CH_2CF_3$ | 0 | H | H | H | iso-$C_4H_9$ |
| Cl | H | $CH_2CF_3$ | 0 | H | H | H | $CH_2CF_3$ |
| Cl | H | $CH_2CF_3$ | 1 | H | H | H | $CH_3$ |
| Cl | H | $CH_2CF_3$ | 1 | H | H | H | $C_2H_5$ |
| Cl | H | $CH_2CF_3$ | 1 | H | H | H | $CH_2CF_3$ |
| Cl | H | $CH_2CF_3$ | 1 | H | H | H | n-$C_3H_7$ |
| Cl | H | $CH_2CF_3$ | 1 | H | H | H | iso-$C_3H_7$ |
| Cl | H | $CH_2CF_3$ | 1 | H | H | H | iso-$C_4H_9$ |
| Cl | H | $CH_2CF_3$ | 2 | H | H | H | $CH_3$ |
| Cl | H | $CH_2CF_3$ | 2 | H | H | H | $C_2H_5$ |
| Cl | H | $CH_2CF_3$ | 2 | H | H | H | $CH_2CF_3$ |

TABLE 1-continued

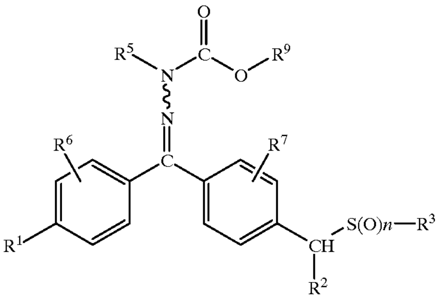

| $R^1$ | $R^2$ | $R^3$ | n | $R^5$ | $R^6$ | $R^7$ | $R^9$ |
|---|---|---|---|---|---|---|---|
| Cl | H | $CH_2CF_3$ | 2 | H | H | H | n-$C_3H_7$ |
| Cl | H | $CH_2CF_3$ | 2 | H | H | H | iso-$C_3H_7$ |
| Cl | H | $CH_2CF_3$ | 2 | H | H | H | iso-$C_4H_9$ |
| Cl | H | $CH_2CH_2Cl$ | 0 | H | H | H | $C_2H_5$ |
| Cl | H | $CH_2CH_2Cl$ | 2 | H | H | H | $C_2H_5$ |
| Cl | H | $CH_2CH_2CH_3F$ | 0 | H | H | H | $C_2H_5$ |
| Cl | H | $CH_2CH_2CH_3F$ | 2 | H | H | H | $C_2H_5$ |
| Cl | H | $CH_2CF_2CF_2H$ | 0 | H | H | H | $C_2H_5$ |
| Cl | H | $CF_2CF_2CF_3$ | 0 | H | H | H | $C_2H_5$ |
| Cl | H | $CH_2CH_2CH_2Cl$ | 0 | H | H | H | $C_2H_5$ |
| Cl | H | $CH{=}CH_2$ | 0 | H | H | H | $CH_3$ |
| Cl | H | $CH{=}CH_2$ | 0 | H | H | H | $C_2H_5$ |
| Cl | H | $CH_2CH{=}CH_2$ | 0 | H | H | H | $C_2H_5$ |
| Cl | H | $CH_2CH{=}CH_2$ | 1 | H | H | H | $C_2H_5$ |
| Cl | H | $CH_2CH{=}CH_2$ | 2 | H | H | H | $C_2H_5$ |
| Cl | H | $CH_2C{\equiv}CH$ | 0 | H | H | H | $C_2H_5$ |
| Cl | H | $CH_2C{\equiv}CH$ | 0 | H | H | H | $CH_3$ |
| Cl | H | $CH_2C{\equiv}CH$ | 1 | H | H | H | $C_2H_5$ |
| Cl | H | $CH_2C{\equiv}CH$ | 2 | H | H | H | $C_2H_5$ |
| Cl | H | $CH_2CN$ | 0 | H | H | H | $CH_3$ |
| Cl | H | $CH_2CN$ | 0 | H | H | H | $C_2H_5$ |
| Cl | H | $CH_2CN$ | 1 | H | H | H | $C_2H_5$ |
| Cl | H | $CH_2CN$ | 2 | H | H | H | $C_2H_5$ |
| Cl | $CH_3$ | $CH_3$ | 0 | H | H | H | $CH_3$ |
| Cl | $CH_3$ | $CH_3$ | 0 | H | H | H | $C_2H_5$ |
| Cl | $CH_3$ | $CH_3$ | 0 | H | H | H | iso-$C_4H_9$ |
| Cl | $CH_3$ | $CH_3$ | 0 | H | H | H | n-$C_4H_9$ |
| Cl | $CH_3$ | $CH_3$ | 0 | H | H | H | $CH_2CF_3$ |
| Cl | $CH_3$ | $CH_3$ | 1 | H | H | H | $CH_3$ |
| Cl | $CH_3$ | $CH_3$ | 1 | H | H | H | $C_2H_5$ |
| Cl | $CH_3$ | $CH_3$ | 1 | H | H | H | iso-$C_4H_9$ |
| Cl | $CH_3$ | $CH_3$ | 1 | H | H | H | $CH_2CF_3$ |
| Cl | $CH_3$ | $CH_3$ | 2 | H | H | H | $CH_3$ |
| Cl | $CH_3$ | $CH_3$ | 2 | H | H | H | $C_2H_5$ |
| Cl | $CH_3$ | $CH_3$ | 2 | H | H | H | iso-$C_4H_9$ |
| Cl | $CH_3$ | $CH_3$ | 2 | H | H | H | $CH_2CF_3$ |
| Cl | $C_2H_5$ | $CH_3$ | 0 | H | H | H | $CH_3$ |
| Cl | $C_2H_5$ | $CH_3$ | 0 | H | H | H | $C_2H_5$ |
| Cl | $C_2H_5$ | $CH_3$ | 1 | H | H | H | $C_2H_5$ |
| Cl | $C_2H_5$ | $CH_3$ | 2 | H | H | H | $C_2H_5$ |
| Cl | n-$C_3H_7$ | $CH_3$ | 0 | H | H | H | $C_2H_5$ |
| Br | H | $CH_3$ | 0 | H | H | H | $CH_3$ |
| Br | H | $CH_3$ | 0 | H | H | H | $C_2H_5$ |
| Br | H | $CH_3$ | 0 | H | H | H | n-$C_3H_7$ |
| Br | H | $CH_3$ | 0 | H | H | H | iso-$C_3H_7$ |
| Br | H | $CH_3$ | 0 | H | H | H | n-$C_4H_9$ |
| Br | H | $CH_3$ | 0 | H | H | H | sec-$C_4H_9$ |
| Br | H | $CH_3$ | 0 | H | H | H | iso-$C_4H_9$ |
| Br | H | $CH_3$ | 0 | H | H | H | tert-$C_4H_9$ |
| Br | H | $CH_3$ | 0 | H | H | H | n-$C_5H_{11}$ |
| Br | H | $CH_3$ | 0 | H | H | H | n-$C_6H_{13}$ |
| Br | H | $CH_3$ | 0 | H | H | H | $CH_2C{\equiv}CH$ |
| Br | H | $CH_3$ | 0 | H | H | H | $CH_2C_6H_5$ |
| Br | H | $CH_3$ | 0 | H | H | H | $CH_2CF_3$ |
| Br | H | $CH_3$ | 0 | $CH_3$ | H | H | $CH_3$ |
| Br | H | $CH_3$ | 0 | $CH_3$ | H | H | $C_2H_5$ |
| Br | H | $CH_3$ | 0 | $C_2H_5$ | H | H | $CH_3$ |
| Br | H | $CH_3$ | 0 | $C_2H_5$ | H | H | $C_2H_5$ |
| Br | H | $CH_3$ | 0 | $C_2H_5$ | H | H | n-$C_3H_7$ |
| Br | H | $CH_3$ | 0 | $C_2H_5$ | H | H | iso-$C_3H_7$ |
| Br | H | $CH_3$ | 0 | $C_2H_5$ | H | H | n-$C_4H_9$ |

TABLE 1-continued

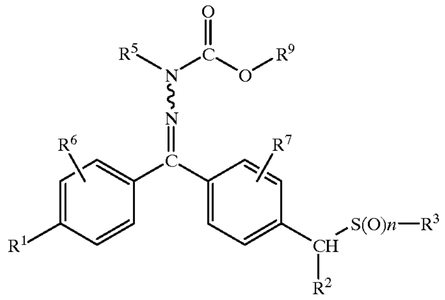

| $R^1$ | $R^2$ | $R^3$ | n | $R^5$ | $R^6$ | $R^7$ | $R^9$ |
|---|---|---|---|---|---|---|---|
| Br | H | $CH_3$ | 0 | $C_2H_5$ | H | H | iso-$C_4H_9$ |
| Br | H | $CH_3$ | 0 | $C_2H_5$ | H | H | sec-$C_4H_9$ |
| Br | H | $CH_3$ | 0 | $C_2H_5$ | H | H | $CH_2CF_3$ |
| Br | H | $CH_3$ | 0 | iso-$C_3H_7$ | H | H | $CH_3$ |
| Br | H | $CH_3$ | 0 | iso-$C_3H_7$ | H | H | $C_2H_5$ |
| Br | H | $CH_3$ | 0 | iso-$C_3H_7$ | H | H | n-$C_3H_7$ |
| Br | H | $CH_3$ | 0 | iso-$C_3H_7$ | H | H | iso-$C_3H_7$ |
| Br | H | $CH_3$ | 0 | iso-$C_3H_7$ | H | H | iso-$C_4H_9$ |
| Br | H | $CH_3$ | 0 | iso-$C_3H_7$ | H | H | $CH_2CF_3$ |
| Br | H | $CH_3$ | 0 | $CH_2SCH_3$ | H | H | $CH_3$ |
| Br | H | $CH_3$ | 0 | $CH_2OCH_3$ | H | H | $CH_3$ |
| Br | H | $CH_3$ | 0 | $CH_2OCH_3$ | H | H | $C_2H_5$ |
| Br | H | $CH_3$ | 0 | $CH_2OC_2H_5$ | H | H | $C_2H_5$ |
| Br | H | $CH_3$ | 0 | $CH_2SCH_3$ | H | H | $C_2H_5$ |
| Br | H | $CH_3$ | 0 | CHO | H | H | $C_2H_5$ |
| Br | H | $CH_3$ | 0 | $COCH_3$ | H | H | $CH_3$ |
| Br | H | $CH_3$ | 0 | $COCH_3$ | H | H | $C_2H_5$ |
| Br | H | $CH_3$ | 0 | $COC_2H_5$ | H | H | $CH_3$ |
| Br | H | $CH_3$ | 0 | $COC_2H_5$ | H | H | $C_2H_5$ |
| Br | H | $CH_3$ | 0 | $COC_2H_5$ | H | H | n-$C_3H_7$ |
| Br | H | $CH_3$ | 0 | $COC_3H_7$-n | H | H | $CH_3$ |
| Br | H | $CH_3$ | 0 | $COC_3H_7$-n | H | H | $C_2H_5$ |
| Br | H | $CH_3$ | 0 | $COC_3H_7$-n | H | H | iso-$C_3H_7$ |
| Br | H | $CH_3$ | 0 | $COC_3H_7$-n | H | H | iso-$C_4H_9$ |
| Br | H | $CH_3$ | 0 | $COCH_3$-n | H | H | n-$C_3H_7$ |
| Br | H | $CH_3$ | 0 | $COCH_2OCH_3$ | H | H | n-$C_3H_7$ |
| Br | H | $CH_3$ | 0 | $COC_6H_5$ | H | H | $CH_3$ |
| Br | H | $CH_3$ | 0 | $COC_6H_5$ | H | H | $C_2H_5$ |
| Br | H | $CH_3$ | 0 | 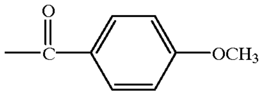 | H | H | $C_2H_5$ |
| Br | H | $CH_3$ | 0 | $COCH{=}CHC_6H_5$ | H | H | $C_2H_5$ |
| Br | H | $CH_3$ | 0 | $COCH_2OCH_3$ | H | H | $CH_3$ |
| Br | H | $CH_3$ | 0 | $COCH_2OCH_3$ | H | H | $C_2H_5$ |
| Br | H | $CH_3$ | 1 | H | H | H | $CH_3$ |
| Br | H | $CH_3$ | 1 | H | H | H | $C_2H_5$ |
| Br | H | $CH_3$ | 1 | H | H | H | n-$C_3H_7$ |
| Br | H | $CH_3$ | 1 | H | H | H | iso-$C_3H_7$ |
| Br | H | $CH_3$ | 1 | H | H | H | iso-$C_4H_9$ |
| Br | H | $CH_3$ | 1 | H | H | H | $CH_2CF_3$ |
| Br | H | $CH_3$ | 1 | $C_2H_5$ | H | H | $CH_3$ |
| Br | H | $CH_3$ | 1 | $C_2H_5$ | H | H | $C_2H_5$ |
| Br | H | $CH_3$ | 1 | $C_2H_5$ | H | H | n-$C_3H_7$ |
| Br | H | $CH_3$ | 1 | $C_2H_5$ | H | H | iso-$C_3H_7$ |
| Br | H | $CH_3$ | 1 | iso-$C_3H_7$ | H | H | $CH_3$ |
| Br | H | $CH_3$ | 1 | iso-$C_3H_7$ | H | H | $C_2H_5$ |
| Br | H | $CH_3$ | 1 | iso-$C_3H_7$ | H | H | n-$C_3H_7$ |
| Br | H | $CH_3$ | 1 | iso-$C_3H_7$ | H | H | iso-$C_3H_7$ |
| Br | H | $CH_3$ | 1 | $COC_2H_5$ | H | H | $CH_3$ |
| Br | H | $CH_3$ | 1 | $COC_2H_5$ | H | H | $C_2H_5$ |
| Br | H | $CH_3$ | 1 | $COC_3H_7$-n | H | H | $CH_3$ |
| Br | H | $CH_3$ | 1 | $COC_3H_7$-n | H | H | $C_2H_5$ |
| Br | H | $CH_3$ | 1 | $COC_2H_5$ | H | H | n-$C_3H_7$ |
| Br | H | $CH_3$ | 1 | $COC_3H_7$-n | H | H | n-$C_3H_7$ |
| Br | H | $CH_3$ | 1 | $COCH_2OCH_3$ | H | H | n-$C_3H_7$ |
| Br | H | $CH_3$ | 1 | $COCH_2OCH_3$ | H | H | $C_2H_5$ |
| Br | H | $CH_3$ | 1 | $COCH_2OCH_3$ | H | H | $CH_3$ |

TABLE 1-continued

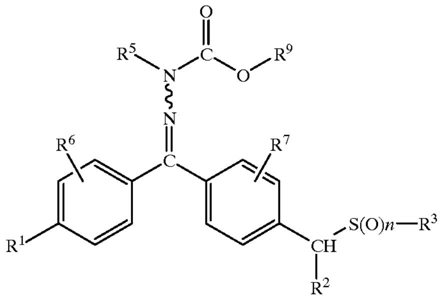

| $R^1$ | $R^2$ | $R^3$ | n | $R^5$ | $R^6$ | $R^7$ | $R^9$ |
|---|---|---|---|---|---|---|---|
| Br | H | $CH_3$ | 1 | $COC_3H_7$-n | H | H | iso-$C_3H_7$ |
| Br | H | $CH_3$ | 2 | H | H | H | $CH_3$ |
| Br | H | $CH_3$ | 2 | H | H | H | $C_2H_5$ |
| Br | H | $CH_3$ | 2 | H | H | H | iso-$C_3H_7$ |
| Br | H | $CH_3$ | 2 | H | H | H | iso-$C_4H_9$ |
| Br | H | $CH_3$ | 2 | H | H | H | n-$C_3H_7$ |
| Br | H | $CH_3$ | 2 | H | H | H | $CH_2CF_3$ |
| Br | H | $CH_3$ | 2 | $C_2H_5$ | H | H | $CH_3$ |
| Br | H | $CH_3$ | 2 | $C_2H_5$ | H | H | $C_2H_5$ |
| Br | H | $CH_3$ | 2 | $C_2H_5$ | H | H | n-$C_3H_7$ |
| Br | H | $CH_3$ | 2 | $C_2H_5$ | H | H | iso-$C_3H_7$ |
| Br | H | $CH_3$ | 2 | iso-$C_3H_7$ | H | H | $CH_3$ |
| Br | H | $CH_3$ | 2 | iso-$C_3H_7$ | H | H | $C_2H_5$ |
| Br | H | $CH_3$ | 2 | iso-$C_3H_7$ | H | H | n-$C_3H_7$ |
| Br | H | $CH_3$ | 2 | iso-$C_3H_7$ | H | H | iso-$C_3H_7$ |
| Br | H | $CH_3$ | 2 | $CH_2OCH_3$ | H | H | $CH_3$ |
| Br | H | $CH_3$ | 2 | $COC_2H_5$ | H | H | $C_2H_5$ |
| Br | H | $CH_3$ | 2 | $COCH_2OCH_3$ | H | H | $C_2H_5$ |
| Br | H | $CH_3$ | 2 | $COC_2H_5$ | H | H | $CH_3$ |
| Br | H | $CH_3$ | 2 | $COC_2H_5$ | H | H | n-$C_3H_7$ |
| Br | H | $CH_3$ | 2 | $COC_3H_7$-n | H | H | $CH_3$ |
| Br | H | $CH_3$ | 2 | $COC_3H_7$-n | H | H | $C_2H_5$ |
| Br | H | $CH_3$ | 2 | $COC_3H_7$-n | H | H | n-$C_3H_7$ |
| Br | H | $CH_3$ | 2 | $COC_3H_7$-n | H | H | iso-$C_3H_7$ |
| Br | H | $CH_3$ | 2 | $COCH_2OCH_3$ | H | H | n-$C_3H_7$ |
| Br | H | $CH_3$ | 2 | $COCH_2OCH_3$ | H | H | $CH_3$ |
| Br | H | $CH_3$ | 2 | $COC_6H_5$ | H | H | $C_2H_5$ |
| Br | H | $C_2H_5$ | 0 | H | H | H | $CH_3$ |
| Br | H | $C_2H_5$ | 0 | H | H | H | $C_2H_5$ |
| Br | H | $C_2H_5$ | 0 | H | H | H | n-$C_3H_7$ |
| Br | H | $C_2H_5$ | 0 | H | H | H | iso-$C_4H_9$ |
| Br | H | $C_2H_5$ | 0 | H | H | H | $CH_2CF_3$ |
| Br | H | $C_2H_5$ | 0 | $CH_3$ | H | H | $CH_3$ |
| Br | H | $C_2H_5$ | 0 | $CH_3$ | H | H | $C_2H_5$ |
| Br | H | $C_2H_5$ | 0 | $C_2H_5$ | H | H | $CH_3$ |
| Br | H | $C_2H_5$ | 0 | $C_2H_5$ | H | H | $C_2H_5$ |
| Br | H | $C_2H_5$ | 0 | $C_2H_5$ | H | H | n-$C_3H_7$ |
| Br | H | $C_2H_5$ | 0 | $C_2H_5$ | H | H | iso-$C_3H_7$ |
| Br | H | $C_2H_5$ | 0 | $C_2H_5$ | H | H | n-$C_4H_9$ |
| Br | H | $C_2H_5$ | 0 | $C_2H_5$ | H | H | iso-$C_4H_9$ |
| Br | H | $C_2H_5$ | 0 | $C_2H_5$ | H | H | sec-$C_4H_9$ |
| Br | H | $C_2H_5$ | 0 | $C_2H_5$ | H | H | $CH_2CF_3$ |
| Br | H | $C_2H_5$ | 0 | iso-$C_3H_7$ | H | H | $CH_3$ |
| Br | H | $C_2H_5$ | 0 | iso-$C_3H_7$ | H | H | $C_2H_5$ |
| Br | H | $C_2H_5$ | 0 | iso-$C_3H_7$ | H | H | n-$C_3H_7$ |
| Br | H | $C_2H_5$ | 0 | iso-$C_3H_7$ | H | H | iso-$C_3H_7$ |
| Br | H | $C_2H_5$ | 0 | iso-$C_3H_7$ | H | H | iso-$C_4H_9$ |
| Br | H | $C_2H_5$ | 0 | iso-$C_3H_7$ | H | H | $CH_2CF_3$ |
| Br | H | $C_2H_5$ | 0 | $CH_2OCH_3$ | H | H | $CH_3$ |
| Br | H | $C_2H_5$ | 0 | $CH_2OCH_3$ | H | H | $C_2H_5$ |
| Br | H | $C_2H_5$ | 0 | $CH_2SCH_3$ | H | H | $CH_3$ |
| Br | H | $C_2H_5$ | 0 | $CH_2SCH_3$ | H | H | $C_2H_5$ |
| Br | H | $C_2H_5$ | 0 | CHO | H | H | $C_2H_5$ |
| Br | H | $C_2H_5$ | 0 | $COCH_3$ | H | H | $C_2H_5$ |
| Br | H | $C_2H_5$ | 0 | $COC_2H_5$ | H | H | $CH_3$ |
| Br | H | $C_2H_5$ | 0 | $COC_2H_5$ | H | H | $C_2H_5$ |
| Br | H | $C_2H_5$ | 0 | $COC_2H_5$ | H | H | n-$C_3H_7$ |
| Br | H | $C_2H_5$ | 0 | $COC_2H_5$ | H | H | iso-$C_3H_7$ |
| Br | H | $C_2H_5$ | 0 | $COC_3H_7$-n | H | H | $CH_3$ |
| Br | H | $C_2H_5$ | 0 | $COC_3H_7$-n | H | H | $C_2H_5$ |
| Br | H | $C_2H_5$ | 0 | $COC_3H_7$-n | H | H | n-$C_3H_7$ |

TABLE 1-continued

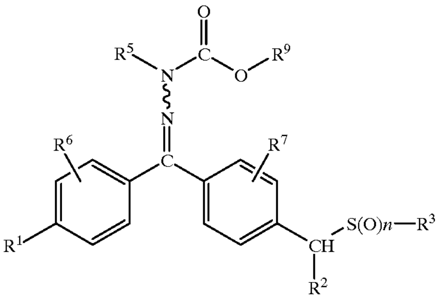

| $R^1$ | $R^2$ | $R^3$ | n | $R^5$ | $R^6$ | $R^7$ | $R^9$ |
|---|---|---|---|---|---|---|---|
| Br | H | $C_2H_5$ | 0 | $COC_3H_7$-n | H | H | iso-$C_3H_7$ |
| Br | H | $C_2H_5$ | 0 | $COC_3H_7$-n | H | H | iso-$C_4H_9$ |
| Br | H | $C_2H_5$ | 0 | $COCH_2OCH_3$ | H | H | $CH_3$ |
| Br | H | $C_2H_5$ | 0 | $COCH_2OCH_3$ | H | H | $C_2H_5$ |
| Br | H | $C_2H_5$ | 0 | $COCH_2OCH_3$ | H | H | n-$C_3H_7$ |
| Br | H | $C_2H_5$ | 0 | $COC_6H_5$ | H | H | $CH_3$ |
| Br | H | $C_2H_5$ | 0 | $COC_6H_5$ | H | H | $C_2H_5$ |
| Br | H | $C_2H_5$ | 1 | H | H | H | $CH_3$ |
| Br | H | $C_2H_5$ | 1 | H | H | H | $C_2H_5$ |
| Br | H | $C_2H_5$ | 1 | H | H | H | n-$C_3H_7$ |
| Br | H | $C_2H_5$ | 1 | H | H | H | iso-$C_3H_7$ |
| Br | H | $C_2H_5$ | 1 | H | H | H | iso-$C_4H_9$ |
| Br | H | $C_2H_5$ | 1 | H | H | H | $CH_2CF_3$ |
| Br | H | $C_2H_5$ | 1 | $C_2H_5$ | H | H | $CH_3$ |
| Br | H | $C_2H_5$ | 1 | $C_2H_5$ | H | H | $C_2H_5$ |
| Br | H | $C_2H_5$ | 1 | $C_2H_5$ | H | H | n-$C_3H_7$ |
| Br | H | $C_2H_5$ | 1 | $C_2H_5$ | H | H | iso-$C_3H_7$ |
| Br | H | $C_2H_5$ | 1 | iso-$C_3H_7$ | H | H | $CH_3$ |
| Br | H | $C_2H_5$ | 1 | is6-$C_3H_7$ | H | H | $C_2H_5$ |
| Br | H | $C_2H_5$ | 1 | iso-$C_3H_7$ | H | H | n-$C_3H_7$ |
| Br | H | $C_2H_5$ | 1 | $COC_2H_5$ | H | H | $CH_3$ |
| Br | H | $C_2H_5$ | 1 | $COC_2H_5$ | H | H | $C_2H_5$ |
| Br | H | $C_2H_5$ | 1 | $COC_2H_5$ | H | H | n-$C_3H_7$ |
| Br | H | $C_2H_5$ | 1 | $COC_3H_7$-n | H | H | $CH_3$ |
| Br | H | $C_2H_5$ | 1 | $COC_3H_7$-n | H | H | $C_2H_5$ |
| Br | H | $C_2H_5$ | 1 | $COC_3H_7$-n | H | H | n-$C_3H_7$ |
| Br | H | $C_2H_5$ | 1 | $COC_3H_7$-n | H | H | iso-$C_3H_7$ |
| Br | H | $C_2H_5$ | 1 | iso-$C_3H_7$ | H | H | iso-$C_3H_7$ |
| Br | H | $C_2H_5$ | 1 | $COCH_2OCH_3$ | H | H | $CH_3$ |
| Br | H | $C_2H_5$ | 1 | $COCH_2OCH_3$ | H | H | $C_2H_5$ |
| Br | H | $C_2H_5$ | 1 | $COCH_2OCH_3$ | H | H | n-$C_3H_7$ |
| Br | H | $C_2H_5$ | 2 | H | H | H | $CH_3$ |
| Br | H | $C_2H_5$ | 2 | H | H | H | $C_2H_5$ |
| Br | H | $C_2H_5$ | 2 | H | H | H | n-$C_3H_7$ |
| Br | H | $C_2H_5$ | 2 | H | H | H | iso-$C_3H_7$ |
| Br | H | $C_2H_5$ | 2 | H | H | H | iso-$C_4H_9$ |
| Br | H | $C_2H_5$ | 2 | H | H | H | $CH_2CF_3$ |
| Br | H | $C_2H_5$ | 2 | $C_2H_5$ | H | H | $CH_3$ |
| Br | H | $C_2H_5$ | 2 | $C_2H_5$ | H | H | $C_2H_5$ |
| Br | H | $C_2H_5$ | 2 | $C_2H_5$ | H | H | n-$C_3H_7$ |
| Br | H | $C_2H_5$ | 2 | $C_2H_5$ | H | H | iso-$C_3H_7$ |
| Br | H | $C_2H_5$ | 2 | iso-$C_3H_7$ | H | H | $CH_3$ |
| Br | H | $C_2H_5$ | 2 | iso-$C_3H_7$ | H | H | $C_2H_5$ |
| Br | H | $C_2H_5$ | 2 | iso-$C_3H_7$ | H | H | n-$C_3H_7$ |
| Br | H | $C_2H_5$ | 2 | iso-$C_3H_7$ | H | H | iso-$C_3H_7$ |
| Br | H | $C_2H_5$ | 2 | $CH_2OCH_3$ | H | H | $C_2H_5$— |
| Br | H | $C_2H_5$ | 2 | $COC_2H_5$ | H | H | $CH_3$ |
| Br | H | $C_2H_5$ | 2 | $COC_2H_5$ | H | H | $C_2H_5$ |
| Br | H | $C_2H_5$ | 2 | $COC_2H_5$ | H | H | n-$C_3H_7$ |
| Br | H | $C_2H_5$ | 2 | $COC_3H_7$-n | H | H | $CH_3$ |
| Br | H | $C_2H_5$ | 2 | $COC_3H_7$-n | H | H | $C_2H_5$ |
| Br | H | $C_2H_5$ | 2 | $COC_3H_7$-n | H | H | iso-$C_3H_7$ |
| Br | H | $C_2H_5$ | 2 | $COC_3H_7$-n | H | H | n-$C_3H_7$ |
| Br | H | $C_2H_5$ | 2 | $COCH_2OCH_3$ | H | H | $CH_3$ |
| Br | H | $C_2H_5$ | 2 | $COCH_2OCH_3$ | H | H | $C_2H_5$ |
| Br | H | $C_2H_5$ | 2 | $COCH_2OCH_3$ | H | H | n-$C_3H_7$ |
| Br | H | n-$C_3H_7$ | 0 | H | H | H | $C_2H_5$ |
| Br | H | n-$C_3H_7$ | 1 | H | H | H | $CH_3$ |
| Br | H | n-$C_3H_7$ | 1 | H | H | H | $C_2H_5$ |
| Br | H | n-$C_3H_7$ | 1 | H | H | H | n-$C_3H_7$ |
| Br | H | n-$C_3H_7$ | 1 | H | H | H | iso-$C_3H_7$ |

TABLE 1-continued

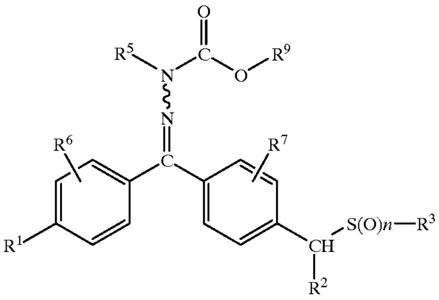

| $R^1$ | $R^2$ | $R^3$ | n | $R^5$ | $R^6$ | $R^7$ | $R^9$ |
|---|---|---|---|---|---|---|---|
| Br | H | n-$C_3H_7$ | 1 | H | H | H | iso-$C_4H_9$ |
| Br | H | n-$C_3H_7$ | 1 | H | H | H | $CH_2CF_3$ |
| Br | H | n-$C_3H_7$ | 2 | H | H | H | $CH_3$ |
| Br | H | n-$C_3H_7$ | 2 | H | H | H | $C_2H_5$ |
| Br | H | n-$C_3H_7$ | 2 | H | H | H | n-$C_3H_7$ |
| Br | H | n-$C_3H_7$ | 2 | H | H | H | iso-$C_3H_7$ |
| Br | H | n-$C_3H_7$ | 2 | H | H | H | iso-$C_4H_9$ |
| Br | H | n-$C_3H_7$ | 2 | H | H | H | $CH_2CF_3$ |
| Br | H | $CH_2CH{=}CH_2$ | 0 | H | H | H | $C_2H_5$ |
| Br | H | $CH_2CH{=}CH_2$ | 2 | H | H | H | $C_2H_5$ |
| Br | H | $CH_2F$ | 1 | H | H | H | $CH_3$ |
| Br | H | $CH_2F$ | 1 | H | H | H | $C_2H_5$ |
| Br | H | $CH_2F$ | 1 | H | H | H | n-$C_3H_7$ |
| Br | H | $CH_2F$ | 1 | H | H | H | iso-$C_3H_7$ |
| Br | H | $CH_2F$ | 1 | H | H | H | iso-$C_4H_9$ |
| Br | H | $CH_2F$ | 1 | H | H | H | $CH_2CF_3$ |
| Br | H | $CHF_2$ | 0 | H | H | H | $C_2H_5$ |
| Br | H | $CHF_2$ | 0 | H | H | H | $CH_2CF_3$ |
| Br | H | $CHF_2$ | 0 | H | H | H | $CH_3$ |
| Br | H | $CHF_2$ | 0 | H | H | H | iso-$C_4H_9$ |
| Br | H | $CHF_2$ | 0 | H | H | H | n-$C_3H_7$ |
| Br | H | $CHF_2$ | 1 | H | H | H | $CH_3$ |
| Br | H | $CHF_2$ | 1 | H | H | H | $C_2H_5$ |
| Br | H | $CHF_2$ | 1 | H | H | H | n-$C_3H_7$ |
| Br | H | $CHF_2$ | 1 | H | H | H | iso-$C_3H_7$ |
| Br | H | $CHF_2$ | 1 | H | H | H | iso-$C_4H_9$ |
| Br | H | $CHF_2$ | 1 | H | H | H | $CH_2CF_3$ |
| Br | H | $CF_3$ | 0 | H | H | H | $C_2H_5$ |
| Br | H | $CF_3$ | 0 | H | H | H | $CH_2CF_3$ |
| Br | H | $CF_3$ | 0 | H | H | H | $CH_3$ |
| Br | H | $CF_3$ | 0 | H | H | H | iso-$C_4H_9$ |
| Br | H | $CF_3$ | 0 | H | H | H | n-$C_4H_9$ |
| Br | H | $CH_2CH_2F$ | 0 | H | H | H | $CH_3$ |
| Br | H | $CH_2CH_2F$ | 0 | H | H | H | $C_2H_5$ |
| Br | H | $CH_2CH_2F$ | 1 | H | H | H | $CH_3$ |
| Br | H | $CH_2CH_2F$ | 1 | H | H | H | $C_2H_5$ |
| Br | H | $CH_2CH_2F$ | 1 | H | H | H | n-$C_3H_7$ |
| Br | H | $CH_2CH_2F$ | 1 | H | H | H | iso-$C_3H_7$ |
| Br | H | $CH_2CH_2F$ | 1 | H | H | H | iso-$C_4H_9$ |
| Br | H | $CH_2CH_2F$ | 1 | H | H | H | $CH_2CF_3$ |
| Br | H | $CH_2CH_2F$ | 2 | H | H | H | $CH_3$ |
| Br | H | $CH_2CH_2F$ | 2 | H | H | H | $C_2H_5$ |
| Br | H | $CH_2CH_2F$ | 2 | H | H | H | n-$C_3H_7$ |
| Br | H | $CH_2CH_2F$ | 2 | H | H | H | iso-$C_3H_7$ |
| Br | H | $CH_2CH_2F$ | 2 | H | H | H | iso-$C_4H_9$ |
| Br | H | $CH_2CH_2F$ | 2 | H | H | H | $CH_2CF_3$ |
| Br | H | $CH_2CHF_2$ | 0 | H | H | H | $C_2H_5$ |
| Br | H | $CH_2CHF_2$ | 0 | H | H | H | $CH_3$ |
| Br | H | $CH_2CHF_2$ | 1 | H | H | H | $CH_3$ |
| Br | H | $CH_2CHF_2$ | 1 | H | H | H | $C_2H_5$ |
| Br | H | $CH_2CHF_2$ | 1 | H | H | H | n-$C_3H_7$ |
| Br | H | $CH_2CHF_2$ | 1 | H | H | H | iso-$C_3H_7$ |
| Br | H | $CH_2CHF_2$ | 1 | H | H | H | iso-$C_4H_9$ |
| Br | H | $CH_2CHF_2$ | 1 | H | H | H | $CH_2CF_3$ |
| Br | H | $CH_2CHF_2$ | 2 | H | H | H | $C_2H_5$ |
| Br | H | $CH_2CHF_2$ | 2 | H | H | H | $CH_3$ |
| Br | H | $CH_2CF_3$ | 0 | H | H | H | $C_2H_5$ |
| Br | H | $CH_2CF_3$ | 0 | H | H | H | $CH_3$ |
| Br | H | $CH_2CF_3$ | 0 | $C_2H_5$ | H | H | $C_2H_5$ |
| Br | H | $CH_2CF_3$ | 0 | $C_2H_5$ | H | H | $CH_3$ |
| Br | H | $CH_2CF_3$ | 1 | H | H | H | $CH_3$ |

TABLE 1-continued

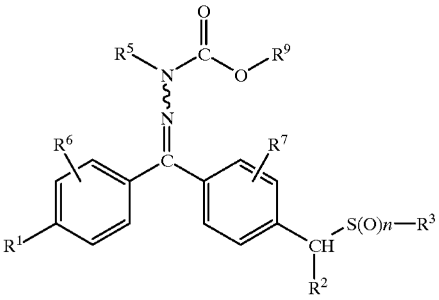

| $R^1$ | $R^2$ | $R^3$ | n | $R^5$ | $R^6$ | $R^7$ | $R^9$ |
|---|---|---|---|---|---|---|---|
| Br | H | $CH_2CF_3$ | 1 | H | H | H | $C_2H_5$ |
| Br | H | $CH_2CF_3$ | 1 | H | H | H | n-$C_3H_7$ |
| Br | H | $CH_2CF_3$ | 1 | H | H | H | iso-$C_3H_7$ |
| Br | H | $CH_2CF_3$ | 1 | H | H | H | iso-$C_4H_9$ |
| Br | H | $CH_2CF_3$ | 1 | H | H | H | $CH_2CF_3$ |
| Br | H | $CH_2CF_3$ | 2 | H | H | H | $CH_3$ |
| Br | H | $CH_2CF_3$ | 2 | H | H | H | $C_2H_5$ |
| Br | H | $CH_2CF_3$ | 2 | H | H | H | n-$C_3H_7$ |
| Br | H | $CH_2CF_3$ | 2 | H | H | H | iso-$C_3H_7$ |
| Br | H | $CH_2CF_3$ | 2 | H | H | H | iso-$C_4H_9$ |
| Br | H | $CH_2CF_3$ | 2 | H | H | H | $CH_2CF_3$ |
| Br | $CH_3$ | $CH_3$ | 0 | H | H | H | $CH_3$ |
| Br | $CH_3$ | $CH_3$ | 0 | H | H | H | $C_2H_5$ |
| Br | $CH_3$ | $CH_3$ | 1 | H | H | H | $CH_3$ |
| Br | $CH_3$ | $CH_3$ | 1 | H | H | H | $C_2H_5$ |
| Br | $CH_3$ | $CH_3$ | 2 | H | H | H | $CH_3$ |
| Br | $CH_3$ | $CH_3$ | 2 | H | H | H | $C_2H_5$ |
| I | H | $CH_3$ | 0 | H | H | H | $CH_3$ |
| I | H | $CH_3$ | 0 | H | H | H | $C_2H_5$ |
| I | H | $CH_3$ | 0 | H | H | H | iso-$C_4H_9$ |
| I | H | $CH_3$ | 1 | H | H | H | $C_2H_5$ |
| I | H | $CH_3$ | 1 | H | H | H | $CH_3$ |
| I | H | $CH_3$ | 1 | H | H | H | iso-$C_4H_9$ |
| I | H | $CH_3$ | 2 | H | H | H | $CH_3$ |
| I | H | $CH_3$ | 2 | H | H | H | $C_2H_5$ |
| I | H | $CH_3$ | 2 | H | H | H | iso-$C_4H_9$ |
| I | H | $C_2H_5$ | 0 | H | H | H | $C_2H_5$ |
| I | H | $C_2H_5$ | 1 | H | H | H | $CH_3$ |
| I | H | $C_2H_5$ | 1 | H | H | H | $C_2H_5$ |
| I | H | $C_2H_5$ | 2 | H | H | H | $C_2H_5$ |
| I | H | $C_2H_5$ | 2 | H | H | H | $CH_3$ |
| I | H | $CHF_2$ | 0 | H | H | H | $C_2H_5$ |
| I | H | $CF_3$ | 0 | H | H | H | $C_2H_5$ |
| I | H | $CH_2CH_2F$ | 0 | H | H | H | $C_2H_5$ |
| I | H | $CH_2CHF_2$ | 0 | H | H | H | $C_2H_5$ |
| I | H | $CH_2CF_3$ | 0 | H | H | H | $C_2H_5$ |
| Cl | H | $CH_3$ | 0 | $CH_2CN$ | H | H | $CH_3$ |
| Cl | H | $CH_3$ | 0 | $CH_2CN$ | H | H | $C_2H_5$ |
| Cl | H | $CH_3$ | 0 | $CH{=}CH_2$ | H | H | $CH_3$ |
| Cl | H | $CH_3$ | 0 | $CH{=}CH_2$ | H | H | $C_2H_5$ |
| Cl | H | $CH_3$ | 0 | $CH_2CH{=}CH_2$ | H | H | $CH_3$ |
| Cl | H | $CH_3$ | 0 | $CH_2CH{=}CH_2$ | H | H | $C_2H_5$ |
| Cl | H | $CH_3$ | 0 | $CH_2C{\equiv}CH$ | H | H | $CH_3$ |
| Cl | H | $CH_3$ | 0 | $CH_2C{\equiv}CH$ | H | H | $C_2H_5$ |
| Cl | H | $CH_3$ | 0 | $CO_2CH_3$ | H | H | $CH_3$ |
| Cl | H | $CH_3$ | 0 | $CO_2CH_3$ | H | H | $C_2H_5$ |
| Cl | H | $CH_3$ | 0 | $CO_2CH_3$ | H | H | n-$C_3H_7$ |
| Cl | H | $CH_3$ | 0 | $CO_2CH_3$ | H | H | iso-$C_3H_7$ |
| Cl | H | $CH_3$ | 0 | $CO_2CH_3$ | H | H | n-$C_4H_9$ |
| Cl | H | $CH_3$ | 0 | $CO_2CH_3$ | H | H | iso-$C_4H_9$ |
| Cl | H | $CH_3$ | 0 | $CO_2CH_3$ | H | H | sec-$C_4H_9$ |
| Cl | H | $CH_3$ | 0 | $CO_2CH_3$ | H | H | $CH_2CF_3$ |
| Cl | H | $CH_3$ | 0 | $CO_2CH_3$ | H | H | 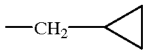 |
| Cl | H | $CH_3$ | 0 | $CO_2C_2H_5$ | H | H | $C_2H_5$ |
| Cl | H | $CH_3$ | 0 | $CO_2C_2H_5$ | H | H | n-$C_3H_7$ |
| Cl | H | $CH_3$ | 0 | $CO_2C_2H_5$ | H | H | iso-$C_3H_7$ |
| Cl | H | $CH_3$ | 0 | $CO_2C_2H_5$ | H | H | n-$C_4H_9$ |

TABLE 1-continued

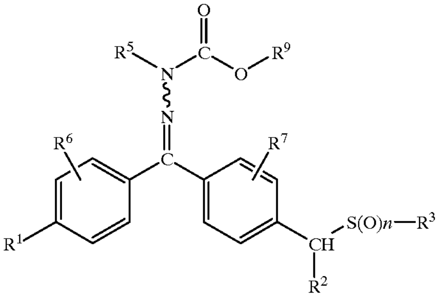

| $R^1$ | $R^2$ | $R^3$ | n | $R^5$ | $R^6$ | $R^7$ | $R^9$ |
|---|---|---|---|---|---|---|---|
| Cl | H | $CH_3$ | 0 | $CO_2C_2H_5$ | H | H | iso-$C_4H_9$ |
| Cl | H | $CH_3$ | 0 | $CO_2C_2H_5$ | H | H | sec-$C_4H_9$ |
| Cl | H | $CH_3$ | 0 | $CO_2C_2H_5$ | H | H | $CH_2CF_3$ |
| Cl | H | $CH_3$ | 0 | $CO_2C_2H_5$ | H | H | 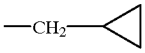 |
| Cl | H | $CH_3$ | 1 | $CO_2CH_3$ | H | H | $CH_3$ |
| Cl | H | $CH_3$ | 1 | $CO_2CH_3$ | H | H | $C_2H_5$ |
| Cl | H | $CH_3$ | 1 | $CO_2CH_3$ | H | H | n-$C_3H_7$ |
| Cl | H | $CH_3$ | 1 | $CO_2CH_3$ | H | H | iso-$C_3H_7$ |
| Cl | H | $CH_3$ | 1 | $CO_2CH_3$ | H | H | n-$C_4H_9$ |
| Cl | H | $CH_3$ | 1 | $CO_2CH_3$ | H | H | iso-$C_4H_9$ |
| Cl | H | $CH_3$ | 1 | $CO_2CH_3$ | H | H | sec-$C_4H_9$ |
| Cl | H | $CH_3$ | 1 | $CO_2CH_3$ | H | H | $CH_2CF_3$ |
| Cl | H | $CH_3$ | 1 | $CO_2CH_3$ | H | H | 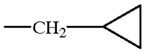 |
| Cl | H | $CH_3$ | 1 | $CO_2C_2H_5$ | H | H | $C_2H_5$ |
| Cl | H | $CH_3$ | 1 | $CO_2C_2H_5$ | H | H | n-$C_3H_7$ |
| Cl | H | $CH_3$ | 1 | $CO_2C_2H_5$ | H | H | iso-$C_3H_7$ |
| Cl | H | $CH_3$ | 1 | $CO_2C_2H_5$ | H | H | n-$C_4H_9$ |
| Cl | H | $CH_3$ | 1 | $CO_2C_2H_5$ | H | H | iso-$C_4H_9$ |
| Cl | H | $CH_3$ | 1 | $CO_2C_2H_5$ | H | H | sec-$C_4H_9$ |
| Cl | H | $CH_3$ | 1 | $CO_2C_2H_5$ | H | H | $CH_2CF_3$ |
| Cl | H | $CH_3$ | 1 | $CO_2C_2H_5$ | H | H | 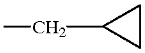 |
| Cl | H | $CH_3$ | 2 | $CO_2CH_3$ | H | H | $CH_3$ |
| Cl | H | $CH_3$ | 2 | $CO_2CH_3$ | H | H | $C_2H_5$ |
| Cl | H | $CH_3$ | 2 | $CO_2CH_3$ | H | H | n-$C_3H_7$ |
| Cl | H | $CH_3$ | 2 | $CO_2CH_3$ | H | H | iso-$C_3H_7$ |
| Cl | H | $CH_3$ | 2 | $CO_2CH_3$ | H | H | n-$C_4H_9$ |
| Cl | H | $CH_3$ | 2 | $CO_2CH_3$ | H | H | iso-$C_4H_9$ |
| Cl | H | $CH_3$ | 2 | $CO_2CH_3$ | H | H | sec-$C_4H_9$ |
| Cl | H | $CH_3$ | 2 | $CO_2CH_3$ | H | H | $CH_2CF_3$ |
| Cl | H | $CH_3$ | 2 | $CO_2CH_3$ | H | H | 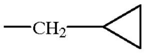 |
| Cl | H | $CH_3$ | 2 | $CO_2C_2H_5$ | H | H | $C_2H_5$ |
| Cl | H | $CH_3$ | 2 | $CO_2C_2H_5$ | H | H | n-$C_3H_7$ |
| Cl | H | $CH_3$ | 2 | $CO_2C_2H_5$ | H | H | iso-$C_3H_7$ |
| Cl | H | $CH_3$ | 2 | $CO_2C_2H_5$ | H | H | n-$C_4H_9$ |
| Cl | H | $CH_3$ | 2 | $CO_2C_2H_5$ | H | H | iso-$C_4H_9$ |
| Cl | H | $CH_3$ | 2 | $CO_2C_2H_5$ | H | H | sec-$C_4H_9$ |
| Cl | H | $CH_3$ | 2 | $CO_2C_2H_5$ | H | H | $CH_2CF_3$ |
| Cl | H | $CH_3$ | 2 | $CO_2C_2H_5$ | H | H | 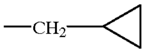 |
| Br | H | $CH_3$ | 2 | $CO_2CH_3$ | H | H | $CH_3$ |
| Br | H | $CH_3$ | 2 | $CO_2CH_3$ | H | H | $C_2H_5$ |
| Br | H | $CH_3$ | 2 | $CO_2CH_3$ | H | H | n-$C_3H_7$ |

TABLE 1-continued

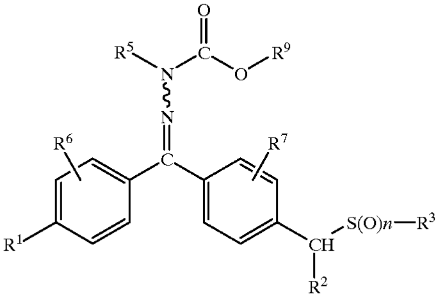

| $R^1$ | $R^2$ | $R^3$ | n | $R^5$ | $R^6$ | $R^7$ | $R^9$ |
|---|---|---|---|---|---|---|---|
| Br | H | $CH_3$ | 2 | $CO_2CH_3$ | H | H | iso-$C_3H_7$ |
| Br | H | $CH_3$ | 2 | $CO_2CH_3$ | H | H | n-$C_4H_9$ |
| Br | H | $CH_3$ | 2 | $CO_2CH_3$ | H | H | iso-$C_4H_9$ |
| Br | H | $CH_3$ | 2 | $CO_2CH_3$ | H | H | sec-$C_4H_9$ |
| Br | H | $CH_3$ | 2 | $CO_2CH_3$ | H | H | $CH_2CF_3$ |
| Br | H | $CH_3$ | 2 | $CO_2CH_3$ | H | H | 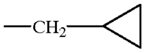 |
| Br | H | $CH_3$ | 2 | $CO_2C_2H_5$ | H | H | $C_2H_5$ |
| Br | H | $CH_3$ | 2 | $CO_2C_2H_5$ | H | H | n-$C_3H_7$ |
| Br | H | $CH_3$ | 2 | $CO_2C_2H_5$ | H | H | iso-$C_3H_7$ |
| Br | H | $CH_3$ | 2 | $CO_2C_2H_5$ | H | H | n-$C_4H_9$ |
| Br | H | $CH_3$ | 2 | $CO_2C_2H_5$ | H | H | iso-$C_4H_9$ |
| Br | H | $CH_3$ | 2 | $CO_2C_2H_5$ | H | H | sec-$C_4H_9$ |
| Br | H | $CH_3$ | 2 | $CO_2C_2H_5$ | H | H | $CH_2CF_3$ |
| Br | H | $CH_3$ | 2 | $CO_2C_2H_5$ | H | H | 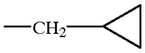 |
| Br | H | $CH_3$ | 1 | $CO_2CH_3$ | H | H | $CH_3$ |
| Br | H | $CH_3$ | 1 | $CO_2CH_3$ | H | H | $C_2H_5$ |
| Br | H | $CH_3$ | 1 | $CO_2CH_3$ | H | H | n-$C_3H_7$ |
| Br | H | $CH_3$ | 1 | $CO_2CH_3$ | H | H | iso-$C_3H_7$ |
| Br | H | $CH_3$ | 1 | $CO_2CH_3$ | H | H | n-$C_4H_9$ |
| Br | H | $CH_3$ | 1 | $CO_2CH_3$ | H | H | iso-$C_4H_9$ |
| Br | H | $CH_3$ | 1 | $CO_2CH_3$ | H | H | sec-$C_4H_9$ |
| Br | H | $CH_3$ | 1 | $CO_2CH_3$ | H | H | $CH_2CF_3$ |
| Br | H | $CH_3$ | 1 | $CO_2CH_3$ | H | H | 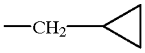 |
| Br | H | $CH_3$ | 1 | $CO_2C_2H_5$ | H | H | $C_2H_5$ |
| Br | H | $CH_3$ | 1 | $CO_2C_2H_5$ | H | H | n-$C_3H_7$ |
| Br | H | $CH_3$ | 1 | $CO_2C_2H_5$ | H | H | iso-$C_3H_7$ |
| Br | H | $CH_3$ | 1 | $CO_2C_2H_5$ | H | H | n-$C_4H_9$ |
| Br | H | $CH_3$ | 1 | $CO_2C_2H_5$ | H | H | iso-$C_4H_9$ |
| Br | H | $CH_3$ | 1 | $CO_2C_2H_5$ | H | H | sec-$C_4H_9$ |
| Br | H | $CH_3$ | 1 | $CO_2C_2H_5$ | H | H | $CH_2CF_3$ |
| Br | H | $CH_3$ | 1 | $CO_2C_2H_5$ | H | H | 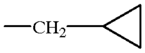 |
| Br | H | $CH_3$ | 0 | $CO_2CH_3$ | H | H | $CH_3$ |
| Br | H | $CH_3$ | 0 | $CO_2CH_3$ | H | H | $C_2H_5$ |
| Br | H | $CH_3$ | 0 | $CO_2CH_3$ | H | H | n-$C_3H_7$ |
| Br | H | $CH_3$ | 0 | $CO_2CH_3$ | H | H | iso-$C_3H_7$ |
| Br | H | $CH_3$ | 0 | $CO_2CH_3$ | H | H | n-$C_4H_9$ |
| Br | H | $CH_3$ | 0 | $CO_2CH_3$ | H | H | iso-$C_4H_9$ |
| Br | H | $CH_3$ | 0 | $CO_2CH_3$ | H | H | sec-$C_4H_9$ |
| Br | H | $CH_3$ | 0 | $CO_2CH_3$ | H | H | $CH_2CF_3$ |
| Br | H | $CH_3$ | 0 | $CO_2CH_3$ | H | H | 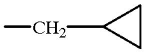 |
| Br | H | $CH_3$ | 0 | $CO_2C_2H_5$ | H | H | $C_2H_5$ |

TABLE 1-continued

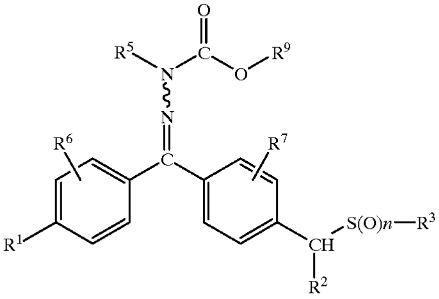

| $R^1$ | $R^2$ | $R^3$ | n | $R^5$ | $R^6$ | $R^7$ | $R^9$ |
|---|---|---|---|---|---|---|---|
| Br | H | $CH_3$ | 0 | $CO_2C_2H_5$ | H | H | n-$C_3H_7$ |
| Br | H | $CH_3$ | 0 | $CO_2C_2H_5$ | H | H | iso-$C_3H_7$ |
| Br | H | $CH_3$ | 0 | $CO_2C_2H_5$ | H | H | n-$C_4H_9$ |
| Br | H | $CH_3$ | 0 | $CO_2C_2H_5$ | H | H | iso-$C_4H_9$ |
| Br | H | $CH_3$ | 0 | $CO_2C_2H_5$ | H | H | sec-$C_4H_9$ |
| Br | H | $CH_3$ | 0 | $CO_2C_2H_5$ | H | H | $CH_2CF_3$ |
| Br | H | $CH_3$ | 0 | $CO_2C_2H_5$ | H | H | 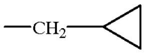 |
| Br | H | $C_2H_5$ | 0 | $C_2H_5$ | H | H | 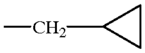 |
| Br | H | $C_2H_5$ | 0 | $C_2H_5$ | H | H | $CH_2Si(CH_3)_3$ |
| Br | H | $C_2H_5$ | 0 | $CH_3$ | H | H | $CH_2CF_3$ |
| Br | H | $C_2H_5$ | 0 | $CH_3$ | H | H | 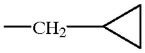 |
| Br | H | $C_2H_5$ | 0 | $CH_3$ | H | H | $CH_2Si(CH_3)_3$ |
| Br | H | $C_2H_5$ | 0 | H | H | H | sec-$C_4H_9$ |
| Br | H | $C_2H_5$ | 0 | H | H | H | 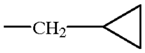 |
| Br | H | $C_2H_5$ | 0 | H | H | H | $CH_2Si(CH_3)_3$ |
| Br | H | $C_2H_5$ | 0 | iso-$C_3H_7$ | H | H | 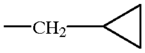 |
| Br | H | $C_2H_5$ | 0 | iso-$C_3H_7$ | H | H | $CH_2Si(CH_3)_3$ |
| Br | H | $C_2H_5$ | 0 | iso-$C_3H_7$ | H | H | n-$C_4H_9$ |
| Br | H | $C_2H_5$ | 0 | n-$C_3H_7$ | H | H | $CH_3$ |
| Br | H | $C_2H_5$ | 0 | n-$C_3H_7$ | H | H | $C_2H_5$ |
| Br | H | $C_2H_5$ | 0 | n-$C_3H_7$ | H | H | $CH_2CF_3$ |
| Br | H | $C_2H_5$ | 0 | n-$C_3H_7$ | H | H | 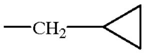 |
| Br | H | $C_2H_5$ | 0 | n-$C_3H_7$ | H | H | $CH_2Si(CH_3)_3$ |
| Br | H | $C_2H_5$ | 0 | n-$C_4H_9$ | H | H | $CH_3$ |
| Br | H | $C_2H_5$ | 0 | n-$C_4H_9$ | H | H | $C_2H_5$ |
| Br | H | $C_2H_5$ | 1 | $C_2H_5$ | H | H | $CH_2CF_3$ |
| Br | H | $C_2H_5$ | 1 | $C_2H_5$ | H | H | 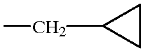 |
| Br | H | $C_2H_5$ | 1 | $C_2H_5$ | H | H | $CH_2Si(CH_3)_3$ |
| Br | H | $C_2H_5$ | 1 | $CH_3$ | H | H | $CH_3$ |
| Br | H | $C_2H_5$ | 1 | $CH_3$ | H | H | $C_2H_5$ |
| Br | H | $C_2H_5$ | 1 | $CH_3$ | H | H | $CH_2CF_3$ |

TABLE 1-continued

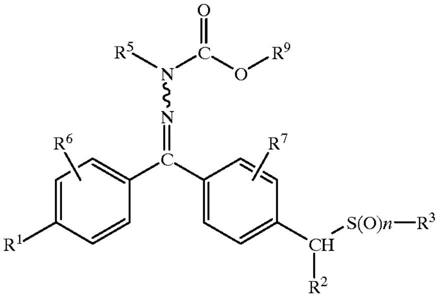

| $R^1$ | $R^2$ | $R^3$ | n | $R^5$ | $R^6$ | $R^7$ | $R^9$ |
|---|---|---|---|---|---|---|---|
| Br | H | $C_2H_5$ | 1 | $CH_3$ | H | H | 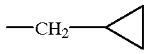 |
| Br | H | $C_2H_5$ | 1 | $CH_3$ | H | H | $CH_2Si(CH_3)_3$ |
| Br | H | $C_2H_5$ | 1 | H | H | H | n-$C_4H_9$ |
| Br | H | $C_2H_5$ | 1 | H | H | H | sec-$C_4H_9$ |
| Br | H | $C_2H_5$ | 1 | H | H | H | 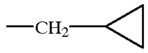 |
| Br | H | $C_2H_5$ | 1 | H | H | H | $CH_2Si(CH_3)_3$ |
| Br | H | $C_2H_5$ | 1 | iso-$C_3H_7$ | H | H | iso-$C_3H_7$ |
| Br | H | $C_2H_5$ | 1 | iso-$C_3H_7$ | H | H | $CH_2CF_3$ |
| Br | H | $C_2H_5$ | 1 | iso-$C_3H_7$ | H | H | 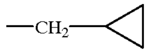 |
| Br | H | $C_2H_5$ | 1 | iso-$C_3H_7$ | H | H | $CH_2Si(CH_3)_3$ |
| Br | H | $C_2H_5$ | 1 | n-$C_3H_7$ | H | H | $CH_3$ |
| Br | H | $C_2H_5$ | 1 | n-$C_3H_7$ | H | H | $C_2H_5$ |
| Br | H | $C_2H_5$ | 1 | n-$C_3H_7$ | H | H | $CH_2CF_3$ |
| Br | H | $C_2H_5$ | 1 | n-$C_3H_7$ | H | H | 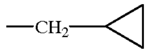 |
| Br | H | $C_2H_5$ | 1 | n-$C_3H_7$ | H | H | $CH_2Si(CH_3)_3$ |
| Br | H | $C_2H_5$ | 1 | n-$C_4H_9$ | H | H | $CH_3$ |
| Br | H | $C_2H_5$ | 1 | n-$C_4H_9$ | H | H | $C_2H_5$ |
| Br | H | $C_2H_5$ | 2 | $C_2H_5$ | H | H | $CH_2CF_3$ |
| Br | H | $C_2H_5$ | 2 | $C_2H_5$ | H | H | 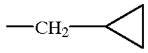 |
| Br | H | $C_2H_5$ | 2 | $C_2H_5$ | H | H | $CH_2Si(CH_3)_3$ |
| Br | H | $C_2H_5$ | 2 | $CH_3$ | H | H | $CH_3$ |
| Br | H | $C_2H_5$ | 2 | $CH_3$ | H | H | $C_2H_5$ |
| Br | H | $C_2H_5$ | 2 | $CH_3$ | H | H | $CH_2CF_3$ |
| Br | H | $C_2H_5$ | 2 | $CH_3$ | H | H | 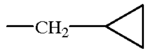 |
| Br | H | $C_2H_5$ | 2 | $CH_3$ | H | H | $CH_2Si(CH_3)_3$ |
| Br | H | $C_2H_5$ | 2 | H | H | H | n-$C_4H_9$ |
| Br | H | $C_2H_5$ | 2 | H | H | H | sec-$C_4H_9$ |
| Br | H | $C_2H_5$ | 2 | H | H | H | 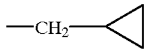 |
| Br | H | $C_2H_5$ | 2 | H | H | H | $CH_2Si(CH_3)_3$ |
| Br | H | $C_2H_5$ | 2 | iso-$C_3H_7$ | H | H | $CH_2CF_3$ |
| Br | H | $C_2H_5$ | 2 | iso-$C_3H_7$ | H | H | 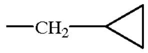 |

TABLE 1-continued

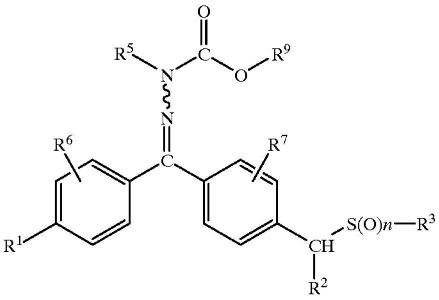

| $R^1$ | $R^2$ | $R^3$ | n | $R^5$ | $R^6$ | $R^7$ | $R^9$ |
|---|---|---|---|---|---|---|---|
| Br | H | $C_2H_5$ | 2 | iso-$C_3H_7$ | H | H | $CH_2Si(CH_3)_3$ |
| Br | H | $C_2H_5$ | 2 | n-$C_3H_7$ | H | H | $CH_3$ |
| Br | H | $C_2H_5$ | 2 | n-$C_3H_7$ | H | H | $C_2H_5$ |
| Br | H | $C_2H_5$ | 2 | n-$C_3H_7$ | H | H | $CH_2CF_3$ |
| Br | H | $C_2H_5$ | 2 | n-$C_3H_7$ | H | H | 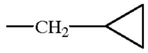 |
| Br | H | $C_2H_5$ | 2 | n-$C_3H_7$ | H | H | $CH_2Si(CH_3)_3$ |
| Br | H | $C_2H_5$ | 2 | n-$C_4H_9$ | H | H | $CH_3$ |
| Br | H | $C_2H_5$ | 2 | n-$C_4H_9$ | H | H | $C_2H_5$ |
| Br | H | $CH_2CF_3$ | 0 | H | H | H | n-$C_3H_7$ |
| Br | H | $CH_2CF_3$ | 0 | H | H | H | iso-$C_3H_7$ |
| Br | H | $CH_2CF_3$ | 0 | H | H | H | iso-$C_4H_9$ |
| Br | H | $CH_2CF_3$ | 0 | H | H | H | $CH_2CF_3$ |
| Br | H | $CH_3$ | 0 | $C_2H_5$ | H | H | 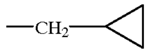 |
| Br | H | $CH_3$ | 0 | $C_2H_5$ | H | H | $CH_2Si(CH_3)_3$ |
| Br | H | $CH_3$ | 0 | $CH_3$ | H | H | $CH_2CF_3$ |
| Br | H | $CH_3$ | 0 | $CH_3$ | H | H | 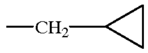 |
| Br | H | $CH_3$ | 0 | $CH_3$ | H | H | $CH_2Si(CH_3)_3$ |
| Br | H | $CH_3$ | 0 | H | H | H | 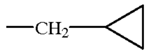 |
| Br | H | $CH_3$ | 0 | H | H | H | $CH_2Si(CH_3)_3$ |
| Br | H | $CH_3$ | 0 | iso-$C_3H_7$ | H | H | 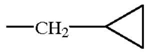 |
| Br | H | $CH_3$ | 0 | iso-$C_3H_7$ | H | H | $CH_2Si(CH_3)_3$ |
| Br | H | $CH_3$ | 0 | iso-$C_3H_7$ | H | H | n-$C_4H_9$ |
| Br | H | $CH_3$ | 0 | n-$C_3H_7$ | H | H | $C_2H_5$ |
| Br | H | $CH_3$ | 0 | n-$C_3H_7$ | H | H | $CH_3$ |
| Br | H | $CH_3$ | 0 | n-$C_3H_7$ | H | H | $CH_2CF_3$ |
| Br | H | $CH_3$ | 0 | n-$C_3H_7$ | H | H | 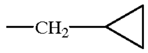 |
| Br | H | $CH_3$ | 0 | n-$C_3H_7$ | H | H | $CH_2Si(CH_3)_3$ |
| Br | H | $CH_3$ | 0 | n-$C_4H_9$ | H | H | $CH_3$ |
| Br | H | $CH_3$ | 0 | n-$C_4H_9$ | H | H | $C_2H_5$ |
| Br | H | $CH_3$ | 1 | $C_2H_5$ | H | H | $CH_2CF_3$ |
| Br | H | $CH_3$ | 1 | $C_2H_5$ | H | H | 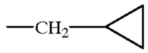 |
| Br | H | $CH_3$ | 1 | $C_2H_5$ | H | H | $CH_2Si(CH_3)_3$ |

TABLE 1-continued

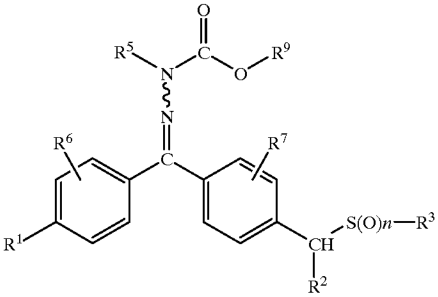

| $R^1$ | $R^2$ | $R^3$ | n | $R^5$ | $R^6$ | $R^7$ | $R^9$ |
|---|---|---|---|---|---|---|---|
| Br | H | $CH_3$ | 1 | $CH_3$ | H | H | $C_2H_5$ |
| Br | H | $CH_3$ | 1 | $CH_3$ | H | H | $CH_3$ |
| Br | H | $CH_3$ | 1 | $CH_3$ | H | H | $CH_2CF_3$ |
| Br | H | $CH_3$ | 1 | $CH_3$ | H | H | 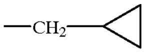 |
| Br | H | $CH_3$ | 2 | iso-$C_3H_7$ | H | H | $CH_2Si(CH_3)_3$ |
| Br | H | $CH_3$ | 2 | n-$C_3H_7$ | H | H | $C_2H_5$ |
| Br | H | $CH_3$ | 2 | n-$C_3H_7$ | H | H | $CH_3$ |
| Br | H | $CH_3$ | 2 | n-$C_3H_7$ | H | H | $CH_2CF_3$ |
| Br | H | $CH_3$ | 2 | n-$C_3H_7$ | H | H | 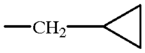 |
| Br | H | $CH_3$ | 1 | $CH_3$ | H | H | $CH_2Si(CH_3)_3$ |
| Br | H | $CH_3$ | 1 | H | H | H | n-$C_4H_9$ |
| Br | H | $CH_3$ | 1 | H | H | H | sec-$C_4H_9$ |
| Br | H | $CH_3$ | 1 | H | H | H | 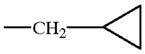 |
| Br | H | $CH_3$ | 1 | H | H | H | $CH_2Si(CH_3)_3$ |
| Br | H | $CH_3$ | 1 | iso-$C_3H_7$ | H | H | $CH_2CF_3$ |
| Br | H | $CH_3$ | 1 | iso-$C_3H_7$ | H | H | 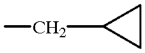 |
| Br | H | $CH_3$ | 1 | iso-$C_3H_7$ | H | H | $CH_2Si(CH_3)_3$ |
| Br | H | $CH_3$ | 1 | n-$C_3H_7$ | H | H | $C_2H_5$ |
| Br | H | $CH_3$ | 1 | n-$C_3H_7$ | H | H | $CH_3$ |
| Br | H | $CH_3$ | 1 | n-$C_3H_7$ | H | H | $CH_2CF_3$ |
| Br | H | $CH_3$ | 1 | n-$C_3H_7$ | H | H | 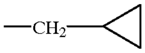 |
| Br | H | $CH_3$ | 1 | n-$C_3H_7$ | H | H | $CH_2Si(CH_3)_3$ |
| Br | H | $CH_3$ | 1 | n-$C_4H_9$ | H | H | $CH_3$ |
| Br | H | $CH_3$ | 1 | n-$C_4H_9$ | H | H | $C_2H_5$ |
| Br | H | $CH_3$ | 2 | $C_2H_5$ | H | H | $CH_2CF_3$ |
| Br | H | $CH_3$ | 2 | $C_2H_5$ | H | H | 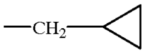 |
| Br | H | $CH_3$ | 2 | $C_2H_5$ | H | H | $CH_2Si(CH_3)_3$ |
| Br | H | $CH_3$ | 2 | $CH_3$ | H | H | $C_2H_5$ |
| Br | H | $CH_3$ | 2 | $CH_3$ | H | H | $CH_3$ |
| Br | H | $CH_3$ | 2 | $CH_3$ | H | H | $CH_2CF_3$ |
| Br | H | $CH_3$ | 2 | $CH_3$ | H | H | 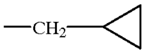 |
| Br | H | $CH_3$ | 2 | $CH_3$ | H | H | $CH_2Si(CH_3)_3$ |
| Br | H | $CH_3$ | 2 | H | H | H | n-$C_4H_9$ |

TABLE 1-continued

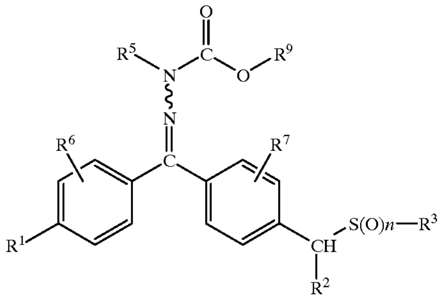

| $R^1$ | $R^2$ | $R^3$ | n | $R^5$ | $R^6$ | $R^7$ | $R^9$ |
|---|---|---|---|---|---|---|---|
| Br | H | $CH_3$ | 2 | H | H | H | sec-$C_4H_9$ |
| Br | H | $CH_3$ | 2 | H | H | H | 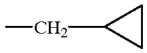 |
| Br | H | $CH_3$ | 2 | H | H | H | iso-$C_4H_9$ |
| Br | H | $CH_3$ | 2 | H | H | H | $CH_2Si(CH_3)_3$ |
| Br | H | $CH_3$ | 2 | iso-$C_3H_7$ | H | H | $CH_2CF_3$ |
| Br | H | $CH_3$ | 2 | iso-$C_3H_7$ | H | H | 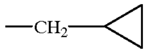 |
| Br | H | $CH_3$ | 2 | n-$C_3H_7$ | H | H | $CH_2Si(CH_3)_3$ |
| Br | H | $CH_3$ | 2 | n-$C_4H_9$ | H | H | $CH_3$ |
| Br | H | $CH_3$ | 2 | n-$C_4H_9$ | H | H | $C_2H_5$ |
| Cl | H | $C_2H_5$ | 0 | $C_2H_5$ | H | H | 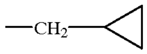 |
| Cl | H | $C_2H_5$ | 0 | $C_2H_5$ | H | H | $CH_2Si(CH_3)_3$ |
| Cl | H | $C_2H_5$ | 0 | $C_2H_5$ | H | H | $CH_2CF_2CHF_2$ |
| Cl | H | $C_2H_5$ | 0 | $CH{=}CH_2$ | H | H | $C_2H_5$ |
| Cl | H | $C_2H_5$ | 0 | $CH_2CF_3$ | H | H | $C_2H_5$ |
| Cl | H | $C_2H_5$ | 0 | $CH_2CHF_2$ | H | H | $C_2H_5$ |
| Cl | H | $C_2H_5$ | 0 | $CH_3$ | H | H | $CH_2CF_3$ |
| Cl | H | $C_2H_5$ | 0 | $CH_3$ | H | H | 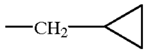 |
| Cl | H | $C_2H_5$ | 0 | $CH_3$ | H | H | $CH_2Si(CH_3)_3$ |
| Cl | H | $C_2H_5$ | 0 | $CH_3$ | H | H | $CH_2CF_2CHF_2$ |
| Cl | H | $C_2H_5$ | 0 | H | H | H | 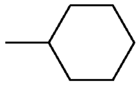 |
| Cl | H | $C_2H_5$ | 0 | H | H | H | 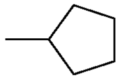 |
| Cl | H | $C_2H_5$ | 0 | H | H | H | 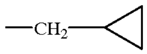 |
| Cl | H | $C_2H_5$ | 0 | H | H | H | $CH_2CF_2CHF_2$ |
| Cl | H | $C_2H_5$ | 0 | iso-$C_3H_7$ | H | H | 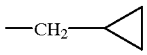 |
| Cl | H | $C_2H_5$ | 0 | iso-$C_3H_7$ | H | H | $CH_2Si(CH_3)_3$ |
| Cl | H | $C_2H_5$ | 0 | n-$C_3H_7$ | H | H | $CH_2CF_3$ |

TABLE 1-continued

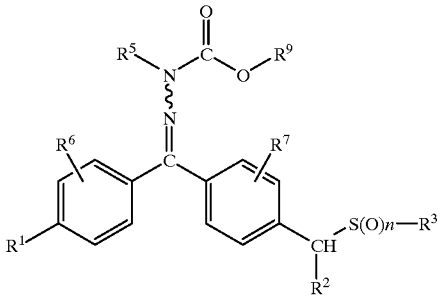

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 0 | n-$C_3H_7$ | H | H | 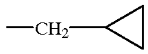 |
| Cl | H | $C_2H_5$ | 0 | n-$C_3H_7$ | H | H | $CH_2Si(CH_3)_3$ |
| Cl | H | $C_2H_5$ | 0 | n-$C_3H_7$ | H | H | $CH_2CF_2CHF_2$ |
| Cl | H | $C_2H_5$ | 1 | $C_2H_5$ | H | H | 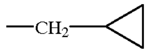 |
| Cl | H | $C_2H_5$ | 1 | $C_2H_5$ | H | H | $CH_2Si(CH_3)_3$ |
| Cl | H | $C_2H_5$ | 1 | $C_2H_5$ | H | H | $CH_2CF_2CHF_2$ |
| Cl | H | $C_2H_5$ | 1 | $CH_3$ | H | H | $C_2H_5$ |
| Cl | H | $C_2H_5$ | 1 | $CH_3$ | H | H | $CH_3$ |
| Cl | H | $C_2H_5$ | 1 | $CH_3$ | H | H | n-$C_3H_7$ |
| Cl | H | $C_2H_5$ | 1 | $CH_3$ | H | H | iso-$C_3H_7$ |
| Cl | H | $C_2H_5$ | 1 | $CH_3$ | H | H | $CH_2CF_3$ |
| Cl | H | $C_2H_5$ | 1 | $CH_3$ | H | H | 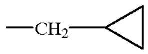 |
| Cl | H | $C_2H_5$ | 1 | $CH_3$ | H | H | $CH_2Si(CH_3)_3$ |
| Cl | H | $C_2H_5$ | 1 | H | H | H | n-$C_4H_9$ |
| Cl | H | $C_2H_5$ | 1 | H | H | H | sec-$C_4H_9$ |
| Cl | H | $C_2H_5$ | 1 | H | H | H | 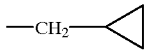 |
| Cl | H | $C_2H_5$ | 1 | H | H | H | $CH_2Si(CH_3)_3$ |
| Cl | H | $C_2H_5$ | 1 | H | H | H | $CH_2CF_2CHF_2$ |
| Cl | H | $C_2H_5$ | 1 | iso-$C_3H_7$ | H | H | $CH_2CF_3$ |
| Cl | H | $C_2H_5$ | 1 | iso-$C_3H_7$ | H | H | 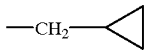 |
| Cl | H | $C_2H_5$ | 1 | iso-$C_3H_7$ | H | H | $CH_2Si(CH_3)_3$ |
| Cl | H | $C_2H_5$ | 1 | n-$C_3H_7$ | H | H | $C_2H_5$ |
| Cl | H | $C_2H_5$ | 1 | n-$C_3H_7$ | H | H | $CH_3$ |
| Cl | H | $C_2H_5$ | 1 | n-$C_3H_7$ | H | H | n-$C_3H_7$ |
| Cl | H | $C_2H_5$ | 1 | n-$C_3H_7$ | H | H | iso-$C_3H_7$ |
| Cl | H | $C_2H_5$ | 1 | n-$C_3H_7$ | H | H | $CH_2CF_3$ |
| Cl | H | $C_2H_5$ | 1 | n-$C_3H_7$ | H | H | 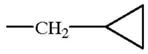 |
| Cl | H | $C_2H_5$ | 1 | n-$C_3H_7$ | H | H | $CH_2Si(CH_3)_3$ |
| Cl | H | $C_2H_5$ | 1 | n-$C_3H_7$ | H | H | $CH_2CF_2CHF_2$ |
| Cl | H | $C_2H_5$ | 1 | n-$C_4H_9$ | H | H | $CH_3$ |
| Cl | H | $C_2H_5$ | 1 | n-$C_4H_9$ | H | H | $C_2H_5$ |
| Cl | H | $C_2H_5$ | 2 | $C_2H_5$ | H | H | 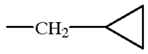 |
| Cl | H | $C_2H_5$ | 2 | $C_2H_5$ | H | H | $CH_2Si(CH_3)_3$ |
| Cl | H | $C_2H_5$ | 2 | $C_2H_5$ | H | H | $CH_2CF_2CHF_2$ |

TABLE 1-continued

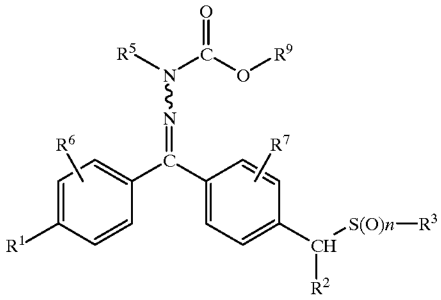

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 2 | $CH_3$ | H | H | $C_2H_5$ |
| Cl | H | $C_2H_5$ | 2 | $CH_3$ | H | H | $CH_3$ |
| Cl | H | $C_2H_5$ | 2 | $CH_3$ | H | H | n-$C_3H_7$ |
| Cl | H | $C_2H_5$ | 2 | $CH_3$ | H | H | iso-$C_3H_7$ |
| Cl | H | $C_2H_5$ | 2 | $CH_3$ | H | H | $CH_2CF_3$ |
| Cl | H | $C_2H_5$ | 2 | $CH_3$ | H | H | 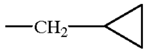 |
| Cl | H | $C_2H_5$ | 2 | $CH_3$ | H | H | $CH_2Si(CH_3)_3$ |
| Cl | H | $C_2H_5$ | 2 | H | H | H | n-$C_4H_9$ |
| Cl | H | $C_2H_5$ | 2 | H | H | H | iso-$C_4H_9$ |
| Cl | H | $C_2H_5$ | 2 | H | H | H | sec-$C_4H_9$ |
| Cl | H | $C_2H_5$ | 2 | H | H | H | 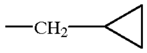 |
| Cl | H | $C_2H_5$ | 2 | H | H | H | $CH_2Si(CH_3)_3$ |
| Cl | H | $C_2H_5$ | 2 | H | H | H | $CH_2CF_2CHF_2$ |
| Cl | H | $C_2H_5$ | 2 | iso-$C_3H_7$ | H | H | $CH_2CF_3$ |
| Cl | H | $C_2H_5$ | 2 | iso-$C_3H_7$ | H | H | 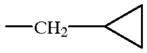 |
| Cl | H | $C_2H_5$ | 2 | iso-$C_3H_7$ | H | H | $CH_2Si(CH_3)_3$ |
| Cl | H | $C_2H_5$ | 2 | n-$C_3H_7$ | H | H | $C_2H_5$ |
| Cl | H | $C_2H_5$ | 2 | n-$C_3H_7$ | H | H | $CH_3$ |
| Cl | H | $C_2H_5$ | 2 | n-$C_3H_7$ | H | H | n-$C_3H_7$ |
| Cl | H | $C_2H_5$ | 2 | n-$C_3H_7$ | H | H | iso-$C_3H_7$ |
| Cl | H | $C_2H_5$ | 2 | n-$C_3H_7$ | H | H | $CH_2CF_3$ |
| Cl | H | $C_2H_5$ | 2 | n-$C_3H_7$ | H | H | 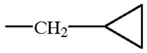 |
| Cl | H | $C_2H_5$ | 2 | n-$C_3H_7$ | H | H | $CH_2Si(CH_3)_3$ |
| Cl | H | $C_2H_5$ | 2 | n-$C_3H_7$ | H | H | $CH_2CF_2CHF_2$ |
| Cl | H | $C_2H_5$ | 2 | n-$C_4H_9$ | H | H | $CH_3$ |
| Cl | H | $C_2H_5$ | 2 | n-$C_4H_9$ | H | H | $C_2H_5$ |
| Cl | H | $CH_2CH{=}CHCH_3$ | 0 | H | H | H | $C_2H_5$ |
| Cl | H | $CH_2CH_2CH_3F$ | 1 | H | H | H | $C_2H_5$ |
| Cl | H | $CH_2CH_2Cl$ | 1 | H | H | H | $C_2H_5$ |
| Cl | H | $CH_3$ | 0 | $C_2H_5$ | H | H | 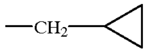 |
| Cl | H | $CH_3$ | 0 | $C_2H_5$ | H | H | $CH_2Si(CH_3)_3$ |
| Cl | H | $CH_3$ | 0 | $C_2H_5$ | H | H | $CH_2CF_2CHF_2$ |
| Cl | H | $CH_3$ | 0 | $CH_2C{\equiv}CH$ | H | H | $C_2H_5$ |
| Cl | H | $CH_3$ | 0 | $CH_2CH{=}CH_2$ | H | H | $C_2H_5$ |
| Cl | H | $CH_3$ | 0 | $CH_2CH_2Cl$ | H | H | $C_2H_5$ |
| Cl | H | $CH_3$ | 0 | $CH_2CH_3F$ | H | H | $C_2H_5$ |
| Cl | H | $CH_3$ | 0 | $CH_2CN$ | H | H | $C_2H_5$ |
| Cl | H | $CH_3$ | 0 | $CH_3$ | H | H | n-$C_4H_9$ |
| Cl | H | $CH_3$ | 0 | $CH_3$ | H | H | iso-$C_4H_9$ |
| Cl | H | $CH_3$ | 0 | $CH_3$ | H | H | sec-$C_4H_9$ |

TABLE 1-continued

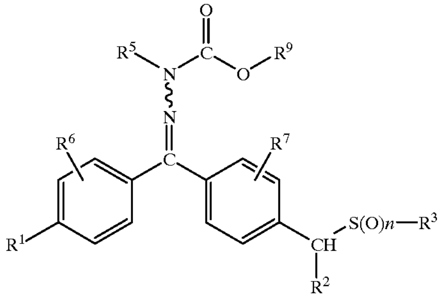

| $R^1$ | $R^2$ | $R^3$ | n | $R^5$ | $R^6$ | $R^7$ | $R^9$ |
|---|---|---|---|---|---|---|---|
| Cl | H | $CH_3$ | 0 | $CH_3$ | H | H | 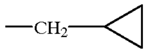 |
| Cl | H | $CH_3$ | 0 | $CH_3$ | H | H | $CH_2Si(CH_3)_3$ |
| Cl | H | $CH_3$ | 0 | $CH_3$ | H | H | $CH_2CF_2CHF_2$ |
| Cl | H | $CH_3$ | 0 | H | H | H | 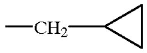 |
| Cl | H | $CH_3$ | 0 | H | H | H | $CH_2CF_2CHF_2$ |
| Cl | H | $CH_3$ | 0 | iso-$C_3H_7$ | H | H | 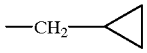 |
| Cl | H | $CH_3$ | 0 | iso-$C_3H_7$ | H | H | $CH_2Si(CH_3)_3$ |
| Cl | H | $CH_3$ | 0 | iso-$C_4H_9$ | H | H | $C_2H_5$ |
| Cl | H | $CH_3$ | 0 | iso-$C_4H_9$ | H | H | $CH_3$ |
| Cl | H | $CH_3$ | 0 | n-$C_3H_7$ | H | H | 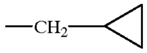 |
| Cl | H | $CH_3$ | 0 | n-$C_3H_7$ | H | H | $CH_2Si(CH_3)_3$ |
| Cl | H | $CH_3$ | 0 | n-$C_3H_7$ | H | H | $CH_2CF_2CHF_2$ |
| Cl | H | $CH_3$ | 0 | n-$C_6H_{13}$ | H | H | $C_2H_5$ |
| Cl | H | $CH_3$ | 0 | n-$C_7H_{15}$ | H | H | $C_2H_5$ |
| Cl | H | $CH_3$ | 1 | $C_2H_5$ | H | H | 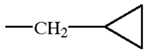 |
| Cl | H | $CH_3$ | 1 | $C_2H_5$ | H | H | $CH_2Si(CH_3)_3$ |
| Cl | H | $CH_3$ | 1 | $C_2H_5$ | H | H | $CH_2CF_2CHF_2$ |
| Cl | H | $CH_3$ | 1 | $CH_3$ | H | H | $CH_3$ |
| Cl | H | $CH_3$ | 1 | $CH_3$ | H | H | n-$C_3H_7$ |
| Cl | H | $CH_3$ | 1 | $CH_3$ | H | H | iso-$C_3H_7$ |
| Cl | H | $CH_3$ | 1 | $CH_3$ | H | H | 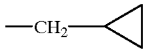 |
| Cl | H | $CH_3$ | 1 | $CH_3$ | H | H | $CH_2Si(CH_3)_3$ |
| Cl | H | $CH_3$ | 1 | H | H | H | n-$C_4H_9$ |
| Cl | H | $CH_3$ | 1 | H | H | H | sec-$C_4H_9$ |
| Cl | H | $CH_3$ | 1 | H | H | H | 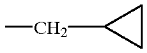 |
| Cl | H | $CH_3$ | 1 | H | H | H | $CH_2Si(CH_3)_3$ |
| Cl | H | $CH_3$ | 1 | H | H | H | $CH_2CF_2CHF_2$ |
| Cl | H | $CH_3$ | 1 | iso-$C_3H_7$ | H | H | $CH_2CF_3$ |
| Cl | H | $CH_3$ | 1 | iso-$C_3H_7$ | H | H | 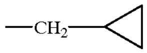 |
| Cl | H | $CH_3$ | 1 | iso-$C_3H_7$ | H | H | $CH_2Si(CH_3)_3$ |

TABLE 1-continued

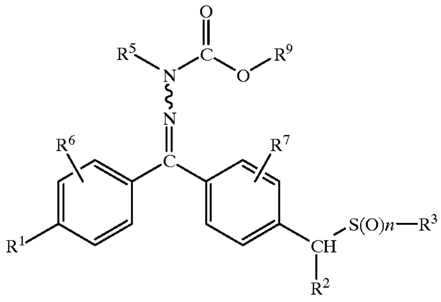

| $R^1$ | $R^2$ | $R^3$ | n | $R^5$ | $R^6$ | $R^7$ | $R^9$ |
|---|---|---|---|---|---|---|---|
| Cl | H | $CH_3$ | 1 | n-$C_3H_7$ | H | H | $C_2H_5$ |
| Cl | H | $CH_3$ | 1 | n-$C_3H_7$ | H | H | $CH_3$ |
| Cl | H | $CH_3$ | 1 | n-$C_3H_7$ | H | H | $CH_2CF_3$ |
| Cl | H | $CH_3$ | 1 | n-$C_3H_7$ | H | H | 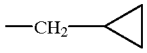 |
| Cl | H | $CH_3$ | 1 | n-$C_3H_7$ | H | H | $CH_2Si(CH_3)_3$ |
| Cl | H | $CH_3$ | 1 | n-$C_3H_7$ | H | H | $CH_2CF_2CHF_2$ |
| Cl | H | $CH_3$ | 1 | n-$C_4H_9$ | H | H | $C_2H_5$ |
| Cl | H | $CH_3$ | 1 | n-$C_4H_9$ | H | H | $CH_3$ |
| Cl | H | $CH_3$ | 2 | $C_2H_5$ | H | H | 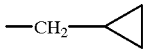 |
| Cl | H | $CH_3$ | 2 | $C_2H_5$ | H | H | $CH_2Si(CH_3)_3$ |
| Cl | H | $CH_3$ | 2 | $C_2H_5$ | H | H | $CH_2CF_2CHF_2$ |
| Cl | H | $CH_3$ | 2 | $CH_3$ | H | H | $CH_3$ |
| Cl | H | $CH_3$ | 2 | $CH_3$ | H | H | n-$C_3H_7$ |
| Cl | H | $CH_3$ | 2 | $CH_3$ | H | H | iso-$C_3H_7$ |
| Cl | H | $CH_3$ | 2 | $CH_3$ | H | H | $CH_2CF_3$ |
| Cl | H | $CH_3$ | 2 | $CH_3$ | H | H | 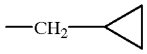 |
| Cl | H | $CH_3$ | 2 | $CH_3$ | H | H | $CH_2Si(CH_3)_3$ |
| Cl | H | $CH_3$ | 2 | H | H | H | n-$C_4H_9$ |
| Cl | H | $CH_3$ | 2 | H | H | H | 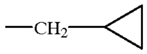 |
| Cl | H | $CH_3$ | 2 | H | H | H | $CH_2Si(CH_3)_3$ |
| Cl | H | $CH_3$ | 2 | H | H | H | $CH_2CF_2CHF_2$ |
| Cl | H | $CH_3$ | 2 | iso-$C_3H_7$ | H | H | $CH_2CF_3$ |
| Cl | H | $CH_3$ | 2 | iso-$C_3H_7$ | H | H | 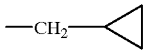 |
| Cl | H | $CH_3$ | 2 | iso-$C_3H_7$ | H | H | $CH_2Si(CH_3)_3$ |
| Cl | H | $CH_3$ | 2 | n-$C_3H_7$ | H | H | $C_2H_5$ |
| Cl | H | $CH_3$ | 2 | n-$C_3H_7$ | H | H | $CH_3$ |
| Cl | H | $CH_3$ | 2 | n-$C_3H_7$ | H | H | $CH_2CF_3$ |
| Cl | H | $CH_3$ | 2 | n-$C_3H_7$ | H | H | 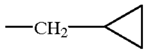 |
| Cl | H | $CH_3$ | 2 | n-$C_3H_7$ | H | H | $CH_2Si(CH_3)_3$ |
| Cl | H | $CH_3$ | 2 | n-$C_3H_7$ | H | H | $CH_2CF_2CHF_2$ |
| Cl | H | $CH_3$ | 2 | n-$C_4H_9$ | H | H | $C_2H_5$ |
| Cl | H | $CH_3$ | 2 | n-$C_4H_9$ | H | H | $CH_3$ |
| Cl | H | $CN_3$ | 0 | H | H | H | $C_2H_5$ |
| Cl | H | $CSOC_2H_3$ | 0 | H | H | H | $C_2H_5$ |
| Cl | H | $COCH_3$ | 0 | H | H | H | $C_2H_5$ |
| Cl | H | sec-$C_4H_9$ | 0 | H | H | H | $CH_3$ |
| F | H | n-$C_3H_7$ | 0 | H | H | H | $C_2H_5$ |

TABLE 1-continued
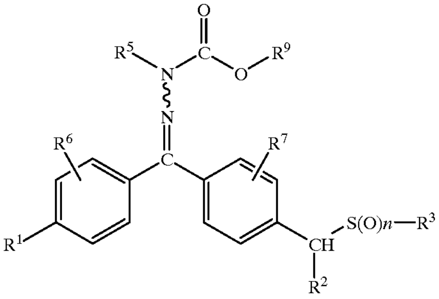
| $R^1$ | $R^2$ | $R^3$ | n | $R^5$ | $R^6$ | $R^7$ | $R^9$ |
|---|---|---|---|---|---|---|---|
| F | H | $n\text{-}C_3H_7$ | 0 | H | H | H | $CH_3$ |
| Cl | H | $CH_3$ | 0 | $CO_2CH_3$ | H | H | 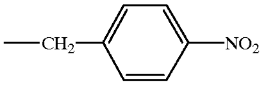 |
| Cl | H | $CH_3$ | 1 | $CO_2CH_3$ | H | H | 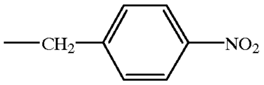 |
| Cl | H | $CH_3$ | 2 | $CO_2CH_3$ | H | H | 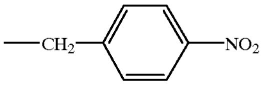 |
| Cl | H | $CH_3$ | 0 | $CO_2CH_3$ | H | H | 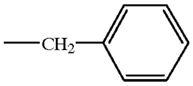 |
| Cl | H | $CH_3$ | 1 | $CO_2CH_3$ | H | H | 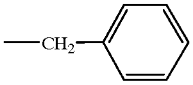 |
| Cl | H | $CH_3$ | 2 | $CO_2CH_3$ | H | H | 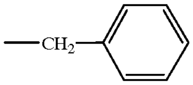 |
| Cl | H | $CH_3$ | 0 | $CO_2C_2H_5$ | H | H | 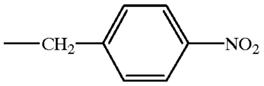 |
| Cl | H | $CH_3$ | 1 | $CO_2C_2H_5$ | H | H | 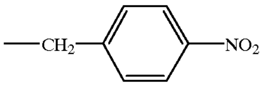 |
| Cl | H | $CH_3$ | 2 | $CO_2C_2H_5$ | H | H | 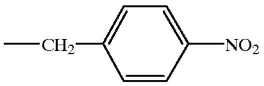 |
| Cl | H | $CH_3$ | 0 | $CO_2C_2H_5$ | H | H | 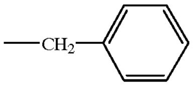 |
| Cl | H | $CH_3$ | 1 | $CO_2C_2H_5$ | H | H | 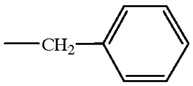 |

TABLE 1-continued

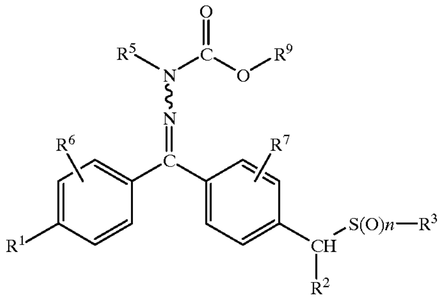

| $R^1$ | $R^2$ | $R^3$ | n | $R^5$ | $R^6$ | $R^7$ | $R^9$ |
|---|---|---|---|---|---|---|---|
| Cl | H | $CH_3$ | 2 | $CO_2C_2H_5$ | H | H | 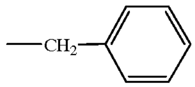 |
| Cl | H | $C_2H_5$ | 0 | $CO_2CH_3$ | H | H | $CH_3$ |
| Cl | H | $C_2H_5$ | 0 | $CO_2CH_3$ | H | H | $C_2H_5$ |
| Cl | H | $C_2H_5$ | 0 | $CO_2CH_3$ | H | H | n-$C_3H_7$ |
| Cl | H | $C_2H_5$ | 0 | $CO_2CH_3$ | H | H | iso-$C_3H_7$ |
| Cl | H | $C_2H_5$ | 0 | $CO_2CH_3$ | H | H | n-$C_4H_9$ |
| Cl | H | $C_2H_5$ | 0 | $CO_2CH_3$ | H | H | iso-$C_4H_9$ |
| Cl | H | $C_2H_5$ | 0 | $CO_2CH_3$ | H | H | sec-$C_4H_9$ |
| Cl | H | $C_2H_5$ | 0 | $CO_2CH_3$ | H | H | $CH_2CF_3$ |
| Cl | H | $C_2H_5$ | 0 | $CO_2CH_3$ | H | H | 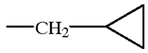 |
| Cl | H | $C_2H_5$ | 0 | $CO_2C_2H_5$ | H | H | $C_2H_5$ |
| Cl | H | $C_2H_5$ | 0 | $CO_2C_2H_5$ | H | H | n-$C_3H_7$ |
| Cl | H | $C_2H_5$ | 0 | $CO_2C_2H_5$ | H | H | iso-$C_3H_7$ |
| Cl | H | $C_2H_5$ | 0 | $CO_2C_2H_5$ | H | H | n-$C_4H_9$ |
| Cl | H | $C_2H_5$ | 0 | $CO_2C_2H_5$ | H | H | iso-$C_4H_9$ |
| Cl | H | $C_2H_5$ | 0 | $CO_2C_2H_5$ | H | H | sec-$C_4H_9$ |
| Cl | H | $C_2H_5$ | 0 | $CO_2C_2H_5$ | H | H | $CH_2CF_3$ |
| Cl | H | $C_2H_5$ | 0 | $CO_2C_2H_5$ | H | H | 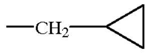 |
| Cl | H | $C_2H_5$ | 1 | $CO_2CH_3$ | H | H | $CH_3$ |
| Cl | H | $C_2H_5$ | 1 | $CO_2CH_3$ | H | H | $C_2H_5$ |
| Cl | H | $C_2H_5$ | 1 | $CO_2CH_3$ | H | H | n-$C_3H_7$ |
| Cl | H | $C_2H_5$ | 1 | $CO_2CH_3$ | H | H | iso-$C_3H_7$ |
| Cl | H | $C_2H_5$ | 1 | $CO_2CH_3$ | H | H | n-$C_4H_9$ |
| Cl | H | $C_2H_5$ | 1 | $CO_2CH_3$ | H | H | iso-$C_4H_9$ |
| Cl | H | $C_2H_5$ | 1 | $CO_2CH_3$ | H | H | sec-$C_4H_9$ |
| Cl | H | $C_2H_5$ | 1 | $CO_2CH_3$ | H | H | $CH_2CF_3$ |
| Cl | H | $C_2H_5$ | 1 | $CO_2CH_3$ | H | H | 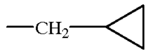 |
| Cl | H | $C_2H_5$ | 1 | $CO_2C_2H_5$ | H | H | $C_2H_5$ |
| Cl | H | $C_2H_5$ | 1 | $CO_2C_2H_5$ | H | H | n-$C_3H_7$ |
| Cl | H | $C_2H_5$ | 1 | $CO_2C_2H_5$ | H | H | iso-$C_3H_7$ |
| Cl | H | $C_2H_5$ | 1 | $CO_2C_2H_5$ | H | H | n-$C_4H_9$ |
| Cl | H | $C_2H_5$ | 1 | $CO_2C_2H_5$ | H | H | iso-$C_4H_9$ |
| Cl | H | $C_2H_5$ | 1 | $CO_2C_2H_5$ | H | H | sec-$C_4H_9$ |
| Cl | H | $C_2H_5$ | 1 | $CO_2C_2H_5$ | H | H | $CH_2CF_3$ |
| Cl | H | $C_2H_5$ | 1 | $CO_2C_2H_5$ | H | H | 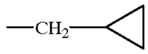 |
| Cl | H | $C_2H_5$ | 2 | $CO_2CH_3$ | H | H | $CH_3$ |
| Cl | H | $C_2H_5$ | 2 | $CO_2CH_3$ | H | H | $C_2H_5$ |
| Cl | H | $C_2H_5$ | 2 | $CO_2CH_3$ | H | H | n-$C_3H_7$ |
| Cl | H | $C_2H_5$ | 2 | $CO_2CH_3$ | H | H | iso-$C_3H_7$ |
| Cl | H | $C_2H_5$ | 2 | $CO_2CH_3$ | H | H | n-$C_4H_9$ |
| Cl | H | $C_2H_5$ | 2 | $CO_2CH_3$ | H | H | iso-$C_4H_9$ |

TABLE 1-continued

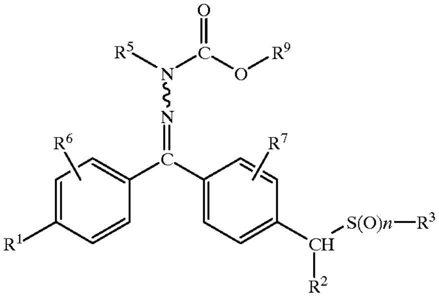

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 2 | $CO_2CH_3$ | H | H | sec-$C_4H_9$ |
| Cl | H | $C_2H_5$ | 2 | $CO_2CH_3$ | H | H | $CH_2CF_3$ |
| Cl | H | $C_2H_5$ | 2 | $CO_2CH_3$ | H | H | 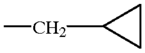 |
| Cl | H | $C_2H_5$ | 2 | $CO_2C_2H_5$ | H | H | $C_2H_5$ |
| Cl | H | $C_2H_5$ | 2 | $CO_2C_2H_5$ | H | H | n-$C_3H_7$ |
| Cl | H | $C_2H_5$ | 2 | $CO_2C_2H_5$ | H | H | iso-$C_3H_7$ |
| Cl | H | $C_2H_5$ | 2 | $CO_2C_2H_5$ | H | H | n-$C_4H_9$ |
| Cl | H | $C_2H_5$ | 2 | $CO_2C_2H_5$ | H | H | iso-$C_4H_9$ |
| Cl | H | $C_2H_5$ | 2 | $CO_2C_2H_5$ | H | H | sec-$C_4H_9$ |
| Cl | H | $C_2H_5$ | 2 | $CO_2C_2H_5$ | H | H | $CH_2CF_3$ |
| Cl | H | $C_2H_5$ | 2 | $CO_2C_2H_5$ | H | H | 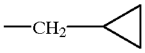 |
| Br | H | $C_2H_5$ | 2 | $CO_2CH_3$ | H | H | $CH_3$ |
| Br | H | $C_2H_5$ | 2 | $CO_2CH_3$ | H | H | $C_2H_5$ |
| Br | H | $C_2H_5$ | 2 | $CO_2CH_3$ | H | H | n-$C_3H_7$ |
| Br | H | $C_2H_5$ | 2 | $CO_2CH_3$ | H | H | iso-$C_3H_7$ |
| Br | H | $C_2H_5$ | 2 | $CO_2CH_3$ | H | H | n-$C_4H_9$ |
| Br | H | $C_2H_5$ | 2 | $CO_2CH_3$ | H | H | iso-$C_4H_9$ |
| Br | H | $C_2H_5$ | 2 | $CO_2CH_3$ | H | H | sec-$C_4H_9$ |
| Br | H | $C_2H_5$ | 2 | $CO_2CH_3$ | H | H | $CH_2CF_3$ |
| Br | H | $C_2H_5$ | 2 | $CO_2CH_3$ | H | H | 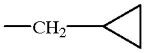 |
| Br | H | $C_2H_5$ | 2 | $CO_2C_2H_5$ | H | H | $C_2H_5$ |
| Br | H | $C_2H_5$ | 2 | $CO_2C_2H_5$ | H | H | n-$C_3H_7$ |
| Br | H | $C_2H_5$ | 2 | $CO_2C_2H_5$ | H | H | iso-$C_3H_7$ |
| Br | H | $C_2H_5$ | 2 | $CO_2C_2H_5$ | H | H | n-$C_4H_9$ |
| Br | H | $C_2H_5$ | 2 | $CO_2C_2H_5$ | H | H | iso-$C_4H_9$ |
| Br | H | $C_2H_5$ | 2 | $CO_2C_2H_5$ | H | H | sec-$C_4H_9$ |
| Br | H | $C_2H_5$ | 2 | $CO_2C_2H_5$ | H | H | $CH_2CF_3$ |
| Br | H | $C_2H_5$ | 2 | $CO_2C_2H_5$ | H | H | 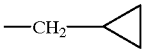 |
| Br | H | $C_2H_5$ | 1 | $CO_2CH_3$ | H | H | $CH_3$ |
| Br | H | $C_2H_5$ | 1 | $CO_2CH_3$ | H | H | $C_2H_5$ |
| Br | H | $C_2H_5$ | 1 | $CO_2CH_3$ | H | H | n-$C_3H_7$ |
| Br | H | $C_2H_5$ | 1 | $CO_2CH_3$ | H | H | iso-$C_3H_7$ |
| Br | H | $C_2H_5$ | 1 | $CO_2CH_3$ | H | H | n-$C_4H_9$ |
| Br | H | $C_2H_5$ | 1 | $CO_2CH_3$ | H | H | iso-$C_4H_9$ |
| Br | H | $C_2H_5$ | 1 | $CO_2CH_3$ | H | H | sec-$C_4H_9$ |
| Br | H | $C_2H_5$ | 1 | $CO_2CH_3$ | H | H | $CH_2CF_3$ |
| Br | H | $C_2H_5$ | 1 | $CO_2CH_3$ | H | H | 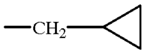 |
| Br | H | $C_2H_5$ | 1 | $CO_2C_2H_5$ | H | H | $C_2H_5$ |
| Br | H | $C_2H_5$ | 1 | $CO_2C_2H_5$ | H | H | n-$C_3H_7$ |
| Br | H | $C_2H_5$ | 1 | $CO_2C_2H_5$ | H | H | iso-$C_3H_7$ |
| Br | H | $C_2H_5$ | 1 | $CO_2C_2H_5$ | H | H | n-$C_4H_9$ |

TABLE 1-continued

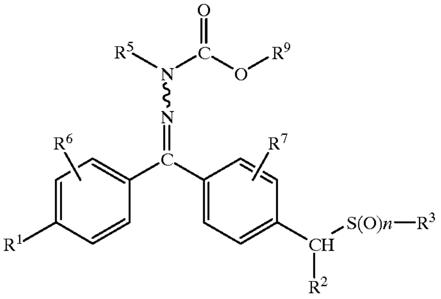

| $R^1$ | $R^2$ | $R^3$ | n | $R^5$ | $R^6$ | $R^7$ | $R^9$ |
|---|---|---|---|---|---|---|---|
| Br | H | $C_2H_5$ | 1 | $CO_2C_2H_5$ | H | H | iso-$C_4H_9$ |
| Br | H | $C_2H_5$ | 1 | $CO_2C_2H_5$ | H | H | sec-$C_4H_9$ |
| Br | H | $C_2H_5$ | 1 | $CO_2C_2H_5$ | H | H | $CH_2CF_3$ |
| Br | H | $C_2H_5$ | 1 | $CO_2C_2H_5$ | H | H | 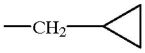 |
| Br | H | $C_2H_5$ | 0 | $CO_2CH_3$ | H | H | $CH_3$ |
| Br | H | $C_2H_5$ | 0 | $CO_2CH_3$ | H | H | $C_2H_5$ |
| Br | H | $C_2H_5$ | 0 | $CO_2CH_3$ | H | H | n-$C_3H_7$ |
| Br | H | $C_2H_5$ | 0 | $CO_2CH_3$ | H | H | iso-$C_3H_7$ |
| Br | H | $C_2H_5$ | 0 | $CO_2CH_3$ | H | H | n-$C_4H_9$ |
| Br | H | $C_2H_5$ | 0 | $CO_2CH_3$ | H | H | iso-$C_4H_9$ |
| Br | H | $C_2H_5$ | 0 | $CO_2CH_3$ | H | H | sec-$C_4H_9$ |
| Br | H | $C_2H_5$ | 0 | $CO_2CH_3$ | H | H | $CH_2CF_3$ |
| Br | H | $C_2H_5$ | a | $CO_2CH_3$ | H | H | 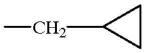 |
| Br | H | $C_2H_5$ | 0 | $CO_2C_2H_5$ | H | H | $C_2H_5$ |
| Br | H | $C_2H_5$ | 0 | $CO_2C_2H_5$ | H | H | n-$C_3H_7$ |
| Br | H | $C_2H_5$ | 0 | $CO_2C_2H_5$ | H | H | iso-$C_3H_7$ |
| Br | H | $C_2H_5$ | 0 | $CO_2C_2H_5$ | H | H | n-$C_4H_9$ |
| Br | H | $C_2H_5$ | 0 | $CO_2C_2H_5$ | H | H | iso-$C_4H_9$ |
| Br | H | $C_2H_5$ | 0 | $CO_2C_2H_5$ | H | H | sec-$C_4H_9$ |
| Br | H | $C_2H_5$ | 0 | $CO_2C_2H_5$ | H | H | $CH_2CF_3$ |
| Br | H | $C_2H_5$ | 0 | $CO_2C_2H_5$ | H | H | 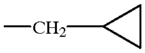 |
| Cl | H | $C_2H_5$ | 0 | $CO_2CH_3$ | H | H | 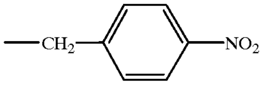 |
| Cl | H | $C_2H_5$ | 1 | $CO_2CH_3$ | H | H | 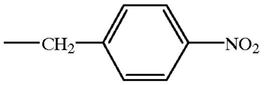 |
| Cl | H | $C_2H_5$ | 2 | $CO_2CH_3$ | H | H | 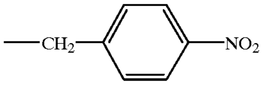 |
| Cl | H | $C_2H_5$ | 0 | $CO_2CH_3$ | H | H | 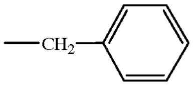 |
| Cl | H | $C_2H_5$ | 1 | $CO_2CH_3$ | H | H | 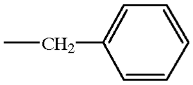 |

TABLE 1-continued

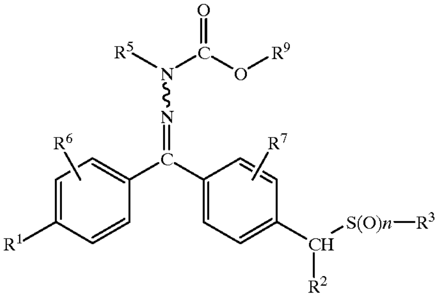

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 2 | $CO_2CH_3$ | H | H | 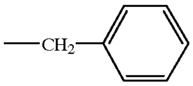 |
| Cl | H | $C_2H_5$ | 0 | $CO_2C_2H_5$ | H | H | 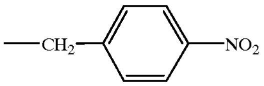 |
| Cl | H | $C_2H_5$ | 1 | $CO_2C_2H_5$ | H | H | 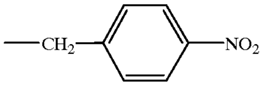 |
| Cl | H | $C_2H_5$ | 2 | $CO_2C_2H_5$ | H | H | 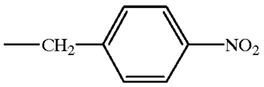 |
| Cl | H | $C_2H_5$ | 0 | $CO_2C_2H_5$ | H | H | 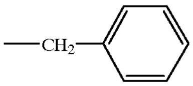 |
| Cl | H | $C_2H_5$ | 1 | $CO_2C_2H_5$ | H | H | 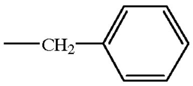 |
| Cl | H | $C_2H_5$ | 2 | $CO_2C_2H_5$ | H | H | 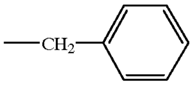 |
| Cl | H | $CH_3$ | 1 | $COCH_3$ | H | H | $CH_3$ |
| Cl | H | $CH_3$ | 1 | $COC_4H_9$-n | H | H | $CH_3$ |
| Cl | H | $CH_3$ | 2 | $COC_4H_9$-n | H | H | $CH_3$ |
| Br | H | $CH_3$ | 0 | $COC_4H_9$-n | H | H | $CH_3$ |
| Br | H | $CH_3$ | 1 | $COC_4H_9$-n | H | H | $CH_3$ |
| Br | H | $CH_3$ | 2 | $COC_4H_9$-n | H | H | $CH_3$ |
| Br | H | $CH_3$ | 0 | 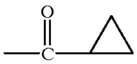 | H | H | $CH_3$ |
| Br | H | $CH_3$ | 1 | 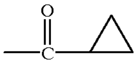 | H | H | $CH_3$ |
| Br | H | $CH_3$ | 2 | 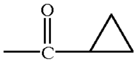 | H | H | $CH_3$ |
| Cl | H | $CH_3$ | 1 | $COC_4H_9$-n | H | H | $C_2H_5$ |
| Cl | H | $CH_3$ | 2 | $COC_4H_9$-n | H | H | $C_2H_5$ |
| Br | H | $CH_3$ | 0 | $COC_4H_9$-n | H | H | $C_2H_5$ |

TABLE 1-continued

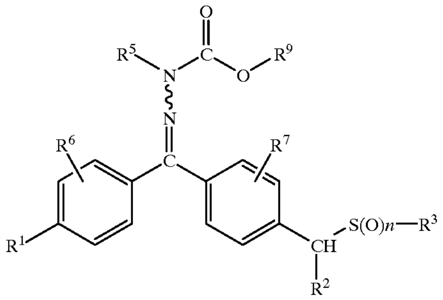

| $R^1$ | $R^2$ | $R^3$ | n | $R^5$ | $R^6$ | $R^7$ | $R^9$ |
|---|---|---|---|---|---|---|---|
| Br | H | $CH_3$ | 1 | $COC_4H_9$-n | H | H | $C_2H_5$ |
| Br | H | $CH_3$ | 2 | $COC_4H_9$-n | H | H | $C_2H_5$ |
| Br | H | $CH_3$ | 0 | 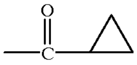 | H | H | $C_2H_5$ |
| Br | H | $CH_3$ | 1 | 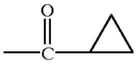 | H | H | $C_2H_5$ |
| Br | H | $CH_3$ | 2 | 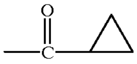 | H | H | $C_2H_5$ |
| Br | H | $CH_3$ | 1 | $COC_6H_5$ | H | H | $C_2H_5$ |
| Cl | H | $CH_3$ | 1 | $COCH_3$ | H | H | n-$C_3H_7$ |
| Cl | H | $CH_3$ | 1 | $COC_4H_9$-n | H | H | n-$C_3H_7$ |
| Cl | H | $CH_3$ | 2 | $COC_4H_9$-n | H | H | n-$C_3H_7$ |
| Br | H | $CH_3$ | 0 | $COC_4H_9$-n | H | H | n-$C_3H_7$ |
| Br | H | $CH_3$ | 1 | $COC_4H_9$-n | H | H | n-$C_3H_7$ |
| Br | H | $CH_3$ | 2 | $COC_4H_9$-n | H | H | n-$C_3H_7$ |
| Br | H | $CH_3$ | 0 | 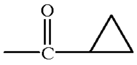 | H | H | n-$C_3H_7$ |
| Br | H | $CH_3$ | 1 | 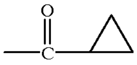 | H | H | n-$C_3H_7$ |
| Br | H | $CH_3$ | 2 | 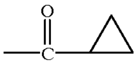 | H | H | n-$C_3H_7$ |
| Cl | H | $CH_3$ | 0 | $COCH_2OCH_3$ | H | H | n-$C_3H_7$ |
| Cl | H | $CH_3$ | 0 | $COCH_2OCH_3$ | H | H | iso-$C_3H_7$ |
| Cl | H | $CH_3$ | 1 | $COCH_2OCH_3$ | H | H | iso-$C_3H_7$ |
| Cl | H | $CH_3$ | 2 | $COCH_2OCH_3$ | H | H | iso-$C_3H_7$ |
| Cl | H | $CH_3$ | 1 | $COCH_3$ | H | H | iso-$C_3H_7$ |
| Cl | H | $CH_3$ | 0 | $COC_3H_7$-iso | H | H | iso-$C_3H_7$ |
| Cl | H | $CH_3$ | 1 | $COC_4H_9$-n | H | H | iso-$C_3H_7$ |
| Cl | H | $CH_3$ | 2 | $COC_4H_9$-n | H | H | iso-$C_3H_7$ |
| Cl | H | $CH_3$ | 0 | 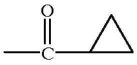 | H | H | iso-$C_3H_7$ |
| Cl | H | $CH_3$ | 1 | $COC_2H_5$ | H | H | $CH_2CF_3$ |
| Cl | H | $CH_3$ | 2 | $COC_2H_5$ | H | H | $CH_2CF_3$ |
| Cl | H | $CH_3$ | 1 | $COC_3H_7$-n | H | H | $CH_2CF_3$ |
| Cl | H | $CH_3$ | 2 | $COC_3H_7$-n | H | H | $CH_2CF_3$ |
| Cl | H | $CH_3$ | 0 | $COC_4H_9$-n | H | H | $CH_2CF_3$ |
| Cl | H | $CH_3$ | 1 | $COC_4H_9$-n | H | H | $CH_2CF_3$ |
| Cl | H | $CH_3$ | 2 | $COC_4H_9$-n | H | H | $CH_2CF_3$ |

TABLE 1-continued
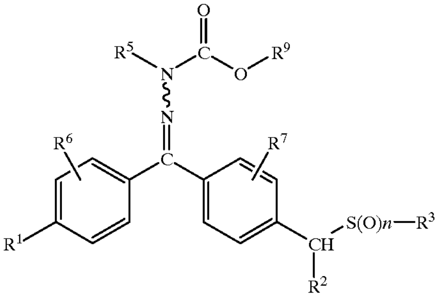
| $R^1$ | $R^2$ | $R^3$ | n | $R^5$ | $R^6$ | $R^7$ | $R^9$ |
|---|---|---|---|---|---|---|---|
| Cl | H | $CH_3$ | 0 | 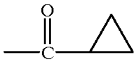 | H | H | $CH_2CF_3$ |
| Cl | H | $CH_3$ | 1 | 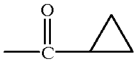 | H | H | $CH_2CF_3$ |
| Cl | H | $CH_3$ | 2 | 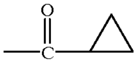 | H | H | $CH_2CF_3$ |
| Cl | H | $CH_3$ | 0 | $COC_2H_5$ | H | H | 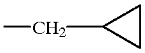 |
| Cl | H | $CH_3$ | 1 | $COC_2H_5$ | H | H | 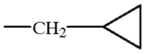 |
| Cl | H | $CH_3$ | 2 | $COC_2H_5$ | H | H | 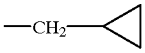 |
| Cl | H | $CH_3$ | 0 | $COC_3H_7$-n | H | H | 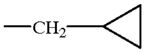 |
| Cl | H | $CH_3$ | 1 | $COC_3H_7$-n | H | H | 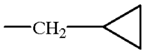 |
| Cl | H | $CH_3$ | 2 | $COC_3H_7$-n | H | H | 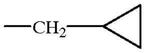 |
| Cl | H | $CH_3$ | 0 | $COC_4H_9$-n | H | H | 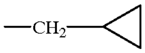 |
| Cl | H | $CH_3$ | 1 | $COC_4H_9$-n | H | H | 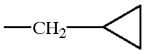 |
| Cl | H | $CH_3$ | 2 | $COC_4H_9$-n | H | H | 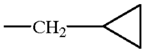 |
| Cl | H | $CH_3$ | 0 | 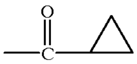 | H | H | 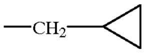 |
| Cl | H | $CH_3$ | 1 | 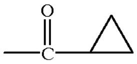 | H | H | 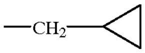 |
| Cl | H | $CH_3$ | 2 | 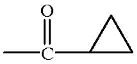 | H | H | 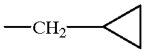 |

TABLE 1-continued

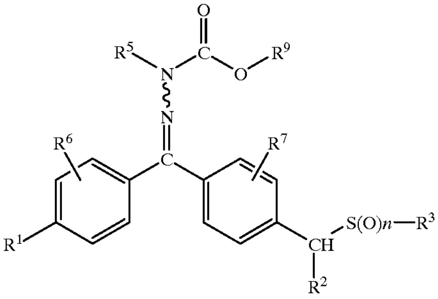

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 1 | $COCH_3$ | H | H | $CH_3$ |
| Cl | H | $C_2H_5$ | 2 | $COCH_3$ | H | H | $CH_3$ |
| Cl | H | $C_2H_5$ | 1 | $COC_4H_9$-n | H | H | $CH_3$ |
| Cl | H | $C_2H_5$ | 2 | $COC_4H_9$-n | H | H | $CH_3$ |
| Br | H | $C_2H_5$ | 0 | $COCH_3$ | H | H | $CH_3$ |
| Br | H | $C_2H_5$ | 0 | $COC_4H_9$-n | H | H | $CH_3$ |
| Br | H | $C_2H_5$ | 1 | $COC_4H_9$-n | H | H | $CH_3$ |
| Br | H | $C_2H_5$ | 2 | $COC_4H_9$-n | H | H | $CH_3$ |
| Cl | H | $C_2H_5$ | 1 | $COCH_3$ | H | H | $C_2H_5$ |
| Cl | H | $C_2H_5$ | 2 | $COCH_3$ | H | H | $C_2H_5$ |
| Cl | H | $C_2H_5$ | 1 | $COC_4H_9$-n | H | H | $C_2H_5$ |
| Cl | H | $C_2H_5$ | 2 | $COC_4H_9$-n | H | H | $C_2H_5$ |
| Br | H | $C_2H_5$ | 1 | $COCH_3$ | H | H | $C_2H_5$ |
| Br | H | $C_2H_5$ | 2 | $COCH_3$ | H | H | $C_2H_5$ |
| Br | H | $C_2H_5$ | 0 | $COC_4H_9$-n | H | H | $C_2H_5$ |
| Br | H | $C_2H_5$ | 1 | $COC_4H_9$-n | H | H | $C_2H_5$ |
| Br | H | $C_2H_5$ | 2 | $COC_4H_9$-n | H | H | $C_2H_5$ |
| Cl | H | $C_2H_5$ | 1 | $COCH_3$ | H | H | n-$C_3H_7$ |
| Cl | H | $C_2H_5$ | 2 | $COCH_3$ | H | H | n-$C_3H_7$ |
| Cl | H | $C_2H_5$ | 1 | $COC_4H_9$-n | H | H | n-$C_3H_7$ |
| Cl | H | $C_2H_5$ | 2 | $COC_4H_9$-n | H | H | n-$C_3H_7$ |
| Br | H | $C_2H_5$ | 0 | $COC_4H_9$-n | H | H | n-$C_3H_7$ |
| Br | H | $C_2H_5$ | 1 | $COC_4H_9$-n | H | H | n-$C_3H_7$ |
| Br | H | $C_2H_5$ | 2 | $COC_4H_9$-n | H | H | n-$C_3H_7$ |
| Cl | H | $C_2H_5$ | 0 | $COC_3H_7$-iso | H | H | iso-$C_3H_7$ |
| Cl | H | $C_2H_5$ | 1 | $COC_4H_9$-n | H | H | iso-$C_3H_7$ |
| Cl | H | $C_2H_5$ | 2 | $COC_4H_9$-n | H | H | iso-$C_3H_7$ |
| Cl | H | $C_2H_5$ | 0 | 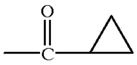 | H | H | iso-$C_3H_7$ |
| Cl | H | $C_2H_5$ | 2 | $COC_6H_5$ | H | H | iso-$C_3H_7$ |
| Br | H | $C_2H_5$ | 1 | $COC_2H_5$ | H | H | iso-$C_3H_7$ |
| Br | H | $C_2H_5$ | 2 | $COC_2H_5$ | H | H | iso-$C_3H_7$ |
| Cl | H | $C_2H_5$ | 1 | $COC_2H_5$ | H | H | $CH_2CF_3$ |
| Cl | H | $C_2H_5$ | 2 | $COC_2H_5$ | H | H | $CH_2CF_3$ |
| Cl | H | $C_2H_5$ | 1 | $COC_3H_7$-n | H | H | $CH_2CF_3$ |
| Cl | H | $C_2H_5$ | 2 | $COC_3H_7$-n | H | H | $CH_2CF_3$ |
| Cl | H | $C_2H_5$ | 0 | $COC_4H_9$-n | H | H | $CH_2CF_3$ |
| Cl | H | $C_2H_5$ | 1 | $COC_4H_9$-n | H | H | $CH_2CF_3$ |
| Cl | H | $C_2H_5$ | 2 | $COC_4H_9$-n | H | H | $CH_2CF_3$ |
| Cl | H | $C_2H_5$ | 0 | $COC_2H_5$ | H | H | 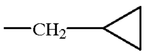 |
| Cl | H | $C_2H_5$ | 1 | $COC_2H_5$ | H | H | 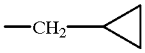 |
| Cl | H | $C_2H_5$ | 2 | $COC_2H_5$ | H | H | 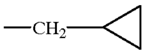 |
| Cl | H | $C_2H_5$ | 0 | $COC_3H_7$-n | H | H | 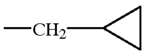 |

TABLE 1-continued

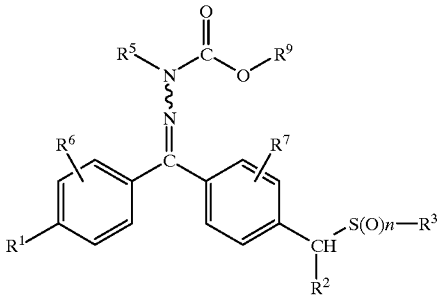

| $R^1$ | $R^2$ | $R^3$ | n | $R^5$ | $R^6$ | $R^7$ | $R^9$ |
|---|---|---|---|---|---|---|---|
| Cl | H | $C_2H_5$ | 1 | $COC_3H_7$-n | H | H | 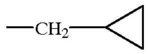 |
| Cl | H | $C_2H_5$ | 2 | $COC_3H_7$-n | H | H | 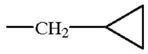 |
| Cl | H | $C_2H_5$ | 0 | $COC_4H_9$-n | H | H | 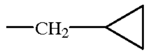 |
| Cl | H | $C_2H_5$ | 1 | $COC_4H_9$-n | H | H | 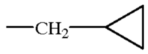 |
| Cl | H | $C_2H_5$ | 2 | $COC_4H_9$-n | H | H | 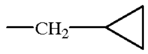 |
| Cl | H | $CH_3$ | 0 | $CO_2CH_3$ | H | H | $CH_2CH{=}CH_2$ |
| Cl | H | $CH_3$ | 1 | $CO_2CH_3$ | H | H | $CH_2CH{=}CH_2$ |
| Cl | H | $CH_3$ | 2 | $CO_2CH_3$ | H | H | $CH_2CH{=}CH_2$ |
| Cl | H | $CH_3$ | 0 | $CO_2C_2H_5$ | H | H | $CH_2CH{=}CH_2$ |
| Cl | H | $CH_3$ | 1 | $CO_2C_2H_5$ | H | H | $CH_2CH{=}CH_2$ |
| Cl | H | $CH_3$ | 2 | $CO_2C_2H_5$ | H | H | $CH_2CH{=}CH_2$ |
| Cl | H | $C_2H_5$ | 0 | $CO_2CH_3$ | H | H | $CH_2CH{=}CH_2$ |
| Cl | H | $C_2H_5$ | 1 | $CO_2CH_3$ | H | H | $CH_2CH{=}CH_2$ |
| Cl | H | $C_2H_5$ | 2 | $CO_2CH_3$ | H | H | $CH_2CH{=}CH_2$ |
| Cl | H | $C_2H_5$ | 0 | $CO_2C_2H_5$ | H | H | $CH_2CH{=}CH_2$ |
| Cl | H | $C_2H_5$ | 1 | $CO_2C_2H_5$ | H | H | $CH_2CH{=}CH_2$ |
| Cl | H | $C_2H_5$ | 2 | $CO_2C_2H_5$ | H | H | $CH_2CH{=}CH_2$ |

TABLE 2

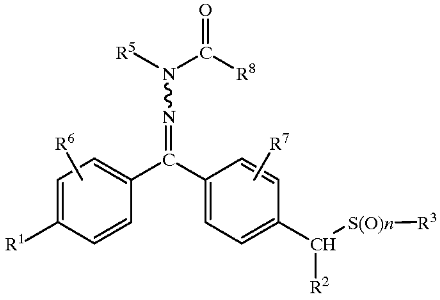

| $R^1$ | $R^2$ | $R^3$ | n | $R^5$ | $R^6$ | $R^7$ | $R^8$ |
|---|---|---|---|---|---|---|---|
| F | H | $CH_3$ | 0 | H | H | H | $CH_3$ |
| F | H | $CH_3$ | 0 | H | H | H | $C_2H_5$ |
| F | H | $CH_3$ | 0 | H | H | H | n-$C_3H_7$ |
| F | H | $CH_3$ | 0 | H | H | H | iso-$C_3H_7$ |
| F | H | $CH_3$ | 0 | H | H | H | n-$C_4H_9$ |
| F | H | $CH_3$ | 0 | H | H | H | iso-$C_4H_9$ |
| F | H | $CH_3$ | 0 | H | H | H | tert-$C_4H_9$ |

TABLE 2-continued

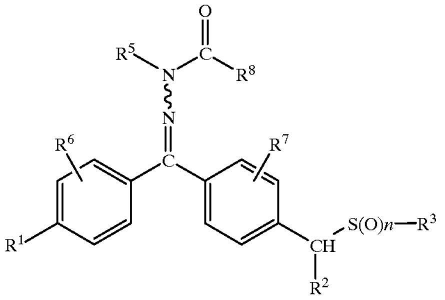

| $R^1$ | $R^2$ | $R^3$ | n | $R^5$ | $R^6$ | $R^7$ | $R^8$ |
|---|---|---|---|---|---|---|---|
| F | H | $CH_3$ | 0 | H | H | H | $(CH_2)_3Cl$ |
| F | H | $CH_3$ | 0 | H | H | H | $CH_2CN$ |
| F | H | $CH_3$ | 0 | H | H | H | $C_6H_5$ |
| F | H | $CH_3$ | 0 | H | H | H | 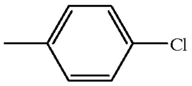 |
| F | H | $CH_3$ | 0 | H | H | H | 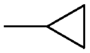 |
| F | H | $CH_3$ | 0 | H | H | H | 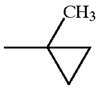 |
| F | H | $CH_3$ | 1 | H | H | H | $CH_3$ |
| F | H | $CH_3$ | 1 | H | H | H | $C_2H_5$ |
| F | H | $CH_3$ | 1 | H | H | H | n-$C_3H_7$ |
| F | H | $CH_3$ | 1 | H | H | H | iso-$C_3H_7$ |
| F | H | $CH_3$ | 1 | H | H | H | n-$C_4H_9$ |
| F | H | $CH_3$ | 1 | H | H | H | iso-$C_4H_9$ |
| F | H | $CH_3$ | 1 | H | H | H | tert-$C_4H_9$ |
| F | H | $CH_3$ | 1 | H | H | H | $(CH_2)_3Cl$ |
| F | H | $CH_3$ | 1 | H | H | H | $CH_2CN$ |
| F | H | $CH_3$ | 1 | H | H | H | $C_6H_5$ |
| F | H | $CH_3$ | 1 | H | H | H | 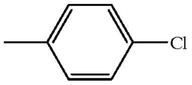 |
| F | H | $CH_3$ | 1 | H | H | H | 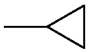 |
| F | H | $CH_3$ | 1 | H | H | H | 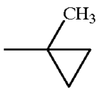 |
| F | H | $CH_3$ | 2 | H | H | H | $CH_3$ |
| F | H | $CH_3$ | 2 | H | H | H | $C_2H_5$ |
| F | H | $CH_3$ | 2 | H | H | H | n-$C_3H_7$ |
| F | H | $CH_3$ | 2 | H | H | H | iso-$C_3H_7$ |
| F | H | $CH_3$ | 2 | H | H | H | n-$C_4H_9$ |
| F | H | $CH_3$ | 2 | H | H | H | iso-$C_4H_9$ |
| F | H | $CH_3$ | 2 | H | H | H | tert-$C_4H_9$ |
| F | H | $CH_3$ | 2 | H | H | H | $(CH_2)_3Cl$ |
| F | H | $CH_3$ | 2 | H | H | H | $CH_2CN$ |
| F | H | $CH_3$ | 2 | H | H | H | $C_6H_5$ |
| F | H | $CH_3$ | 2 | H | H | H | 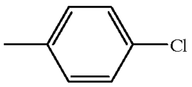 |

TABLE 2-continued

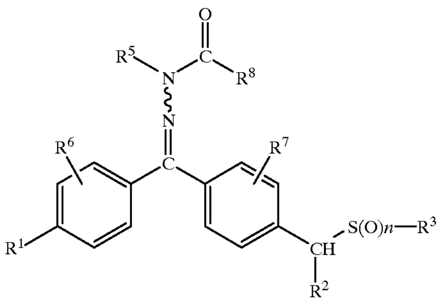

| $R^1$ | $R^2$ | $R^3$ | n | $R^5$ | $R^6$ | $R^7$ | $R^8$ |
|---|---|---|---|---|---|---|---|
| F | H | $CH_3$ | 2 | H | H | H | 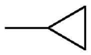 |
| F | H | $CH_3$ | 2 | H | H | H | 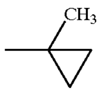 |
| F | H | $C_2H_5$ | 0 | H | H | H | $CH_3$ |
| F | H | $C_2H_5$ | 0 | H | H | H | $C_2H_5$ |
| F | H | $C_2H_5$ | 0 | H | H | H | n-$C_3H_7$ |
| F | H | $C_2H_5$ | 0 | H | H | H | iso-$C_3H_7$ |
| F | H | $C_2H_5$ | 0 | H | H | H | n-$C_4H_9$ |
| F | H | $C_2H_5$ | 0 | H | H | H | iso-$C_4H_9$ |
| F | H | $C_2H_5$ | 0 | H | H | H | tert-$C_4H_9$ |
| F | H | $C_2H_5$ | 0 | H | H | H | $(CH_2)_3Cl$ |
| F | H | $C_2H_5$ | 0 | H | H | H | $CH_2CN$ |
| F | H | $C_2H_5$ | 0 | H | H | H | $C_6H_5$ |
| F | H | $C_2H_5$ | 0 | H | H | H | 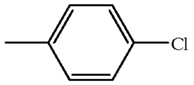 |
| F | H | $C_2H_5$ | 0 | H | H | H | 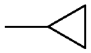 |
| F | H | $C_2H_5$ | 0 | H | H | H | 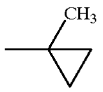 |
| F | H | $C_2H_5$ | 1 | H | H | H | $CH_3$ |
| F | H | $C_2H_5$ | 1 | H | H | H | $C_2H_5$ |
| F | H | $C_2H_5$ | 1 | H | H | H | n-$C_3H_7$ |
| F | H | $C_2H_5$ | 1 | H | H | H | iso-$C_3H_7$ |
| F | H | $C_2H_5$ | 1 | H | H | H | n-$C_4H_9$ |
| F | H | $C_2H_5$ | 1 | H | H | H | iso-$C_4H_9$ |
| F | H | $C_2H_5$ | 1 | H | H | H | tert-$C_4H_9$ |
| F | H | $C_2H_5$ | 1 | H | H | H | $(CH_2)_3Cl$ |
| F | H | $C_2H_5$ | 1 | H | H | H | $CH_2CN$ |
| F | H | $C_2H_5$ | 1 | H | H | H | $C_6H_5$ |
| F | H | $C_2H_5$ | 1 | H | H | H | 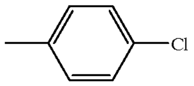 |
| F | H | $C_2H_5$ | 1 | H | H | H | 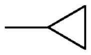 |

TABLE 2-continued

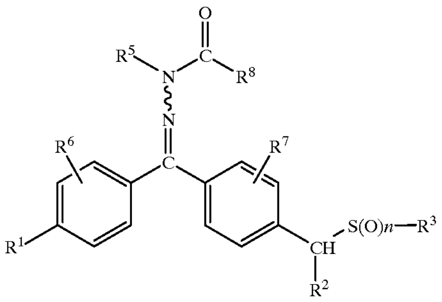

| $R^1$ | $R^2$ | $R^3$ | n | $R^5$ | $R^6$ | $R^7$ | $R^8$ |
|---|---|---|---|---|---|---|---|
| F | H | $C_2H_5$ | 1 | H | H | H | 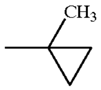 |
| F | H | $C_2H_5$ | 2 | H | H | H | $CH_3$ |
| F | H | $C_2H_5$ | 2 | H | H | H | $C_2H_5$ |
| F | H | $C_2H_5$ | 2 | H | H | H | n-$C_3H_7$ |
| F | H | $C_2H_5$ | 2 | H | H | H | iso-$C_3H_7$ |
| F | H | $C_2H_5$ | 2 | H | H | H | n-$C_4H_9$ |
| F | H | $C_2H_5$ | 2 | H | H | H | iso-$C_4H_9$ |
| F | H | $C_2H_5$ | 2 | H | H | H | tert-$C_4H_9$ |
| F | H | $C_2H_5$ | 2 | H | H | H | $(CH_2)_3Cl$ |
| F | H | $C_2H_5$ | 2 | H | H | H | $CH_2CN$ |
| F | H | $C_2H_5$ | 2 | H | H | H | $C_6H_5$ |
| F | H | $C_2H_5$ | 2 | H | H | H | 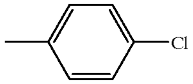 |
| F | H | $C_2H_5$ | 2 | H | H | H | 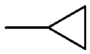 |
| F | H | $C_2H_5$ | 2 | H | H | H | 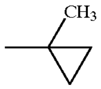 |
| Cl | H | $CH_3$ | 0 | H | H | H | H |
| Cl | H | $CH_3$ | 0 | H | H | H | $CH_3$ |
| Cl | H | $CH_3$ | 0 | H | H | H | $C_2H_5$ |
| Cl | H | $CH_3$ | 0 | H | H | H | n-$C_3H_7$ |
| Cl | H | $CH_3$ | 0 | H | H | H | iso-$C_3H_7$ |
| Cl | H | $CH_3$ | 0 | H | H | H | n-$C_4H_9$ |
| Cl | H | $CH_3$ | 0 | H | H | H | sec-$C_4H_9$ |
| Cl | H | $CH_3$ | 0 | H | H | H | iso-$C_4H_9$ |
| Cl | H | $CH_3$ | 0 | H | H | H | tert-$C_4H_9$ |
| Cl | H | $CH_3$ | 0 | H | H | H | n-$C_5H_{11}$ |
| Cl | H | $CH_3$ | 0 | H | H | H | n-$C_5H_{13}$ |
| Cl | H | $CH_3$ | 0 | H | H | H | $C_6H_5$ |
| Cl | H | $CH_3$ | 0 | H | H | H | 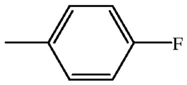 |
| Cl | H | $CH_3$ | 0 | H | H | H | 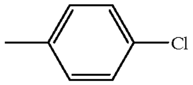 |
| Cl | H | $CH_3$ | 0 | H | H | H | 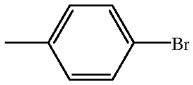 |

TABLE 2-continued

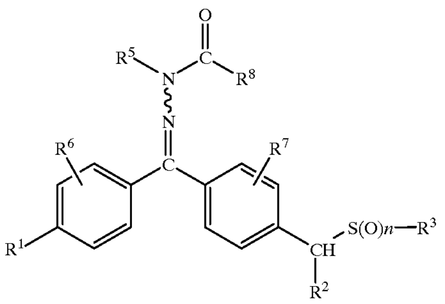

| $R^1$ | $R^2$ | $R^3$ | n | $R^5$ | $R^6$ | $R^7$ | $R^8$ |
|---|---|---|---|---|---|---|---|
| Cl | H | $CH_3$ | 0 | H | H | H | 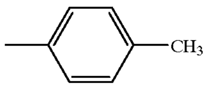 |
| Cl | H | $CH_3$ | 0 | H | H | H | 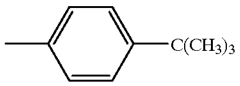 |
| Cl | H | $CH_3$ | 0 | H | H | H | 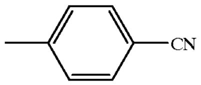 |
| Cl | H | $CH_3$ | 0 | H | H | H | 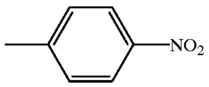 |
| Cl | H | $CH_3$ | 0 | H | H | H | 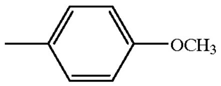 |
| Cl | H | $CH_3$ | 0 | H | H | H | 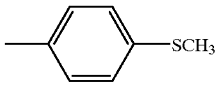 |
| Cl | H | $CH_3$ | 0 | H | H | H | $CH{=}CH_2$ |
| Cl | H | $CH_3$ | 0 | H | H | H | $CH{=}CHC_6H_5$ |
| Cl | H | $CH_3$ | 0 | H | H | H | $CH{=}CHCH_3$ |
| Cl | H | $CH_3$ | 0 | H | H | H | $C({=}CH_2)CH_3$ |
| Cl | H | $CH_3$ | 0 | H | H | H | $CH_2CF{=}CF_2$ |
| Cl | H | $CH_3$ | 0 | H | H | H | 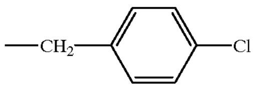 |
| Cl | H | $CH_3$ | 0 | H | H | H | $CH_2CH_2Cl$ |
| Cl | H | $CH_3$ | 0 | H | H | H | $(CH_2)_4Cl$ |
| Cl | H | $CH_3$ | 0 | H | H | H | $(CH_2)_3Cl$ |
| Cl | H | $CH_3$ | 0 | H | H | H | $CH_2OCH_3$ |
| Cl | H | $CH_3$ | 0 | H | H | H | $CH_2CH_2OCH_3$ |
| Cl | H | $CH_3$ | 0 | H | H | H | $CH_2CN$ |
| Cl | H | $CH_3$ | 0 | H | H | H | $CH_2CO_2C_2H_5$ |
| Cl | H | $CH_3$ | 0 | H | H | H | 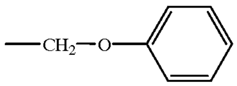 |
| Cl | H | $CH_3$ | 0 | H | H | H | 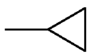 |

TABLE 2-continued

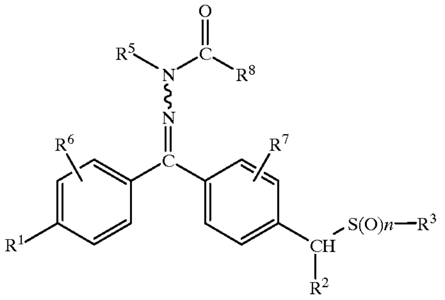

| $R^1$ | $R^2$ | $R^3$ | n | $R^5$ | $R^6$ | $R^7$ | $R^8$ |
|---|---|---|---|---|---|---|---|
| Cl | H | $CH_3$ | 0 | H | H | H | 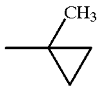 |
| Cl | H | $CH_3$ | 0 | H | H | H | 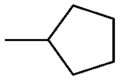 |
| Cl | H | $CH_3$ | 0 | H | H | H | 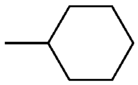 |
| Cl | H | $CH_3$ | 0 | H | 2-Cl | H | $CH_3$ |
| Cl | H | $CH_3$ | 0 | H | 2-Cl | H | $C_2H_5$ |
| Cl | H | $CH_3$ | 0 | H | 2-Cl | H | n-$C_3H_7$ |
| Cl | H | $CH_3$ | 0 | H | 2-Cl | H | n-$C_4H_9$ |
| Cl | H | $CH_3$ | 0 | H | 3-Cl | H | $CH_3$ |
| Cl | H | $CH_3$ | 0 | H | 3-Cl | H | $C_2H_5$ |
| Cl | H | $CH_3$ | 0 | H | 3-Cl | H | n-$C_3H_7$ |
| Cl | H | $CH_3$ | 0 | H | 3-Cl | H | n-$C_4H_9$ |
| Cl | H | $CH_3$ | 0 | H | 2-F | H | $CH_3$ |
| Cl | H | $CH_3$ | 0 | H | 2-F | H | $C_2H_5$ |
| Cl | H | $CH_3$ | 0 | H | 2-F | H | n-$C_3H_7$ |
| Cl | H | $CH_3$ | 0 | H | 2-F | H | n-$C_4H_9$ |
| Cl | H | $CH_3$ | 0 | H | 3-F | H | $CH_3$ |
| Cl | H | $CH_3$ | 0 | H | 3-F | H | $C_2H_5$ |
| Cl | H | $CH_3$ | 0 | H | 3-F | H | n-$C_3H_7$ |
| Cl | H | $CH_3$ | 0 | H | 3-F | H | n-$C_4H_9$ |
| Cl | H | $CH_3$ | 0 | H | 3-F | H | sec-$C_4H_9$ |
| Cl | H | $CH_3$ | 0 | $CH_3$ | H | H | $CH_3$ |
| Cl | H | $CH_3$ | 0 | $CH_3$ | H | H | $C_2H_5$ |
| Cl | H | $CH_3$ | 0 | $CH_3$ | H | H | n-$C_3H_7$ |
| Cl | H | $CH_3$ | 0 | $CH_3$ | H | H | iso-$C_3H_7$ |
| Cl | H | $CH_3$ | 0 | $CH_3$ | H | H | n-$C_4H_9$ |
| Cl | H | $CH_3$ | 0 | $CH_3$ | H | H | sec-$C_4H_9$ |
| Cl | H | $CH_3$ | 0 | $CH_3$ | H | H | tert-$C_4H_9$ |
| Cl | H | $CH_3$ | 0 | $CH_3$ | H | H | iso-$C_4H_9$ |
| Cl | H | $CH_3$ | 0 | $CH_3$ | H | H | $C_6H_5$ |
| Cl | H | $CH_3$ | 0 | $CH_3$ | H | H | 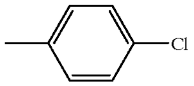 |
| Cl | H | $CH_3$ | 0 | $CH_3$ | H | H | $(CH_2)_3Cl$ |
| Cl | H | $CH_3$ | 0 | $CH_3$ | H | H | $(CH_2)_4Cl$ |
| Cl | H | $CH_3$ | 0 | $CH_3$ | H | H | $CH_2CN$ |
| Cl | H | $CH_3$ | 0 | $CH_3$ | H | H | $CH_2OCH_3$ |
| Cl | H | $CH_3$ | 0 | $CH_3$ | H | H | $CH_2CO_2C_2H_5$ |
| Cl | H | $CH_3$ | 0 | $C_2H_5$ | H | H | 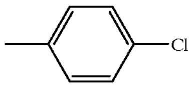 |

TABLE 2-continued

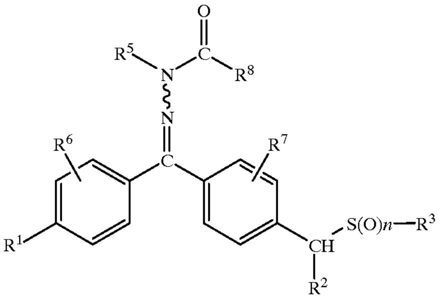

| $R^1$ | $R^2$ | $R^3$ | n | $R^5$ | $R^6$ | $R^7$ | $R^8$ |
|---|---|---|---|---|---|---|---|
| Cl | H | $CH_3$ | 0 | $C_2H_5$ | H | H | $CH_3$ |
| Cl | H | $CH_3$ | 0 | $C_2H_5$ | H | H | $C_2H_5$ |
| Cl | H | $CH_3$ | 0 | $C_2H_5$ | H | H | n-$C_3H_7$ |
| Cl | H | $CH_3$ | 0 | $C_2H_5$ | H | H | iso-$C_3H_7$ |
| Cl | H | $CH_3$ | 0 | $C_2H_5$ | H | H | n-$C_4H_9$ |
| Cl | H | $CH_3$ | 0 | $C_2H_5$ | H | H | iso-$C_4H_9$ |
| Cl | H | $CH_3$ | 0 | $C_2H_5$ | H | H | sec-$C_4H_9$ |
| Cl | H | $CH_3$ | 0 | $C_2H_5$ | H | H | tert-$C_4H_9$ |
| Cl | H | $CH_3$ | 0 | $C_2H_5$ | H | H | $(CH_2)_3Cl$ |
| Cl | H | $CH_3$ | 0 | $C_2H_5$ | H | H | $(CH_2)_4Cl$ |
| Cl | H | $CH_3$ | 0 | $C_2H_5$ | H | H | $CH_2CN$ |
| Cl | H | $CH_3$ | 0 | $C_2H_5$ | H | H | $CH_2OCH_3$ |
| Cl | H | $CH_3$ | 0 | $C_2H_5$ | H | H | $CH_2CO_2C_2H_5$ |
| Cl | H | $CH_3$ | 0 | $C_2H_5$ | H | H | $C_6H_5$ |
| Cl | H | $CH_3$ | 0 | n-$C_3H_7$ | H | H | 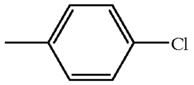 |
| Cl | H | $CH_3$ | 0 | n-$C_3H_7$ | H | H | $CH_3$ |
| Cl | H | $CH_3$ | 0 | n-$C_3H_7$ | H | H | $C_2H_5$ |
| Cl | H | $CH_3$ | 0 | n-$C_3H_7$ | H | H | n-$C_3H_7$ |
| Cl | H | $CH_3$ | 0 | n-$C_3H_7$ | H | H | iso-$C_3H_7$ |
| Cl | H | $CH_3$ | 0 | n-$C_3H_7$ | H | H | n-$C_4H_9$ |
| Cl | H | $CH_3$ | 0 | n-$C_3H_7$ | H | H | iso-$C_4H_9$ |
| Cl | H | $CH_3$ | 0 | n-$C_3H_7$ | H | H | sec-$C_4H_9$ |
| Cl | H | $CH_3$ | 0 | n-$C_3H_7$ | H | H | tert-$C_4H_9$ |
| Cl | H | $CH_3$ | 0 | n-$C_3H_7$ | H | H | $(CH_2)_3Cl$ |
| Cl | H | $CH_3$ | 0 | n-$C_3H_7$ | H | H | $(CH_2)_4Cl$ |
| Cl | H | $CH_3$ | 0 | n-$C_3H_7$ | H | H | $CH_2CN$ |
| Cl | H | $CH_3$ | 0 | n-$C_3H_7$ | H | H | $CH_2CO_2C_2H_5$ |
| Cl | H | $CH_3$ | 0 | n-$C_3H_7$ | H | H | $CH_2OCH_3$ |
| Cl | H | $CH_3$ | 0 | n-$C_3H_7$ | H | H | $C_6H_5$ |
| Cl | H | $CH_3$ | 0 | iso-$C_3H_7$ | H | H | $CH_3$ |
| Cl | H | $CH_3$ | 0 | iso-$C_3H_7$ | H | H | $C_2H_5$ |
| Cl | H | $CH_3$ | 0 | iso-$C_3H_7$ | H | H | n-$C_3H_7$ |
| Cl | H | $CH_3$ | 0 | iso-$C_3H_7$ | H | H | iso-$C_3H_7$ |
| Cl | H | $CH_3$ | 0 | iso-$C_3H_7$ | H | H | n-$C_4H_9$ |
| Cl | H | $CH_3$ | 0 | iso-$C_3H_7$ | K | H | iso-$C_4H_9$ |
| Cl | H | $CH_3$ | 0 | iso-$C_3H_7$ | H | H | sec-$C_4H_9$ |
| Cl | H | $CH_3$ | 0 | iso-$C_3H_7$ | H | H | tert-$C_4H_9$ |
| Cl | H | $CH_3$ | 0 | iso-$C_3H_7$ | H | H | $(CH_2)_3Cl$ |
| Cl | H | $CH_3$ | 0 | iso-$C_3H_7$ | H | H | $(CH_2)_4Cl$ |
| Cl | H | $CH_3$ | 0 | iso-$C_3H_7$ | H | H | $CH_2CN$ |
| Cl | H | $CH_3$ | 0 | iso-$C_3H_7$ | H | H | $CH_2CO_2C_2H_5$ |
| Cl | H | $CH_3$ | 0 | iso-$C_3H_7$ | H | H | $CH_2OCH_3$ |
| Cl | H | $CH_3$ | 0 | iso-$C_3H_7$ | H | H | $C_6H_5$ |
| Cl | H | $CH_3$ | 0 | iso-$C_3H_7$ | H | H | 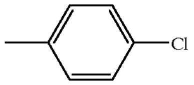 |
| Cl | H | $CH_3$ | 0 | $CH_2OCH_3$ | H | H | $CH_3$ |
| Cl | H | $CH_3$ | 0 | $CH_2OCH_3$ | H | H | $C_6H_5$ |
| Cl | H | $CH_3$ | 0 | $CH_2OC_2H_5$ | H | H | $CH_3$ |
| Cl | H | $CH_3$ | 0 | $CH_2OC_2H_5$ | H | H | $C_2H_5$ |
| Cl | H | $CH_3$ | 0 | $CH_2SCH_3$ | H | H | $CH_3$ |
| Cl | H | $CH_3$ | 0 | $CH_2SCH_3$ | H | H | $C_6H_5$ |

TABLE 2-continued

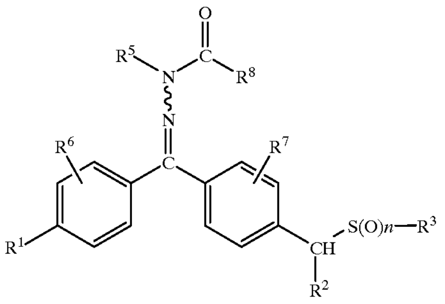

| $R^1$ | $R^2$ | $R^3$ | n | $R^5$ | $R^6$ | $R^7$ | $R^8$ |
|---|---|---|---|---|---|---|---|
| Cl | H | $CH_3$ | 0 | $COCH_3$ | H | H | $CH_3$ |
| Cl | H | $CH_3$ | 0 | $COC_2H_5$ | H | H | $CH_3$ |
| Cl | H | $CH_3$ | 0 | $COC_2H_5$ | H | H | $C_2H_5$ |
| Cl | H | $CH_3$ | 1 | H | H | H | $CH_3$ |
| Cl | H | $CH_3$ | 1 | H | H | H | $C_2H_5$ |
| Cl | H | $CH_3$ | 1 | H | H | H | n-$C_3H_7$ |
| Cl | H | $CH_3$ | 1 | H | H | H | iso-$C_3H_7$ |
| Cl | H | $CH_3$ | 1 | H | H | H | n-$C_4H_9$ |
| Cl | H | $CH_3$ | 1 | H | H | H | iso-$C_4H_9$ |
| Cl | H | $CH_3$ | 1 | H | H | H | tert-$C_4H_9$ |
| Cl | H | $CH_3$ | 1 | H | H | H | $(CH_2)_3Cl$ |
| Cl | H | $CH_3$ | 1 | H | H | H | $CH_2CN$ |
| Cl | H | $CH_3$ | 1 | H | H | H | $CH_2OCH_3$ |
| Cl | H | $CH_3$ | 1 | H | H | H | $CH_2CO_2C_2H_5$ |
| Cl | H | $CH_3$ | 1 | H | H | H | 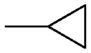 |
| Cl | H | $CH_3$ | 1 | H | H | H | 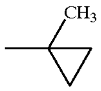 |
| Cl | H | $CH_3$ | 1 | H | H | H | $C_6H_5$ |
| Cl | H | $CH_3$ | 1 | H | H | H | 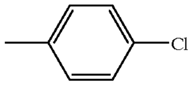 |
| Cl | H | $CH_3$ | 1 | H | 2-Cl | H | $C_2H_5$ |
| Cl | H | $CH_3$ | 1 | H | 3-Cl | H | $CH_3$ |
| Cl | H | $CH_3$ | 1 | $CH_3$ | H | H | $CH_3$ |
| Cl | H | $CH_3$ | 1 | $CH_3$ | H | H | $C_2H_5$ |
| Cl | H | $CH_3$ | 1 | $CH_3$ | H | H | n-$C_3H_7$ |
| Cl | H | $CH_3$ | 1 | $CH_3$ | H | H | iso-$C_3H_7$ |
| Cl | H | $CH_3$ | 1 | $CH_3$ | H | H | n-$C_4H_9$ |
| Cl | H | $CH_3$ | 1 | $CH_3$ | H | H | iso-$C_4H_9$ |
| Cl | H | $CH_3$ | 1 | $CH_3$ | H | H | sec-$C_4H_9$ |
| Cl | H | $CH_3$ | 1 | $CH_3$ | H | H | tert-$C_4H_9$ |
| Cl | H | $CH_3$ | 1 | $CH_3$ | H | H | $(CH_2)_3Cl$ |
| Cl | H | $CH_3$ | 1 | $CH_3$ | H | H | $(CH_2)_4Cl$ |
| Cl | H | $CH_3$ | 1 | $CH_3$ | H | H | $CH_2CN$ |
| Cl | H | $CH_3$ | 1 | $CH_3$ | H | H | $CH_2CO_2C_2H_5$ |
| Cl | H | $CH_3$ | 1 | $CH_3$ | H | H | $CH_2OCH_3$ |
| Cl | H | $CH_3$ | 1 | $CH_3$ | H | H | $C_6H_5$ |
| Cl | H | $CH_3$ | 1 | $CH_3$ | H | H | 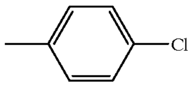 |
| Cl | H | $CH_3$ | 1 | $C_2H_5$ | H | H | $CH_3$ |
| Cl | H | $CH_3$ | 1 | $C_2H_5$ | H | H | $C_2H_5$ |
| Cl | H | $CH_3$ | 1 | $C_2H_5$ | H | H | n-$C_3H_7$ |
| Cl | H | $CH_3$ | 1 | $C_2H_5$ | H | H | iso-$C_3H_7$ |
| Cl | H | $CH_3$ | 1 | $C_2H_5$ | H | H | n-$C_4H_9$ |
| Cl | H | $CH_3$ | 1 | $C_2H_5$ | H | H | iso-$C_4H_9$ |
| Cl | H | $CH_3$ | 1 | $C_2H_5$ | H | H | sec-$C_4H_9$ |

TABLE 2-continued

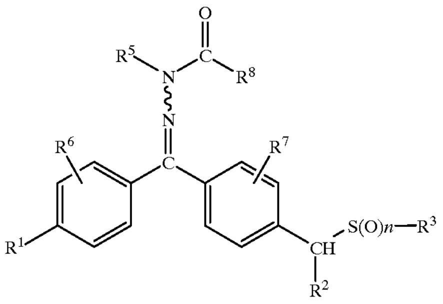

| $R^1$ | $R^2$ | $R^3$ | n | $R^5$ | $R^6$ | $R^7$ | $R^8$ |
|---|---|---|---|---|---|---|---|
| Cl | H | $CH_3$ | 1 | $C_2H_5$ | H | H | tert-$C_4H_9$ |
| Cl | H | $CH_3$ | 1 | $C_2H_5$ | H | H | $(CH_2)_3Cl$ |
| Cl | H | $CH_3$ | 1 | $C_2H_5$ | H | H | $(CH_2)_4Cl$ |
| Cl | H | $CH_3$ | 1 | $C_2H_5$ | H | H | $CH_2CN$ |
| Cl | H | $CH_3$ | 1 | $C_2H_5$ | H | H | $CH_2CO_2C_2H_5$ |
| Cl | H | $CH_3$ | 1 | $C_2H_5$ | H | H | $CH_2OCH_3$ |
| Cl | H | $CH_3$ | 1 | $C_2H_5$ | H | H | $C_6H_5$ |
| Cl | H | $CH_3$ | 1 | $C_2H_5$ | H | H | 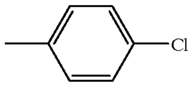 |
| Cl | H | $CH_3$ | 1 | n-$C_3H_7$ | H | H | $CH_3$ |
| Cl | H | $CH_3$ | 1 | n-$C_3H_7$ | H | H | $C_2H_5$ |
| Cl | H | $CH_3$ | 1 | n-$C_3H_7$ | H | H | n-$C_3H_7$ |
| Cl | H | $CH_3$ | 1 | n-$C_3H_7$ | H | H | iso-$C_3H_7$ |
| Cl | H | $CH_3$ | 1 | n-$C_3H_7$ | H | H | n-$C_4H_9$ |
| Cl | H | $CH_3$ | 1 | n-$C_3H_7$ | H | H | iso-$C_4H_9$ |
| Cl | H | $CH_3$ | 1 | n-$C_3H_7$ | H | H | sec-$C_4H_9$ |
| Cl | H | $CH_3$ | 1 | n-$C_3H_7$ | H | H | tert-$C_4H_9$ |
| Cl | H | $CH_3$ | 1 | n-$C_3H_7$ | H | H | $(CH_2)_3Cl$ |
| Cl | H | $CH_3$ | 1 | n-$C_3H_7$ | H | H | $(CH_2)ACl$ |
| Cl | H | $CH_3$ | 1 | n-$C_3H_7$ | H | H | $CH_2CN$ |
| Cl | H | $CH_3$ | 1 | n-$C_3H_7$ | H | H | $CH_2CO_2C_2H_5$ |
| Cl | H | $CH_3$ | 1 | n-$C_3H_7$ | H | H | $CH_2OCH_3$ |
| Cl | H | $CH_3$ | 1 | n-$C_3H_7$ | H | H | $C_6H_5$ |
| Cl | H | $CH_3$ | 1 | n-$C_3H_7$ | H | H | 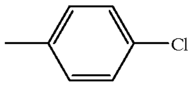 |
| Cl | H | $CH_3$ | 1 | iso-$C_3H_7$ | H | H | $CH_3$ |
| Cl | H | $CH_3$ | 1 | iso-$C_3H_7$ | H | H | $C_2H_5$ |
| Cl | H | $CH_3$ | 1 | iso-$C_3H_7$ | H | H | n-$C_3H_7$ |
| Cl | H | $CH_3$ | 1 | iso-$C_3H_7$ | H | H | iso-$C_3H_7$ |
| Cl | H | $CH_3$ | 1 | iso-$C_3H_7$ | H | H | n-$C_4H_9$ |
| Cl | H | $CH_3$ | 1 | iso-$C_3H_7$ | H | H | iso-$C_4H_9$ |
| Cl | H | $CH_3$ | 1 | iso-$C_3H_7$ | H | H | sec-$C_4H_9$ |
| Cl | H | $CH_3$ | 1 | iso-$C_3H_7$ | H | H | tert-$C_4H_9$ |
| Cl | H | $CH_3$ | 1 | iso-$C_3H_7$ | H | H | $(CH_2)_3Cl$ |
| Cl | H | $CH_3$ | 1 | iso-$C_3H_7$ | H | H | $(CH_2)_4Cl$ |
| Cl | H | $CH_3$ | 1 | iso-$C_3H_7$ | H | H | $CH_2CN$ |
| Cl | H | $CH_3$ | 1 | iso-$C_3H_7$ | H | H | $CH_2CO_2C_2H_5$ |
| Cl | H | $CH_3$ | 1 | iso-$C_3H_7$ | H | H | $CH_2OCH_3$ |
| Cl | H | $CH_3$ | 1 | iso-$C_3H_7$ | H | H | $C_6H_5$ |
| Cl | H | $CH_3$ | 1 | iso-$C_3H_7$ | H | H | 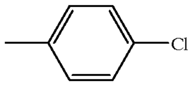 |
| Cl | H | $CH_3$ | 2 | H | H | H | $CH_3$ |
| Cl | H | $CH_3$ | 2 | H | H | H | $C_2H_5$ |
| Cl | H | $CH_3$ | 2 | H | H | H | n-$C_3H_7$ |
| Cl | H | $CH_3$ | 2 | H | H | H | iso-$C_3H_7$ |
| Cl | H | $CH_3$ | 2 | H | H | H | n-$C_4H_9$ |
| Cl | H | $CH_3$ | 2 | H | H | H | iso-$C_4H_9$ |
| Cl | H | $CH_3$ | 2 | H | H | H | tert-$C_4H_9$ |

TABLE 2-continued

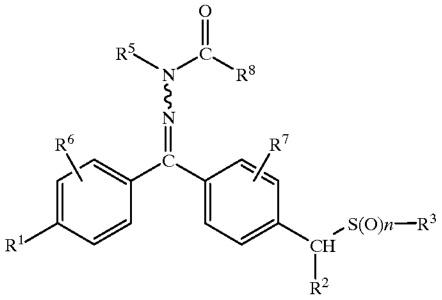

| $R^1$ | $R^2$ | $R^3$ | n | $R^5$ | $R^6$ | $R^7$ | $R^8$ |
|---|---|---|---|---|---|---|---|
| Cl | H | $CH_3$ | 2 | H | H | H | $(CH_2)_3Cl$ |
| Cl | H | $CH_3$ | 2 | H | H | H | $CH_2CN$ |
| Cl | H | $CH_3$ | 2 | H | H | H | $CH_2OCH_3$ |
| Cl | H | $CH_3$ | 2 | H | H | H | $CH_2CO_2C_2H_5$ |
| Cl | H | $CH_3$ | 2 | H | H | H | 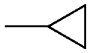 |
| Cl | H | $CH_3$ | 2 | H | H | H | 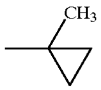 |
| Cl | H | $CH_3$ | 2 | H | H | H | $C_6H_5$ |
| Cl | H | $CH_3$ | 2 | H | H | H | 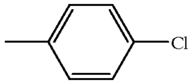 |
| Cl | H | $CH_3$ | 2 | H | 2-Cl | H | $C_2H_5$ |
| Cl | H | $CH_3$ | 2 | H | 3-Cl | H | $C_2H_5$ |
| Cl | H | $CH_3$ | 2 | $CH_3$ | H | H | $CH_3$ |
| Cl | H | $CH_3$ | 2 | $CH_3$ | H | H | $C_2H_5$ |
| Cl | H | $CH_3$ | 2 | $CH_3$ | H | H | n-$C_3H_7$ |
| Cl | H | $CH_3$ | 2 | $CH_3$ | H | H | iso-$C_3H_7$ |
| Cl | H | $CH_3$ | 2 | $CH_3$ | H | H | n-$C_4H_9$ |
| Cl | H | $CH_3$ | 2 | $CH_3$ | H | H | iso-$C_4H_9$ |
| Cl | H | $CH_3$ | 2 | $CH_3$ | H | H | sec-$C_4H_9$ |
| Cl | H | $CH_3$ | 2 | $CH_3$ | H | H | tert-$C_4H_9$ |
| Cl | H | $CH_3$ | 2 | $CH_3$ | H | H | $(CH_2)_3Cl$ |
| Cl | H | $CH_3$ | 2 | $CH_3$ | H | H | $(CH_2)_4Cl$ |
| Cl | H | $CH_3$ | 2 | $CH_3$ | H | H | $CH_2CN$ |
| Cl | H | $CH_3$ | 2 | $CH_3$ | H | H | $CH_2CO_2C_2H_5$ |
| Cl | H | $CH_3$ | 2 | $CH_3$ | H | H | $CH_2OCH_3$ |
| Cl | H | $CH_3$ | 2 | $CH_3$ | H | H | $C_6H_5$ |
| Cl | H | $CH_3$ | 2 | $CH_3$ | H | H | 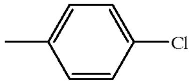 |
| Cl | H | $CH_3$ | 2 | $C_2H_5$ | H | H | $CH_3$ |
| Cl | H | $CH_3$ | 2 | $C_2H_5$ | H | H | $C_2H_5$ |
| Cl | H | $CH_3$ | 2 | $C_2H_5$ | H | H | n-$C_3H_7$ |
| Cl | H | $CH_3$ | 2 | $C_2H_5$ | H | H | iso-$C_3H_7$ |
| Cl | H | $CH_3$ | 2 | $C_2H_5$ | H | H | n-$C_2H_5$ |
| Cl | H | $CH_3$ | 2 | $C_2H_5$ | H | H | iso-$C_4H_9$ |
| Cl | H | $CH_3$ | 2 | $C_2H_5$ | H | H | sec-$C_4H_9$ |
| Cl | H | $CH_3$ | 2 | $C_2H_5$ | H | H | tert-$C_4H_9$ |
| Cl | H | $CH_3$ | 2 | $C_2H_5$ | H | H | $(CH_2)_3Cl$ |
| Cl | H | $CH_3$ | 2 | $C_2H_5$ | H | H | $(CH_2)_4Cl$ |
| Cl | H | $CH_3$ | 2 | $C_2H_5$ | H | H | $CH_2CN$ |
| Cl | H | $CH_3$ | 2 | $C_2H_5$ | H | H | $CH_2CO_2C_2H_5$ |
| Cl | H | $CH_3$ | 2 | $C_2H_5$ | H | H | $CH_2OCH_3$ |
| Cl | H | $CH_3$ | 2 | $C_2H_5$ | H | H | $C_6H_5$ |

TABLE 2-continued

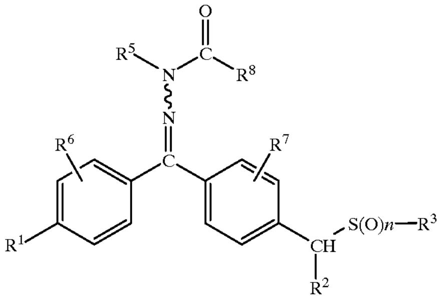

| $R^1$ | $R^2$ | $R^3$ | n | $R^5$ | $R^6$ | $R^7$ | $R^8$ |
|---|---|---|---|---|---|---|---|
| Cl | H | $CH_3$ | 2 | $C_2H_5$ | H | H | 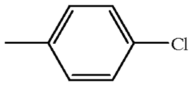 |
| Cl | H | $CH_3$ | 2 | n-$C_3H_7$ | H | H | $CH_3$ |
| Cl | H | $CH_3$ | 2 | n-$C_3H_7$ | H | H | $C_2H_5$ |
| Cl | H | $CH_3$ | 2 | n-$C_3H_7$ | H | H | n-$C_3H_7$ |
| Cl | H | $CH_3$ | 2 | n-$C_3H_7$ | H | H | iso-$C_3H_7$ |
| Cl | H | $CH_3$ | 2 | n-$C_3H_7$ | H | H | n-$C_4H_9$ |
| Cl | H | $CH_3$ | 2 | n-$C_3H_7$ | H | H | iso-$C_4H_9$ |
| Cl | H | $CH_3$ | 2 | n-$C_3H_7$ | H | H | sec-$C_4H_9$ |
| Cl | H | $CH_3$ | 2 | n-$C_3H_7$ | H | H | tert-$C_4H_9$ |
| Cl | H | $CH_3$ | 2 | n-$C_3H_7$ | H | H | $(CH_2)_3Cl$ |
| Cl | H | $CH_3$ | 2 | n-$C_3H_7$ | H | H | $(CH_2)_4Cl$ |
| Cl | H | $CH_3$ | 2 | n-$C_3H_7$ | H | H | $CH_2CN$ |
| Cl | H | $CH_3$ | 2 | n-$C_3H_7$ | H | H | $CH_2CO_2C_2H_5$ |
| Cl | H | $CH_3$ | 2 | n-$C_3H_7$ | H | H | $CH_2OCH_3$ |
| Cl | H | $CH_3$ | 2 | n-$C_3H_7$ | H | H | $C_6H_5$ |
| Cl | H | $CH_3$ | 2 | n-$C_3H_7$ | H | H | 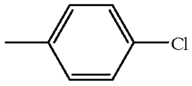 |
| Cl | H | $CH_3$ | 2 | iso-$C_3H_7$ | H | H | $CH_3$ |
| Cl | H | $CH_3$ | 2 | iso-$C_3H_7$ | H | H | $C_2H_5$ |
| Cl | H | $CH_3$ | 2 | iso-$C_3H_7$ | H | H | n-$C_3H_7$ |
| Cl | H | $CH_3$ | 2 | iso-$C_3H_7$ | H | H | iso-$C_3H_7$ |
| Cl | H | $CH_3$ | 2 | iso-$C_3H_7$ | H | H | n-$C_4H_9$ |
| Cl | H | $CH_3$ | 2 | iso-$C_3H_7$ | H | H | iso-$C_4H_9$ |
| Cl | H | $CH_3$ | 2 | iso-$C_3H_7$ | H | H | sec-$C_4H_9$ |
| Cl | H | $CH_3$ | 2 | iso-$C_3H_7$ | H | H | tert-$C_4H_9$ |
| Cl | H | $CH_3$ | 2 | iso-$C_3H_7$ | H | H | $C_6H_5$ |
| Cl | H | $CH_3$ | 2 | iso-$C_3H_7$ | H | H | 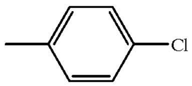 |
| Cl | H | $CH_3$ | 2 | iso-$C_3H_7$ | H | H | $(CH_2)_3Cl$ |
| Cl | H | $CH_3$ | 2 | iso-$C_3H_7$ | H | H | $(CH_2)_4Cl$ |
| Cl | H | $CH_3$ | 2 | iso-$C_3H_7$ | H | H | $CH_2CN$ |
| Cl | H | $CH_3$ | 2 | iso-$C_3H_7$ | H | H | $CH_2CO_2C_2H_5$ |
| Cl | H | $CH_3$ | 2 | iso-$C_3H_7$ | H | H | $CH_2OCH_3$ |
| Cl | H | $C_2H_5$ | 0 | H | H | H | $CH_3$ |
| Cl | H | $C_2H_5$ | 0 | H | H | H | $C_2H_5$ |
| Cl | H | $C_2H_5$ | 0 | H | H | H | n-$C_3H_7$ |
| Cl | H | $C_2H_5$ | 0 | H | H | H | iso-$C_3H_7$ |
| Cl | H | $C_2H_5$ | 0 | H | H | H | n-$C_4H_9$ |
| Cl | H | $C_2H_5$ | 0 | H | H | H | iso-$C_4H_9$ |
| Cl | H | $C_2H_5$ | 0 | H | H | H | sec-$C_4H_9$ |
| Cl | H | $C_2H_5$ | 0 | H | H | H | tert-$C_4H_9$ |
| Cl | H | $C_2H_5$ | 0 | H | H | H | n-$C_5H_{11}$ |
| Cl | H | $C_2H_5$ | 0 | H | H | H | n-$C_6H_{13}$ |
| Cl | H | $C_2H_5$ | 0 | H | H | H | $C_6H_5$ |

TABLE 2-continued

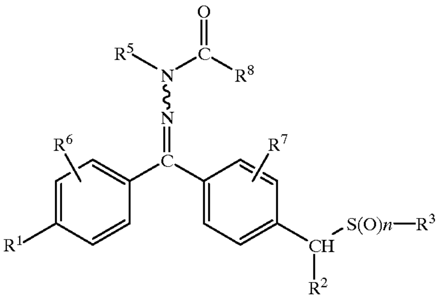

| $R^1$ | $R^2$ | $R^3$ | n | $R^5$ | $R^6$ | $R^7$ | $R^8$ |
|---|---|---|---|---|---|---|---|
| Cl | H | $C_2H_5$ | 0 | H | H | H | 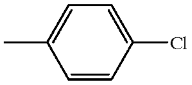 |
| Cl | H | $C_2H_5$ | 0 | H | H | H | 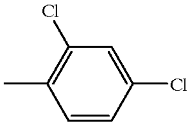 |
| Cl | H | $C_2H_5$ | 0 | H | H | H | 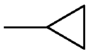 |
| Cl | H | $C_2H_5$ | 0 | H | H | H | 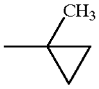 |
| Cl | H | $C_2H_5$ | 0 | H | H | H | 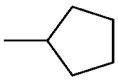 |
| Cl | H | $C_2H_5$ | 0 | H | H | H | 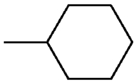 |
| Cl | H | $C_2H_5$ | 0 | H | H | H | $CH{=}CH_2$ |
| Cl | H | $C_2H_5$ | 0 | H | H | H | $CH{=}CHC_6H_5$ |
| Cl | H | $C_2H_5$ | 0 | H | H | H | $CH_2CF{=}CF_2$ |
| Cl | H | $C_2H_5$ | 0 | H | H | H | $(CH_2)_4Cl$ |
| Cl | H | $C_2H_5$ | 0 | H | H | H | $(CH_2)_3Cl$ |
| Cl | H | $C_2H_5$ | 0 | H | H | H | $CH_2CN$ |
| Cl | H | $C_2H_5$ | 0 | H | H | H | $CH_2OCH_3$ |
| Cl | H | $C_2H_5$ | 0 | H | H | H | $CH_2CO_2C_2H_5$ |
| Cl | H | $C_2H_5$ | 0 | $CH_3$ | H | H | $CH_3$ |
| Cl | H | $C_2H_5$ | 0 | $CH_3$ | H | H | $CH_3$ |
| Cl | H | $C_2H_5$ | 0 | $CH_3$ | H | H | $C_2H_5$ |
| Cl | H | $C_2H_5$ | 0 | $CH_3$ | H | H | n-$C_3H_7$ |
| Cl | H | $C_2H_5$ | 0 | $CH_3$ | H | H | iso-$C_3H_7$ |
| Cl | H | $C_2H_5$ | 0 | $CH_3$ | H | H | n-$C_4H_9$ |
| Cl | H | $C_2H_5$ | 0 | $CH_3$ | H | H | iso-$C_4H_9$ |
| Cl | H | $C_2H_5$ | 0 | $CH_3$ | H | H | sec-$C_4H_9$ |
| Cl | H | $C_2H_5$ | 0 | $CH_3$ | H | H | tert-$C_4H_9$ |
| Cl | H | $C_2H_5$ | 0 | $CH_3$ | H | H | $(CH_2)_3Cl$ |
| Cl | H | $C_2H_5$ | 0 | $CH_3$ | H | H | $(CH_2)_4Cl$ |
| Cl | H | $C_2H_5$ | 0 | $CH_3$ | H | H | $CH_2CN$ |
| Cl | H | $C_2H_5$ | 0 | $CH_3$ | H | H | $CH_2OCH_3$ |
| Cl | H | $C_2H_5$ | 0 | $CH_3$ | H | H | $CH_2CO_2C_2H_5$ |
| Cl | H | $C_2H_5$ | 0 | $CH_3$ | H | H | $C_6H_5$ |

TABLE 2-continued

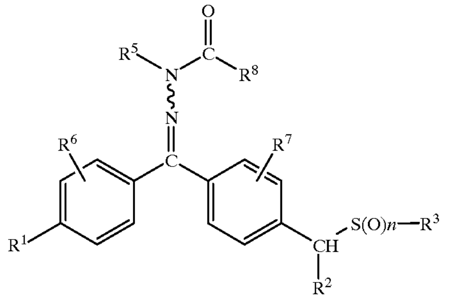

| $R^1$ | $R^2$ | $R^3$ | n | $R^5$ | $R^6$ | $R^7$ | $R^8$ |
|---|---|---|---|---|---|---|---|
| Cl | H | $C_2H_5$ | 0 | $CH_3$ | H | H | 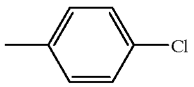 |
| Cl | H | $C_2H_5$ | 0 | $C_2H_5$ | H | H | $CH_3$ |
| Cl | H | $C_2H_5$ | 0 | $C_2H_5$ | H | H | $C_2H_5$ |
| Cl | H | $C_2H_5$ | 0 | $C_2H_5$ | H | H | n-$C_3H_7$ |
| Cl | H | $C_2H_5$ | 0 | $C_2H_5$ | H | H | iso-$C_3H_7$ |
| Cl | H | $C_2H_5$ | 0 | $C_2H_5$ | H | H | n-$C_4H_9$ |
| Cl | H | $C_2H_5$ | 0 | $C_2H_5$ | H | H | iso-$C_4H_9$ |
| Cl | H | $C_2H_5$ | 0 | $C_2H_5$ | H | H | sec-$C_4H_9$ |
| Cl | H | $C_2H_5$ | 0 | $C_2H_5$ | H | H | tert-$C_4H_9$ |
| Cl | H | $C_2H_5$ | 0 | $C_2H_5$ | H | H | $(CH_2)_3Cl$ |
| Cl | H | $C_2H_5$ | 0 | $C_2H_5$ | H | H | $(CH_2)_4Cl$ |
| Cl | H | $C_2H_5$ | 0 | $C_2H_5$ | H | H | $CH_2CN$ |
| Cl | H | $C_2H_5$ | 0 | $C_2H_5$ | H | H | $CH_2OCH_3$ |
| Cl | H | $C_2H_5$ | 0 | $C_2H_5$ | H | H | $CH_2CO_2C_2H_5$ |
| Cl | H | $C_2H_5$ | 0 | $C_2H_5$ | H | H | $C_6H_5$ |
| Cl | H | $C_2H_5$ | 0 | $C_2H_5$ | H | H | 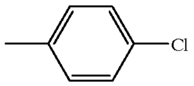 |
| Cl | H | $C_2H_5$ | 0 | n-$C_3H_7$ | H | H | $CH_3$ |
| Cl | H | $C_2H_5$ | 0 | n-$C_3H_7$ | H | H | $C_2H_5$ |
| Cl | H | $C_2H_5$ | 0 | n-$C_3H_7$ | H | H | n-$C_3H_7$ |
| Cl | H | $C_2H_5$ | 0 | n-$C_3H_7$ | H | H | iso-$C_3H_7$ |
| Cl | H | $C_2H_5$ | 0 | n-$C_3H_7$ | H | H | n-$C_4H_9$ |
| Cl | H | $C_2H_5$ | 0 | n-$C_3H_7$ | H | H | iso-$C_4H_9$ |
| Cl | H | $C_2H_5$ | 0 | n-$C_3H_7$ | H | H | sec-$C_4H_9$ |
| Cl | H | $C_2H_5$ | 0 | n-$C_3H_7$ | H | H | tert-$C_4H_9$ |
| Cl | H | $C_2H_5$ | 0 | n-$C_3H_7$ | H | H | $(CH_2)_3Cl$ |
| Cl | H | $C_2H_5$ | 0 | n-$C_3H_7$ | H | H | $(CH_2)_4Cl$ |
| Cl | H | $C_2H_5$ | 0 | n-$C_3H_7$ | H | H | $CH_2CN$ |
| Cl | H | $C_2H_5$ | 0 | n-$C_3H_7$ | H | H | $CH_2CO_2C_2H_5$ |
| Cl | H | $C_2H_5$ | 0 | n-$C_3H_7$ | H | H | $CH_2OCH_3$ |
| Cl | H | $C_2H_5$ | 0 | n-$C_3H_7$ | H | H | $C_6H_5$ |
| Cl | H | $C_2H_5$ | 0 | n-$C_3H_7$ | H | H | 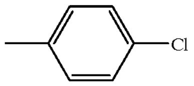 |
| Cl | H | $C_2H_5$ | 0 | iso-$C_3H_7$ | H | H | $CH_3$ |
| Cl | H | $C_2H_5$ | 0 | iso-$C_3H_7$ | H | H | $C_2H_5$ |
| Cl | H | $C_2H_5$ | 0 | iso-$C_3H_7$ | H | H | n-$C_3H_7$ |
| Cl | H | $C_2H_5$ | 0 | iso-$C_3H_7$ | H | H | iso-$C_3H_7$ |
| Cl | H | $C_2H_5$ | 0 | iso-$C_3H_7$ | H | H | n-$C_4H_9$ |
| Cl | H | $C_2H_5$ | 0 | iso-$C_3H_7$ | H | H | iso-$C_4H_9$ |
| Cl | H | $C_2H_5$ | 0 | iso-$C_3H_7$ | H | H | sec-$C_4H_9$ |
| Cl | H | $C_2H_5$ | 0 | $CH_3$ | H | H | $CH_2CN$ |
| Cl | H | $C_2H_5$ | 0 | $CH_3$ | H | H | $CH_2CH_3$ |
| Cl | H | $C_2H_5$ | 0 | iso-$C_3H_7$ | H | H | tert-$C_4H_9$ |
| Cl | H | $C_2H_5$ | 0 | iso-$C_3H_7$ | H | H | $(CH_2)_3Cl$ |
| Cl | H | $C_2H_5$ | 0 | iso-$C_3H_7$ | H | H | $(CH_2)_4Cl$ |
| Cl | H | $C_2H_5$ | 0 | iso-$C_3H_7$ | H | H | $CH_2CN$ |
| Cl | H | $C_2H_5$ | 0 | iso-$C_3H_7$ | H | H | $CH_2OCH_3$ |
| Cl | H | $C_2H_5$ | 0 | iso-$C_3H_7$ | H | H | $CH_2CO_2C_2H_5$ |

TABLE 2-continued

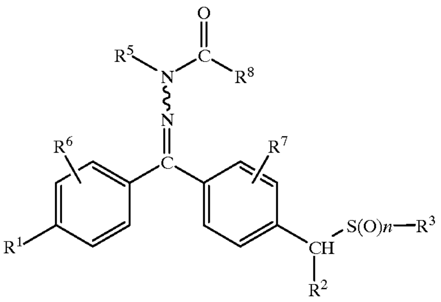

| $R^1$ | $R^2$ | $R^3$ | n | $R^5$ | $R^6$ | $R^7$ | $R^8$ |
|---|---|---|---|---|---|---|---|
| Cl | H | $C_2H_5$ | 0 | iso-$C_3H_7$ | H | H | $C_6H_5$ |
| Cl | H | $C_2H_5$ | 0 | iso-$C_3H_7$ | H | H | 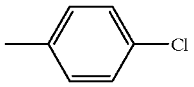 |
| Cl | H | $C_2H_5$ | 0 | $CH_2OCH_3$ | H | H | $CH_3$ |
| Cl | H | $C_2H_5$ | 0 | $CH_2SCH_3$ | H | H | $CH_3$ |
| Cl | H | $C_2H_5$ | 0 | $COC_2H_5$ | H | H | $CH_3$ |
| Cl | H | $C_2H_5$ | 0 | $COC_2H_5$ | H | H | $C_2H_5$ |
| Cl | H | $C_2H_5$ | 0 | $COC_3H_7$-n | H | H | $CH_3$ |
| Cl | H | $C_2H_5$ | 1 | H | H | H | $CH_3$ |
| Cl | H | $C_2H_5$ | 1 | H | H | H | $C_2H_5$ |
| Cl | H | $C_2H_5$ | 1 | H | H | H | n-$C_3H_7$ |
| Cl | H | $C_2H_5$ | 1 | H | H | H | iso-$C_3H_7$ |
| Cl | H | $C_2H_5$ | 1 | H | H | H | n-$C_4H_9$ |
| Cl | H | $C_2H_5$ | 1 | H | H | H | iso-$C_4H_9$ |
| Cl | H | $C_2H_5$ | 1 | H | H | H | tert-$C_4H_9$ |
| Cl | H | $C_2H_5$ | 1 | H | H | H | $(CH_2)_3Cl$ |
| Cl | H | $C_2H_5$ | 1 | H | H | H | $CH_2CN$ |
| Cl | H | $C_2H_5$ | 1 | H | H | H | $CH_2OCH_3$ |
| Cl | H | $C_2H_5$ | 1 | H | H | H | $CH_2CO_2C_2H_5$ |
| Cl | H | $C_2H_5$ | 1 | H | H | H | 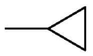 |
| Cl | H | $C_2H_5$ | 1 | H | H | H | 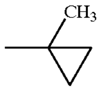 |
| Cl | H | $C_2H_5$ | 1 | H | H | H | $C_6H_5$ |
| Cl | H | $C_2H_5$ | 1 | H | H | H | 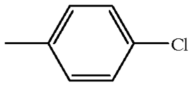 |
| Cl | H | $C_2H_5$ | 1 | $CH_3$ | H | H | $CH_3$ |
| Cl | H | $C_2H_5$ | 1 | $CH_3$ | H | H | $C_2H_5$ |
| Cl | H | $C_2H_5$ | 1 | $CH_3$ | H | H | n-$C_3H_7$ |
| Cl | H | $C_2H_5$ | 1 | $CH_3$ | H | H | iso-$C_3H_7$ |
| Cl | H | $C_2H_5$ | 1 | $CH_3$ | H | H | n-$C_4H_9$ |
| Cl | H | $C_2H_5$ | 1 | $CH_3$ | H | H | iso-$C_4H_9$ |
| Cl | H | $C_2H_5$ | 1 | $CH_3$ | H | H | sec-$C_4H_9$ |
| Cl | H | $C_2H_5$ | 1 | $CH_3$ | H | H | tert-$C_4H_9$ |
| Cl | H | $C_2H_5$ | 1 | $CH_3$ | H | H | $(CH_2)_3Cl$ |
| Cl | H | $C_2H_5$ | 1 | $CH_3$ | H | H | $(CH_2)_4Cl$ |
| Cl | H | $C_2H_5$ | 1 | $CH_3$ | H | H | $CH_2CN$ |
| Cl | H | $C_2H_5$ | 1 | $CH_3$ | H | H | $CH_2CO_2C_2H_5$ |
| Cl | H | $C_2H_5$ | 1 | $CH_3$ | H | H | $CH_2OCH_3$ |
| Cl | H | $C_2H_5$ | 1 | $CH_3$ | H | H | $C_6H_5$ |
| Cl | H | $C_2H_5$ | 1 | $CH_3$ | H | H | 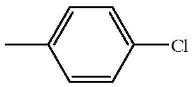 |

TABLE 2-continued

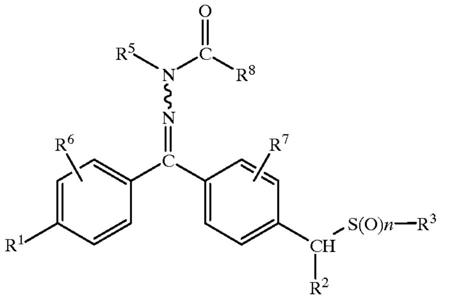

| $R^1$ | $R^2$ | $R^3$ | n | $R^5$ | $R^6$ | $R^7$ | $R^8$ |
|---|---|---|---|---|---|---|---|
| Cl | H | $C_2H_5$ | 1 | $C_2H_5$ | H | H | $CH_3$ |
| Cl | H | $C_2H_5$ | 1 | $C_2H_5$ | H | H | $C_2H_5$ |
| Cl | H | $C_2H_5$ | 1 | $C_2H_5$ | H | H | n-$C_3H_7$ |
| Cl | H | $C_2H_5$ | 1 | $C_2H_5$ | H | H | iso-$C_3H_7$ |
| Cl | H | $C_2H_5$ | 1 | $C_2H_5$ | H | H | n-$C_4H_9$ |
| Cl | H | $C_2H_5$ | 1 | $C_2H_5$ | H | H | iso-$C_4H_9$ |
| Cl | H | $C_2H_5$ | 1 | $C_2H_5$ | H | H | sec-$C_4H_9$ |
| Cl | H | $C_2H_5$ | 1 | $C_2H_5$ | H | H | tert-$C_4H_9$ |
| Cl | H | $C_2H_5$ | 1 | $C_2H_5$ | H | H | $(CH_2)_3Cl$ |
| Cl | H | $C_2H_5$ | 1 | $C_2H_5$ | H | H | $(CH_2)_4Cl$ |
| Cl | H | $C_2H_5$ | 1 | $C_2H_5$ | H | H | $CH_2CN$ |
| Cl | H | $C_2H_5$ | 1 | $C_2H_5$ | H | H | $CH_2OCH_3$ |
| Cl | H | $C_2H_5$ | 1 | $C_2H_5$ | H | H | $CH_2CO_2C_2H_5$ |
| Cl | H | $C_2H_5$ | 1 | $C_2H_5$ | H | H | $C_6H_5$ |
| Cl | H | $C_2H_5$ | 1 | $C_2H_5$ | H | H | 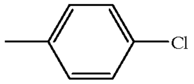 |
| Cl | H | $C_2H_5$ | 1 | n-$C_3H_7$ | H | H | $CH_3$ |
| Cl | H | $C_2H_5$ | 1 | n-$C_3H_7$ | H | H | $C_2H_5$ |
| Cl | H | $C_2H_5$ | 1 | n-$C_3H_7$ | H | H | n-$C_3H_7$ |
| Cl | H | $C_2H_5$ | 1 | n-$C_3H_7$ | H | H | iso-$C_3H_7$ |
| Cl | H | $C_2H_5$ | 1 | n-$C_3H_7$ | H | H | n-$C_4H_9$ |
| Cl | H | $C_2H_5$ | 1 | n-$C_3H_7$ | H | H | iso-$C_4H_9$ |
| Cl | H | $C_2H_5$ | 1 | n-$C_3H_7$ | H | H | sec-$C_4H_9$ |
| Cl | H | $C_2H_5$ | 1 | n-$C_3H_7$ | H | H | tert-$C_4H_9$ |
| Cl | H | $C_2H_5$ | 1 | n-$C_3H_7$ | H | H | $(CH_2)_3Cl$ |
| Cl | H | $C_2H_5$ | 1 | n-$C_3H_7$ | H | H | $(CH_2)_4Cl$ |
| Cl | H | $C_2H_5$ | 1 | n-$C_3H_7$ | H | H | $CH_2CN$ |
| Cl | H | $C_2H_5$ | 1 | n-$C_3H_7$ | H | H | $CH_2CO_2C_2H_5$ |
| Cl | H | $C_2H_5$ | 1 | n-$C_3H_7$ | H | H | $CH_2OCH_3$ |
| Cl | H | $C_2H_5$ | 1 | n-$C_3H_7$ | H | H | $C_6H_5$ |
| Cl | H | $C_2H_5$ | 1 | n-$C_3H_7$ | H | H | 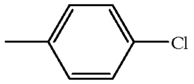 |
| Cl | H | $C_2H_5$ | 1 | iso-$C_3H_7$ | H | H | $CH_3$ |
| Cl | H | $C_2H_5$ | 1 | iso-$C_3H_7$ | H | H | $C_2H_5$ |
| Cl | H | $C_2H_5$ | 1 | iso-$C_3H_7$ | H | H | n-$C_3H_7$ |
| Cl | H | $C_2H_5$ | 1 | iso-$C_3H_7$ | H | H | iso-$C_3H_7$ |
| Cl | H | $C_2H_5$ | 1 | iso-$C_3H_7$ | H | H | n-$C_4H_9$ |
| Cl | H | $C_2H_5$ | 1 | iso-$C_3H_7$ | H | H | iso-$C_4H_9$ |
| Cl | H | $C_2H_5$ | 1 | iso-$C_3H_7$ | H | H | sec-$C_4H_9$ |
| Cl | H | $C_2H_5$ | 1 | iso-$C_3H_7$ | H | H | tert-$C_4H_9$ |
| Cl | H | $C_2H_5$ | 1 | iso-$C_3H_7$ | H | H | $(CH_2)_3Cl$ |
| Cl | H | $C_2H_5$ | 1 | iso-$C_3H_7$ | H | H | $(CH_2)_4Cl$ |
| Cl | H | $C_2H_5$ | 1 | iso-$C_3H_7$ | H | H | $CH_2CN$ |
| Cl | H | $C_2H_5$ | 1 | iso-$C_3H_7$ | H | H | $CH_2OCH_3$ |
| Cl | H | $C_2H_5$ | 1 | iso-$C_3H_7$ | H | H | $CH_2CO_2C_2H_5$ |
| Cl | H | $C_2H_5$ | 1 | iso-$C_3H_7$ | H | H | $C_6H_5$ |
| Cl | H | $C_2H_5$ | 1 | iso-$C_3H_7$ | H | H | 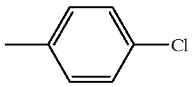 |

TABLE 2-continued

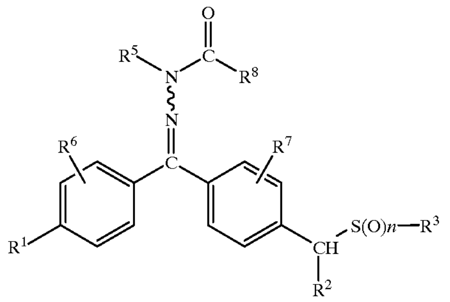

| $R^1$ | $R^2$ | $R^3$ | n | $R^5$ | $R^6$ | $R^7$ | $R^8$ |
|---|---|---|---|---|---|---|---|
| Cl | H | $C_2H_5$ | 2 | H | H | H | $CH_3$ |
| Cl | H | $C_2H_5$ | 2 | H | H | H | $C_2H_5$ |
| Cl | H | $C_2H_5$ | 2 | H | H | H | n-$C_3H_7$ |
| Cl | H | $C_2H_5$ | 2 | H | H | H | iso-$C_3H_7$ |
| Cl | H | $C_2H_5$ | 2 | H | H | H | n-$C_4H_9$ |
| Cl | H | $C_2H_5$ | 2 | H | H | H | iso-$C_4H_9$ |
| Cl | H | $C_2H_5$ | 2 | H | H | H | tert-$C_4H_9$ |
| Cl | H | $C_2H_5$ | 2 | H | H | H | $(CH_2)_3Cl$ |
| Cl | H | $C_2H_5$ | 2 | H | H | H | $CH_2CN$ |
| Cl | H | $C_2H_5$ | 2 | H | H | H | $CH_2OCH_3$ |
| Cl | H | $C_2H_5$ | 2 | H | H | H | $CH_2CO_2C_2H_5$ |
| Cl | H | $C_2H_5$ | 2 | H | H | H | 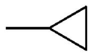 |
| Cl | H | $C_2H_5$ | 2 | H | H | H | 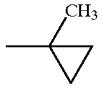 |
| Cl | H | $C_2H_5$ | 2 | H | H | H | $C_6H_5$ |
| Cl | H | $C_2H_5$ | 2 | H | H | H | 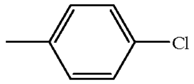 |
| Cl | H | $C_2H_5$ | 2 | $CH_3$ | H | H | $CH_3$ |
| Cl | H | $C_2H_5$ | 2 | $CH_3$ | H | H | $C_2H_5$ |
| Cl | H | $C_2H_5$ | 2 | $CH_3$ | H | H | n-$C_3H_7$ |
| Cl | H | $C_2H_5$ | 2 | $CH_3$ | H | H | iso-$C_3H_7$ |
| Cl | H | $C_2H_5$ | 2 | $CH_3$ | H | H | n-$C_4H_9$ |
| Cl | H | $C_2H_5$ | 2 | $CH_3$ | H | H | iso-$C_4H_9$ |
| Cl | H | $C_2H_5$ | 2 | $CH_3$ | H | H | sec-$C_4H_9$ |
| Cl | H | $C_2H_5$ | 2 | $CH_3$ | H | H | tert-$C_4H_9$ |
| Cl | H | $C_2H_5$ | 2 | $CH_3$ | H | H | $(CH_2)_3Cl$ |
| Cl | H | $C_2H_5$ | 2 | $CH_3$ | H | H | $(CH_2)_4Cl$ |
| Cl | H | $C_2H_5$ | 2 | $CH_3$ | H | H | $CH_2CN$ |
| Cl | H | $C_2H_5$ | 2 | $CH_3$ | H | H | $CH_2CO_2C_2H_5$ |
| Cl | H | $C_2H_5$ | 2 | $CH_3$ | H | H | $CH_2OCH_3$ |
| Cl | H | $C_2H_5$ | 2 | $CH_3$ | H | H | $C_6H_5$ |
| Cl | H | $C_2H_5$ | 2 | $CH_3$ | H | H | 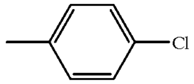 |
| Cl | H | $C_2H_5$ | 2 | $C_2H_5$ | H | H | $CH_3$ |
| Cl | H | $C_2H_5$ | 2 | $C_2H_5$ | H | H | $C_2H_5$ |
| Cl | H | $C_2H_5$ | 2 | $C_2H_5$ | H | H | n-$C_3H_7$ |
| Cl | H | $C_2H_5$ | 2 | $C_2H_5$ | H | H | iso-$C_3H_7$ |
| Cl | H | $C_2H_5$ | 2 | $C_2H_5$ | H | H | n-$C_4H_9$ |
| Cl | H | $C_2H_5$ | 2 | $C_2H_5$ | H | H | iso-$C_4H_9$ |
| Cl | H | $C_2H_5$ | 2 | $C_2H_5$ | H | H | sec-$C_4H_9$ |
| Cl | H | $C_2H_5$ | 2 | $C_2H_5$ | H | H | tert-$C_4H_9$ |
| Cl | H | $C_2H_5$ | 2 | $C_2H_5$ | H | H | $(CH_2)_3Cl$ |
| Cl | H | $C_2H_5$ | 2 | $C_2H_5$ | H | H | $(CH_2)_4Cl$ |
| Cl | H | $C_2H_5$ | 2 | $C_2H_5$ | H | H | $CH_2CN$ |

TABLE 2-continued

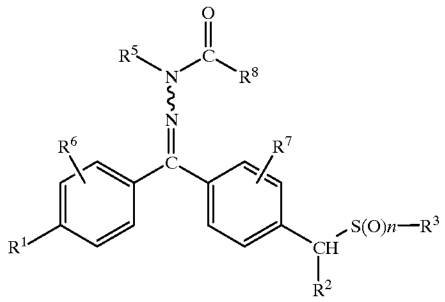

| $R^1$ | $R^2$ | $R^3$ | n | $R^5$ | $R^6$ | $R^7$ | $R^8$ |
|---|---|---|---|---|---|---|---|
| Cl | H | $C_2H_5$ | 2 | $C_2H_5$ | H | H | $CH_2CO_2C_2H_5$ |
| Cl | H | $C_2H_5$ | 2 | $C_2H_5$ | H | H | $CH_2OCH_3$ |
| Cl | H | $C_2H_5$ | 2 | $C_2H_5$ | H | H | $C_6H_5$ |
| Cl | H | $C_2H_5$ | 2 | $C_2H_5$ | H | H | 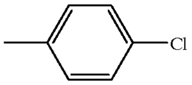 |
| Cl | H | $C_2H_5$ | 2 | n-$C_3H_7$ | H | H | $CH_3$ |
| Cl | H | $C_2H_5$ | 2 | n-$C_3H_7$ | H | H | $C_2H_5$ |
| Cl | H | $C_2H_5$ | 2 | n-$C_3H_7$ | H | H | n-$C_3H_7$ |
| Cl | H | $C_2H_5$ | 2 | n-$C_3H_7$ | H | H | iso-$C_3H_7$ |
| Cl | H | $C_2H_5$ | 2 | n-$C_3H_7$ | H | H | n-$C_4H_9$ |
| Cl | H | $C_2H_5$ | 2 | n-$C_3H_7$ | H | H | iso-$C_4H_9$ |
| Cl | H | $C_2H_5$ | 2 | n-$C_3H_7$ | H | H | sec-$C_4H_9$ |
| Cl | H | $C_2H_5$ | 2 | n-$C_3H_7$ | H | H | tert-$C_4H_9$ |
| Cl | H | $C_2H_5$ | 2 | n-$C_3H_7$ | H | H | $(CH_2)_3Cl$ |
| Cl | H | $C_2H_5$ | 2 | n-$C_3H_7$ | H | H | $(CH_2)_4Cl$ |
| Cl | H | $C_2H_5$ | 2 | n-$C_3H_7$ | H | H | $CH_2CN$ |
| Cl | H | $C_2H_5$ | 2 | n-$C_3H_7$ | H | H | $CH_2CO_2C_2H_5$ |
| Cl | H | $C_2H_5$ | 2 | n-$C_3H_7$ | H | H | $CH_2OCH_3$ |
| Cl | H | $C_2H_5$ | 2 | n-$C_3H_7$ | H | H | $C_6H_5$ |
| Cl | H | $C_2H_5$ | 2 | n-$C_3H_7$ | H | H | 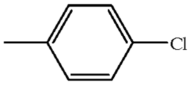 |
| Cl | H | $C_2H_5$ | 2 | iso-$C_3H_7$ | H | H | $CH_3$ |
| Cl | H | $C_2H_5$ | 2 | iso-$C_3H_7$ | H | H | $C_2H_5$ |
| Cl | H | $C_2H_5$ | 2 | iso-$C_3H_7$ | H | H | n-$C_3H_7$ |
| Cl | H | $C_2H_5$ | 2 | iso-$C_3H_7$ | H | H | iso-$C_3H_7$ |
| Cl | H | $C_2H_5$ | 2 | iso-$C_3H_7$ | H | H | n-$C_4H_9$ |
| Cl | H | $C_2H_5$ | 2 | iso-$C_3H_7$ | H | H | iso-$C_4H_9$ |
| Cl | H | $C_2H_5$ | 2 | iso-$C_3H_7$ | H | H | sec-$C_4H_9$ |
| Cl | H | $C_2H_5$ | 2 | iso-$C_3H_7$ | H | H | tert-$C_4H_9$ |
| Cl | H | $C_2H_5$ | 2 | iso-$C_3H_7$ | H | H | $(CH_2)_3Cl$ |
| Cl | H | $C_2H_5$ | 2 | iso-$C_3H_7$ | H | H | $(CH_2)_4Cl$ |
| Cl | H | $C_2H_5$ | 2 | iso-$C_3H_7$ | H | H | $CH_2CN$ |
| Cl | H | $C_2H_5$ | 2 | iso-$C_3H_7$ | H | H | $CH_2CO_2C_2H_5$ |
| Cl | H | $C_2H_5$ | 2 | iso-$C_3H_7$ | H | H | $CH_2OCH_3$ |
| Cl | H | $C_2H_5$ | 2 | iso-$C_3H_7$ | H | H | $C_6H_5$ |
| Cl | H | $C_2H_5$ | 2 | iso-$C_3H_7$ | H | H | 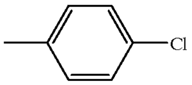 |
| Cl | H | n-$C_3H_7$ | 0 | H | H | H | $CH_3$ |
| Cl | H | n-$C_3H_7$ | 0 | H | H | H | $C_2H_5$ |
| Cl | H | n-$C_3H_7$ | 0 | H | H | H | n-$C_3H_7$ |
| Cl | H | n-$C_3H_7$ | 0 | H | H | H | iso-$C_3H_7$ |
| Cl | H | n-$C_3H_7$ | 0 | H | H | H | n-$C_4H_9$ |
| Cl | H | n-$C_3H_7$ | 0 | H | H | H | iso-$C_4H_9$ |
| Cl | H | n-$C_3H_7$ | 0 | H | H | H | tert-$C_4H_9$ |
| Cl | H | n-$C_3H_7$ | 0 | H | H | H | $(CH_2)_3Cl$ |
| Cl | H | n-$C_3H_7$ | 0 | H | H | H | $CH_2CN$ |
| Cl | H | n-$C_3H_7$ | 0 | H | H | H | $CH_2OCH_3$ |
| Cl | H | n-$C_3H_7$ | 0 | H | H | H | $CH_2CO_2C_2H_5$ |

TABLE 2-continued

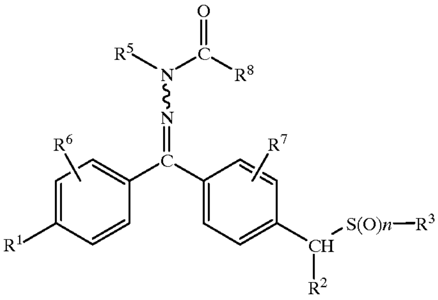

| $R^1$ | $R^2$ | $R^3$ | n | $R^5$ | $R^6$ | $R^7$ | $R^8$ |
|---|---|---|---|---|---|---|---|
| Cl | H | n-$C_3H_7$ | 0 | H | H | H | 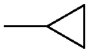 |
| Cl | H | n-$C_3H_7$ | 0 | H | H | H | 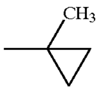 |
| Cl | H | n-$C_3H_7$ | 0 | H | H | H | $C_6H_5$ |
| Cl | H | n-$C_3H_7$ | 0 | H | H | H | 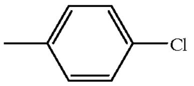 |
| Cl | H | n-$C_3H_7$ | 1 | H | H | H | $CH_3$ |
| Cl | H | n-$C_3H_7$ | 1 | H | H | H | $C_2H_5$ |
| Cl | H | n-$C_3H_7$ | 1 | H | H | H | n-$C_3H_7$ |
| Cl | H | n-$C_3H_7$ | 1 | H | H | H | iso-$C_3H_7$ |
| Cl | H | n-$C_3H_7$ | 1 | H | H | H | n-$C_4H_9$ |
| Cl | H | n-$C_3H_7$ | 1 | H | H | H | iso-$C_4H_9$ |
| Cl | H | n-$C_3H_7$ | 1 | H | H | H | tert-$C_4H_9$ |
| Cl | H | n-$C_3H_7$ | 1 | H | H | H | $(CH_2)_3Cl$ |
| Cl | H | n-$C_3H_7$ | 1 | H | H | H | $CH_2CN$ |
| Cl | H | n-$C_3H_7$ | 1 | H | H | H | $CH_2OCH_3$ |
| Cl | H | n-$C_3H_7$ | 1 | H | H | H | $CH_2CO_2C_2H_5$ |
| Cl | H | n-$C_3H_7$ | 1 | H | H | H | 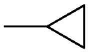 |
| Cl | H | n-$C_3H_7$ | 1 | H | H | H | 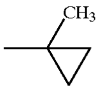 |
| Cl | H | n-$C_3H_7$ | 1 | H | H | H | $C_6H_5$ |
| Cl | H | n-$C_3H_7$ | 1 | H | H | H | 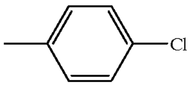 |
| Cl | H | n-$C_3H_7$ | 2 | H | H | H | $CH_3$ |
| Cl | H | n-$C_3H_7$ | 2 | H | H | H | $C_2H_5$ |
| Cl | H | n-$C_3H_7$ | 2 | H | H | H | n-$C_3H_7$ |
| Cl | H | n-$C_3H_7$ | 2 | H | H | H | iso-$C_3H_7$ |
| Cl | H | n-$C_3H_7$ | 2 | H | H | H | n-$C_4H_9$ |
| Cl | H | n-$C_3H_7$ | 2 | H | H | H | iso-$C_4H_9$ |
| Cl | H | n-$C_3H_7$ | 2 | H | H | H | tert-$C_4H_9$ |
| Cl | H | n-$C_3H_7$ | 2 | H | H | H | $(CH_2)_3Cl$ |
| Cl | H | n-$C_3H_7$ | 2 | H | H | H | $CH_2CN$ |
| Cl | H | n-$C_3H_7$ | 2 | H | H | H | $CH_2OCH_3$ |
| Cl | H | n-$C_3H_7$ | 2 | H | H | H | $CH_2CO_2C_2H_5$ |

TABLE 2-continued

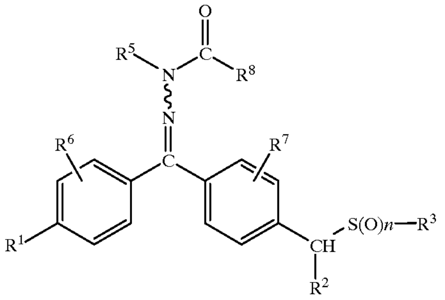

| $R^1$ | $R^2$ | $R^3$ | n | $R^5$ | $R^6$ | $R^7$ | $R^8$ |
|---|---|---|---|---|---|---|---|
| Cl | H | n-$C_3H_7$ | 2 | H | H | H | 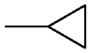 |
| Cl | H | n-$C_3H_7$ | 2 | H | H | H | 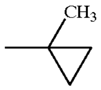 |
| Cl | H | n-$C_3H_7$ | 2 | H | H | H | $C_6H_5$ |
| Cl | H | n-$C_3H_7$ | 2 | H | H | H | 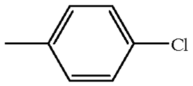 |
| Cl | H | $CH_2F$ | 0 | H | H | H | $CH_3$ |
| Cl | H | $CH_2F$ | 0 | H | H | H | $C_2H_5$ |
| Cl | H | $CH_2F$ | 0 | H | H | H | n-$C_3H_7$ |
| Cl | H | $CH_2F$ | 0 | H | H | H | iso-$C_3H_7$ |
| Cl | H | $CH_2F$ | 0 | H | H | H | n-$C_4H_9$ |
| Cl | H | $CH_2F$ | 0 | H | H | H | iso-$C_4H_9$ |
| Cl | H | $CH_2F$ | 0 | H | H | H | tert-$C_4H_9$ |
| Cl | H | $CH_2F$ | 0 | H | H | H | $(CH_2)_3Cl$ |
| Cl | H | $CH_2F$ | 0 | H | H | H | $CH_2CN$ |
| Cl | H | $CH_2F$ | 0 | H | H | H | $CH_2OCH_3$ |
| Cl | H | $CH_2F$ | 0 | H | H | H | $CH_2CO_2C_2H_5$ |
| Cl | H | $CH_2F$ | 0 | H | H | H | 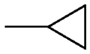 |
| Cl | H | $CH_2F$ | 0 | H | H | H | 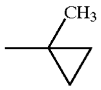 |
| Cl | H | $CH_2F$ | 0 | H | H | H | $C_6H_5$ |
| Cl | H | $CH_2F$ | 0 | H | H | H | 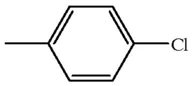 |
| Cl | H | $CH_2F$ | 1 | H | H | H | $CH_3$ |
| Cl | H | $CH_2F$ | 1 | H | H | H | $C_2H_5$ |
| Cl | H | $CH_2F$ | 1 | H | H | H | n-$C_3H_7$ |
| Cl | H | $CH_2F$ | 1 | H | H | H | iso-$C_3H_7$ |
| Cl | H | $CH_2F$ | 1 | H | H | H | n-$C_4H_9$ |
| Cl | H | $CH_2F$ | 1 | H | H | H | iso-$C_4H_9$ |
| Cl | H | $CH_2F$ | 1 | H | H | H | tert-$C_4H_9$ |
| Cl | H | $CH_2F$ | 1 | H | H | H | $(CH_2)_3Cl$ |
| Cl | H | $CH_2F$ | 1 | H | H | H | $CH_2CN$ |
| Cl | H | $CH_2F$ | 1 | H | H | H | $CH_2OCH_3$ |
| Cl | H | $CH_2F$ | 1 | H | H | H | $CH_2CO_2C_2H_5$ |
| Cl | H | $CH_2F$ | 1 | H | H | H | 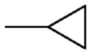 |

TABLE 2-continued

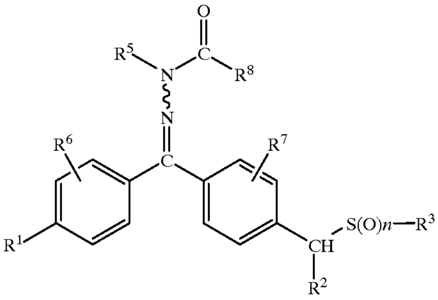

| $R^1$ | $R^2$ | $R^3$ | n | $R^5$ | $R^6$ | $R^7$ | $R^8$ |
|---|---|---|---|---|---|---|---|
| Cl | H | $CH_2F$ | 1 | H | H | H | 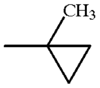 |
| Cl | H | $CH_2F$ | 1 | H | H | H | $C_6H_5$ |
| Cl | H | $CH_2F$ | 1 | H | H | H | 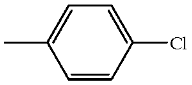 |
| Cl | H | $CH_2F$ | 2 | H | H | H | $CH_3$ |
| Cl | H | $CH_2F$ | 2 | H | H | H | $C_2H_5$ |
| Cl | H | $CH_2F$ | 2 | H | H | H | n-$C_3H_7$ |
| Cl | H | $CH_2F$ | 2 | H | H | H | iso-$C_3H_7$ |
| Cl | H | $CH_2F$ | 2 | H | H | H | n-$C_4H_9$ |
| Cl | H | $CH_2F$ | 2 | H | H | H | iso-$C_4H_9$ |
| Cl | H | $CH_2F$ | 2 | H | H | H | tert-$C_4H_9$ |
| Cl | H | $CH_2F$ | 2 | H | H | H | $(CH_2)_3Cl$ |
| Cl | H | $CH_2F$ | 2 | H | H | H | $CH_2CN$ |
| Cl | H | $CH_2F$ | 2 | H | H | H | $CH_2OCH_3$ |
| Cl | H | $CH_2F$ | 2 | H | H | H | $CH_2CO_2C_2H_5$ |
| Cl | H | $CH_2F$ | 2 | H | H | H | 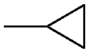 |
| Cl | H | $CH_2F$ | 2 | H | H | H | 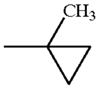 |
| Cl | H | $CH_2F$ | 2 | H | H | H | $C_6H_5$ |
| Cl | H | $CH_2F$ | 2 | H | H | H | 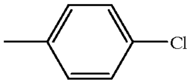 |
| Cl | H | $CHF_2$ | 0 | H | H | H | $CH_3$ |
| Cl | H | $CHF_2$ | 0 | H | H | H | $C_2H_5$ |
| Cl | H | $CHF_2$ | 0 | H | H | H | n-$C_3H_7$ |
| Cl | H | $CHF_2$ | 0 | H | H | H | iso-$C_3H_7$ |
| Cl | H | $CHF_2$ | 0 | H | H | H | n-$C_4H_9$ |
| Cl | H | $CHF_2$ | 0 | H | H | H | iso-$C_4H_9$ |
| Cl | H | $CHF_2$ | 0 | H | H | H | tert-$C_4H_9$ |
| Cl | H | $CHF_2$ | 0 | H | H | H | $(CH_2)_3Cl$ |
| Cl | H | $CHF_2$ | 0 | H | H | H | $CH_2CN$ |
| Cl | H | $CHF_2$ | 0 | H | H | H | $CH_2OCH_3$ |
| Cl | H | $CHF_2$ | 0 | H | H | H | $CH_2CO_2H_5$ |
| Cl | H | $CHF_2$ | 0 | H | H | H | 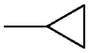 |

TABLE 2-continued

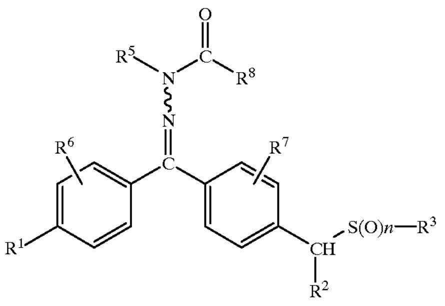

| $R^1$ | $R^2$ | $R^3$ | n | $R^5$ | $R^6$ | $R^7$ | $R^8$ |
|---|---|---|---|---|---|---|---|
| Cl | H | $CHF_2$ | 0 | H | H | H | 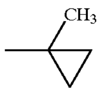 |
| Cl | H | $CHF_2$ | 0 | H | H | H | $C_6H_5$ |
| Cl | H | $CHF_2$ | 0 | H | H | H | 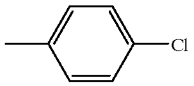 |
| Cl | H | $CHF_2$ | 1 | H | H | H | $CH_3$ |
| Cl | H | $CHF_2$ | 1 | H | H | H | $C_2H_5$ |
| Cl | H | $CHF_2$ | 1 | H | H | H | n-$C_3H_7$ |
| Cl | H | $CHF_2$ | 1 | H | H | H | iso-$C_3H_7$ |
| Cl | H | $CHF_2$ | 1 | H | H | H | n-$C_4H_9$ |
| Cl | H | $CHF_2$ | 1 | H | H | H | iso-$C_4H_9$ |
| Cl | H | $CHF_2$ | 1 | H | H | H | tert-$C_4H_9$ |
| Cl | H | $CHF_2$ | 1 | H | H | H | $(CH_2)_3Cl$ |
| Cl | H | $CHF_2$ | 1 | H | H | H | $CH_2CN$ |
| Cl | H | $CHF_2$ | 1 | H | H | H | $CH_2OCH_3$ |
| Cl | H | $CHF_2$ | 1 | H | H | H | $CH_2CO_2C_2H_5$ |
| Cl | H | $CHF_2$ | 1 | H | H | H | 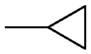 |
| Cl | H | $CHF_2$ | 1 | H | H | H | 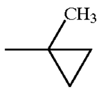 |
| Cl | H | $CHF_2$ | 1 | H | H | H | $C_6H_5$ |
| Cl | H | $CHF_2$ | 1 | H | H | H | 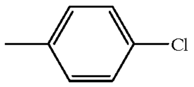 |
| Cl | H | $CHF_2$ | 2 | H | H | H | $CH_3$ |
| Cl | H | $CHF_2$ | 2 | H | H | H | $C_2H_5$ |
| Cl | H | $CHF_2$ | 2 | H | H | H | n-$C_3H_7$ |
| Cl | H | $CHF_2$ | 2 | H | H | H | iso-$C_3H_7$ |
| Cl | H | $CHF_2$ | 2 | H | H | H | n-$C_4H_9$ |
| Cl | H | $CHF_2$ | 2 | H | H | H | iso-$C_4H_9$ |
| Cl | H | $CHF_2$ | 2 | H | H | H | tert-$C_4H_9$ |
| Cl | H | $CHF_2$ | 2 | H | H | H | $(CH_2)_3Cl$ |
| Cl | H | $CHF_2$ | 2 | H | H | H | $CH_2CN$ |
| Cl | H | $CHF_2$ | 2 | H | H | H | $CH_2OCH_3$ |
| Cl | H | $CHF_2$ | 2 | H | H | H | $CH_2CO_2C_2H_5$ |
| Cl | H | $CHF_2$ | 2 | H | H | H | 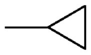 |

TABLE 2-continued

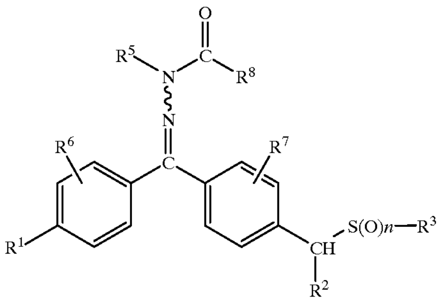

| $R^1$ | $R^2$ | $R^3$ | n | $R^5$ | $R^6$ | $R^7$ | $R^8$ |
|---|---|---|---|---|---|---|---|
| Cl | H | $CHF_2$ | 2 | H | H | H | 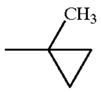 |
| Cl | H | $CHF_2$ | 2 | H | H | H | $C_6H_5$ |
| Cl | H | $CHF_2$ | 2 | H | H | H | 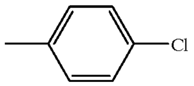 |
| Cl | H | $CF_3$ | 0 | H | H | H | $CH_3$ |
| Cl | H | $CH_2CH_2F$ | 0 | H | H | H | $CH_3$ |
| Cl | H | $CH_2CH_2F$ | 0 | H | H | H | $C_2H_5$ |
| Cl | H | $CH_2CH_2F$ | 0 | H | H | H | n-$C_3H_7$ |
| Cl | H | $CH_2CH_2F$ | 0 | H | H | H | iso-$C_3H_7$ |
| Cl | H | $CH_2CH_2F$ | 0 | H | H | H | n-$C_4H_9$ |
| Cl | H | $CH_2CH_2F$ | 0 | H | H | H | iso-$C_4H_9$ |
| Cl | H | $CH_2CH_2F$ | 0 | H | H | H | tert-$C_4H_9$ |
| Cl | H | $CH_2CH_2F$ | 0 | H | H | H | $(CH_2)_3Cl$ |
| Cl | H | $CH_2CH_2F$ | 0 | H | H | H | $CH_2CN$ |
| Cl | H | $CH_2CH_2F$ | 0 | H | H | H | $CH_2OCH_3$ |
| Cl | H | $CH_2CH_2F$ | 0 | H | H | H | $CH_2CO_2C_2H_5$ |
| Cl | H | $CH_2CH_2F$ | 0 | H | H | H | 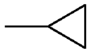 |
| Cl | H | $CH_2CH_2F$ | 0 | H | H | H | 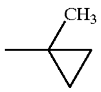 |
| Cl | H | $CH_2CH_2F$ | 0 | H | H | H | $C_6H_5$ |
| Cl | H | $CH_2CH_2F$ | 0 | H | H | H | 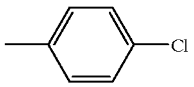 |
| Cl | H | $CH_2CH_2F$ | 1 | H | H | H | $CH_3$ |
| Cl | H | $CH_2CH_2F$ | 1 | H | H | H | $C_2H_5$ |
| Cl | H | $CH_2CH_2F$ | 1 | H | H | H | n-$C_3H_7$ |
| Cl | H | $CH_2CH_2F$ | 1 | H | H | H | iso-$C_3H_7$ |
| Cl | H | $CH_2CH_2F$ | 1 | H | H | H | n-$C_4H_9$ |
| Cl | H | $CH_2CH_2F$ | 1 | H | H | H | iso-$C_4H_9$ |
| Cl | H | $CH_2CH_2F$ | 1 | H | H | H | tert-$C_4H_9$ |
| Cl | H | $CH_2CH_2F$ | 1 | H | H | H | $(CH_2)_3Cl$ |
| Cl | H | $CH_2CH_2F$ | 1 | H | H | H | $CH_2CN$ |
| Cl | H | $CH_2CH_2F$ | 1 | H | H | H | $CH_2OCH_3$ |
| Cl | H | $CH_2CH_2F$ | 1 | H | H | H | $CH_2CO_2C_2H_5$ |
| Cl | H | $CH_2CH_2F$ | 1 | H | H | H | 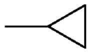 |

TABLE 2-continued

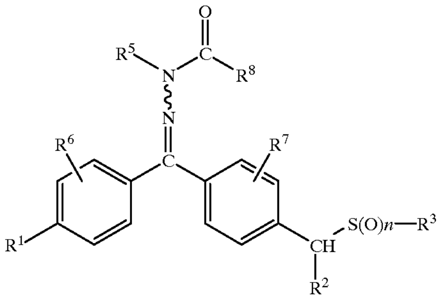

| $R^1$ | $R^2$ | $R^3$ | n | $R^5$ | $R^6$ | $R^7$ | $R^8$ |
|---|---|---|---|---|---|---|---|
| Cl | H | $CH_2CH_2F$ | 1 | H | H | H | 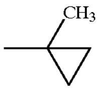 |
| Cl | H | $CH_2CH_2F$ | 1 | H | H | H | $C_6H_5$ |
| Cl | H | $CH_2CH_2F$ | 1 | H | H | H | 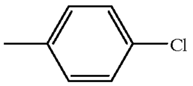 |
| Cl | H | $CH_2CH_2F$ | 2 | H | H | H | $CH_3$ |
| Cl | H | $CH_2CH_2F$ | 2 | H | H | H | $C_2H_5$ |
| Cl | H | $CH_2CH_2F$ | 2 | H | H | H | n-$C_3H_7$ |
| Cl | H | $CH_2CH_2F$ | 2 | H | H | H | iso-$C_3H_7$ |
| Cl | H | $CH_2CH_2F$ | 2 | H | H | H | n-$C_4H_9$ |
| Cl | H | $CH_2CH_2F$ | 2 | H | H | H | iso-$C_4H_9$ |
| Cl | H | $CH_2CH_2F$ | 2 | H | H | H | tert-$C_4H_9$ |
| Cl | H | $CH_2CH_2F$ | 2 | H | H | H | $(CH_2)_3Cl$ |
| Cl | H | $CH_2CH_2F$ | 2 | H | H | H | $CH_2CN$ |
| Cl | H | $CH_2CH_2F$ | 2 | H | H | H | $CH_2OCH_3$ |
| Cl | H | $CH_2CH_2F$ | 2 | H | H | H | $CH_2CO_2C_2H_5$ |
| Cl | H | $CH_2CH_2F$ | 2 | H | H | H | 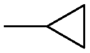 |
| Cl | H | $CH_2CH_2F$ | 2 | H | H | H | 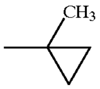 |
| Cl | H | $CH_2CH_2F$ | 2 | H | H | H | $C_6H_5$ |
| Cl | H | $CH_2CH_2F$ | 2 | H | H | H | 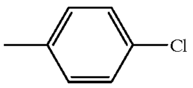 |
| Cl | H | $CH_2CHF_2$ | 0 | H | H | H | $CH_3$ |
| Cl | H | $CH_2CHF_2$ | 0 | H | H | H | $C_2H_5$ |
| Cl | H | $CH_2CHF_2$ | 0 | H | H | H | n-$C_3H_7$ |
| Cl | H | $CH_2CHF_2$ | 0 | H | H | H | iso-$C_3H_7$ |
| Cl | H | $CH_2CHF_2$ | 0 | H | H | H | n-$C_4H_9$ |
| Cl | H | $CH_2CHF_2$ | 0 | H | H | H | iso-$C_4H_9$ |
| Cl | H | $CH_2CHF_2$ | 0 | H | H | H | tert-$C_4H_9$ |
| Cl | H | $CH_2CHF_2$ | 0 | H | H | H | $(CH_2)_3Cl$ |
| Cl | H | $CH_2CHF_2$ | 0 | H | H | H | $CH_2CN$ |
| Cl | H | $CH_2CHF_2$ | 0 | H | H | H | $CH_2OCH_3$ |
| Cl | H | $CH_2CHF_2$ | 0 | H | H | H | $CH_2CO_2C_2H_5$ |
| Cl | H | $CH_2CHF_2$ | 0 | H | H | H | 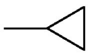 |

TABLE 2-continued

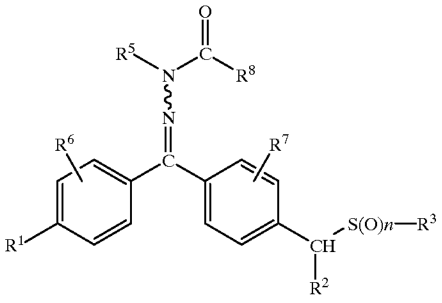

| $R^1$ | $R^2$ | $R^3$ | n | $R^5$ | $R^6$ | $R^7$ | $R^8$ |
|---|---|---|---|---|---|---|---|
| Cl | H | $CH_2CHF_2$ | 0 | H | H | H | 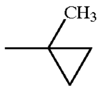 |
| Cl | H | $CH_2CHF_2$ | 0 | H | H | H | $C_6H_5$ |
| Cl | H | $CH_2CHF_2$ | 0 | H | H | H | 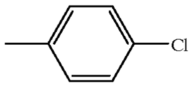 |
| Cl | H | $CH_2CHF_2$ | 1 | H | H | H | $CH_3$ |
| Cl | H | $CH_2CHF_2$ | 1 | H | H | H | $C_2H_5$ |
| Cl | H | $CH_2CHF_2$ | 1 | H | H | H | n-$C_3H_7$ |
| Cl | H | $CH_2CHF_2$ | 1 | H | H | H | iso-$C_3H_7$ |
| Cl | H | $CH_2CHF_2$ | 1 | H | H | H | n-$C_4H_9$ |
| Cl | H | $CH_2CHF_2$ | 1 | H | H | H | iso-$C_4H_9$ |
| Cl | H | $CH_2CHF_2$ | 1 | H | H | H | tert-$C_4H_9$ |
| Cl | H | $CH_2CHF_2$ | 1 | H | H | H | $(CH_2)_3Cl$ |
| Cl | H | $CH_2CHF_2$ | 1 | H | H | H | $CH_2CN$ |
| Cl | H | $CH_2CHF_2$ | 1 | H | H | H | $CH_2OCH_3$ |
| Cl | H | $CH_2CHF_2$ | 1 | H | H | H | $CH_2CO_2C_2H_5$ |
| Cl | H | $CH_2CHF_2$ | 1 | H | H | H | 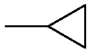 |
| Cl | H | $CH_2CHF_2$ | 1 | H | H | H | 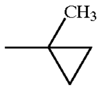 |
| Cl | H | $CH_2CHF_2$ | 1 | H | H | H | $C_6H_5$ |
| Cl | H | $CH_2CHF_2$ | 1 | H | H | H | 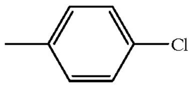 |
| Cl | H | $CH_2CHF_2$ | 2 | H | H | H | $CH_3$ |
| Cl | H | $CH_2CHF_2$ | 2 | H | H | H | $C_2H_5$ |
| Cl | H | $CH_2CHF_2$ | 2 | H | H | H | n-$C_3H_7$ |
| Cl | H | $CH_2CHF_2$ | 2 | H | H | H | iso-$C_3H_7$ |
| Cl | H | $CH_2CHF_2$ | 2 | H | H | H | n-$C_4H_9$ |
| Cl | H | $CH_2CHF_2$ | 2 | H | H | H | iso-$C_4H_9$ |
| Cl | H | $CH_2CHF_2$ | 2 | H | H | H | tert-$C_4H_9$ |
| Cl | H | $CH_2CHF_2$ | 2 | H | H | H | $(CH_2)_3Cl$ |
| Cl | H | $CH_2CHF_2$ | 2 | H | H | H | $CH_2CN$ |
| Cl | H | $CH_2CHF_2$ | 2 | H | H | H | $CH_2OCH_3$ |
| Cl | H | $CH_2CHF_2$ | 2 | H | H | H | $CH_2CO_2C_2H_5$ |
| Cl | H | $CH_2CHF_2$ | 2 | H | H | H | 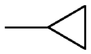 |

TABLE 2-continued

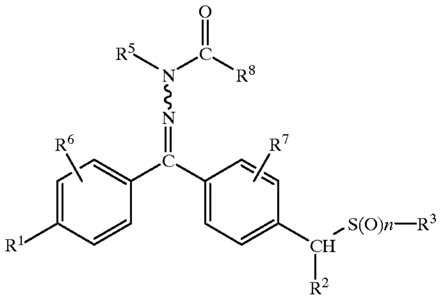

| $R^1$ | $R^2$ | $R^3$ | n | $R^5$ | $R^6$ | $R^7$ | $R^8$ |
|---|---|---|---|---|---|---|---|
| Cl | H | $CH_2CHF_2$ | 2 | H | H | H | 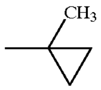 |
| Cl | H | $CH_2CHF_2$ | 2 | H | H | H | $C_6H_5$ |
| Cl | H | $CH_2CHF_2$ | 2 | H | H | H | 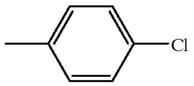 |
| Cl | H | $CH_2CF_3$ | 0 | H | H | H | $CH_3$ |
| Cl | H | $CH_2CF_3$ | 0 | H | H | H | $C_2H_5$ |
| Cl | H | $CH_2CF_3$ | 0 | H | H | H | n-$C_3H_7$ |
| Cl | H | $CH_2CF_3$ | 0 | H | H | H | iso-$C_3H_7$ |
| Cl | H | $CH_2CF_3$ | 0 | H | H | H | n-$C_4H_9$ |
| Cl | H | $CH_2CF_3$ | 0 | H | H | H | iso-$C_4H_9$ |
| Cl | H | $CH_2CF_3$ | 0 | H | H | H | tert-$C_4H_9$ |
| Cl | H | $CH_2CF_3$ | 0 | H | H | H | $(CH_2)_3Cl$ |
| Cl | H | $CH_2CF_3$ | 0 | H | H | H | $CH_2CN$ |
| Cl | H | $CH_2CF_3$ | 0 | H | H | H | $CH_2OCH_3$ |
| Cl | H | $CH_2CF_3$ | 0 | H | H | H | $CH_2CO_2C_2H_5$ |
| Cl | H | $CH_2CF_3$ | 0 | H | H | H | 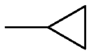 |
| Cl | H | $CH_2CF_3$ | 0 | H | H | H | 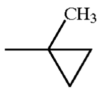 |
| Cl | H | $CH_2CF_3$ | 0 | H | H | H | $C_6H_5$ |
| Cl | H | $CH_2CF_3$ | 0 | H | H | H | 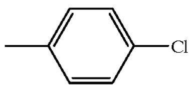 |
| Cl | H | $CH_2CF_3$ | 1 | H | H | H | $CH_3$ |
| Cl | H | $CH_2CF_3$ | 1 | H | H | H | $C_2H_5$ |
| Cl | H | $CH_2CF_3$ | 1 | H | H | H | n-$C_3H_7$ |
| Cl | H | $CH_2CF_3$ | 1 | H | H | H | iso-$C_3H_7$ |
| Cl | H | $CH_2CF_3$ | 1 | H | H | H | n-$C_4H_9$ |
| Cl | H | $CH_2CF_3$ | 1 | H | H | H | iso-$C_4H_9$ |
| Cl | H | $CH_2CF_3$ | 1 | H | H | H | tert-$C_4H_9$ |
| Cl | H | $CH_2CF_3$ | 1 | H | H | H | $(CH_2)_3Cl$ |
| Cl | H | $CH_2CF_3$ | 1 | H | H | H | $CH_2CN$ |
| Cl | H | $CH_2CF_3$ | 1 | H | H | H | $CH_2OCH_3$ |
| Cl | H | $CH_2CF_3$ | 1 | H | H | H | $CH_2CO_2C_2H_5$ |
| Cl | H | $CH_2CF_3$ | 1 | H | H | H | 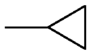 |

TABLE 2-continued

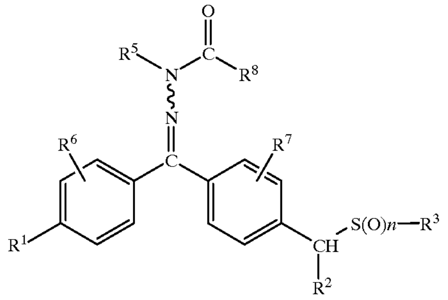

| $R^1$ | $R^2$ | $R^3$ | n | $R^5$ | $R^6$ | $R^7$ | $R^8$ |
|---|---|---|---|---|---|---|---|
| Cl | H | $CH_2CF_3$ | 1 | H | H | H | 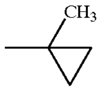 |
| Cl | H | $CH_2CF_3$ | 1 | H | H | H | $C_6H_5$ |
| Cl | H | $CH_2CF_3$ | 1 | H | H | H | 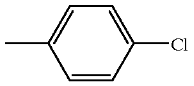 |
| Cl | H | $CH_2CF_3$ | 2 | H | H | H | $CH_3$ |
| Cl | H | $CH_2CF_3$ | 2 | H | H | H | $C_2H_5$ |
| Cl | H | $CH_2CF_3$ | 2 | H | H | H | n-$C_3H_7$ |
| Cl | H | $CH_2CF_3$ | 2 | H | H | H | iso-$C_3H_7$ |
| Cl | H | $CH_2CF_3$ | 2 | H | H | H | n-$C_4H_9$ |
| Cl | H | $CH_2CF_3$ | 2 | H | H | H | iso-$C_4H_9$ |
| Cl | H | $CH_2CF_3$ | 2 | H | H | H | tert-$C_4H_9$ |
| Cl | H | $CH_2CF_3$ | 2 | H | H | H | $(CH_2)_3Cl$ |
| Cl | H | $CH_2CF_3$ | 2 | H | H | H | $CH_2CN$ |
| Cl | H | $CH_2CF_3$ | 2 | H | H | H | $CH_2OCH_3$ |
| Cl | H | $CH_2CF_3$ | 2 | H | H | H | $CH_2CO_2C_2H_5$ |
| Cl | H | $CH_2CF_3$ | 2 | H | H | H | 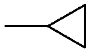 |
| Cl | H | $CH_2CF_3$ | 2 | H | H | H | 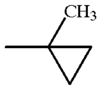 |
| Cl | H | $CH_2CF_3$ | 2 | H | H | H | $C_6H_5$ |
| Cl | H | $CH_2CF_3$ | 2 | H | H | H | 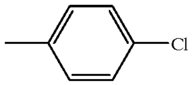 |
| Cl | $CH_3$ | $CH_3$ | 0 | H | H | H | $CH_3$ |
| Cl | $CH_3$ | $CH_3$ | 1 | H | H | H | $CH_3$ |
| Cl | $CH_3$ | $CH_3$ | 2 | H | H | H | $CH_3$ |
| Br | H | $CH_3$ | 0 | H | H | H | $CH_2OCH_3$ |
| Br | H | $CH_3$ | 0 | H | H | H | $CH_2CO_2C_2H_5$ |
| Br | H | $CH_3$ | 0 | H | H | H | $CH_3$ |
| Br | H | $CH_3$ | 0 | H | H | H | $C_2H_5$ |
| Br | H | $CH_3$ | 0 | H | H | H | n-$C_3H_7$ |
| Br | H | $CH_3$ | 0 | H | H | H | iso-$C_3H_7$ |
| Br | H | $CH_3$ | 0 | H | H | H | n-$C_4H_9$ |
| Br | H | $CH_3$ | 0 | H | H | H | sec-$C_4H_9$ |
| Br | H | $CH_3$ | 0 | H | H | H | iso-$C_4H_9$ |
| Br | H | $CH_3$ | 0 | H | H | H | tert-$C_4H_9$ |
| Br | H | $CH_3$ | 0 | H | H | H | n-$C_5H_{11}$ |
| Br | H | $CH_3$ | 0 | H | H | H | n-$C_6H_{13}$ |
| Br | H | $CH_3$ | 0 | H | H | H | 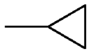 |

TABLE 2-continued

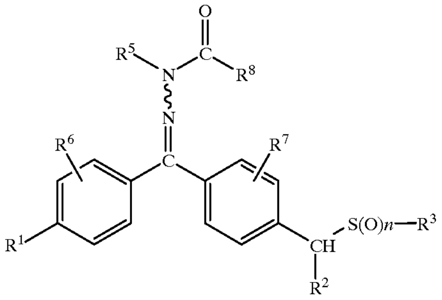

| $R^1$ | $R^2$ | $R^3$ | n | $R^5$ | $R^6$ | $R^7$ | $R^8$ |
|---|---|---|---|---|---|---|---|
| Br | H | $CH_3$ | 0 | H | H | H | 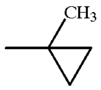 |
| Br | H | $CH_3$ | 0 | H | H | H | 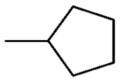 |
| Br | H | $CH_3$ | 0 | H | H | H | 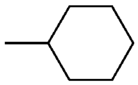 |
| Br | H | $CH_3$ | 0 | H | H | H | $C_6H_5$ |
| Br | H | $CH_3$ | 0 | H | H | H | 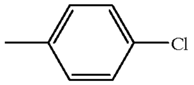 |
| Br | H | $CH_3$ | 0 | H | H | H | 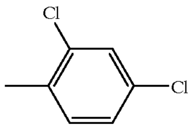 |
| Br | H | $CH_3$ | 0 | H | H | H | $CH{=}CH_2$ |
| Br | H | $CH_3$ | 0 | H | H | H | $CH{=}CHCH_3$ |
| Br | H | $CH_3$ | 0 | H | H | H | $C({=}CH_2)CH_3$ |
| Br | H | $CH_3$ | 0 | H | H | H | $CH{=}CHC_6H_5$ |
| Br | H | $CH_3$ | 0 | H | H | H | 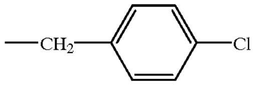 |
| Br | H | $CH_3$ | 0 | H | H | H | $(CH_2)_4Cl$ |
| Br | H | $CH_3$ | 0 | H | H | H | $(CH_2)_3Cl$ |
| Br | H | $CH_3$ | 0 | H | H | H | $CH_2CN$ |
| Br | H | $CH_3$ | 0 | H | H | H | $CH_2OC_6H_5$ |
| Br | H | $CH_3$ | 0 | $CH_3$ | H | H | $CH_3$ |
| Br | H | $CH_3$ | 0 | $CH_3$ | H | H | $C_2H_5$ |
| Br | H | $CH_3$ | 0 | $CH_3$ | H | H | n-$C_3H_7$ |
| Br | H | $CH_3$ | 0 | $CH_3$ | H | H | iso-$C_3H_7$ |
| Br | H | $CH_3$ | 0 | $CH_3$ | H | H | n-$C_4H_9$ |
| Br | H | $CH_3$ | 0 | $CH_3$ | H | H | iso-$C_4H_9$ |
| Br | H | $CH_3$ | 0 | $CH_3$ | H | H | sec-$C_4H_9$ |
| Br | H | $CH_3$ | 0 | $CH_3$ | H | H | tert-$C_4H_9$ |
| Br | H | $CH_3$ | 0 | $CH_3$ | H | H | $(CH_2)_3Cl$ |
| Br | H | $CH_3$ | 0 | $CH_3$ | H | H | $(CH_2)_4Cl$ |
| Br | H | $CH_3$ | 0 | $CH_3$ | H | H | $CH_2CN$ |
| Br | H | $CH_3$ | 0 | $CH_3$ | H | H | $CH_2CO_2C_2H_5$ |
| Br | H | $CH_3$ | 0 | $CH_3$ | H | H | $CH_2OCH_3$ |
| Br | H | $CH_3$ | 0 | $CH_3$ | H | H | $C_6H_5$ |

TABLE 2-continued

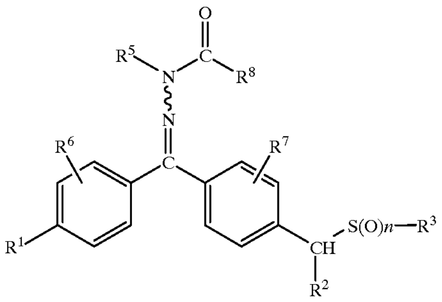

| $R^1$ | $R^2$ | $R^3$ | n | $R^5$ | $R^6$ | $R^7$ | $R^8$ |
|---|---|---|---|---|---|---|---|
| Br | H | $CH_3$ | 0 | $CH_3$ | H | H | 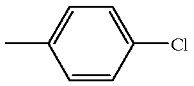 |
| Br | H | $CH_3$ | 0 | $C_2H_5$ | H | H | $CH_3$ |
| Br | H | $CH_3$ | 0 | $C_2H_5$ | H | H | $C_2H_5$ |
| Br | H | $CH_3$ | 0 | $C_2H_5$ | H | H | n-$C_3H_7$ |
| Br | H | $CH_3$ | 0 | $C_2H_5$ | H | H | iso-$C_3H_7$ |
| Br | H | $CH_3$ | 0 | $C_2H_5$ | H | H | n-$C_4H_9$ |
| Br | H | $CH_3$ | 0 | $C_2H_5$ | H | H | iso-$C_4H_9$ |
| Br | H | $CH_3$ | 0 | $C_2H_5$ | H | H | sec-$C_4H_9$ |
| Br | H | $CH_3$ | 0 | $C_2H_5$ | H | H | tert-$C_4H_9$ |
| Br | H | $CH_3$ | 0 | $C_2H_5$ | H | H | $(CH_2)_3Cl$ |
| Br | H | $CH_3$ | 0 | $C_2H_5$ | H | H | $(CH_2)_4Cl$ |
| Br | H | $CH_3$ | 0 | $C_2H_5$ | H | H | $CH_2CN$ |
| Br | H | $CH_3$ | 0 | $C_2H_5$ | H | H | $CH_2CO_2C_2H_5$ |
| Br | H | $CH_3$ | 0 | $C_2H_5$ | H | H | $CH_2OCH_3$ |
| Br | H | $CH_3$ | 0 | $C_2H_5$ | H | H | $C_6H_5$ |
| Br | H | $CH_3$ | 0 | $C_2H_5$ | H | H | 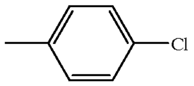 |
| Br | H | $CH_3$ | 0 | n-$C_5$H7 | H | H | $CH_3$ |
| Br | H | $CH_3$ | 0 | n-$C_3H_7$ | H | H | $C_2H_5$ |
| Br | H | $CH_3$ | 0 | n-$C_3H_7$ | H | H | n-$C_3H_7$ |
| Br | H | $CH_3$ | 0 | n-$C_3H_7$ | H | H | iso-$C_3H_7$ |
| Br | H | $CH_3$ | 0 | n-$C_3H_7$ | H | H | n-$C_4H_9$ |
| Br | H | $CH_3$ | 0 | n-$C_3H_7$ | H | H | iso-$C_4H_9$ |
| Br | H | $CH_3$ | 0 | n-$C_3H_7$ | H | H | sec-$C_4H_9$ |
| Br | H | $CH_3$ | 0 | n-$C_3H_7$ | H | H | tert-$C_4H_9$ |
| Br | H | $CH_3$ | 0 | n-$C_3H_7$ | H | H | $(CH_2)_3Cl$ |
| Br | H | $CH_3$ | 0 | n-$C_3H_7$ | H | H | $(CH_2)_4Cl$ |
| Br | H | $CH_3$ | 0 | n-$C_3H_7$ | H | H | $CH_2CN$ |
| Br | H | $CH_3$ | 0 | n-$C_3H_7$ | H | H | $CH_2CO_2C_2H_5$ |
| Br | H | $CH_3$ | 0 | n-$C_3H_7$ | H | H | $CH_2OCH_3$ |
| Br | H | $CH_3$ | 0 | n-$C_3H_7$ | H | H | $C_6H_5$ |
| Br | H | $CH_3$ | 0 | n-$C_3H_7$ | H | H | 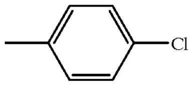 |
| Br | H | $CH_3$ | 0 | iso-$C_3H_7$ | H | H | $CH_3$ |
| Br | H | $CH_3$ | 0 | iso-$C_3H_7$ | H | H | $C_2H_5$ |
| Br | H | $CH_3$ | 0 | iso-$C_3H_7$ | H | H | n-$C_3H_7$ |
| Br | H | $CH_3$ | 0 | iso-$C_3H_7$ | H | H | iso-$C_3H_7$ |
| Br | H | $CH_3$ | 0 | iso-$C_3H_7$ | H | H | n-$C_4H_9$ |
| Br | H | $CH_3$ | 0 | iso-$C_3H_7$ | H | H | iso-$C_4H_9$ |
| Br | H | $CH_3$ | 0 | iso-$C_3H_7$ | H | H | sec-$C_4H_9$ |
| Br | H | $CH_3$ | 0 | iso-$C_3H_7$ | H | H | tert-$C_4H_9$ |
| Br | H | $CH_3$ | 0 | iso-$C_3H_7$ | H | H | $(CH_2)_3Cl$ |
| Br | H | $CH_3$ | 0 | iso-$C_3H_7$ | H | H | $(CH_2)_4Cl$ |
| Br | H | $CH_3$ | 0 | iso-$C_3H_7$ | H | H | $CH_2CN$ |
| Br | H | $CH_3$ | 0 | iso-$C_3H_7$ | H | H | $CH_2CO_2C_2H_5$ |
| Br | H | $CH_3$ | 0 | iso-$C_3H_7$ | H | H | $CH_2OCH_3$ |
| Br | H | $CH_3$ | 0 | iso-$C_3H_7$ | H | H | $C_6H_5$ |

TABLE 2-continued

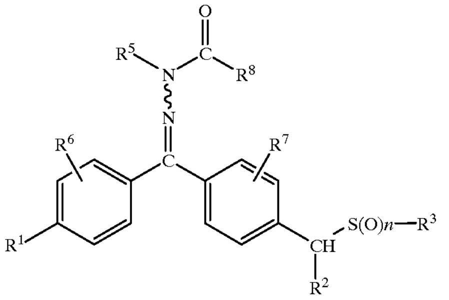

| $R^1$ | $R^2$ | $R^3$ | n | $R^5$ | $R^6$ | $R^7$ | $R^8$ |
|---|---|---|---|---|---|---|---|
| Br | H | $CH_3$ | 0 | iso-$C_3H_7$ | H | H | 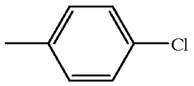 |
| Br | H | $CH_3$ | 0 | $CH_2CH_3$ | H | H | $CH_3$ |
| Br | H | $CH_3$ | 0 | $CH_2OCH_3$ | H | H | $C_6H_5$ |
| Br | H | $CH_3$ | 0 | $CH_2OC_2H_5$ | H | H | $CH_3$ |
| Br | H | $CH_3$ | 0 | $CH_2OC_2H_5$ | H | H | $C_6H_5$ |
| Br | H | $CH_3$ | 1 | H | H | H | $CH_3$ |
| Br | H | $CH_3$ | 1 | H | H | H | $C_2H_5$ |
| Br | H | $CH_3$ | 1 | H | H | H | n-$C_3H_7$ |
| Br | H | $CH_3$ | 1 | H | H | H | iso-$C_3H_7$ |
| Br | H | $CH_3$ | 1 | H | H | H | n-$C_4H_9$ |
| Br | H | $CH_3$ | 1 | H | H | H | iso-$C_4H_9$ |
| Br | H | $CH_3$ | 1 | H | H | H | tert-$C_4H_9$ |
| Br | H | $CH_3$ | 1 | H | H | H | $(CH_2)_3Cl$ |
| Br | H | $CH_3$ | 1 | H | H | H | $CH_2CN$ |
| Br | H | $CH_3$ | 1 | H | H | H | $CH_2OCH_3$ |
| Br | H | $CH_3$ | 1 | H | H | H | $CH_2CO_2C_2H_5$ |
| Br | H | $CH_3$ | 1 | H | H | H | 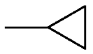 |
| Br | H | $CH_3$ | 1 | H | H | H | 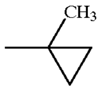 |
| Br | H | $CH_3$ | 1 | H | H | H | $C_6H_5$ |
| Br | H | $CH_3$ | 1 | H | H | H | 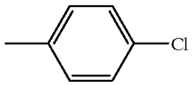 |
| Br | H | $CH_3$ | 1 | $CH_3$ | H | H | $CH_3$ |
| Br | H | $CH_3$ | 1 | $CH_3$ | H | H | $C_2H_5$ |
| Br | H | $CH_3$ | 1 | $CH_3$ | H | H | n-$C_3H_7$ |
| Br | H | $CH_3$ | 1 | $CH_3$ | H | H | iso-$C_3H_7$ |
| Br | H | $CH_3$ | 1 | $CH_3$ | H | H | n-$C_4H_9$ |
| Br | H | $CH_3$ | 1 | $CH_3$ | H | H | iso-$C_4H_9$ |
| Br | H | $CH_3$ | 1 | $CH_3$ | H | H | sec-$C_4H_9$ |
| Br | H | $CH_3$ | 1 | $CH_3$ | H | H | tert-$C_4H_9$ |
| Br | H | $CH_3$ | 1 | $CH_3$ | H | H | $(CH_2)_3Cl$ |
| Br | H | $CH_3$ | 1 | $CH_3$ | H | H | $(CH_2)_4Cl$ |
| Br | H | $CH_3$ | 1 | $CH_3$ | H | H | $CH_2CN$ |
| Br | H | $CH_3$ | 1 | $CH_3$ | H | H | $CH_2OCH_3$ |
| Br | H | $CH_3$ | 1 | $CH_3$ | H | H | $CH_2CO_2C_2H_5$ |
| Br | H | $CH_3$ | 1 | $CH_3$ | H | H | $C_6H_5$ |
| Br | H | $CH_3$ | 1 | $CH_3$ | H | H | 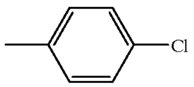 |
| Br | H | $CH_3$ | 1 | $C_2H_5$ | H | H | $CH_3$ |

TABLE 2-continued

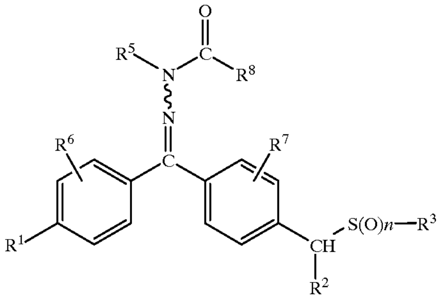

| $R^1$ | $R^2$ | $R^3$ | n | $R^5$ | $R^6$ | $R^7$ | $R^8$ |
|---|---|---|---|---|---|---|---|
| Br | H | $CH_3$ | 1 | $C_2H_5$ | H | H | $C_2H_5$ |
| Br | H | $CH_3$ | 1 | $C_2H_5$ | H | H | n-$C_3H_7$ |
| Br | H | $CH_3$ | 1 | $C_2H_5$ | H | H | iso-$C_3H_7$ |
| Br | H | $CH_3$ | 1 | $C_2H_5$ | H | H | n-$C_4H_9$ |
| Br | H | $CH_3$ | 1 | $C_2H_5$ | H | H | iso-$C_4H_9$ |
| Br | H | $CH_3$ | 1 | $C_2H_5$ | H | H | sec-$C_4H_9$ |
| Br | H | $CH_3$ | 1 | $C_2H_5$ | H | H | tert-$C_4H_9$ |
| Br | H | $CH_3$ | 1 | $C_2H_5$ | H | H | $(CH_2)_3Cl$ |
| Br | H | $CH_3$ | 1 | $C_2H_5$ | H | H | $(CH_2)_4Cl$ |
| Br | H | $CH_3$ | 1 | $C_2H_5$ | H | H | $CH_2CN$ |
| Br | H | $CH_3$ | 1 | $C_2H_5$ | H | H | $CH_2CO_2C_2H_5$ |
| Br | H | $CH_3$ | 1 | $C_2H_5$ | H | H | $CH_2OCH_3$ |
| Br | H | $CH_3$ | 1 | $C_2H_5$ | H | H | $C_6H_5$ |
| Br | H | $CH_3$ | 1 | $C_2H_5$ | H | H | 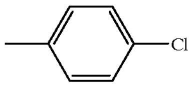 |
| Br | H | $CH_3$ | 1 | n-$C_3H_7$ | H | H | $CH_3$ |
| Br | H | $CH_3$ | 1 | n-$C_3H_7$ | H | H | $C_2H_5$ |
| Br | H | $CH_3$ | 1 | n-$C_3H_7$ | H | H | n-$C_3H_7$ |
| Br | H | $CH_3$ | 1 | n-$C_3H_7$ | H | H | iso-$C_3H_7$ |
| Br | H | $CH_3$ | 1 | n-$C_3H_7$ | H | H | n-$C_4H_9$ |
| Br | H | $CH_3$ | 1 | n-$C_3H_7$ | H | H | iso-$C_4H_9$ |
| Br | H | $CH_3$ | 1 | n-$C_3H_7$ | H | H | sec-$C_4H_9$ |
| Br | H | $CH_3$ | 1 | n-$C_3H_7$ | H | H | tert-$C_4H_9$ |
| Br | H | $CH_3$ | 1 | n-$C_3H_7$ | H | H | $(CH_2)_3Cl$ |
| Br | H | $CH_3$ | 1 | n-$C_3H_7$ | H | H | $(CH_2)_4Cl$ |
| Br | H | $CH_3$ | 1 | n-$C_3H_7$ | H | H | $CH_2CN$ |
| Br | H | $CH_3$ | 1 | n-$C_3H_7$ | H | H | $CH_2CO_2C_2H_5$ |
| Br | H | $CH_3$ | 1 | n-$C_3H_7$ | H | H | $CH_2OCH_3$ |
| Br | H | $CH_3$ | 1 | n-$C_3H_7$ | H | H | $C_6H_5$ |
| Br | H | $CH_3$ | 1 | n-$C_3H_7$ | H | H | 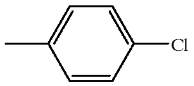 |
| Br | H | $CH_3$ | 1 | iso-$C_3H_7$ | H | H | $CH_3$ |
| Br | H | $CH_3$ | 1 | iso-$C_3H_7$ | H | H | $C_2H_5$ |
| Br | H | $CH_3$ | 1 | iso-$C_3H_7$ | H | H | n-$C_3H_7$ |
| Br | H | $CH_3$ | 1 | iso-$C_3H_7$ | H | H | iso-$C_3H_7$ |
| Br | H | $CH_3$ | 1 | iso-$C_3H_7$ | H | H | n-$C_4H_9$ |
| Br | H | $CH_3$ | 1 | iso-$C_3H_7$ | H | H | iso-$C_4H_9$ |
| Br | H | $CH_3$ | 1 | iso-$C_3H_7$ | H | H | sec-$C_4H_9$ |
| Br | H | $CH_3$ | 1 | iso-$C_3H_7$ | H | H | tert-$C_4H_9$ |
| Br | H | $CH_3$ | 1 | iso-$C_3H_7$ | H | H | $(CH_2)_3Cl$ |
| Br | H | $CH_3$ | 1 | iso-$C_3H_7$ | H | H | $(CH_2)_4Cl$ |
| Br | H | $CH_3$ | 1 | iso-$C_3H_7$ | H | H | $CH_2CN$ |
| Br | H | $CH_3$ | 1 | iso-$C_3H_7$ | H | H | $CH_2CO_2C_2H_5$ |
| Br | H | $CH_3$ | 1 | iso-$C_3H_7$ | H | H | $CH_2OCH_3$ |
| Br | H | $CH_3$ | 1 | iso-$C_3H_7$ | H | H | $C_6H_5$ |
| Br | H | $CH_3$ | 1 | iso-$C_3H_7$ | H | H | 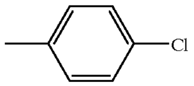 |
| Br | H | $CH_3$ | 2 | H | H | H | $CH_3$ |

TABLE 2-continued

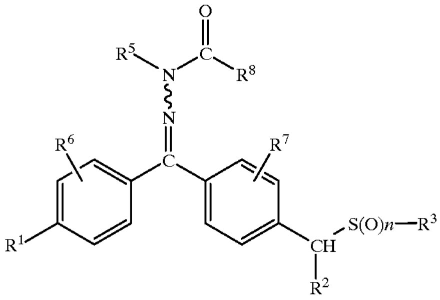

| $R^1$ | $R^2$ | $R^3$ | n | $R^5$ | $R^6$ | $R^7$ | $R^8$ |
|---|---|---|---|---|---|---|---|
| Br | H | $CH_3$ | 2 | H | H | H | $C_2H_5$ |
| Br | H | $CH_3$ | 2 | H | H | H | n-$C_3H_7$ |
| Br | H | $CH_3$ | 2 | H | H | H | iso-$C_3H_7$ |
| Br | H | $CH_3$ | 2 | H | H | H | n-$C_4H_9$ |
| Br | H | $CH_3$ | 2 | H | H | H | iso-$C_4H_9$ |
| Br | H | $CH_3$ | 2 | H | H | H | tert-$C_4H_9$ |
| Br | H | $CH_3$ | 2 | H | H | H | $(CH_2)_3Cl$ |
| Br | H | $CH_3$ | 2 | H | H | H | $CH_2CN$ |
| Br | H | $CH_3$ | 2 | H | H | H | $CH_2OCH_3$ |
| Br | H | $CH_3$ | 2 | H | H | H | $CH_2CO_2C_2H_5$ |
| Br | H | $CH_3$ | 2 | H | H | H | 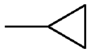 |
| Br | H | $CH_3$ | 2 | H | H | H | 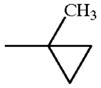 |
| Br | H | $CH_3$ | 2 | H | H | H | $C_6H_5$ |
| Br | H | $CH_3$ | 2 | H | H | H | 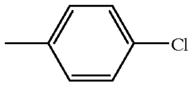 |
| Br | H | $CH_3$ | 2 | $CH_3$ | H | H | $CH_3$ |
| Br | H | $CH_3$ | 2 | $CH_3$ | H | H | $C_2H_5$ |
| Br | H | $CH_3$ | 2 | $CH_3$ | H | H | n-$C_3H_7$ |
| Br | H | $CH_3$ | 2 | $CH_3$ | H | H | iso-$C_3H_7$ |
| Br | H | $CH_3$ | 2 | $CH_3$ | H | H | n-$C_4H_9$ |
| Br | H | $CH_3$ | 2 | $CH_3$ | H | H | iso-$C_4H_9$ |
| Br | H | $CH_3$ | 2 | $CH_3$ | H | H | sec-$C_4H_9$ |
| Br | H | $CH_3$ | 2 | $CH_3$ | H | H | tert-$C_4H_9$ |
| Br | H | $CH_3$ | 2 | $CH_3$ | H | H | $(CH_2)_3Cl$ |
| Br | H | $CH_3$ | 2 | $CH_3$ | H | H | $(CH_2)_4Cl$ |
| Br | H | $CH_3$ | 2 | $CH_3$ | H | H | $C_6H_5$ |
| Br | H | $CH_3$ | 2 | $CH_3$ | H | H | 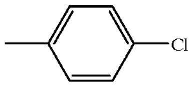 |
| Br | H | $CH_3$ | 2 | $C_2H_5$ | H | H | $CH_3$ |
| Br | H | $CH_3$ | 2 | $C_2H_5$ | H | H | $C_2H_5$ |
| Br | H | $CH_3$ | 2 | $C_2H_5$ | H | H | n-$C_3H_7$ |
| Br | H | $CH_3$ | 2 | $C_2H_5$ | H | H | iso-$C_3H_7$ |
| Br | H | $CH_3$ | 2 | $CH_3$ | H | H | $CH_2CN$ |
| Br | H | $CH_3$ | 2 | $CH_3$ | H | H | $CH_2CO_2C_2H_5$ |
| Br | H | $CH_3$ | 2 | $CH_3$ | H | H | $CH_2OCH_3$ |
| Br | H | $CH_3$ | 2 | $C_2H_5$ | H | H | n-$C_4H_9$ |
| Br | H | $CH_3$ | 2 | $C_2H_5$ | H | H | iso-$C_4H_9$ |
| Br | H | $CH_3$ | 2 | $C_2H_5$ | H | H | sec-$C_4H_9$ |
| Br | H | $CH_3$ | 2 | $C_2H_5$ | H | H | tert-$C_4H_9$ |
| Br | H | $CH_3$ | 2 | $C_2H_5$ | H | H | $(CH_2)_3Cl$ |
| Br | H | $CH_3$ | 2 | $C_2H_5$ | H | H | $(CH_2)_4Cl$ |
| Br | H | $CH_3$ | 2 | $C_2H_5$ | H | H | $CH_2CN$ |
| Br | H | $CH_3$ | 2 | $C_2H_5$ | H | H | $CH_2CO_2C_2H_5$ |
| Br | H | $CH_3$ | 2 | $C_2H_5$ | H | H | $CH_2OCH_3$ |

TABLE 2-continued

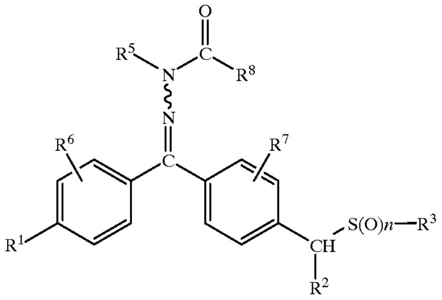

| $R^1$ | $R^2$ | $R^3$ | n | $R^5$ | $R^6$ | $R^7$ | $R^8$ |
|---|---|---|---|---|---|---|---|
| Br | H | $CH_3$ | 2 | $C_2H_5$ | H | H | $C_6H_5$ |
| Br | H | $CH_3$ | 2 | $C_2H_5$ | H | H | 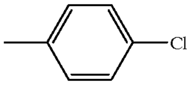 |
| Br | H | $CH_3$ | 2 | n-$C_3H_7$ | H | H | $CH_3$ |
| Br | H | $CH_3$ | 2 | n-$C_3H_7$ | H | H | $C_2H_5$ |
| Br | H | $CH_3$ | 2 | n-$C_3H_7$ | H | H | n-$C_3H_7$ |
| Br | H | $CH_3$ | 2 | n-$C_3H_7$ | H | H | iso-$C_3H_7$ |
| Br | H | $CH_3$ | 2 | n-$C_3H_7$ | H | H | n-$C_4H_9$ |
| Br | H | $CH_3$ | 2 | n-$C_3H_7$ | H | H | iso-$C_4H_9$ |
| Br | H | $CH_3$ | 2 | n-$C_3H_7$ | H | H | sec-$C_4H_9$ |
| Br | H | $CH_3$ | 2 | n-$C_3H_7$ | H | H | tert-$C_4H_9$ |
| Br | H | $CH_3$ | 2 | n-$C_3H_7$ | H | H | $(CH_2)_3Cl$ |
| Br | H | $CH_3$ | 2 | n-$C_3H_7$ | H | H | $(CH_2)_4Cl$ |
| Br | H | $CH_3$ | 2 | n-$C_3H_7$ | H | H | $CH_2CN$ |
| Br | H | $CH_3$ | 2 | n-$C_3H_7$ | H | H | $CH_2CO_2C_2H_5$ |
| Br | H | $CH_3$ | 2 | n-$C_3H_7$ | H | H | $CH_2OCH_3$ |
| Br | H | $CH_3$ | 2 | n-$C_3H_7$ | H | H | $C_6H_5$ |
| Br | H | $CH_3$ | 2 | n-$C_3H_7$ | H | H | 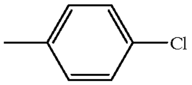 |
| Br | H | $CH_3$ | 2 | iso-$C_3H_7$ | H | H | $CH_3$ |
| Br | H | $CH_3$ | 2 | iso-$C_3H_7$ | H | H | $C_2H_5$ |
| Br | H | $CH_3$ | 2 | iso-$C_3H_7$ | H | H | n-$C_3H_7$ |
| Br | H | $CH_3$ | 2 | iso-$C_3H_7$ | H | H | iso-$C_3H_7$ |
| Br | H | $CH_3$ | 2 | iso-$C_3H_7$ | H | H | n-$C_4H_9$ |
| Br | H | $CH_3$ | 2 | iso-$C_3H_7$ | H | H | iso-$C_4H_9$ |
| Br | H | $CH_3$ | 2 | iso-$C_3H_7$ | H | H | sec-$C_4H_9$ |
| Br | H | $CH_3$ | 2 | iso-$C_3H_7$ | H | H | tert-$C_4H_9$ |
| Br | H | $CH_3$ | 2 | iso-$C_3H_7$ | H | H | $(CH_2)_3Cl$ |
| Br | H | $CH_3$ | 2 | iso-$C_3H_7$ | H | H | $(CH_2)_4Cl$ |
| Br | H | $CH_3$ | 2 | iso-$C_3H_7$ | H | H | $CH_2CN$ |
| Br | H | $CH_3$ | 2 | iso-$C_3H_7$ | H | H | $CH_2CO_2C_2H_5$ |
| Br | H | $CH_3$ | 2 | iso-$C_3H_7$ | H | H | $CH_2OCH_3$ |
| Br | H | $CH_3$ | 2 | iso-$C_3H_7$ | H | H | $C_6H_5$ |
| Br | H | $CH_3$ | 2 | iso-$C_3H_7$ | H | H | 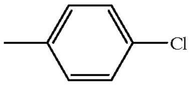 |
| Br | H | $C_2H_5$ | 0 | H | H | H | $CH_3$ |
| Br | H | $C_2H_5$ | 0 | H | H | H | $C_2H_5$ |
| Br | H | $C_2H_5$ | 0 | H | H | H | n-$C_3H_7$ |
| Br | H | $C_2H_5$ | 0 | H | H | H | iso-$C_3H_7$ |
| Br | H | $C_2H_5$ | 0 | H | H | H | n-$C_4H_9$ |
| Br | H | $C_2H_5$ | 0 | H | H | H | iso-$C_4H_9$ |
| Br | H | $C_2H_5$ | 0 | H | H | H | sec-$C_4H_9$ |
| Br | H | $C_2H_5$ | 0 | H | H | H | tert-$C_4H_9$ |
| Br | H | $C_2H_5$ | 0 | H | H | H | n-$C_5H_{11}$ |
| Br | H | $C_2H_5$ | 0 | H | H | H | n-$C_5H_{13}$ |
| Br | H | $C_2H_5$ | 0 | H | H | H | $(CH_2)_4Cl$ |
| Br | H | $C_2H_5$ | 0 | H | H | H | $(CH_2)_3Cl$ |
| Br | H | $C_2H_5$ | 0 | H | H | H | $CH_2CN$ |

TABLE 2-continued

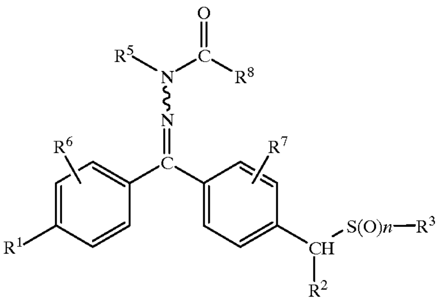

| $R^1$ | $R^2$ | $R^3$ | n | $R^5$ | $R^6$ | $R^7$ | $R^8$ |
|---|---|---|---|---|---|---|---|
| Br | H | $C_2H_5$ | 0 | H | H | H | 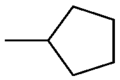 |
| Br | H | $C_2H_5$ | 0 | H | H | H | 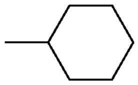 |
| Br | H | $C_2H_5$ | 0 | $CH_3$ | H | H | $CH_3$ |
| Br | H | $C_2H_5$ | 0 | $CH_3$ | H | H | $C_2H_5$ |
| Br | H | $C_2H_5$ | 0 | $CH_3$ | H | H | n-$C_3H_7$ |
| Br | H | $C_2H_5$ | 0 | $CH_3$ | H | H | iso-$C_3H_7$ |
| Br | H | $C_2H_5$ | 0 | $CH_3$ | H | H | n-$C_4H_9$ |
| Br | H | $C_2H_5$ | 0 | $CH_3$ | H | H | iso-$C_4H_9$ |
| Br | H | $C_2H_5$ | 0 | $CH_3$ | H | H | sec-$C_4H_9$ |
| Br | H | $C_2H_5$ | 0 | $CH_3$ | H | H | tert-$C_4H_9$ |
| Br | H | $C_2H_5$ | 0 | $CH_3$ | H | H | $(CH_2)_3Cl$ |
| Br | H | $C_2H_5$ | 0 | $CH_3$ | H | H | $(CH_2)_4Cl$ |
| Br | H | $C_2H_5$ | 0 | $CH_3$ | H | H | $CH_2CN$ |
| Br | H | $C_2H_5$ | 0 | $CH_3$ | H | H | $CH_2CO_2C_2H_5$ |
| Br | H | $C_2H_5$ | 0 | $CH_3$ | H | H | $CH_2OCH_3$ |
| Br | H | $C_2H_5$ | 0 | $CH_3$ | H | H | $C_6H_5$ |
| Br | H | $C_2H_5$ | 0 | $CH_3$ | H | H | 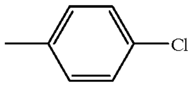 |
| Br | H | $C_2H_5$ | 0 | $C_2H_5$ | H | H | $CH_3$ |
| Br | H | $C_2H_5$ | 0 | $C_2H_5$ | H | H | $C_2H_5$ |
| Br | H | $C_2H_5$ | 0 | $C_2H_5$ | H | H | n-$C_3H_7$ |
| Br | H | $C_2H_5$ | 0 | $C_2H_5$ | H | H | iso-$C_3H_7$ |
| Br | H | $C_2H_5$ | 0 | $C_2H_5$ | H | H | n-$C_4H_9$ |
| Br | H | $C_2H_5$ | 0 | $C_2H_5$ | H | H | iso-$C_4H_9$ |
| Br | H | $C_2H_5$ | 0 | $C_2H_5$ | H | H | sec-$C_4H_9$ |
| Br | H | $C_2H_5$ | 0 | $C_2H_5$ | H | H | tert-$C_4H_9$ |
| Br | H | $C_2H_5$ | 0 | $C_2H_5$ | H | H | $(CH_2)_3Cl$ |
| Br | H | $C_2H_5$ | 0 | $C_2H_5$ | H | H | $(CH_2)_4Cl$ |
| Br | H | $C_2H_5$ | 0 | $C_2H_5$ | H | H | $CH_2CN$ |
| Br | H | $C_2H_5$ | 0 | $C_2H_5$ | H | H | $CH_2CO_2C_2H_5$ |
| Br | H | $C_2H_5$ | 0 | $C_2H_5$ | H | H | $CH_2OCH_3$ |
| Br | H | $C_2H_5$ | 0 | $C_2H_5$ | H | H | $C_6H_5$ |
| Br | H | $C_2H_5$ | 0 | $C_2H_5$ | H | H | 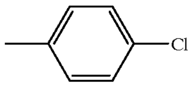 |
| Br | H | $C_2H_5$ | 0 | n-$C_3H_7$ | H | H | $CH_3$ |
| Br | H | $C_2H_5$ | 0 | n-$C_3H_7$ | H | H | $C_2H_5$ |
| Br | H | $C_2H_5$ | 0 | n-$C_3H_7$ | H | H | n-$C_3H_7$ |
| Br | H | $C_2H_5$ | 0 | n-$C_3H_7$ | H | H | iso-$C_3H_7$ |
| Br | H | $C_2H_5$ | 0 | n-$C_3H_7$ | H | H | n-$C_4H_9$ |
| Br | H | $C_2H_5$ | 0 | n-$C_3H_7$ | H | H | iso-$C_4H_9$ |
| Br | H | $C_2H_5$ | 0 | n-$C_3H_7$ | H | H | sec-$C_4H_9$ |
| Br | H | $C_2H_5$ | 0 | n-$C_3H_7$ | H | H | tert-$C_4H_9$ |

TABLE 2-continued

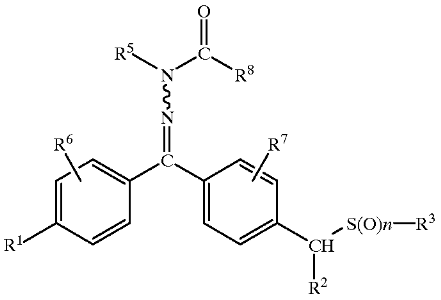

| $R^1$ | $R^2$ | $R^3$ | n | $R^5$ | $R^6$ | $R^7$ | $R^8$ |
|---|---|---|---|---|---|---|---|
| Br | H | $C_2H_5$ | 0 | n-$C_3H_7$ | H | H | $(CH_2)_3Cl$ |
| Br | H | $C_2H_5$ | 0 | n-$C_3H_7$ | H | H | $(CH_2)_4Cl$ |
| Br | H | $C_2H_5$ | 0 | n-$C_3H_7$ | H | H | $CH_2CN$ |
| Br | H | $C_2H_5$ | 0 | n-$C_3H_7$ | H | H | $CH_2CO_2C_2H_5$ |
| Br | H | $C_2H_5$ | 0 | n-$C_3H_7$ | H | H | $CH_2OCH_3$ |
| Br | H | $C_2H_5$ | 0 | n-$C_3H_7$ | H | H | $C_6H_5$ |
| Br | H | $C_2H_5$ | 0 | n-$C_3H_7$ | H | H | 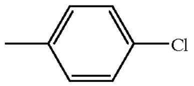 |
| Br | H | $C_2H_5$ | 0 | iso-$C_3H_7$ | H | H | $CH_3$ |
| Br | H | $C_2H_5$ | 0 | iso-$C_3H_7$ | H | H | $C_2H_5$ |
| Br | H | $C_2H_5$ | 0 | iso-$C_3H_7$ | H | H | n-$C_3H_7$ |
| Br | H | $C_2H_5$ | 0 | iso-$C_3H_7$ | H | H | iso-$C_3H_7$ |
| Br | H | $C_2H_5$ | 0 | iso-$C_3H_7$ | H | H | n-$C_4H_9$ |
| Br | H | $C_2H_5$ | 0 | iso-$C_3H_7$ | H | H | iso-$C_4H_9$ |
| Br | H | $C_2H_5$ | 0 | iso-$C_3H_7$ | H | H | sec-$C_4H_9$ |
| Br | H | $C_2H_5$ | 0 | iso-$C_3H_7$ | H | H | tert-$C_4H_9$ |
| Br | H | $C_2H_5$ | 0 | iso-$C_3H_7$ | H | H | $(CH_2)_3Cl$ |
| Br | H | $C_2H_5$ | 0 | iso-$C_3H_7$ | H | H | $(CH_2)_4Cl$ |
| Br | H | $C_2H_5$ | 0 | iso-$C_3H_7$ | H | H | $CH_2CN$ |
| Br | H | $C_2H_5$ | 0 | iso-$C_3H_7$ | H | H | $CH_2CO_2C_2H_5$ |
| Br | H | $C_2H_5$ | 0 | iso-$C_3H_7$ | H | H | $CH_2OCH_3$ |
| Br | H | $C_2H_5$ | 0 | iso-$C_3H_7$ | H | H | $C_6H_5$ |
| Br | H | $C_2H_5$ | 0 | iso-$C_3H_7$ | H | H | 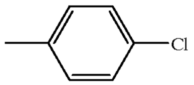 |
| Br | H | $C_2H_5$ | 0 | $CH_2OCH_3$ | H | H | $CH_3$ |
| Br | H | $C_2H_5$ | 0 | $CH_2SCH_3$ | H | H | $CH_3$ |
| Br | H | $C_2H_5$ | 1 | H | H | H | $CH_3$ |
| Br | H | $C_2H_5$ | 1 | H | H | H | $C_2H_5$ |
| Br | H | $C_2H_5$ | 1 | H | H | H | n-$C_3H_7$ |
| Br | H | $C_2H_5$ | 1 | H | H | H | n-$C_4H_9$ |
| Br | H | $C_2H_5$ | 1 | H | H | H | iso-$C_4H_9$ |
| Br | H | $C_2H_5$ | 1 | H | H | H | tert-$C_4H_9$ |
| Br | H | $C_2H_5$ | 1 | H | H | H | $(CH_2)_3Cl$ |
| Br | H | $C_2H_5$ | 1 | H | H | H | $CH_2CN$ |
| Br | H | $C_2H_5$ | 1 | H | H | H | $CH_2OCH_3$ |
| Br | H | $C_2H_5$ | 1 | H | H | H | $CH_2CO_2C_2H_5$ |
| Br | H | $C_2H_5$ | 1 | H | H | H | 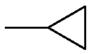 |
| Br | H | $C_2H_5$ | 1 | H | H | H | 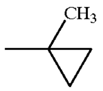 |
| Br | H | $C_2H_5$ | 1 | H | H | H | $C_6H_5$ |

TABLE 2-continued

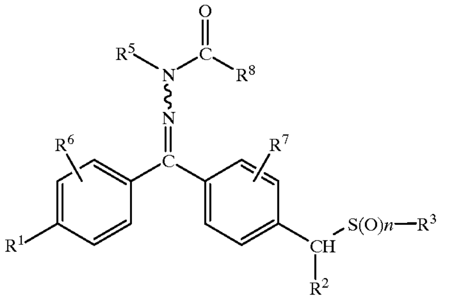

| $R^1$ | $R^2$ | $R^3$ | n | $R^5$ | $R^6$ | $R^7$ | $R^8$ |
|---|---|---|---|---|---|---|---|
| Br | H | $C_2H_5$ | 1 | H | H | H | 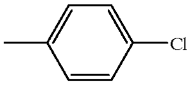 |
| Br | H | $C_2H_5$ | 1 | $CH_3$ | H | H | $CH_3$ |
| Br | H | $C_2H_5$ | 1 | $CH_3$ | H | H | $C_2H_5$ |
| Br | H | $C_2H_5$ | 1 | $CH_3$ | H | H | n-$C_3H_7$ |
| Br | H | $C_2H_5$ | 1 | $CH_3$ | H | H | iso-$C_3H_7$ |
| Br | H | $C_2H_5$ | 1 | $CH_3$ | H | H | n-$C_4H_9$ |
| Br | H | $C_2H_5$ | 1 | $CH_3$ | H | H | iso-$C_4H_9$ |
| Br | H | $C_2H_5$ | 1 | $CH_3$ | H | H | sec-$C_4H_9$ |
| Br | H | $C_2H_5$ | 1 | $CH_3$ | H | H | tert-$C_4H_9$ |
| Br | H | $C_2H_5$ | 1 | $CH_3$ | H | H | $(CH_2)_3Cl$ |
| Br | H | $C_2H_5$ | 1 | $CH_3$ | H | H | $(CH_2)_4Cl$ |
| Br | H | $C_2H_5$ | 1 | $CH_3$ | H | H | $CH_2CN$ |
| Br | H | $C_2H_5$ | 1 | $CH_3$ | H | H | $CH_2CO_2C_2H_5$ |
| Br | H | $C_2H_5$ | 1 | $CH_3$ | H | H | $CH_2OCH_3$ |
| Br | H | $C_2H_5$ | 1 | $CH_3$ | H | H | $C_6H_5$ |
| Br | H | $C_2H_5$ | 1 | $CH_3$ | H | H | 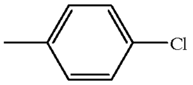 |
| Br | H | $C_2H_5$ | 1 | $C_2H_5$ | H | H | $CH_3$ |
| Br | H | $C_2H_5$ | 1 | $C_2H_5$ | H | H | $C_2H_5$ |
| Br | H | $C_2H_5$ | 1 | $C_2H_5$ | H | H | n-$C_3H_7$ |
| Br | H | $C_2H_5$ | 1 | $C_2H_5$ | H | H | iso-$C_3H_7$ |
| Br | H | $C_2H_5$ | 1 | $C_2H_5$ | H | H | n-$C_4H_9$ |
| Br | H | $C_2H_5$ | 1 | $C_2H_5$ | H | H | iso-$C_4H_9$ |
| Br | H | $C_2H_5$ | 1 | $C_2H_5$ | H | H | sec-$C_4H_9$ |
| Br | H | $C_2H_5$ | 1 | $C_2H_5$ | H | H | tert-$C_4H_9$ |
| Br | H | $C_2H_5$ | 1 | $C_2H_5$ | H | H | $(CH_2)_3Cl$ |
| Br | H | $C_2H_5$ | 1 | $C_2H_5$ | H | H | $(CH_2)_4Cl$ |
| Br | H | $C_2H_5$ | 1 | $C_2H_5$ | H | H | $CH_2CN$ |
| Br | H | $C_2H_5$ | 1 | $C_2H_5$ | H | H | $CH_2CO_2C_2H_5$ |
| Br | H | $C_2H_5$ | 1 | $C_2H_5$ | H | H | $CH_2OCH_3$ |
| Br | H | $C_2H_5$ | 1 | $C_2H_5$ | H | H | $C_6H_5$ |
| Br | H | $C_2H_5$ | 1 | $C_2H_5$ | H | H | 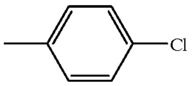 |
| Br | H | $C_2H_5$ | 1 | n-$C_3H_7$ | H | H | $CH_3$ |
| Br | H | $C_2H_5$ | 1 | n-$C_3H_7$ | H | H | $C_2H_5$ |
| Br | H | $C_2H_5$ | 1 | n-$C_3H_7$ | H | H | n-$C_3H_7$ |
| Br | H | $C_2H_5$ | 1 | n-$C_3H_7$ | H | H | iso-$C_3H_7$ |
| Br | H | $C_2H_5$ | 1 | n-$C_3H_7$ | H | H | n-$C_4H_9$ |
| Br | H | $C_2H_5$ | 1 | n-$C_3H_7$ | H | H | iso-$C_4H_9$ |
| Br | H | $C_2H_5$ | 1 | n-$C_3H_7$ | H | H | sec-$C_4H_9$ |
| Br | H | $C_2H_5$ | 1 | n-$C_3H_7$ | H | H | tert-$C_4H_9$ |
| Br | H | $C_2H_5$ | 1 | n-$C_3H_7$ | H | H | $(CH_2)_3Cl$ |
| Br | H | $C_2H_5$ | 1 | n-$C_3H_7$ | H | H | $(CH_2)_4Cl$ |
| Br | H | $C_2H_5$ | 1 | n-$C_3H_7$ | H | H | $CH_2CN$ |
| Br | H | $C_2H_5$ | 1 | n-$C_3H_7$ | H | H | $CH_2CO_2C_2H_5$ |
| Br | H | $C_2H_5$ | 1 | n-$C_3H_7$ | H | H | $CH_2OCH_3$ |
| Br | H | $C_2H_5$ | 1 | n-$C_3H_7$ | H | H | $C_6H_5$ |

TABLE 2-continued

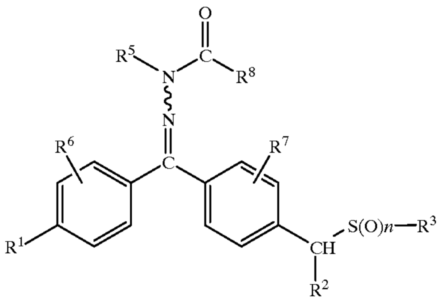

| $R^1$ | $R^2$ | $R^3$ | n | $R^5$ | $R^6$ | $R^7$ | $R^8$ |
|---|---|---|---|---|---|---|---|
| Br | H | $C_2H_5$ | 1 | n-$C_3H_7$ | H | H | 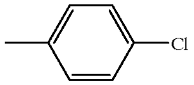 |
| Br | H | $C_2H_5$ | 1 | iso-$C_3H_7$ | H | H | $CH_3$ |
| Br | H | $C_2H_5$ | 1 | iso-$C_3H_7$ | H | H | $C_2H_5$ |
| Br | H | $C_2H_5$ | 1 | iso-$C_3H_7$ | H | H | n-$C_3H_7$ |
| Br | H | $C_2H_5$ | 1 | iso-$C_3H_7$ | H | H | iso-$C_3H_7$ |
| Br | H | $C_2H_5$ | 1 | iso-$C_3H_7$ | H | H | n-$C_4H_9$ |
| Br | H | $C_2H_5$ | 1 | iso-$C_3H_7$ | H | H | iso-$C_4H_9$ |
| Br | H | $C_2H_5$ | 1 | iso-$C_3H_7$ | H | H | sec-$C_4H_9$ |
| Br | H | $C_2H_5$ | 1 | iso-$C_3H_7$ | H | H | tert-$C_4H_9$ |
| Br | H | $C_2H_5$ | 1 | iso-$C_3H_7$ | H | H | $(CH_2)_3Cl$ |
| Br | H | $C_2H_5$ | 1 | iso-$C_3H_7$ | H | H | $(CH_2)_4Cl$ |
| Br | H | $C_2H_5$ | 1 | iso-$C_3H_7$ | H | H | $CH_2CN$ |
| Br | H | $C_2H_5$ | 1 | iso-$C_3H_7$ | H | H | $CH_2CO_2C_2H_5$ |
| Br | H | $C_2H_5$ | 1 | iso-$C_3H_7$ | H | H | $CH_2OCH_3$ |
| Br | H | $C_2H_5$ | 1 | iso-$C_3H_7$ | H | H | $C_6H_5$ |
| Br | H | $C_2H_5$ | 1 | iso-$C_3H_7$ | H | H | 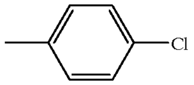 |
| Br | H | $C_2H_5$ | 2 | H | H | H | $CH_3$ |
| Br | H | $C_2H_5$ | 2 | H | H | H | $C_2H_5$ |
| Br | H | $C_2H_5$ | 2 | H | H | H | n-$C_3H_7$ |
| Br | H | $C_2H_5$ | 2 | H | H | H | n-$C_4H_9$ |
| Br | H | $C_2H_5$ | 2 | H | H | H | iso-$C_4H_9$ |
| Br | H | $C_2H_5$ | 2 | H | H | H | tert-$C_4H_9$ |
| Br | H | $C_2H_5$ | 2 | H | H | H | $(CH_2)_3Cl$ |
| Br | H | $C_2H_5$ | 2 | H | H | H | $CH_2CN$ |
| Br | H | $C_2H_5$ | 2 | H | H | H | $CH_2OCH_3$ |
| Br | H | $C_2H_5$ | 2 | H | H | H | $CH_2CO_2C_2H_5$ |
| Br | H | $C_2H_5$ | 2 | H | H | H | 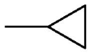 |
| Br | H | $C_2H_5$ | 2 | H | H | H | 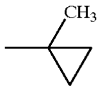 |
| Br | H | $C_2H_5$ | 2 | H | H | H | $C_6H_5$ |
| Br | H | $C_2H_5$ | 2 | H | H | H | 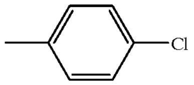 |
| Br | H | $C_2H_5$ | 2 | $CH_3$ | H | H | $CH_3$ |
| Br | H | $C_2H_5$ | 2 | $CH_3$ | H | H | $C_2H_5$ |
| Br | H | $C_2H_5$ | 2 | $CH_3$ | H | H | n-$C_3H_7$ |
| Br | H | $C_2H_5$ | 2 | $CH_3$ | H | H | iso-$C_3H_7$ |
| Br | H | $C_2H_5$ | 2 | $CH_3$ | H | H | n-$C_4H_9$ |
| Br | H | $C_2H_5$ | 2 | $CH_3$ | H | H | iso-$C_4H_9$ |
| Br | H | $C_2H_5$ | 2 | $CH_3$ | H | H | sec-$C_4H_9$ |

TABLE 2-continued

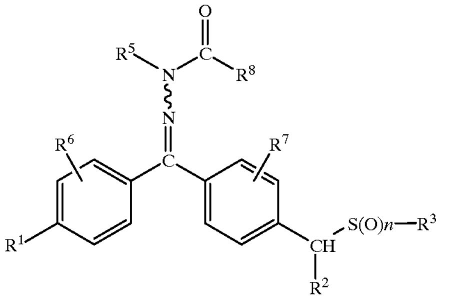

| $R^1$ | $R^2$ | $R^3$ | n | $R^5$ | $R^6$ | $R^7$ | $R^8$ |
|---|---|---|---|---|---|---|---|
| Br | H | $C_2H_5$ | 2 | $CH_3$ | H | H | tert-$C_4H_9$ |
| Br | H | $C_2H_5$ | 2 | $CH_3$ | H | H | $(CH_2)_3Cl$ |
| Br | H | $C_2H_5$ | 2 | $CH_3$ | H | H | $(CH_2)_4Cl$ |
| Br | H | $C_2H_5$ | 2 | $CH_3$ | H | H | $CH_2CN$ |
| Br | H | $C_2H_5$ | 2 | $CH_3$ | H | H | $CH_2CO_2C_2H_5$ |
| Br | H | $C_2H_5$ | 2 | $CH_3$ | H | H | $CH_2OCH_3$ |
| Br | H | $C_2H_5$ | 2 | $CH_3$ | H | H | $C_6H_5$ |
| Br | H | $C_2H_5$ | 2 | $CH_3$ | H | H | 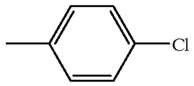 |
| Br | H | $C_2H_5$ | 2 | $C_2H_5$ | H | H | $CH_3$ |
| Br | H | $C_2H_5$ | 2 | $C_2H_5$ | H | H | $C_2H_5$ |
| Br | H | $C_2H_5$ | 2 | $C_2H_5$ | H | H | n-$C_3H_7$ |
| Br | H | $C_2H_5$ | 2 | $C_2H_5$ | H | H | iso-$C_3H_7$ |
| Br | H | $C_2H_5$ | 2 | $C_2H_5$ | H | H | n-$C_4H_9$ |
| Br | H | $C_2H_5$ | 2 | $C_2H_5$ | H | H | iso-$C_4H_9$ |
| Br | H | $C_2H_5$ | 2 | $C_2H_5$ | H | H | sec-$C_4H_9$ |
| Br | H | $C_2H_5$ | 2 | $C_2H_5$ | H | H | tert-$C_4H_9$ |
| Br | H | $C_2H_5$ | 2 | $C_2H_5$ | H | H | $(CH_2)_3Cl$ |
| Br | H | $C_2H_5$ | 2 | $C_2H_5$ | H | H | $(CH_2)_4Cl$ |
| Br | H | $C_2H_5$ | 2 | $C_2H_5$ | H | H | $CH_2CN$ |
| Br | H | $C_2H_5$ | 2 | $C_2H_5$ | H | H | $CH_2CO_2C_2H_5$ |
| Br | H | $C_2H_5$ | 2 | $C_2H_5$ | H | H | $CH_2OCH_3$ |
| Br | H | $C_2H_5$ | 2 | $C_2H_5$ | H | H | $C_6H_5$ |
| Br | H | $C_2H_5$ | 2 | $C_2H_5$ | H | H | 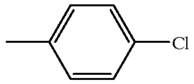 |
| Br | H | $C_2H_5$ | 2 | n-$C_3H_7$ | H | H | $CH_3$ |
| Br | H | $C_2H_5$ | 2 | n-$C_3H_7$ | H | H | $C_2H_5$ |
| Br | H | $C_2H_5$ | 2 | n-$C_3H_7$ | H | H | n-$C_3H_7$ |
| Br | H | $C_2H_5$ | 2 | n-$C_3H_7$ | H | H | iso-$C_3H_7$ |
| Br | H | $C_2H_5$ | 2 | n-$C_3H_7$ | H | H | n-$C_4H_9$ |
| Br | H | $C_2H_5$ | 2 | n-$C_3H_7$ | H | H | iso-$C_4H_9$ |
| Br | H | $C_2H_5$ | 2 | n-$C_3H_7$ | H | H | sec-$C_4H_9$ |
| Br | H | $C_2H_5$ | 2 | n-$C_3H_7$ | H | H | tert-$C_4H_9$ |
| Br | H | $C_2H_5$ | 2 | n-$C_3H_7$ | H | H | $(CH_2)_3Cl$ |
| Br | H | $C_2H_5$ | 2 | n-$C_3H_7$ | H | H | $(CH_2)_4Cl$ |
| Br | H | $C_2H_5$ | 2 | n-$C_3H_7$ | H | H | $CH_2CN$ |
| Br | H | $C_2H_5$ | 2 | n-$C_3H_7$ | H | H | $CH_2CO_2C_2H_5$ |
| Br | H | $C_2H_5$ | 2 | n-$C_3H_7$ | H | H | $CH_2OCH_3$ |
| Br | H | $C_2H_5$ | 2 | n-$C_3H_7$ | H | H | $C_6H_5$ |
| Br | H | $C_2H_5$ | 2 | n-$C_3H_7$ | H | H | 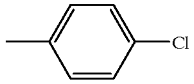 |
| Br | H | $C_2H_5$ | 2 | iso-$C_3H_7$ | H | H | $CH_3$ |
| Br | H | $C_2H_5$ | 2 | iso-$C_3H_7$ | H | H | $C_2H_5$ |
| Br | H | $C_2H_5$ | 2 | iso-$C_3H_7$ | H | H | n-$C_3H_7$ |
| Br | H | $C_2H_5$ | 2 | iso-$C_3H_7$ | H | H | iso-$C_3H_7$ |
| Br | H | $C_2H_5$ | 2 | iso-$C_3H_7$ | H | H | n-$C_4H_9$ |
| Br | H | $C_2H_5$ | 2 | iso-$C_3H_7$ | H | H | iso-$C_4H_9$ |
| Br | H | $C_2H_5$ | 2 | iso-$C_3H_7$ | H | H | sec-$C_4H_9$ |

TABLE 2-continued

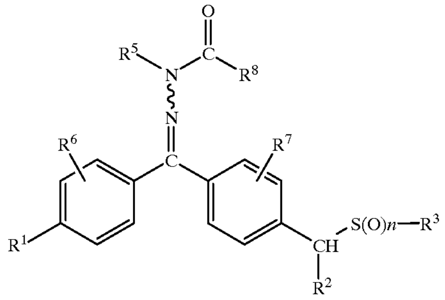

| $R^1$ | $R^2$ | $R^3$ | n | $R^5$ | $R^6$ | $R^7$ | $R^8$ |
|---|---|---|---|---|---|---|---|
| Br | H | $C_2H_5$ | 2 | iso-$C_3H_7$ | H | H | tert-$C_4H_9$ |
| Br | H | $C_2H_5$ | 2 | iso-$C_3H_7$ | H | H | $(CH_2)_3Cl$ |
| Br | H | $C_2H_5$ | 2 | iso-$C_3H_7$ | H | H | $(CH_2)_4Cl$ |
| Br | H | $C_2H_5$ | 2 | iso-$C_3H_7$ | H | H | $CH_2CN$ |
| Br | H | $C_2H_5$ | 2 | iso-$C_3H_7$ | H | H | $CH_2CO_2C_2H_5$ |
| Br | H | $C_2H_5$ | 2 | iso-$C_3H_7$ | H | H | $CH_2OCH_3$ |
| Br | H | $C_2H_5$ | 2 | iso-$C_3H_7$ | H | H | $C_6H_5$ |
| Br | H | $C_2H_5$ | 2 | iso-$C_3H_7$ | H | H | 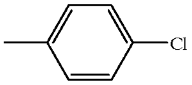 |
| Br | H | n-$C_3H_7$ | 0 | H | H | H | $CH_3$ |
| Br | H | n-$C_3H_7$ | 0 | H | H | H | $C_2H_5$ |
| Br | H | n-$C_3H_7$ | 0 | H | H | H | n-$C_3H_7$ |
| Br | H | n-$C_3H_7$ | 0 | H | H | H | n-$C_4H_9$ |
| Br | H | n-$C_3H_7$ | 0 | H | H | H | iso-$C_4H_9$ |
| Br | H | n-$C_3H_7$ | 0 | H | H | H | tert-$C_4H_9$ |
| Br | H | n-$C_3H_7$ | 0 | H | H | H | $(CH_2)_3Cl$ |
| Br | H | n-$C_3H_7$ | 0 | H | H | H | $CH_2CN$ |
| Br | H | n-$C_3H_7$ | 0 | H | H | H | $CH_2OCH_3$ |
| Br | H | n-$C_3H_7$ | 0 | H | H | H | $CH_2CO_2C_2H_5$ |
| Br | H | n-$C_3H_7$ | 0 | H | H | H | 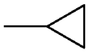 |
| Br | H | n-$C_3H_7$ | 0 | H | H | H | 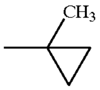 |
| Br | H | n-$C_3H_7$ | 0 | H | H | H | $C_6H_5$ |
| Br | H | n-$C_3H_7$ | 0 | H | H | H | 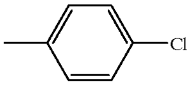 |
| Br | H | n-$C_3H_7$ | 1 | H | H | H | $CH_3$ |
| Br | H | n-$C_3H_7$ | 1 | H | H | H | $C_2H_5$ |
| Br | H | n-$C_3H_7$ | 1 | H | H | H | n-$C_3H_7$ |
| Br | H | n-$C_3H_7$ | 1 | H | H | H | n-$C_4H_9$ |
| Br | H | n-$C_3H_7$ | 1 | H | H | H | iso-$C_4H_9$ |
| Br | H | n-$C_3H_7$ | 1 | H | H | H | tert-$C_4H_9$ |
| Br | H | n-$C_3H_7$ | 1 | H | H | H | $(CH_2)_3Cl$ |
| Br | H | n-$C_3H_7$ | 1 | H | H | H | $CH_2CN$ |
| Br | H | n-$C_3H_7$ | 1 | H | H | H | $CH_2OCH_3$ |
| Br | H | n-$C_3H_7$ | 1 | H | H | H | $CH_2CO_2C_2H_5$ |
| Br | H | n-$C_3H_7$ | 1 | H | H | H | 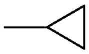 |
| Br | H | n-$C_3H_7$ | 1 | H | H | H | 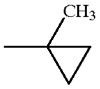 |

TABLE 2-continued

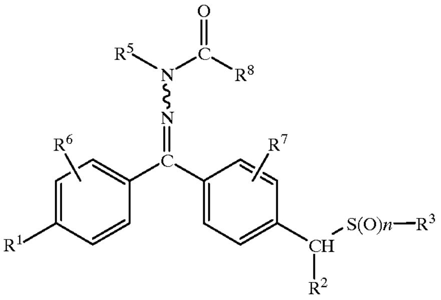

| $R^1$ | $R^2$ | $R^3$ | n | $R^5$ | $R^6$ | $R^7$ | $R^8$ |
|---|---|---|---|---|---|---|---|
| Br | H | n-$C_3H_7$ | 1 | H | H | H | $C_6H_5$ |
| Br | H | n-$C_3H_7$ | 1 | H | H | H | 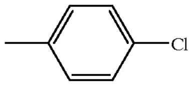 |
| Br | H | n-$C_3H_7$ | 2 | H | H | H | $CH_3$ |
| Br | H | n-$C_3H_7$ | 2 | H | H | H | $C_2H_5$ |
| Br | H | n-$C_3H_7$ | 2 | H | H | H | n-$C_3H_7$ |
| Br | H | n-$C_3H_7$ | 2 | H | H | H | n-$C_4H_9$ |
| Br | H | n-$C_3H_7$ | 2 | H | H | H | iso-$C_4H_9$ |
| Br | H | n-$C_3H_7$ | 2 | H | H | H | tert-$C_4H_9$ |
| Br | H | n-$C_3H_7$ | 2 | H | H | H | $(CH_2)_3Cl$ |
| Br | H | n-$C_3H_7$ | 2 | H | H | H | $CH_2CN$ |
| Br | H | n-$C_3H_7$ | 2 | H | H | H | $CH_2OCH_3$ |
| Br | H | n-$C_3H_7$ | 2 | H | H | H | $CH_2CO_2C_2H_5$ |
| Br | H | n-$C_3H_7$ | 2 | H | H | H | 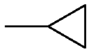 |
| Br | H | n-$C_3H_7$ | 2 | H | H | H | 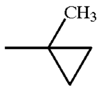 |
| Br | H | n-$C_3H_7$ | 2 | H | H | H | $C_6H_5$ |
| Br | H | n-$C_3H_7$ | 2 | H | H | H | 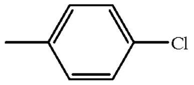 |
| Br | H | $CHF_2$ | 0 | H | H | H | $CH_3$ |
| Br | H | $CHF_2$ | 0 | H | H | H | $C_2H_5$ |
| Br | H | $CHF_2$ | 0 | H | H | H | n-$C_3H_7$ |
| Br | H | $CHF_2$ | 0 | H | H | H | n-$C_4H_9$ |
| Br | H | $CHF_2$ | 0 | H | H | H | iso-$C_4H_9$ |
| Br | H | $CHF_2$ | 0 | H | H | H | tert-$C_4H_9$ |
| Br | H | $CHF_2$ | 0 | H | H | H | $(CH_2)_3Cl$ |
| Br | H | $CHF_2$ | 0 | H | H | H | $CH_2CN$ |
| Br | H | $CHF_2$ | 0 | H | H | H | $CH_2OCH_3$ |
| Br | H | $CHF_2$ | 0 | H | H | H | $CH_2CO_2C_2H_5$ |
| Br | H | $CHF_2$ | 0 | H | H | H | 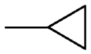 |
| Br | H | $CHF_2$ | 0 | H | H | H | 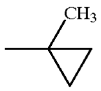 |
| Br | H | $CHF_2$ | 0 | H | H | H | $C_6H_5$ |

TABLE 2-continued

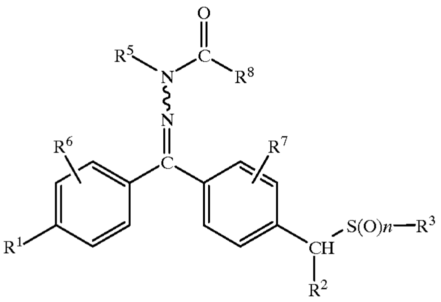

| $R^1$ | $R^2$ | $R^3$ | n | $R^5$ | $R^6$ | $R^7$ | $R^8$ |
|---|---|---|---|---|---|---|---|
| Br | H | $CHF_2$ | 0 | H | H | H | 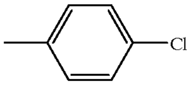 |
| Br | H | $CHF_2$ | 1 | H | H | H | $CH_3$ |
| Br | H | $CHF_2$ | 1 | H | H | H | $C_2H_5$ |
| Br | H | $CHF_2$ | 1 | H | H | H | n-$C_3H_7$ |
| Br | H | $CHF_2$ | 1 | H | H | H | n-$C_4H_9$ |
| Br | H | $CHF_2$ | 1 | H | H | H | iso-$C_4H_9$ |
| Br | H | $CHF_2$ | 1 | H | H | H | tert-$C_4H_9$ |
| Br | H | $CHF_2$ | 1 | H | H | H | $(CH_2)_3Cl$ |
| Br | H | $CHF_2$ | 1 | H | H | H | $CH_2CN$ |
| Br | H | $CHF_2$ | 1 | H | H | H | $CH_2OCH_3$ |
| Br | H | $CHF_2$ | 1 | H | H | H | $CH_2CO_2C_2H_5$ |
| Br | H | $CHF_2$ | 1 | H | H | H | 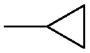 |
| Br | H | $CHF_2$ | 1 | H | H | H | 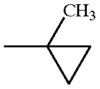 |
| Br | H | $CHF_2$ | 1 | H | H | H | $C_6H_5$ |
| Br | H | $CHF_2$ | 1 | H | H | H | 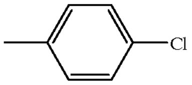 |
| Br | H | $CHF_2$ | 2 | H | H | H | $CH_3$ |
| Br | H | $CHF_2$ | 2 | H | H | H | $C_2H_5$ |
| Br | H | $CHF_2$ | 2 | H | H | H | n-$C_3H_7$ |
| Br | H | $CHF_2$ | 2 | H | H | H | n-$C_4H_9$ |
| Br | H | $CHF_2$ | 2 | H | H | H | iso-$C_4H_9$ |
| Br | H | $CHF_2$ | 2 | H | H | H | tert-$C_4H_9$ |
| Br | H | $CHF_2$ | 2 | H | H | H | $(CH_2)_3Cl$ |
| Br | H | $CHF_2$ | 2 | H | H | H | $CH_2CN$ |
| Br | H | $CHF_2$ | 2 | H | H | H | $CH_2OCH_3$ |
| Br | H | $CHF_2$ | 2 | H | H | H | $CH_2CO_2C_2H_5$ |
| Br | H | $CHF_2$ | 2 | H | H | H | 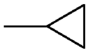 |
| Br | H | $CHF_2$ | 2 | H | H | H | 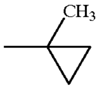 |
| Br | H | $CHF_2$ | 2 | H | H | H | $C_6H_5$ |
| Br | H | $CHF_2$ | 2 | H | H | H | 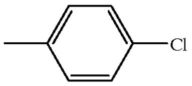 |

TABLE 2-continued

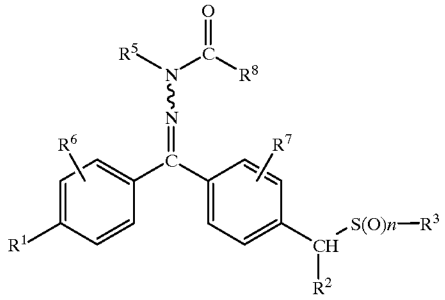

| $R^1$ | $R^2$ | $R^3$ | n | $R^5$ | $R^6$ | $R^7$ | $R^8$ |
|---|---|---|---|---|---|---|---|
| Br | H | $CF_3$ | 0 | H | H | H | $C_6H_5$ |
| Br | H | $CF_3$ | 0 | H | H | H | $CH_3$ |
| Br | H | $CH_2CH_2F$ | 0 | H | H | H | $CH_3$ |
| Br | H | $CH_2CH_2F$ | 0 | H | H | H | $C_2H_5$ |
| Br | H | $CH_2CH_2F$ | 0 | H | H | H | n-$C_3H_7$ |
| Br | H | $CH_2CH_2F$ | 0 | H | H | H | iso-$C_3H_7$ |
| Br | H | $CH_2CH_2F$ | 0 | H | H | H | n-$C_4H_9$ |
| Br | H | $CH_2CH_2F$ | 0 | H | H | H | iso-$C_4H_9$ |
| Br | H | $CH_2CH_2F$ | 0 | H | H | H | tert-$C_4H_9$ |
| Br | H | $CH_2CH_2F$ | 0 | H | H | H | $(CH_2)_3Cl$ |
| Br | H | $CH_2CH_2F$ | 0 | H | H | H | $CH_2CN$ |
| Br | H | $CH_2CH_2F$ | 0 | H | H | H | $CH_2OCH_3$ |
| Br | H | $CH_2CH_2F$ | 0 | H | H | H | $CH_2CO_2C_2H_5$ |
| Br | H | $CH_2CH_2F$ | 0 | H | H | H | 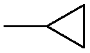 |
| Br | H | $CH_2CH_2F$ | 0 | H | H | H | 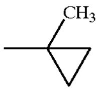 |
| Br | H | $CH_2CH_2F$ | 0 | H | H | H | $C_6H_5$ |
| Br | H | $CH_2CH_2F$ | 0 | H | H | H | 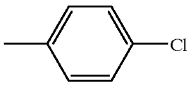 |
| Br | H | $CH_2CH_2F$ | 1 | H | H | H | $CH_3$ |
| Br | H | $CH_2CH_2F$ | 1 | H | H | H | $C_2H_5$ |
| Br | H | $CH_2CH_2F$ | 1 | H | H | H | n-$C_3H_7$ |
| Br | H | $CH_2CH_2F$ | 1 | H | H | H | iso-$C_3H_7$ |
| Br | H | $CH_2CH_2F$ | 1 | H | H | H | n-$C_4H_9$ |
| Br | H | $CH_2CH_2F$ | 1 | H | H | H | iso-$C_4H_9$ |
| Br | H | $CH_2CH_2F$ | 1 | H | H | H | tert-$C_4H_9$ |
| Br | H | $CH_2CH_2F$ | 1 | H | H | H | $(CH_2)_3Cl$ |
| Br | H | $CH_2CH_2F$ | 1 | H | H | H | $CH_2CN$ |
| Br | H | $CH_2CH_2F$ | 1 | H | H | H | $CH_2OCH_3$ |
| Br | H | $CH_2CH_2F$ | 1 | H | H | H | $CH_2CO_2C_2H_5$ |
| Br | H | $CH_2CH_2F$ | 1 | H | H | H | 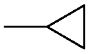 |
| Br | H | $CH_2CH_2F$ | 1 | H | H | H | 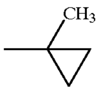 |
| Br | H | $CH_2CH_2F$ | 1 | H | H | H | $C_6H_5$ |
| Br | H | $CH_2CH_2F$ | 1 | H | H | H | 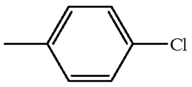 |

TABLE 2-continued

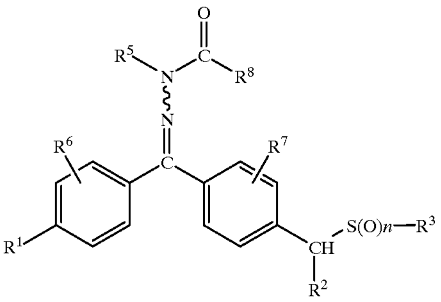

| $R^1$ | $R^2$ | $R^3$ | n | $R^5$ | $R^6$ | $R^7$ | $R^8$ |
|---|---|---|---|---|---|---|---|
| Br | H | $CH_2CH_2F$ | 2 | H | H | H | $CH_3$ |
| Br | H | $CH_2CH_2F$ | 2 | H | H | H | $C_2H_5$ |
| Br | H | $CH_2CH_2F$ | 2 | H | H | H | n-$C_3H_7$ |
| Br | H | $CH_2CH_2F$ | 2 | H | H | H | iso-$C_3H_7$ |
| Br | H | $CH_2CH_2F$ | 2 | H | H | H | n-$C_4H_9$ |
| Br | H | $CH_2CH_2F$ | 2 | H | H | H | iso-$C_4H_9$ |
| Br | H | $CH_2CH_2F$ | 2 | H | H | H | tert-$C_4H_9$ |
| Br | H | $CH_2CH_2F$ | 2 | H | H | H | $(CH_2)_3Cl$ |
| Br | H | $CH_2CH_2F$ | 2 | H | H | H | $CH_2CN$ |
| Br | H | $CH_2CH_2F$ | 2 | H | H | H | $CH_2OCH_3$ |
| Br | H | $CH_2CH_2F$ | 2 | H | H | H | $CH_2CO_2C_2H_5$ |
| Br | H | $CH_2CH_2F$ | 2 | H | H | H | 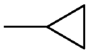 |
| Br | H | $CH_2CH_2F$ | 2 | H | H | H | 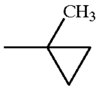 |
| Br | H | $CH_2CH_2F$ | 2 | H | H | H | $C_6H_5$ |
| Br | H | $CH_2CH_2F$ | 2 | H | H | H | 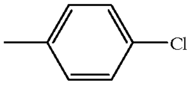 |
| Br | H | $CH_2CHF_2$ | 0 | H | H | H | $CH_3$ |
| Br | H | $CH_2CHF_2$ | 0 | H | H | H | $C_2H_5$ |
| Br | H | $CH_2CHF_2$ | 0 | H | H | H | n-$C_3H_7$ |
| Br | H | $CH_2CHF_2$ | 0 | H | H | H | iso-$C_3H_7$ |
| Br | H | $CH_2CHF_2$ | 0 | H | H | H | n-$C_4H_9$ |
| Br | H | $CH_2CHF_2$ | 0 | H | H | H | iso-$C_4H_9$ |
| Br | H | $CH_2CHF_2$ | 0 | H | H | H | tert-$C_4H_9$ |
| Br | H | $CH_2CHF_2$ | 0 | H | H | H | $(CH_2)_3Cl$ |
| Br | H | $CH_2CHF_2$ | 0 | H | H | H | $CH_2CN$ |
| Br | H | $CH_2CHF_2$ | 0 | H | H | H | $CH_2OCH_3$ |
| Br | H | $CH_2CHF_2$ | 0 | H | H | H | $CH_2CO_2C_2H_5$ |
| Br | H | $CH_2CHF_2$ | 0 | H | H | H | 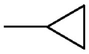 |
| Br | H | $CH_2CHF_2$ | 0 | H | H | H | 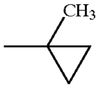 |
| Br | H | $CH_2CHF_2$ | 0 | H | H | H | $C_6H_5$ |
| Br | H | $CH_2CHF_2$ | 0 | H | H | H | 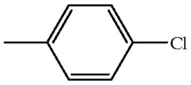 |
| Br | H | $CH_2CHF_2$ | 1 | H | H | H | $CH_3$ |
| Br | H | $CH_2CHF_2$ | 1 | H | H | H | $C_2H_5$ |
| Br | H | $CH_2CHF_2$ | 1 | H | H | H | n-$C_3H_7$ |

TABLE 2-continued

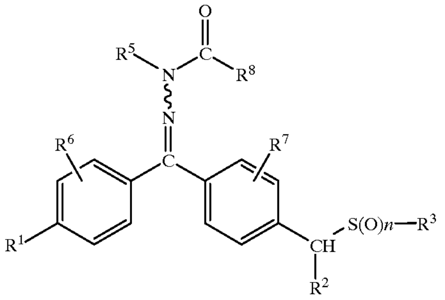

| $R^1$ | $R^2$ | $R^3$ | n | $R^5$ | $R^6$ | $R^7$ | $R^8$ |
|---|---|---|---|---|---|---|---|
| Br | H | $CH_2CHF_2$ | 1 | H | H | H | iso-$C_3H_7$ |
| Br | H | $CH_2CHF_2$ | 1 | H | H | H | n-$C_4H_9$ |
| Br | H | $CH_2CHF_2$ | 1 | H | H | H | iso-$C_4H_9$ |
| Br | H | $CH_2CHF_2$ | 1 | H | H | H | tert-$C_4H_9$ |
| Br | H | $CH_2CHF_2$ | 1 | H | H | H | $(CH_2)_3Cl$ |
| Br | H | $CH_2CHF_2$ | 1 | H | H | H | $CH_2CN$ |
| Br | H | $CH_2CHF_2$ | 1 | H | H | H | $CH_2OCH_3$ |
| Br | H | $CH_2CHF_2$ | 1 | H | H | H | $CH_2CO_2C_2H_5$ |
| Br | H | $CH_2CHF_2$ | 1 | H | H | H | 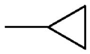 |
| Br | H | $CH_2CHF_2$ | 1 | H | H | H | 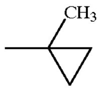 |
| Br | H | $CH_2CHF_2$ | 1 | H | H | H | $C_6H_5$ |
| Br | H | $CH_2CHF_2$ | 1 | H | H | H | 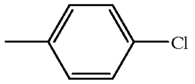 |
| Br | H | $CH_2CHF_2$ | 2 | H | H | H | $CH_3$ |
| Br | H | $CH_2CHF_2$ | 2 | H | H | H | $C_2H_5$ |
| Br | H | $CH_2CHF_2$ | 2 | H | H | H | n-$C_3H_7$ |
| Br | H | $CH_2CHF_2$ | 2 | H | H | H | iso-$C_3H_7$ |
| Br | H | $CH_2CHF_2$ | 2 | H | H | H | n-$C_4H_9$ |
| Br | H | $CH_2CHF_2$ | 2 | H | H | H | iso-$C_4H_9$ |
| Br | H | $CH_2CHF_2$ | 2 | H | H | H | tert-$C_4H_9$ |
| Br | H | $CH_2CHF_2$ | 2 | H | H | H | $(CH_2)_3Cl$ |
| Br | H | $CH_2CHF_2$ | 2 | H | H | H | $CH_2CN$ |
| Br | H | $CH_2CHF_2$ | 2 | H | H | H | $CH_2OCH_3$ |
| Br | H | $CH_2CHF_2$ | 2 | H | H | H | $CH_2CO_2C_2H_5$ |
| Br | H | $CH_2CHF_2$ | 2 | H | H | H | 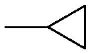 |
| Br | H | $CH_2CHF_2$ | 2 | H | H | H | 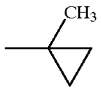 |
| Br | H | $CH_2CHF_2$ | 2 | H | H | H | $C_6H_5$ |
| Br | H | $CH_2CHF_2$ | 2 | H | H | H | 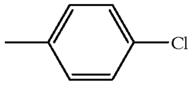 |
| Br | H | $CH_2CF_3$ | 0 | H | H | H | $CH_3$ |
| Br | H | $CH_2CF_3$ | 0 | H | H | H | $C_2H_5$ |
| Br | H | $CH_2CF_3$ | 0 | H | H | H | n-$C_3H_7$ |
| Br | H | $CH_2CF_3$ | 0 | H | H | H | iso-$C_3H_7$ |
| Br | H | $CH_2CF_3$ | 0 | H | H | H | n-$C_4H_9$ |
| Br | H | $CH_2CF_3$ | 0 | H | H | H | iso-$C_4H_9$ |

TABLE 2-continued

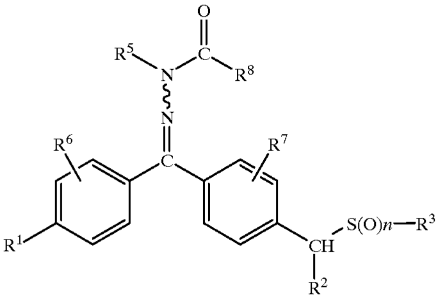

| $R^1$ | $R^2$ | $R^3$ | n | $R^5$ | $R^6$ | $R^7$ | $R^8$ |
|---|---|---|---|---|---|---|---|
| Br | H | $CH_2CF_3$ | 0 | H | H | H | tert-$C_4H_9$ |
| Br | H | $CH_2CF_3$ | 0 | H | H | H | $(CH_2)_3Cl$ |
| Br | H | $CH_2CF_3$ | 0 | H | H | H | $CH_2CN$ |
| Br | H | $CH_2CF_3$ | 0 | H | H | H | $CH_2OCH_3$ |
| Br | H | $CH_2CF_3$ | 0 | H | H | H | $CH_2CO_2C_2H_5$ |
| Br | H | $CH_2CF_3$ | 0 | H | H | H | 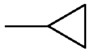 |
| Br | H | $CH_2CF_3$ | 0 | H | H | H | 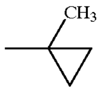 |
| Br | H | $CH_2CF_3$ | 0 | H | H | H | $C_6H_5$ |
| Br | H | $CH_2CF_3$ | 0 | H | H | H | 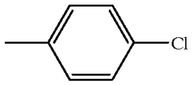 |
| Br | H | $CH_2CF_3$ | 1 | H | H | H | $CH_3$ |
| Br | H | $CH_2CF_3$ | 1 | H | H | H | $C_2H_5$ |
| Br | H | $CH_2CF_3$ | 1 | H | H | H | n-$C_3H_7$ |
| Br | H | $CH_2CF_3$ | 1 | H | H | H | iso-$C_3H_7$ |
| Br | H | $CH_2CF_3$ | 1 | H | H | H | n-$C_4H_9$ |
| Br | H | $CH_2CF_3$ | 1 | H | H | H | iso-$C_4H_9$ |
| Br | H | $CH_2CF_3$ | 1 | H | H | H | tert-$C_4H_9$ |
| Br | H | $CH_2CF_3$ | 1 | H | H | H | $(CH_2)_3Cl$ |
| Br | H | $CH_2CF_3$ | 1 | H | H | H | $CH_2CN$ |
| Br | H | $CH_2CF_3$ | 1 | H | H | H | $CH_2OCH_3$ |
| Br | H | $CH_2CF_3$ | 1 | H | H | H | $CH_2CO_2C_2H_5$ |
| Br | H | $CH_2CF_3$ | 1 | H | H | H | 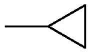 |
| Br | H | $CH_2CF_3$ | 1 | H | H | H | 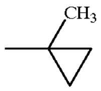 |
| Br | H | $CH_2CF_3$ | 1 | H | H | H | $C_6H_5$ |
| Br | H | $CH_2CF_3$ | 1 | H | H | H | 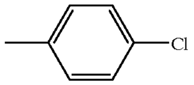 |
| Br | H | $CH_2CF_3$ | 2 | H | H | H | $CH_3$ |
| Br | H | $CH_2CF_3$ | 2 | H | H | H | $C_2H_5$ |
| Br | H | $CH_2CF_3$ | 2 | H | H | H | n-$C_3H_7$ |
| Br | H | $CH_2CF_3$ | 2 | H | H | H | iso-$C_3H_7$ |
| Br | H | $CH_2CF_3$ | 2 | H | H | H | n-$C_4H_9$ |
| Br | H | $CH_2CF_3$ | 2 | H | H | H | iso-$C_4H_9$ |
| Br | H | $CH_2CF_3$ | 2 | H | H | H | tert-$C_4H_9$ |
| Br | H | $CH_2CF_3$ | 2 | H | H | H | $(CH_2)_3Cl$ |
| Br | H | $CH_2CF_3$ | 2 | H | H | H | $CH_2CN$ |

TABLE 2-continued

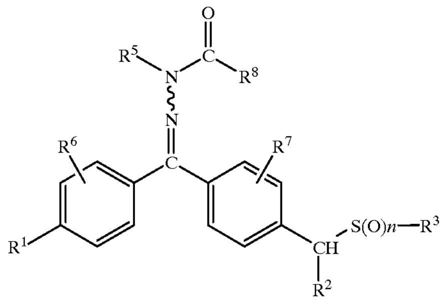

| $R^1$ | $R^2$ | $R^3$ | n | $R^5$ | $R^6$ | $R^7$ | $R^8$ |
|---|---|---|---|---|---|---|---|
| Br | H | $CH_2CF_3$ | 2 | H | H | H | $CH_2OCH_3$ |
| Br | H | $CH_2CF_3$ | 2 | H | H | H | $CH_2CO_2C_2H_5$ |
| Br | H | $CH_2CF_3$ | 2 | H | H | H | 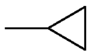 |
| Br | H | $CH_2CF_3$ | 2 | H | H | H | 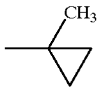 |
| Br | H | $CH_2CF_3$ | 2 | H | H | H | $C_6H_5$ |
| Br | H | $CH_2CF_3$ | 2 | H | H | H | 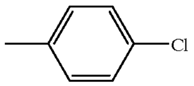 |
| I | H | $C_2H_5$ | 0 | H | H | H | $C_6H_5$ |
| I | H | $CH_3$ | 0 | H | H | H | $CH_3$ |
| I | H | $CH_3$ | 0 | H | H | H | $C_2H_5$ |
| I | H | $CH_3$ | 0 | H | H | H | n-$C_3H_7$ |
| I | H | $CH_3$ | 0 | H | H | H | iso-$C_3H_7$ |
| I | H | $CH_3$ | 0 | H | H | H | n-$C_4H_9$ |
| I | H | $CH_3$ | 2 | H | H | H | $C_2H_5$ |
| I | H | $CH_3$ | 1 | H | H | H | $C_2H_5$ |
| Cl | H | $CH_3$ | 0 | H | H | H | $COCH_3$ |
| Cl | H | $CH_3$ | 1 | H | H | H | $COCH_3$ |
| Cl | H | $CH_3$ | 2 | H | H | H | $COCH_3$ |
| Cl | H | $C_2H_5$ | 0 | H | H | H | $COCH_3$ |
| Cl | H | $CH_3$ | 0 | H | H | H | $CO_2CH_3$ |
| Cl | H | $CH_3$ | 1 | H | H | H | $CO_2CH_3$ |
| Cl | H | $CH_3$ | 2 | H | H | H | $CO_2CH_3$ |
| Cl | H | $C_2H_5$ | 0 | H | H | H | $CO_2CH_3$ |
| Cl | H | $C_2H_5$ | 1 | H | H | H | $CO_2CH_3$ |
| Cl | H | $C_2H_5$ | 2 | H | H | H | $CO_2CH_3$ |
| Cl | H | $CH_3$ | 0 | H | H | H | $CO_2C_2H_5$ |
| Cl | H | $CH_3$ | 1 | H | H | H | $CO_2C_2H_5$ |
| Cl | H | $CH_3$ | 2 | H | H | H | $CO_2C_2H_5$ |
| Cl | H | $C_2H_5$ | 0 | H | H | H | $CO_2C_2H_5$ |
| Cl | H | $C_2H_5$ | 1 | H | H | H | $CO_2C_2H_5$ |
| Cl | H | $C_2H_5$ | 2 | H | H | H | $CO_2C_2H_5$ |
| Br | H | $C_2H_5$ | 0 | H | H | H | 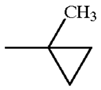 |
| Br | H | $C_2H_5$ | 0 | H | H | H | 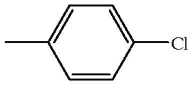 |
| Br | H | $C_2H_5$ | 0 | H | H | H | $C_6H_5$ |
| Br | H | $C_2H_5$ | 0 | H | H | H | $CH_2CO_2C_2H_5$ |
| Br | H | $C_2H_5$ | 0 | H | H | H | $CH_2OCH_3$ |

TABLE 2-continued

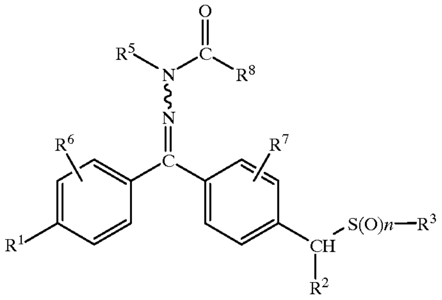

| $R^1$ | $R^2$ | $R^3$ | n | $R^5$ | $R^6$ | $R^7$ | $R^8$ |
|---|---|---|---|---|---|---|---|
| Br | H | $C_2H_5$ | 0 | H | H | H | 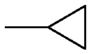 |
| Br | H | $C_2H_5$ | 1 | H | H | H | iso-$C_3H_7$ |
| Br | H | $C_2H_5$ | 1 | H | H | H | sec-$C_4H_9$ |
| Br | H | $C_2H_5$ | 2 | H | H | H | iso-$C_3H_7$ |
| Br | H | $C_2H_5$ | 2 | H | H | H | sec-$C_4H_9$ |
| Br | H | $CH_3$ | 1 | H | H | H | sec-$C_4H_9$ |
| Br | H | $CH_3$ | 2 | H | H | H | sec-$C_4H_9$ |
| Cl | H | $C_2H_5$ | 0 | $C_2H_5$ | H | H | 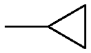 |
| Cl | H | $C_2H_5$ | 0 | $C_2H_5$ | H | H | $COCH_3$ |
| Cl | H | $C_2H_5$ | 0 | $C_2H_5$ | H | H | $CO_2C_2H_5$ |
| Cl | H | $C_2H_5$ | 0 | $C_2H_5$ | H | H | $CO_2CH_3$ |
| Cl | H | $C_2H_5$ | 0 | $CH_2OC_2H_5$ | H | H | $C_2H_5$ |
| Cl | H | $C_2H_5$ | 0 | $CH_2OC_2H_5$ | H | H | $CH_2OCH_3$ |
| Cl | H | $C_2H_5$ | 0 | $CH_2OC_2H_5$ | H | H | n-$C_3H_7$ |
| Cl | H | $C_2H_5$ | 0 | $CH_2OC_2H_5$ | H | H | n-$C_4H_9$ |
| Cl | H | $C_2H_5$ | 0 | $CH_2OC_2H_5$ | H | H | tert-$C_4H_9$ |
| Cl | H | $C_2H_5$ | 0 | $CH_2OCH_3$ | H | H | $C_2H_5$ |
| Cl | H | $C_2H_5$ | 0 | $CH_2OCH_3$ | H | H | $CH_2OCH_3$ |
| Cl | H | $C_2H_5$ | 0 | $CH_2OCH_3$ | H | H | n-$C_3H_7$ |
| Cl | H | $C_2H_5$ | 0 | $CH_2OCH_3$ | H | H | n-$C_4H_9$ |
| Cl | H | $C_2H_5$ | 0 | $CH_2OCH_3$ | H | H | tert-$C_4H_9$ |
| Cl | H | $C_2H_5$ | 0 | $CH_2SCH_3$ | H | H | $C_2H_5$ |
| Cl | H | $C_2H_5$ | 0 | $CH_2SCH_3$ | H | H | $CH_2OCH_3$ |
| Cl | H | $C_2H_5$ | 0 | $CH_2SCH_3$ | H | H | n-$C_3H_7$ |
| Cl | H | $C_2H_5$ | 0 | $CH_2SCH_3$ | H | H | n-$C_4H_9$ |
| Cl | H | $C_2H_5$ | 0 | $CH_2SCH_3$ | H | H | tert-$C_4H_9$ |
| Cl | H | $C_2H_5$ | 0 | $CH_3$ | H | H | 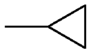 |
| Cl | H | $C_2H_5$ | 0 | $CH_3$ | H | H | $COCH_3$ |
| Cl | H | $C_2H_5$ | 0 | $CH_3$ | H | H | $CO_2C_2H_5$ |
| Cl | H | $C_2H_5$ | 0 | $CH_3$ | H | H | $CO_2CH_3$ |
| Cl | H | $C_2H_5$ | 0 | $COC_2H_5$ | H | H | $CH_2OCH_3$ |
| Cl | H | $C_2H_5$ | 0 | $COC_2H_5$ | H | H | n-$C_3H_7$ |
| Cl | H | $C_2H_5$ | 0 | $COC_2H_5$ | H | H | n-$C_4H_9$ |
| Cl | H | $C_2H_5$ | 0 | $COC_2H_5$ | H | H | tert-$C_4H_9$ |
| Cl | H | $C_2H_5$ | 0 | $COC_3H_7$-n | H | H | $C_2H_5$ |
| Cl | H | $C_2H_5$ | 0 | $COC_3H_7$-n | H | H | $CH_2OCH_3$ |
| Cl | H | $C_2H_5$ | 0 | $COC_3H_7$-n | H | H | n-$C_3H_7$ |
| Cl | H | $C_2H_5$ | 0 | $COC_3H_7$-n | H | H | n-$C_4H_9$ |
| Cl | H | $C_2H_5$ | 0 | $COC_3H_7$-n | H | H | tert-$C_4H_9$ |
| Cl | H | $C_2H_5$ | 0 | $COCH_3$ | H | H | $C_2H_5$ |
| Cl | H | $C_2H_5$ | 0 | $COCH_3$ | H | H | $CH_2OCH_3$ |
| Cl | H | $C_2H_5$ | 0 | $COCH_3$ | H | H | $CH_3$ |
| Cl | H | $C_2H_5$ | 0 | $COCH_3$ | H | H | n-$C_3H_7$ |
| Cl | H | $C_2H_5$ | 0 | $COCH_3$ | H | H | n-$C_4H_9$ |
| Cl | H | $C_2H_5$ | 0 | $COCH_3$ | H | H | tert-$C_4H_9$ |
| Cl | H | $C_2H_5$ | 0 | H | H | H | $(CH_2)_5Br$ |
| Cl | H | $C_2H_5$ | 0 | H | H | H | $CH_2CH_2CO_2H$ |
| Cl | H | $C_2H_5$ | 0 | H | H | H | $CH_2CH_2SCH_3$ |
| Cl | H | $C_2H_5$ | 0 | H | H | H | $CO_2C_2H_5$ |
| Cl | H | $C_2H_5$ | 0 | H | H | H | $CO_2CH_3$ |

TABLE 2-continued

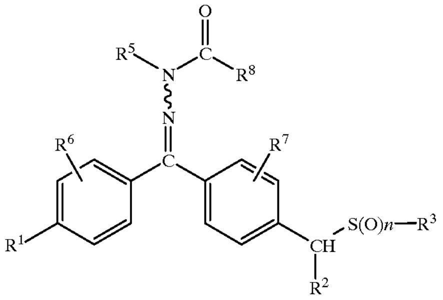

| $R^1$ | $R^2$ | $R^3$ | n | $R^5$ | $R^6$ | $R^7$ | $R^8$ |
|---|---|---|---|---|---|---|---|
| Cl | H | $C_2H_5$ | 0 | H | H | H | $COCH_3$ |
| Cl | H | $C_2H_5$ | 0 | iso-$C_3H_7$ | H | H | 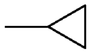 |
| Cl | H | $C_2H_5$ | 0 | iso-$C_3H_7$ | H | H | $COCH_3$ |
| Cl | H | $C_2H_5$ | 0 | iso-$C_3H_7$ | H | H | $CO_2CH_3$ |
| Cl | H | $C_2H_5$ | 0 | n-$C_3H_7$ | H | H | 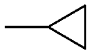 |
| Cl | H | $C_2H_5$ | 0 | n-$C_3H_7$ | H | H | $COCH_3$ |
| Cl | H | $C_2H_5$ | 0 | n-$C_3H_7$ | H | H | $CO_2CH_3$ |
| Cl | H | $C_2H_5$ | 1 | $C_2H_5$ | H | H | 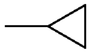 |
| Cl | H | $C_2H_5$ | 1 | $C_2H_5$ | H | H | $COCH_3$ |
| Cl | H | $C_2H_5$ | 1 | $C_2H_5$ | H | H | $CO_2C_2H_5$ |
| Cl | H | $C_2H_5$ | 1 | $C_2H_5$ | H | H | $CO_2CH_3$ |
| Cl | H | $C_2H_5$ | 1 | $CH_2OC_2H_5$ | H | H | $C_2H_5$ |
| Cl | H | $C_2H_5$ | 1 | $CH_2OC_2H_5$ | H | H | $CH_2OCH_3$ |
| Cl | H | $C_2H_5$ | 1 | $CH_2OC_2H_5$ | H | H | $CH_3$ |
| Cl | H | $C_2H_5$ | 1 | $CH_2OC_2H_5$ | H | H | n-$C_3H_7$ |
| Cl | H | $C_2H_5$ | 1 | $CH_2OC_2H_5$ | H | H | n-$C_4H_9$ |
| Cl | H | $C_2H_5$ | 1 | $CH_2OC_2H_5$ | H | H | tert-$C_4H_9$ |
| Cl | H | $C_2H_5$ | 1 | $CH_2OCH_3$ | H | H | $C_2H_5$ |
| Cl | H | $C_2H_5$ | 1 | $CH_2OCH_3$ | H | H | $CH_2OCH_3$ |
| Cl | H | $C_2H_5$ | 1 | $CH_2OCH_3$ | H | H | $CH_3$ |
| Cl | H | $C_2H_5$ | 1 | $CH_2OCH_3$ | H | H | n-$C_3H_7$ |
| Cl | H | $C_2H_5$ | 1 | $CH_2OCH_3$ | H | H | n-$C_4H_9$ |
| Cl | H | $C_2H_5$ | 1 | $CH_2OCH_3$ | H | H | tert-$C_4H_9$ |
| Cl | H | $C_2H_5$ | 1 | $CH_2SCH_3$ | H | H | $C_2H_5$ |
| Cl | H | $C_2H_5$ | 1 | $CH_2SCH_3$ | H | H | $CH_2OCH_3$ |
| Cl | H | $C_2H_5$ | 1 | $CH_2SCH_3$ | H | H | $CH_3$ |
| Cl | H | $C_2H_5$ | 1 | $CH_2SCH_3$ | H | H | n-$C_3H_7$ |
| Cl | H | $C_2H_5$ | 1 | $CH_2SCH_3$ | H | H | n-$C_4H_9$ |
| Cl | H | $C_2H_5$ | 1 | $CH_2SCH_3$ | H | H | tert-$C_4H_9$ |
| Cl | H | $C_2H_5$ | 1 | $CH_3$ | H | H | 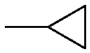 |
| Cl | H | $C_2H_5$ | 1 | $CH_3$ | H | H | $COCH_3$ |
| Cl | H | $C_2H_5$ | 1 | $CH_3$ | H | H | $CO_2C_2H_5$ |
| Cl | H | $C_2H_5$ | 1 | $CH_3$ | H | H | $CO_2CH_3$ |
| Cl | H | $C_2H_5$ | 1 | $COC_2H_5$ | H | H | $C_2H_5$ |
| Cl | H | $C_2H_5$ | 1 | $COC_2H_5$ | H | H | $CH_2OCH_3$ |
| Cl | H | $C_2H_5$ | 1 | $COC_2H_5$ | H | H | $CH_3$ |
| Cl | H | $C_2H_5$ | 1 | $COC_2H_5$ | H | H | n-$C_3H_7$ |
| Cl | H | $C_2H_5$ | 1 | $COC_2H_5$ | H | H | n-$C_4H_9$ |
| Cl | H | $C_2H_5$ | 1 | $COC_2H_5$ | H | H | tert-$C_4H_9$ |
| Cl | H | $C_2H_5$ | 1 | $COC_3H_7$-n | H | H | $C_2H_5$ |
| Cl | H | $C_2H_5$ | 1 | $COC_3H_7$-n | H | H | $CH_2OCH_3$ |
| Cl | H | $C_2H_5$ | 1 | $COC_3H_7$-n | H | H | $CH_3$ |
| Cl | H | $C_2H_5$ | 1 | $COC_3H_7$-n | H | H | n-$C_3H_7$ |
| Cl | H | $C_2H_5$ | 1 | $COC_3H_7$-n | H | H | n-$C_4H_9$ |
| Cl | H | $C_2H_5$ | 1 | $COC_3H_7$-n | H | H | tert-$C_4H_9$ |

TABLE 2-continued

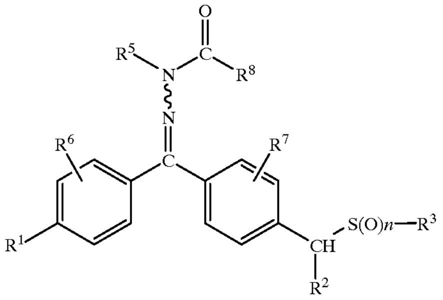

| $R^1$ | $R^2$ | $R^3$ | n | $R^5$ | $R^6$ | $R^7$ | $R^8$ |
|---|---|---|---|---|---|---|---|
| Cl | H | $C_2H_5$ | 1 | $COCH_3$ | H | H | $C_2H_5$ |
| Cl | H | $C_2H_5$ | 1 | $COCH_3$ | H | H | $CH_2OCH_3$ |
| Cl | H | $C_2H_5$ | 1 | $COCH_3$ | H | H | $CH_3$ |
| Cl | H | $C_2H_5$ | 1 | $COCH_3$ | H | H | n-$C_3H_7$ |
| Cl | H | $C_2H_5$ | 1 | $COCH_3$ | H | H | n-$C_4H_9$ |
| Cl | H | $C_2H_5$ | 1 | $COCH_3$ | H | H | tert-$C_4H_9$ |
| Cl | H | $C_2H_5$ | 1 | H | H | H | $(CH_2)sBr$ |
| Cl | H | $C_2H_5$ | 1 | H | H | H | $CH_2CH_2CO_2H$ |
| Cl | H | $C_2H_5$ | 1 | H | H | H | $CH_2CH_2SCH_3$ |
| Cl | H | $C_2H_5$ | 1 | H | H | H | $CO_2C_2H_5$ |
| Cl | H | $C_2H_5$ | 1 | H | H | H | $CO_2CH_3$ |
| Cl | H | $C_2H_5$ | 1 | H | H | H | $COCH_3$ |
| Cl | H | $C_2H_5$ | 1 | H | H | H | 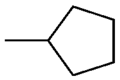 |
| Cl | H | $C_2H_5$ | 1 | H | H | H | 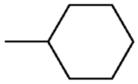 |
| Cl | H | $C_2H_5$ | 1 | H | H | H | sec-$C_4H_9$ |
| Cl | H | $C_2H_5$ | 1 | iso-$C_3H_7$ | H | H | 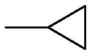 |
| Cl | H | $C_2H_5$ | 1 | iso-$C_3H_7$ | H | H | $COCH_3$ |
| Cl | H | $C_2H_5$ | 1 | iso-$C_3H_7$ | H | H | $CO_2CH_3$ |
| Cl | H | $C_2H_5$ | 1 | n-$C_3H_7$ | H | H | 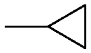 |
| Cl | H | $C_2H_5$ | 1 | n-$C_3H_7$ | H | H | $COCH_3$ |
| Cl | H | $C_2H_5$ | 1 | n-$C_3H_7$ | H | H | $CO_2CH_3$ |
| Cl | H | $C_2H_5$ | 2 | $C_2H_5$ | H | H | 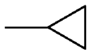 |
| Cl | H | $C_2H_5$ | 2 | $C_2H_5$ | H | H | $COCH_3$ |
| Cl | H | $C_2H_5$ | 2 | $C_2H_5$ | H | H | $CO_2C_2H_5$ |
| Cl | H | $C_2H_5$ | 2 | $C_2H_5$ | H | H | $CO_2CH_3$ |
| Cl | H | $C_2H_5$ | 2 | $CH_2OC_2H_5$ | H | H | $C_2H_5$ |
| Cl | H | $C_2H_5$ | 2 | $CH_2OC_2H_5$ | H | H | $CH_2OCH_3$ |
| Cl | H | $C_2H_5$ | 2 | $CH_2OC_2H_5$ | H | H | $CH_3$ |
| Cl | H | $C_2H_5$ | 2 | $CH_2OC_2H_5$ | H | H | n-$C_3H_7$ |
| Cl | H | $C_2H_5$ | 2 | $CH_2OC_2H_5$ | H | H | n-$C_4H_9$ |
| Cl | H | $C_2H_5$ | 2 | $CH_2OC_2H_5$ | H | H | tert-$C_4H_9$ |
| Cl | H | $C_2H_5$ | 2 | $CH_2OCH_3$ | H | H | $C_2H_5$ |
| Cl | H | $C_2H_5$ | 2 | $CH_2OCH_3$ | H | H | $CH_2OCH_3$ |
| Cl | H | $C_2H_5$ | 2 | $CH_2OCH_3$ | H | H | $CH_3$ |
| Cl | H | $C_2H_5$ | 2 | $CH_2OCH_3$ | H | H | n-$C_3H_7$ |
| Cl | H | $C_2H_5$ | 2 | $CH_2OCH_3$ | H | H | n-$C_4H_9$ |
| Cl | H | $C_2H_5$ | 2 | $CH_2OCH_3$ | H | H | tert-$C_4H_9$ |
| Cl | H | $C_2H_5$ | 2 | $CH_2SCH_3$ | H | H | $C_2H_5$ |
| Cl | H | $C_2H_5$ | 2 | $CH_2SCH_3$ | H | H | $CH_2OCH_3$ |

TABLE 2-continued

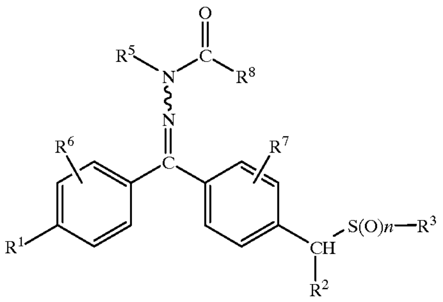

| $R^1$ | $R^2$ | $R^3$ | n | $R^5$ | $R^6$ | $R^7$ | $R^8$ |
|---|---|---|---|---|---|---|---|
| Cl | H | $C_2H_5$ | 2 | $CH_2SCH_3$ | H | H | $CH_3$ |
| Cl | H | $C_2H_5$ | 2 | $CH_2SCH_3$ | H | H | n-$C_3H_7$ |
| Cl | H | $C_2H_5$ | 2 | $CH_2SCH_3$ | H | H | n-$C_4H_9$ |
| Cl | H | $C_2H_5$ | 2 | $CH_2SCH_3$ | H | H | tert-$C_4H_9$ |
| Cl | H | $C_2H_5$ | 2 | $CH_3$ | H | H | 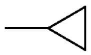 |
| Cl | H | $C_2H_5$ | 2 | $CH_3$ | H | H | $COCH_3$ |
| Cl | H | $C_2H_5$ | 2 | $CH_3$ | H | H | $CO_2C_2H_5$ |
| Cl | H | $C_2H_5$ | 2 | $CH_3$ | H | H | $CO_2CH_3$ |
| Cl | H | $C_2H_5$ | 2 | $COC_2H_5$ | H | H | $C_2H_5$ |
| Cl | H | $C_2H_5$ | 2 | $COC_2H_5$ | H | H | $CH_2OCH_3$ |
| Cl | H | $C_2H_5$ | 2 | $COC_2H_5$ | H | H | $CH_3$ |
| Cl | H | $C_2H_5$ | 2 | $COC_2H_5$ | H | H | n-$C_3H_7$ |
| Cl | H | $C_2H_5$ | 2 | $COC_2H_5$ | H | H | n-$C_4H_9$ |
| Cl | H | $C_2H_5$ | 2 | $COC_2H_5$ | H | H | tert-$C_4H_9$ |
| Cl | H | $C_2H_5$ | 2 | $COC_3H_7$-n | H | H | $C_2H_5$ |
| Cl | H | $C_2H_5$ | 2 | $COC_3H_7$-n | H | H | $CH_2OCH_3$ |
| Cl | H | $C_2H_5$ | 2 | $COC_3H_7$-n | H | H | $CH_3$ |
| Cl | H | $C_2H_5$ | 2 | $COC_3H_7$-n | H | H | n-$C_3H_7$ |
| Cl | H | $C_2H_5$ | 2 | $COC_3H_7$-n | H | H | n-$C_4H_9$ |
| Cl | H | $C_2H_5$ | 2 | $COC_3H_7$-n | H | H | tert-$C_4H_9$ |
| Cl | H | $C_2H_5$ | 2 | $COCH_3$ | H | H | $C_2H_5$ |
| Cl | H | $C_2H_5$ | 2 | $COCH_3$ | H | H | $CH_2OCH_3$ |
| Cl | H | $C_2H_5$ | 2 | $COCH_3$ | H | H | $CH_3$ |
| Cl | H | $C_2H_5$ | 2 | $COCH_3$ | H | H | n-$C_3H_7$ |
| Cl | H | $C_2H_5$ | 2 | $COCH_3$ | H | H | n-$C_4H_9$ |
| Cl | H | $C_2H_5$ | 2 | $COCH_3$ | H | H | tert-$C_4H_9$ |
| Cl | H | $C_2H_5$ | 2 | H | H | H | $(CH_2)_5Br$ |
| Cl | H | $C_2H_5$ | 2 | H | H | H | $CH_2CH_2CO_2H$ |
| Cl | H | $C_2H_5$ | 2 | H | H | H | $CH_2CH_2SCH_3$ |
| Cl | H | $C_2H_5$ | 2 | H | H | H | $CO_2C_2H_5$ |
| Cl | H | $C_2H_5$ | 2 | H | H | H | $CO_2CH_3$ |
| Cl | H | $C_2H_5$ | 2 | H | H | H | $COCH_3$ |
| Cl | H | $C_2H_5$ | 2 | H | H | H | 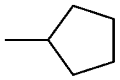 |
| Cl | H | $C_2H_5$ | 2 | H | H | H | 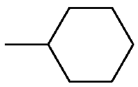 |
| Cl | H | $C_2H_5$ | 2 | H | H | H | sec-$C_4H_9$ |
| Cl | H | $C_2H_5$ | 2 | iso-$C_3H_7$ | H | H | 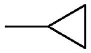 |
| Cl | H | $C_2H_5$ | 2 | iso-$C_3H_7$ | H | H | $COCH_3$ |
| Cl | H | $C_2H_5$ | 2 | iso-$C_3H_7$ | H | H | $CO_2CH_3$ |
| Cl | H | $C_2H_5$ | 2 | n-$C_3H_7$ | H | H | 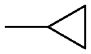 |

TABLE 2-continued

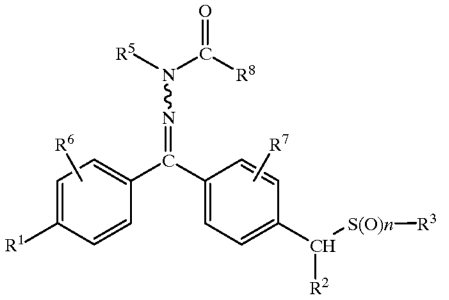

| $R^1$ | $R^2$ | $R^3$ | n | $R^5$ | $R^6$ | $R^7$ | $R^8$ |
|---|---|---|---|---|---|---|---|
| Cl | H | $C_2H_5$ | 2 | n-$C_3H_7$ | H | H | $COCH_3$ |
| Cl | H | $C_2H_5$ | 2 | n-$C_3H_7$ | H | H | $CO_2CH_3$ |
| Cl | H | $CH_2CF_3$ | 0 | $C_2H_5$ | H | H | $C_2H_5$ |
| Cl | H | $CH_2CF_3$ | 0 | $C_2H_5$ | H | H | $CH_2OCH_3$ |
| Cl | H | $CH_2CF_3$ | 0 | $C_2H_5$ | H | H | $CH_3$ |
| Cl | H | $CH_2CF_3$ | 0 | $C_2H_5$ | H | H | n-$C_3H_7$ |
| Cl | H | $CH_2CF_3$ | 0 | $CH_3$ | H | H | $C_2H_5$ |
| Cl | H | $CH_2CF_3$ | 0 | $CH_3$ | H | H | $CH_2OCH_3$ |
| Cl | H | $CH_2CF_3$ | 0 | $CH_3$ | H | H | $CH_3$ |
| Cl | H | $CH_2CF_3$ | 0 | $CH_3$ | H | H | n-$C_3H_7$ |
| Cl | H | $CH_2CF_3$ | 1 | $C_2H_5$ | H | H | $C_2H_5$ |
| Cl | H | $CH_2CF_3$ | 1 | $C_2H_5$ | H | H | $CH_2OCH_3$ |
| Cl | H | $CH_2CF_3$ | 1 | $C_2H_5$ | H | H | $CH_3$ |
| Cl | H | $CH_2CF_3$ | 1 | $C_2H_5$ | H | H | n-$C_3H_7$ |
| Cl | H | $CH_2CF_3$ | 1 | $CH_3$ | H | H | $C_2H_5$ |
| Cl | H | $CH_2CF_3$ | 1 | $CH_3$ | H | H | $CH_2OCH_3$ |
| Cl | H | $CH_2CF_3$ | 1 | $CH_3$ | H | H | $CH_3$ |
| Cl | H | $CH_2CF_3$ | 1 | $CH_3$ | H | H | n-$C_3H_7$ |
| Cl | H | $CH_2CF_3$ | 2 | $C_2H_5$ | H | H | $C_2H_5$ |
| Cl | H | $CH_2CF_3$ | 2 | $C_2H_5$ | H | H | $CH_2OCH_3$ |
| Cl | H | $CH_2CF_3$ | 2 | $C_2H_5$ | H | H | $CH_3$ |
| Cl | H | $CH_2CF_3$ | 2 | $C_2H_5$ | H | H | n-$C_3H_7$ |
| Cl | H | $CH_2CF_3$ | 2 | $CH_3$ | H | H | $C_2H_5$ |
| Cl | H | $CH_2CF_3$ | 2 | $CH_3$ | H | H | $CH_2OCH_3$ |
| Cl | H | $CH_2CF_3$ | 2 | $CH_3$ | H | H | $CH_3$ |
| Cl | H | $CH_2CF_3$ | 2 | $CH_3$ | H | H | n-$C_3H_7$ |
| Cl | H | $CH_3$ | 0 | $C_2H_5$ | H | H | 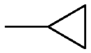 |
| Cl | H | $CH_3$ | 0 | $C_2H_5$ | H | H | $COCH_3$ |
| Cl | H | $CH_3$ | 0 | $C_2H_5$ | H | H | $CO_2C_2H_5$ |
| Cl | H | $CH_3$ | 0 | $C_2H_5$ | H | H | $CO_2CH_3$ |
| Cl | H | $CH_3$ | 0 | $CH_2OC_2H_5$ | H | H | $C_2H_5$ |
| Cl | H | $CH_3$ | 0 | $CH_2OC_2H_5$ | H | H | $CH_2OCH_3$ |
| Cl | H | $CH_3$ | 0 | $CH_2OC_2H_5$ | H | H | n-$C_3H_7$ |
| Cl | H | $CH_3$ | 0 | $CH_2OC_2H_5$ | H | H | n-$C_4H_9$ |
| Cl | H | $CH_3$ | 0 | $CH_2OC_2H_5$ | H | H | tert-$C_4H_9$ |
| Cl | H | $CH_3$ | 0 | $CH_2OCH_3$ | H | H | $C_2H_5$ |
| Cl | H | $CH_3$ | 0 | $CH_2OCH_3$ | H | H | $CH_2OCH_3$ |
| Cl | H | $CH_3$ | 0 | $CH_2CCH_3$ | H | H | n-$C_3H_7$ |
| Cl | H | $CH_3$ | 0 | $CH_2OCH_3$ | H | H | n-$C_4H_9$ |
| Cl | H | $CH_3$ | 0 | $CH_2OCH_3$ | H | H | tert-$C_4H_9$ |
| Cl | H | $CH_3$ | 0 | $CH_2SCH_3$ | H | H | $C_2H_5$ |
| Cl | H | $CH_3$ | 0 | $CH_2SCH_3$ | H | H | $CH_2OCH_3$ |
| Cl | H | $CH_3$ | 0 | $CH_2SCH_3$ | H | H | n-$C_3H_7$ |
| Cl | H | $CH_3$ | 0 | $CH_2SCH_3$ | H | H | n-$C_4H_9$ |
| Cl | H | $CH_3$ | 0 | $CH_2SCH_3$ | H | H | tert-$C_4H_9$ |
| Cl | H | $CH_3$ | 0 | $CH_3$ | H | H | 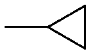 |
| Cl | H | $CH_3$ | 0 | $CH_3$ | H | H | $COCH_3$ |
| Cl | H | $CH_3$ | 0 | $CH_3$ | H | H | $CO_2C_2H_5$ |
| Cl | H | $CH_3$ | 0 | $CH_3$ | H | H | $CO_2CH_3$ |
| Cl | H | $CH_3$ | 0 | $COC_2H_5$ | H | H | $C_2H_5$ |
| Cl | H | $CH_3$ | 0 | $COC_2H_5$ | H | H | $CH_2OCH_3$ |
| Cl | H | $CH_3$ | 0 | $COC_2H_5$ | H | H | n-$C_3H_7$ |
| Cl | H | $CH_3$ | 0 | $COC_2H_5$ | H | H | n-$C_4H_9$ |

TABLE 2-continued

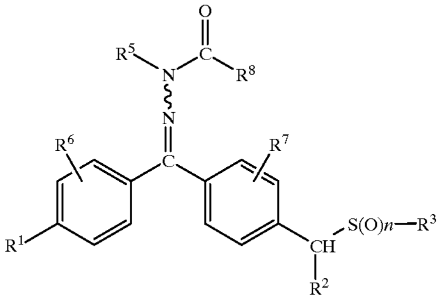

| $R^1$ | $R^2$ | $R^3$ | n | $R^5$ | $R^6$ | $R^7$ | $R^8$ |
|---|---|---|---|---|---|---|---|
| Cl | H | $CH_3$ | 0 | $COC_2H_5$ | H | H | tert-$C_4H_9$ |
| Cl | H | $CH_3$ | 0 | $COC_3H_7$-n | H | H | $C_2H_5$ |
| Cl | H | $CH_3$ | 0 | $COC_3H_7$-n | H | H | $CH_2OCH_3$ |
| Cl | H | $CH_3$ | 0 | $COC_3H_7$-n | H | H | $CH_3$ |
| Cl | H | $CH_3$ | 0 | $COC_3H_7$-n | H | H | n-$C_3H_7$ |
| Cl | H | $CH_3$ | 0 | $COC_3H_7$-n | H | H | n-$C_4H_9$ |
| Cl | H | $CH_3$ | 0 | $CCC_3H_7$-n | H | H | tert-$C_4H_9$ |
| Cl | H | $CH_3$ | 0 | $COC_6H_5$ | H | H | $CH_3$ |
| Cl | H | $CH_3$ | 0 | $COCH_3$ | H | H | $C_2H_5$ |
| Cl | H | $CH_3$ | 0 | $COCH_3$ | H | H | $CH_2OCH_3$ |
| Cl | H | $CH_3$ | 0 | $COCH_3$ | H | H | n-$C_3H_7$ |
| Cl | H | $CH_3$ | 0 | $COCH_3$ | H | H | n-$C_4H_9$ |
| Cl | H | $CH_3$ | 0 | $COCH_3$ | H | H | tert-$C_4H_9$ |
| Cl | H | $CH_3$ | 0 | H | H | H | $(CH_2)_5Br$ |
| Cl | H | $CH_3$ | 0 | H | H | H | $CH_2CH_2CO_2H$ |
| Cl | H | $CH_3$ | 0 | H | H | H | $CH_2CH_2SCH_3$ |
| Cl | H | $CH_3$ | 0 | H | H | H | $CH_2CO_2CH_3$ |
| Cl | H | $CH_3$ | 0 | H | H | H | $CO_2C_2H_5$ |
| Cl | H | $CH_3$ | 0 | H | H | H | $CO_2CH_3$ |
| Cl | H | $CH_3$ | 0 | H | H | H | $COCH_3$ |
| Cl | H | $CH_3$ | 0 | iso-$C_3H_7$ | H | H | 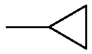 |
| Cl | H | $CH_3$ | 0 | iso-$C_3H_7$ | H | H | $COCH_3$ |
| Cl | H | $CH_3$ | 0 | iso-$C_3H_7$ | H | H | $CO_2CH_3$ |
| Cl | H | $CH_3$ | 0 | n-$C_3H_7$ | H | H | 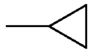 |
| Cl | H | $CH_3$ | 0 | n-$C_3H_7$ | H | H | $COCH_3$ |
| Cl | H | $CH_3$ | 0 | n-$C_3H_7$ | H | H | $CO_2CH_3$ |
| Cl | H | $CH_3$ | 1 | $C_2H_5$ | H | H | 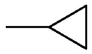 |
| Cl | H | $CH_3$ | 1 | $C_2H_5$ | H | H | $COCH_3$ |
| Cl | H | $CH_3$ | 1 | $C_2H_5$ | H | H | $CO_2C_2H_5$ |
| Cl | H | $CH_3$ | 1 | $C_2H_5$ | H | H | $CO_2CH_3$ |
| Cl | H | $CH_3$ | 1 | $CH_2OC_2H_5$ | H | H | $C_2H_5$ |
| Cl | H | $CH_3$ | 1 | $CH_2OC_2H_5$ | H | H | $CH_2OCH_3$ |
| Cl | H | $CH_3$ | 1 | $CH_2OC_2H_5$ | H | H | $CH_3$ |
| Cl | H | $CH_3$ | 1 | $CH_2OC_2H_5$ | H | H | n-$C_3H_7$ |
| Cl | H | $CH_3$ | 1 | $CH_2OC_2H_5$ | H | H | n-$C_4H_9$ |
| Cl | H | $CH_3$ | 1 | $CH_2OC_2H_5$ | H | H | tert-$C_4H_9$ |
| Cl | H | $CH_3$ | 1 | $CH_2CH_3$ | H | H | $C_2H_5$ |
| Cl | H | $CH_3$ | 1 | $CH_2CH_3$ | H | H | $CH_2OCH_3$ |
| Cl | H | $CH_3$ | 1 | $CH_2OCH_3$ | H | H | $CH_3$ |
| Cl | H | $CH_3$ | 1 | $CH_2OCH_3$ | H | H | n-$C_3H_7$ |
| Cl | H | $CH_3$ | 1 | $CH_2OCH_3$ | H | H | n-$C_4H_9$ |
| Cl | H | $CH_3$ | 1 | $CH_2OCH_3$ | H | H | tert-$C_4H_9$ |
| Cl | H | $CH_3$ | 1 | $CH_2SCH_3$ | H | H | $C_2H_5$ |
| Cl | H | $CH_3$ | 1 | $CH_2SCH_3$ | H | H | $CH_2OCH_3$ |
| Cl | H | $CH_3$ | 1 | $CH_2SCH_3$ | H | H | $CH_3$ |
| Cl | H | $CH_3$ | 1 | $CH_2SCH_3$ | H | H | n-$C_3H_7$ |
| Cl | H | $CH_3$ | 1 | $CH_2SCH_3$ | H | H | n-$C_4H_9$ |
| Cl | H | $CH_3$ | 1 | $CH_2SCH_3$ | H | H | tert-$C_4H_9$ |

TABLE 2-continued

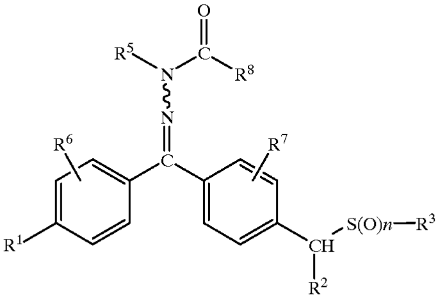

| $R^1$ | $R^2$ | $R^3$ | n | $R^5$ | $R^6$ | $R^7$ | $R^8$ |
|---|---|---|---|---|---|---|---|
| Cl | H | $CH_3$ | 1 | $CH_3$ | H | H | 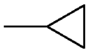 |
| Cl | H | $CH_3$ | 1 | $CH_3$ | H | H | $COCH_3$ |
| Cl | H | $CH_3$ | 1 | $CH_3$ | H | H | $CO_2C_2H_5$ |
| Cl | H | $CH_3$ | 1 | $CH_3$ | H | H | $CO_2CH_3$ |
| Cl | H | $CH_3$ | 1 | $COC_2H_5$ | H | H | $C_2H_5$ |
| Cl | H | $CH_3$ | 1 | $COC_2H_5$ | H | H | $CH_2OCH_3$ |
| Cl | H | $CH_3$ | 1 | $COC_2H_5$ | H | H | $CH_3$ |
| Cl | H | $CH_3$ | 1 | $COC_2H_5$ | H | H | n-$C_3H_7$ |
| Cl | H | $CH_3$ | 1 | $COC_2H_5$ | H | H | n-$C_4H_9$ |
| Cl | H | $CH_3$ | 1 | $COC_2H_5$ | H | H | tert-$C_4H_9$ |
| Cl | H | $CH_3$ | 1 | $COC_3H_7$-n | H | H | $C_2H_5$ |
| Cl | H | $CH_3$ | 1 | $COC_3H_7$-n | H | H | $CH_2OCH_3$ |
| Cl | H | $CH_3$ | 1 | $COC_3H_7$-n | H | H | $CH_3$ |
| Cl | H | $CH_3$ | 1 | $COC_3H_7$-n | H | H | n-$C_3H_7$ |
| Cl | H | $CH_3$ | 1 | $COC_3H_7$-n | H | H | n-$C_4H_9$ |
| Cl | H | $CH_3$ | 1 | $COC_3H_7$-n | H | H | tert-$C_4H_9$ |
| Cl | H | $CH_3$ | 1 | $COCH_3$ | H | H | $C_2H_5$ |
| Cl | H | $CH_3$ | 1 | $COCH_3$ | H | H | $CH_2OCH_3$ |
| Cl | H | $CH_3$ | 1 | $COCH_3$ | H | H | $CH_3$ |
| Cl | H | $CH_3$ | 1 | $COCH_3$ | H | H | n-$C_3H_7$ |
| Cl | H | $CH_3$ | 1 | $COCH_3$ | H | H | n-$C_4H_9$ |
| Cl | H | $CH_3$ | 1 | $COCH_3$ | H | H | tert-$C_4H_9$ |
| Cl | H | $CH_3$ | 1 | H | H | H | $(CH_2)_5Br$ |
| Cl | H | $CH_3$ | 1 | H | H | H | $CH_2CH_2CO_2H$ |
| Cl | H | $CH_3$ | 1 | H | H | H | $CH_2CH_2SCH_3$ |
| Cl | H | $CH_3$ | 1 | H | H | H | $CH_2CO_2CH_3$ |
| Cl | H | $CH_3$ | 1 | H | H | H | $CO_2C_2H_5$ |
| Cl | H | $CH_3$ | 1 | H | H | H | $CO_2CH_3$ |
| Cl | H | $CH_3$ | 1 | H | H | H | $COCH_3$ |
| Cl | H | $CH_3$ | 1 | H | H | H | 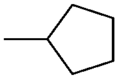 |
| Cl | H | $CH_3$ | 1 | H | H | H | 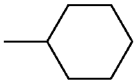 |
| Cl | H | $CH_3$ | 1 | H | H | H | sec-$C_4H_9$ |
| Cl | H | $CH_3$ | 1 | iso-$C_3H_7$ | H | H | 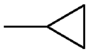 |
| Cl | H | $CH_3$ | 1 | iso-$C_2H$ | H | H | $COCH_3$ |
| Cl | H | $CH_3$ | 1 | iso-$C_3H_7$ | H | H | $CO_2CH_3$ |
| Cl | H | $CH_3$ | 1 | n-$C_2H$ | H | H | 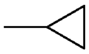 |
| Cl | H | $CH_3$ | 1 | n-$C_3H$ | H | H | $COCH_3$ |
| Cl | H | $CH_3$ | 1 | n-$C_3H$ | H | H | $CO_2CH_3$ |

TABLE 2-continued

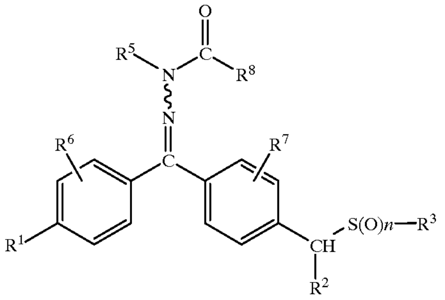

| $R^1$ | $R^2$ | $R^3$ | n | $R^5$ | $R^6$ | $R^7$ | $R^8$ |
|---|---|---|---|---|---|---|---|
| Cl | H | $CH_3$ | 2 | $C_2H_5$ | H | H | 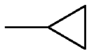 |
| Cl | H | $CH_3$ | 2 | $C_2H_5$ | H | H | $COCH_3$ |
| Cl | H | $CH_3$ | 2 | $C_2H_5$ | H | H | $CO_2C_2H_5$ |
| Cl | H | $CH_3$ | 2 | $C_2H_5$ | H | H | $CO_2CH_3$ |
| Cl | H | $CH_3$ | 2 | $CH_2OC_2H_5$ | H | H | $C_2H_5$ |
| Cl | H | $CH_3$ | 2 | $CH_2OC_2H_5$ | H | H | $CH_2OCH_3$ |
| Cl | H | $CH_3$ | 2 | $CH_2OC_2H_5$ | H | H | $CH_3$ |
| Cl | H | $CH_3$ | 2 | $CH_2OC_2H_5$ | H | H | n-$C_3H_7$ |
| Cl | H | $CH_3$ | 2 | $CH_2OC_2H_5$ | H | H | n-$C_4H_9$ |
| Cl | H | $CH_3$ | 2 | $CH_2OC_2H_5$ | H | H | tert-$C_4H_9$ |
| Cl | H | $CH_3$ | 2 | $CH_2OCH_3$ | H | H | $C_2H_5$ |
| Cl | H | $CH_3$ | 2 | $CH_2OCH_3$ | H | H | $CH_2OCH_3$ |
| Cl | H | $CH_3$ | 2 | $CH_2OCH_3$ | H | H | $CH_3$ |
| Cl | H | $CH_3$ | 2 | $CH_2OCH_3$ | H | H | n-$C_3H_7$ |
| Cl | H | $CH_3$ | 2 | $CH_2OCH_3$ | H | H | n-$C_4H_9$ |
| Cl | H | $CH_3$ | 2 | $CH_2OCH_3$ | H | H | tert-$C_4H_9$ |
| Cl | H | $CH_3$ | 2 | $CH_2SCH_3$ | H | H | $C_2H_5$ |
| Cl | H | $CH_3$ | 2 | $CH_2SCH_3$ | H | H | $CH_2OCH_3$ |
| Cl | H | $CH_3$ | 2 | $CH_2SCH_3$ | H | H | $CH_3$ |
| Cl | H | $CH_3$ | 2 | $CH_2SCH_3$ | H | H | n-$C_3H$ |
| Cl | H | $CH_3$ | 2 | $CH_2SCH_3$ | H | H | n-$C_4H_9$ |
| Cl | H | $CH_3$ | 2 | $CH_2SCH_3$ | H | H | tert-$C_4H_9$ |
| Cl | H | $CH_3$ | 2 | $CH_3$ | H | H | 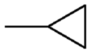 |
| Cl | H | $CH_3$ | 2 | $CH_3$ | H | H | $COCH_3$ |
| Cl | H | $CH_3$ | 2 | $CH_3$ | H | H | $CO_2C_2H_5$ |
| Cl | H | $CH_3$ | 2 | $CH_3$ | H | H | $CO_2CH_3$ |
| Cl | H | $CH_3$ | 2 | $COC_2H_5$ | H | H | $C_2H_5$ |
| Cl | H | $CH_3$ | 2 | $COC_2H_5$ | H | H | $CH_2OCH_3$ |
| Cl | H | $CH_3$ | 2 | $COC_2H_5$ | H | H | $CH_3$ |
| Cl | H | $CH_3$ | 2 | $COC_2H_5$ | H | H | n-$C_3H_7$ |
| Cl | H | $CH_3$ | 2 | $COC_2H_5$ | H | H | n-$C_4H_9$ |
| Cl | H | $CH_3$ | 2 | $COC_2H_5$ | H | H | tert-$C_4H_9$ |
| Cl | H | $CH_3$ | 2 | $COC_3H_7$-n | H | H | $C_2H_5$ |
| Cl | H | $CH_3$ | 2 | $COC_3H_7$-n | H | H | $CH_2OCH_3$ |
| Cl | H | $CH_3$ | 2 | $COC_3H_7$-n | H | H | $CH_3$ |
| Cl | H | $CH_3$ | 2 | $COC_3H_7$-n | H | H | n-$C_3H_7$ |
| Cl | H | $CH_3$ | 2 | $COC_3H_7$-n | H | H | n-$C_4H_9$ |
| Cl | H | $CH_3$ | 2 | $COC_3H_7$-n | H | H | tert-$C_4H_9$ |
| Cl | H | $CH_3$ | 2 | $COCH_3$ | H | H | $C_2H_5$ |
| Cl | H | $CH_3$ | 2 | $COCH_3$ | H | H | $CH_2OCH_3$ |
| Cl | H | $CH_3$ | 2 | $COCH_3$ | H | H | $CH_3$ |
| Cl | H | $CH_3$ | 2 | $COCH_3$ | H | H | n-$C_3H_7$ |
| Cl | H | $CH_3$ | 2 | $COCH_3$ | H | H | n-$C_4H_9$ |
| Cl | H | $CH_3$ | 2 | $COCH_3$ | H | H | tert-$C_4H_9$ |
| Cl | H | $CH_3$ | 2 | H | H | H | $(CH_2)_5Br$ |
| Cl | H | $CH_3$ | 2 | H | H | H | $CH_2CH_2CO_2H$ |
| Cl | H | $CH_3$ | 2 | H | H | H | $CH_2CH_2SCH_3$ |
| Cl | H | $CH_3$ | 2 | H | H | H | $CH_2CO_2CH_3$ |
| Cl | H | $CH_3$ | 2 | H | H | H | $CO_2C_2H_5$ |
| Cl | H | $CH_3$ | 2 | H | H | H | $CO_2CH_3$ |
| Cl | H | $CH_3$ | 2 | H | H | H | $COCH_3$ |

TABLE 2-continued

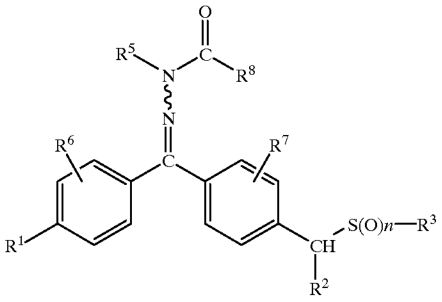

| $R^1$ | $R^2$ | $R^3$ | n | $R^5$ | $R^6$ | $R^7$ | $R^8$ |
|---|---|---|---|---|---|---|---|
| Cl | H | $CH_3$ | 2 | H | H | H | 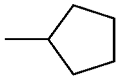 |
| Cl | H | $CH_3$ | 2 | H | H | H | 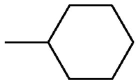 |
| Cl | H | $CH_3$ | 2 | H | H | H | sec-$C_4H_9$ |
| Cl | H | $CH_3$ | 2 | iso-$C_3H_7$ | H | H | 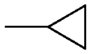 |
| Cl | H | $CH_3$ | 2 | iso-$C_3H_7$ | H | H | $COCH_3$ |
| Cl | H | $CH_3$ | 2 | iso-$C_3H_7$ | H | H | $CO_2CH_3$ |
| Cl | H | $CH_3$ | 2 | n-$C_3H_7$ | H | H | 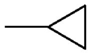 |
| Cl | H | $CH_3$ | 2 | n-$C_3H_7$ | H | H | $COCH_3$ |
| Cl | H | $CH_3$ | 2 | n-$C_3H_7$ | H | H | $CO_2CH_3$ |

TABLE 3

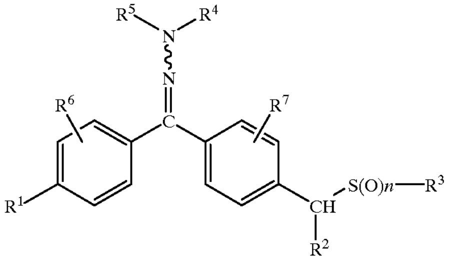

| $R^1$ | $R^2$ | $R^3$ | n | $R^4$ | $R^5$ | $R^6$ | $R^7$ |
|---|---|---|---|---|---|---|---|
| Br | H | $C_2H_5$ | 0 | H | H | H | H |
| Br | H | $C_2H_5$ | 0 | tert-$C_4H_9$ | H | H | H |
| Br | H | $C_2H_5$ | 2 | H | H | H | H |
| Br | H | $C_2H_5$ | 1 | H | H | H | H |
| Br | H | $CH_3$ | 0 | H | H | H | H |
| Br | H | $CH_3$ | 0 | tert-$C_4H_9$ | H | H | H |
| Br | H | $CH_3$ | 2 | H | H | H | H |
| Br | H | $CH_3$ | 2 | $CH_3$ | $CH_3$ | H | H |
| Br | H | $CH_3$ | 2 | $CH_3$ | H | H | H |
| Br | H | $CH_3$ | 2 | $C_6H_5$ | H | H | H |

TABLE 3-continued

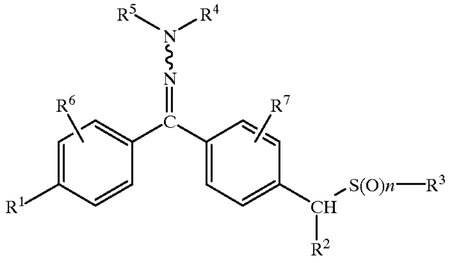

| $R^1$ | $R^2$ | $R^3$ | n | $R^4$ | $R^5$ | $R^6$ | $R^7$ |
|---|---|---|---|---|---|---|---|
| Br | H | $CH_3$ | 2 | 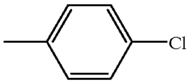 | H | H | H |
| Br | H | $CH_3$ | 1 | H | H | H | H |
| Cl | H | $C_2H_5$ | 0 | H | H | H | H |
| Cl | H | $C_2H_5$ | 0 | tert-$C_4H_9$ | H | H | H |
| Cl | H | $C_2H_5$ | 2 | H | H | H | H |
| Cl | H | $C_2H_5$ | 2 | $CH_3$ | $CH_3$ | H | H |
| Cl | H | $C_2H_5$ | 2 | $CH_3$ | H | H | H |
| Cl | H | $C_2H_5$ | 2 | $C_6H_5$ | H | H | H |
| Cl | H | $C_2H_5$ | 2 | 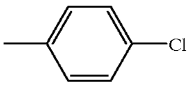 | H | H | H |
| Cl | H | $C_2H_5$ | 2 | 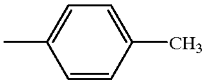 | H | H | H |
| Cl | H | $C_2H_5$ | 1 | H | H | H | H |
| Cl | H | $CH_3$ | 0 | H | H | H | H |
| Cl | H | $CH_3$ | 0 | tert-$C_4H_9$ | H | H | H |
| Cl | H | $CH_3$ | 2 | H | H | H | H |
| Cl | H | $CH_3$ | 2 | $CH_3$ | H | H | H |
| Cl | H | $CH_3$ | 2 | iso-$C_3H_7$ | H | H | H |
| Cl | H | $CH_3$ | 2 | $CH_2CH{=}CH_2$ | H | H | H |
| Cl | H | $CH_3$ | 2 | $CH_3$ | $CH_3$ | H | H |
| Cl | H | $CH_3$ | 2 | n-$C_4H_9$ | H | H | H |
| Cl | H | $CH_3$ | 2 | $CH_2C_6H_5$ | H | H | H |
| Cl | H | $CH_3$ | 2 | $CH_3$ | $C_6H_5$ | H | H |
| Cl | H | $CH_3$ | 2 | $C_6H_5$ | H | H | H |
| Cl | H | $CH_3$ | 2 | 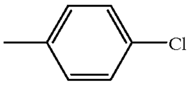 | H | H | H |
| Cl | H | $CH_3$ | 2 | 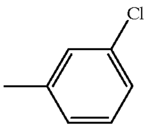 | H | H | H |
| Cl | H | $CH_3$ | 2 | 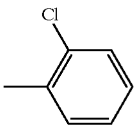 | H | H | H |
| Cl | H | $CH_3$ | 2 | 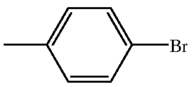 | H | H | H |

TABLE 3-continued
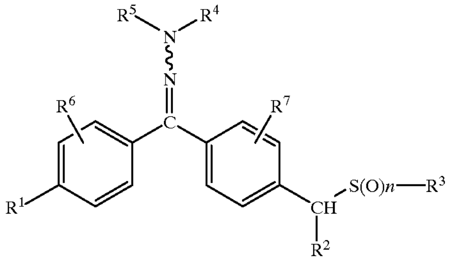
| $R^1$ | $R^2$ | $R^3$ | n | $R^4$ | $R^5$ | $R^6$ | $R^7$ |
|---|---|---|---|---|---|---|---|
| Cl | H | $CH_3$ | 2 | 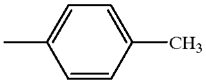 | H | H | H |
| Cl | H | $CH_3$ | 2 | 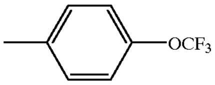 | H | H | H |
| Cl | H | $CH_3$ | 2 | 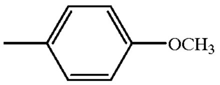 | H | H | H |
| Cl | H | $CH_3$ | 2 | 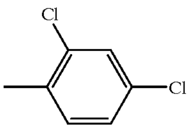 | H | H | H |
| Cl | H | $CH_3$ | 2 | 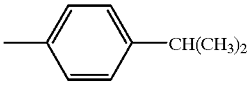 | H | H | H |
| Cl | H | $CH_3$ | 2 | 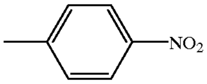 | H | H | H |
| Cl | H | $CH_3$ | 2 | 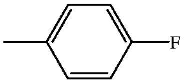 | H | H | H |
| Cl | H | $CH_3$ | 1 | H | H | H | H |
| Cl | H | $CHF_2$ | 0 | H | H | H | H |
| Cl | H | $CHF_2$ | 1 | H | H | H | H |
| Cl | H | $CF_3$ | 0 | H | H | H | H |
| Cl | H | $CH_2CF_3$ | 0 | H | H | H | H |
| Cl | H | $CH_2CH_2F$ | 0 | H | H | H | H |
| Cl | H | $CH_2CHF_2$ | 0 | H | H | H | H |

TABLE 4

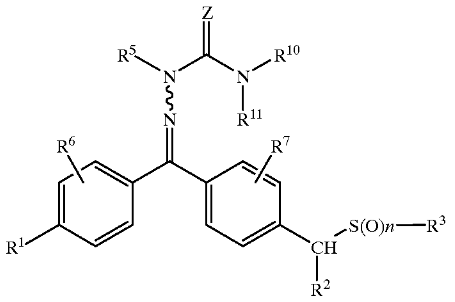

| $R^1$ | $R^2$ | $R^3$ | n | $R^5$ | $R^6$ | $R^7$ | Z | $R^{10}$ | $R^{11}$ |
|---|---|---|---|---|---|---|---|---|---|
| Br | H | $CH_3$ | 0 | H | H | H | O | H | $C_6H_5$ |
| Br | H | $CH_3$ | 0 | H | H | H | O | H | H |
| Br | H | $CH_3$ | 0 | H | H | H | S | H | H |
| Br | H | $CH_3$ | 1 | H | H | H | O | H | H |
| Cl | H | $CH_2CF_3$ | 0 | H | H | H | O | H | H |
| Cl | H | $CH_2CF_3$ | 0 | H | H | H | S | H | H |
| Cl | H | $CH_2CH_2F$ | 0 | H | H | H | O | H | H |
| Cl | H | $CH_2CH_2F$ | 0 | H | H | H | S | H | H |
| Cl | H | $CH_2CHF_2$ | 0 | H | H | H | O | H | H |
| Cl | H | $CH_2CHF_2$ | 0 | H | H | H | S | H | H |
| Cl | H | $CH_3$ | 0 | H | H | H | S | $CH_3$ | $CH_3$ |
| Cl | H | $CH_3$ | 0 | H | H | H | O | H | $C_2H_5$ |
| Cl | H | $CH_3$ | 0 | H | H | H | O | H | 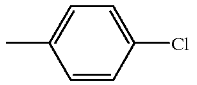 |
| Cl | H | $CH_3$ | 0 | H | H | H | O | H | 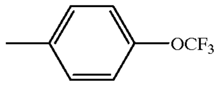 |
| Cl | H | $CH_3$ | 0 | H | H | H | O | H | $C_6H_5$ |
| Cl | H | $CH_3$ | 0 | H | H | H | S | H | $C_6H_5$ |
| Cl | H | $CH_3$ | 0 | H | H | H | O | H | $CH_2CH_2Cl$ |
| Cl | H | $CH_3$ | 0 | H | H | H | O | H | $CH_3$ |
| Cl | H | $CH_3$ | 0 | H | H | H | S | H | $CH_3$ |
| Cl | H | $CH_3$ | 0 | H | H | H | O | H | H |
| Cl | H | $CH_3$ | 0 | H | H | H | S | H | H |
| Cl | H | $CH_3$ | 2 | H | H | H | O | H | $C_2H_5$ |
| Cl | H | $CH_3$ | 2 | H | H | H | S | H | H |
| Cl | H | $CH_3$ | 1 | H | H | H | S | H | H |
| Cl | H | $CH_3$ | 0 | H | H | H | O | H | 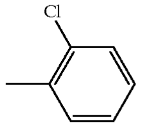 |
| Cl | H | $CH_3$ | 0 | H | H | H | O | H | 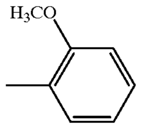 |
| Cl | H | $CH_3$ | 0 | H | H | H | S | H | 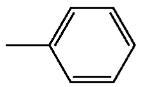 |

In process (a), if, for example, 4-chloro-4'-methylmercaptomethylbenzophenone and ethyl carbazate are used as the starting materials, the reaction is illustrated by the following equation:

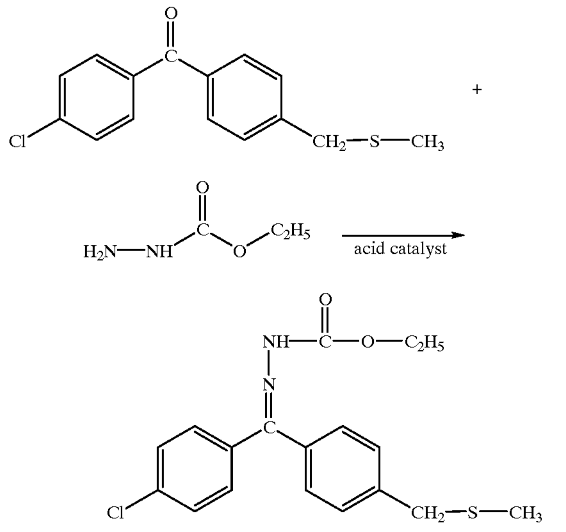

In process (b), if, for example, 4-chloro-4'-methylmercaptomethylbenzophenone hydrazone and 4-trifluoro-methoxyphenyl isocyanate are used as the starting materials, the reaction is illustrated by the following equation:

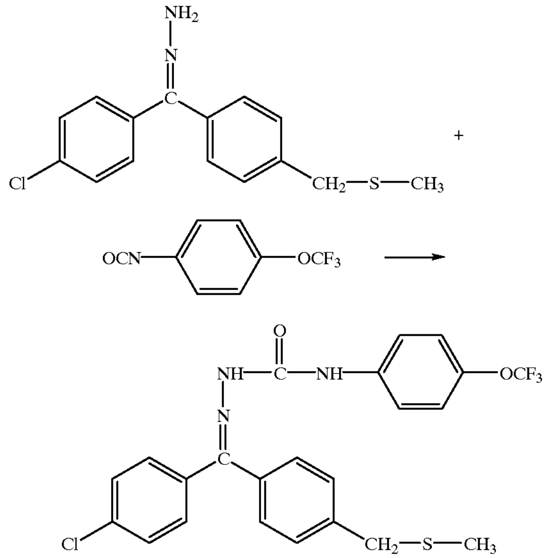

In process (c), if, for example, 4-chloro-4'-methylmercaptomethylbenzophenone 10 hydrazone and isobutyl chiorocarbonate are used as the starting materials, the reaction is illustrated by the following equation:

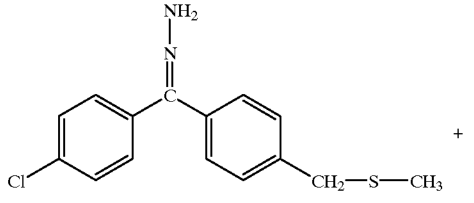

-continued

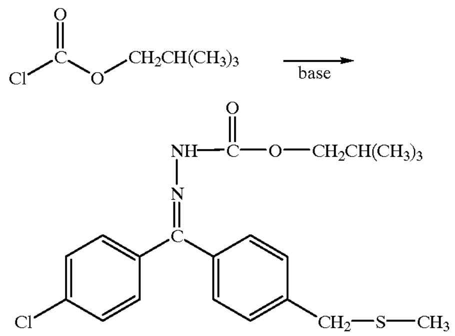

In process (d), if, for example, 4-chloro-4'-methylmercaptomethylbenzophenone ethoxycarbonylhydrazone ane methyliodide are used as the starting materials, the reaction is illustrared by the following equation:

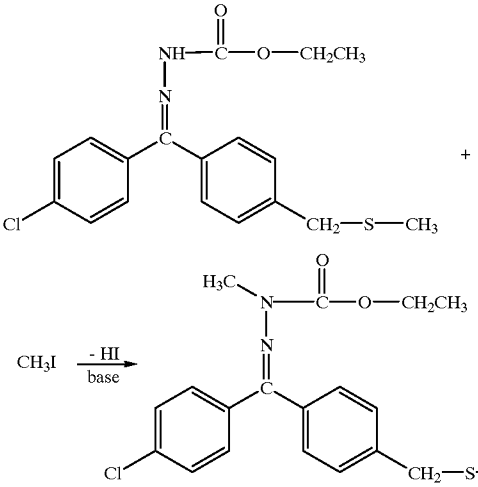

In the process (e), if, for example, 4-chloro-4'-methylmercaptomethylbenzophenone ethoxycarbonylhydrazone is oxidized by sodium periodate, the reaction is illustrated by the following equation:

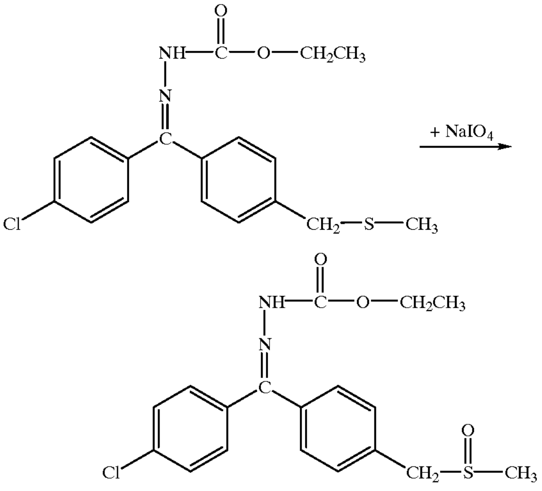

In process (f), if, for example, 4-chloro-4'-methylmercaptomethylbenzophenone ethoxycarbonylhydrazone is oxidized by m-chloroperbenzoic acid, the reaction is illustrated by the following equation:

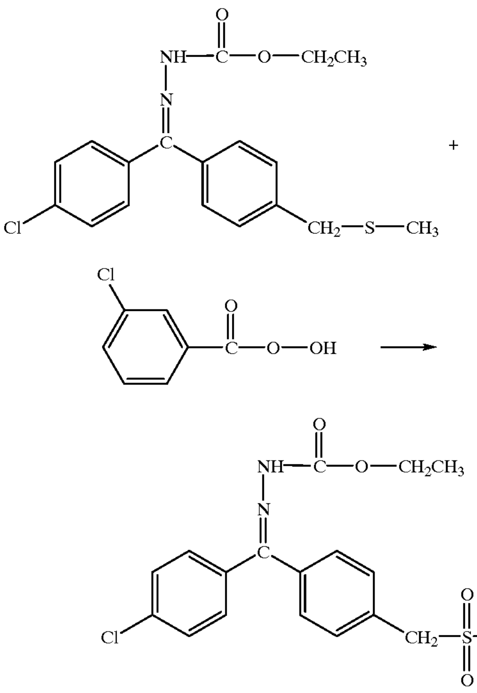

In process (a), the compounds of the formula (II) mean compounds based on the above definitions of $R^1$, $R^2$, $R^3$, $R^6$, $R^7$ and n, preferably compounds based on the above preferred definitions.

The starting compounds of the formula (II) are novel, and can be obtained by the following processes:

(g) in the case where n is 0:

compounds of the formula (XI)

(XI)

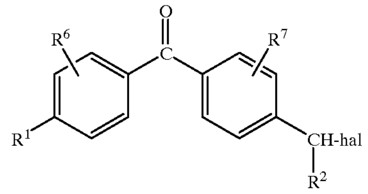

wherein $R^1$, $R^2$, $R^6$, $R^7$ and hal have the same meaning mentioned above, are reacted with compounds of the formula (XII) or salts thereof $R^3$—SH (XII)

wherein $R^3$ has the same meaning mentioned above, in the presence of inert solvent, and if appropriate, in the presence of an acid binder, or (h) in the case where n is 0:

compounds of the formula (XIII) or salts thereof (XIII)

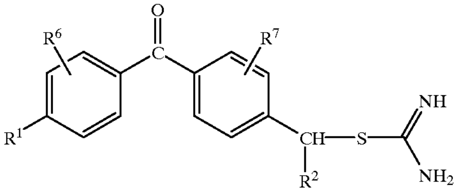

wherein $R^1$, $R^2$, $R^6$ and $R^7$ have the same meaning mentioned above, are reacted with compounds of the formula (XIV)

$R^{15}$—$R^3$ (XIV)

wherein $R^3$ has the same meanings mentioned above, and $R^{15}$ is chlorine, bromine or iodine;

in the presence of an inert solvent, and if appropriate, in the presence of an acid binder, or (j) in the case where n is 0 and $R^1$ is fluorine or chlorine: compounds of the formula (XV)

(XV)

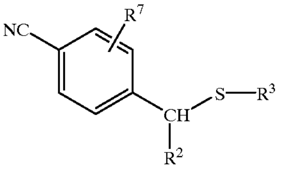

wherein $R^2$, $R^3$ and $R^7$ have the same meaning mentioned above, are reacted with compounds of the formula (XVI)

(XVI)

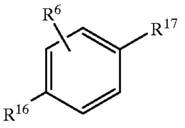

wherein $R^6$ has the same meaning mentioned above and $R^{16}$ is fluorine or chlorine, and $R^{17}$ is lithium, magnesium bromide or magnesium iodide, in the presence of an inert solvent, and if appropriate, in the presence of an acid binder, or (k) in the case where n is 0: compounds of the formula (XVII (XVII)

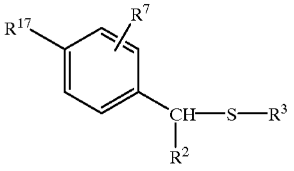

wherein $R^2$, $R^3$, $R^7$ and $R^{16}$ have the same meanings as mentioned above, are reacted with compounds of the formula (XVIII)

(XVIII)

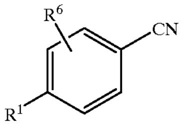

wherein $R^1$ and $R^6$ have the same meanings as mentioned above, in the presence of an inert solvent, or (m) in the case where n is 0, $R^2$ is hydrogen and $R^3$ is perfluoroalkyl, then $R^3$ is replaced by $R^{18}$: compounds of the formula (XIX)

(XIX)

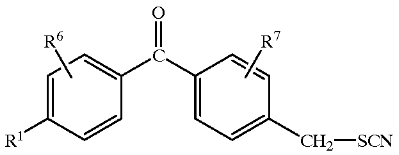

wherein $R^1$, $R^6$ and $R^7$ have same meaning as mentioned above, are reacted with compounds of the formula (XX)

$R^{18}$—I (XX)

wherein $R^{18}$ is $C_{1-4}$ perfluoroalkyl, in the presence of an inert solvent, an if appropriate, in the presence of an acid binder, or (n) in the case where n is 0 and $R^2$ is $C_{1-4}$ alkyl, then $R^2$ is replaced by $R^{19}$: compounds of the formula (XXI)

(XXI)

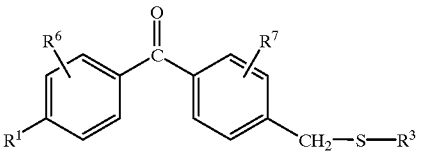

wherein $R^1$, $R^3$, $R^6$ and $R^7$ have same meaning as mentioned above, are reacted with compounds of the formula hal —$R^{19}$ (XXII)

wherein hal has the same meaning as mentioned above and $R^{19}$ is $C_{1-4}$ alkyl, in the presence of an inert solvent, and if appropriate in the presence of an acid binder, or (p) in the case where n is 1: compounds of the formula (XXIII)

(XXIII)

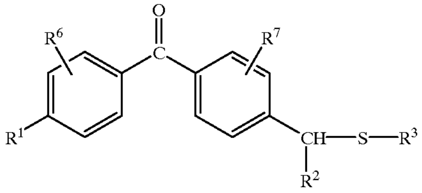

wherein $R^1$, $R^2$, $R^3$, $R^6$ and $R^7$ have the same meaning mentioned above, are oxidized, if appropriate, in the presence of an inert solvent, or (q) in the case where n is 2: compounds of the formula (XXIV)

(XXIV)

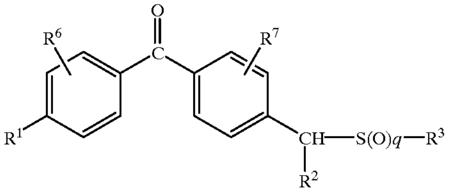

wherein $R^1$, $R^2$, $R^3$, $R^6$, $R^7$ and q have the same meaning mentioned above, are oxidized, if appropriate, in the presence of an inert solvent.

Examples of the compounds of the formula (II) are shown in Table 5.

TABLE 5

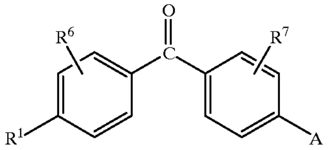

| $R^1$ | $R^6$ | $R^7$ | A | $R^1$ | $R^6$ | $R^7$ | A |
|---|---|---|---|---|---|---|---|
| Br | H | H | $CH(CH_3)SCH_3$ | Cl | H | H | $CH_2S(CH_2)_3F$ |
| Br | H | H | $CH(CH_3)SO_2CH_3$ | Cl | H | H | $CH_2SC_2H_5$ |
| Br | H | H | $CH(CH_3)SOCH_3$ | Cl | H | H | $CH_2SC_3H_7$-iso |
| Br | H | H | $CH_2SC_2H_5$ | Cl | H | H | $CH_2SC_3H_7$-n |
| Br | H | H | $CH_2SC_3H_7$-n | Cl | H | H | $CH_2SC_4H_9$-n |

TABLE 5-continued

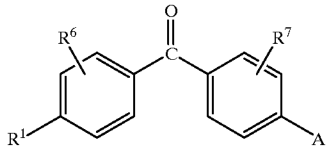

| $R^1$ | $R^6$ | $R^7$ | A | $R^1$ | $R^6$ | $R^7$ | A |
|---|---|---|---|---|---|---|---|
| Br | H | H | $CH_2SCF_3$ | Cl | H | H | $CH_2SC_4H_9$-sec |
| Br | H | H | $CH_2SCH_2CF_3$ | Cl | H | H | $CH_2SCF_2CF_2CF_3$ |
| Br | H | H | $CH_2SCH_2CH{=}CH_2$ | Cl | H | H | $CH_2SCF_2CF_3$ |
| Br | H | H | $CH_2SCH_2CH_2F$ | Cl | H | H | $CH_2SCF_2CHF_2$ |
| Br | H | H | $CH_2SCH_2CHF_2$ | Cl | H | H | $CH_2SCF_3$ |
| Br | H | H | $CH_2SCH_2F$ | Cl | H | H | $CH_2SCH_2C{\equiv}CH$ |
| Br | H | H | $CH_2SCH_3$ | Cl | H | H | $CH_2SCH_2CF_2CF_2H$ |
| Br | H | H | $CH_2SCHF_2$ | Cl | H | H | $CH_2SCH_2CF_2CF_3$ |
| Br | H | H | $CH_2SO_2C_2H_5$ | Cl | H | H | $CH_2SCH_2CF_3$ |
| Br | H | H | $CH_2SO_2C_3H_7$-n | Cl | H | H | $CH_2SCH{=}CH_2$ |
| Br | H | H | $CH_2SO_2CH_2CF_3$ | Cl | H | H | $CH_2SCH_2CH{=}CH_2$ |
| Br | H | H | $CH_2SO_2CH_2CH{=}CH_2$ | Cl | H | H | $CH_2SCH_2CH_2CH_2Cl$ |
| Br | H | H | $CH_2SO_2CH_2CH_2F$ | Cl | H | H | $CH_2SCH_2CH_2Cl$ |
| Br | H | H | $CH_2SO_2CH_2CHF_2$ | Cl | H | H | $CH_2SCH_2CH_2F$ |
| Br | H | H | $CH_2SO_2CH_3$ | Cl | H | H | $CH_2SCH_2CHF_2$ |
| Br | H | H | $CH_2SOC_2H_5$ | Cl | H | H | $CH_2SCH_2CN$ |
| Br | H | H | $CH_2SOC3H_7$-n | Cl | H | H | $CH_2SCH_2F$ |
| Br | H | H | $CH_2SOCH_2CF_3$ | Cl | H | H | $CH_2SCH_2Cl$ |
| Br | H | H | $CH_2SOCH_2CH{=}CH_2$ | Cl | H | H | $CH_2SCH_3$ |
| Br | H | H | $CH_2SOCH_2CH_2F$ | Cl | H | 2-Cl | $CH_2SCH_3$ |
| Br | H | H | $CH_2SOCH_2CHF_2$ | Cl | H | 3-Cl | $CH_2SCH_3$ |
| Br | H | H | $CH_2SOCH_2F$ | Cl | H | 2-F | $CH_2SCH_3$ |
| Br | H | H | $CH_2SOCH_3$ | Cl | H | 3-F | $CH_2SCH_3$ |
| Br | H | H | $CH_2SOCHF_2$ | Cl | H | 2-Br | $CH_2SCH_3$ |
| Cl | H | H | $CH(C_2H_5)SCH_3$ | Cl | H | 3-Br | $CH_2SCH_3$ |
| Cl | H | H | $CH(C_2H_5)SO_2CH_3$ | Cl | H | 3-$CH_3$ | $CH_2SCH_3$ |
| Cl | H | H | $CH(C_2H_5)SOCH_3$ | Cl | H | 2-$CH_3$ | $CH_2SCH_3$ |
| Cl | H | H | $CH(CH_3)SCH_3$ | Cl | H | H | $CH_2SCHF_2$ |
| Cl | H | H | $CH(CH_3)SO_2CH_3$ | Cl | H | H | $CH_2SO_2C_2H_5$ |
| Cl | H | H | $CH(CH_3)SOCH_3$ | Cl | H | H | $CH_2SO_2C_3H_7$-n |
| Cl | H | H | $CH(n\text{-}C_3H_7)SCH_3$ | Cl | H | H | $CH_2SO_2CH_2C{\equiv}CH$ |
| Cl | H | H | $CH_2SO_2CH_2CF_3$ | Cl | 3-F | H | $CH_2SCH_3$ |
| Cl | H | H | $CH_2SO_2CH_2CH{=}CH_2$ | Cl | 2-Cl | H | $CH_2SO_2C_2H_5$ |
| Cl | H | H | $CH_2SO_2CH_2CH_2CH_2F$ | Cl | 2-F | H | $CH_2SO_2C_2H_5$ |
| Cl | H | H | $CH_2SO_2CH_2CH_2CH_2Cl$ | Cl | 3-F | H | $CH_2SO_2C_2H_5$ |
| Cl | H | H | $CH_2SO_2CH_2CH_2Cl$ | Cl | 2-Cl | H | $CH_2SO_2CH_3$ |
| Cl | H | H | $CH_2SO_2CH_2CH_2F$ | Cl | 2-F | H | $CH_2SO_2CH_3$ |
| Cl | H | H | $CH_2SO_2CH_2CHF_2$ | Cl | 3-F | H | $CH_2SO_2CH_3$ |
| Cl | H | H | $CH_2SO_2CH_3$ | Cl | 2-Cl | H | $CH_2SOC_2H_5$ |
| Cl | H | 2-Cl | $CH_2SO_2CH_3$ | Cl | 2-F | H | $CH_2SOC_2H_5$ |
| Cl | H | 3-Cl | $CH_2SO_2CH_3$ | Cl | 3-F | H | $CH_2SOC_2H_5$ |
| Cl | H | 2-F | $CH_2SO_2CH_3$ | Cl | 2-Cl | H | $CH_2SOCH_3$ |
| Cl | H | 3-F | $CH_2SO_2CH_3$ | Cl | 2-F | H | $CH_2SOCH_3$ |
| Cl | H | 2-Br | $CH_2SO_2CH_3$ | Cl | 3-F | H | $CH_2SOCH_3$ |
| Cl | H | 3-Br | $CH_2SO_2CH_3$ | Cl | 3-Cl | H | $CH_2SC_2H_5$ |
| Cl | H | 3-$CH_3$ | $CH_2SO_2CH_3$ | Cl | 3-Cl | H | $CH_2SCH_3$ |
| Cl | H | 2-$CH_3$ | $CH_2SO_2CH_3$ | Cl | 3-Cl | H | $CH_2SO_2C_2H_5$ |
| Cl | H | H | $CH_2SOC_2H_5$ | Cl | 3-Cl | H | $CH_2SO_2CH_3$ |
| Cl | H | H | $CH_2SOC_3H_7$-n | Cl | 3-Cl | H | $CH_2SOC_2H_5$ |
| Cl | H | H | $CH_2SOCH_2C{\equiv}CH$ | Cl | 3-Cl | H | $CH_2SOCH_3$ |
| Cl | H | H | $CH_2SOCH_2CF_3$ | F | H | H | $CH_2SC_2H_5$ |
| Cl | H | H | $CH_2SOCH_2CH{=}CH_2$ | F | H | H | $CH_2SCH_3$ |
| Cl | H | H | $CH_2SOCH_2CH_2CH_2Cl$ | F | H | H | $CH_2SO_2C_2H_5$ |
| Cl | H | H | $CH_2SOCH_2CH_2Cl$ | F | H | H | $CH_2SO_2CH_3$ |
| Cl | H | H | $CH_2SOCH_2CH_2F$ | F | H | H | $CH_2SOC_2H_5$ |
| Cl | H | H | $CH_2SOCH_2CHF_2$ | F | H | H | $CH_2SOCH_3$ |
| Cl | H | H | $CH_2SOCH_2F$ | F | 3-F | H | $CH_2SC_2H_5$ |
| Cl | H | H | $CH_2SOCH_3$ | F | 3-F | H | $CH_2SCH_3$ |
| Cl | H | 2-Cl | $CH_2SOCH_3$ | F | 3-F | H | $CH_2SO_2C_2H_5$ |
| Cl | H | 3-Cl | $CH_2SOCH_3$ | F | 3-F | H | $CH_2SO_2CH_3$ |
| Cl | H | 2-F | $CH_2SOCH_3$ | F | 3-F | H | $CH_2SOC_2H_5$ |
| Cl | H | 3-F | $CH_2SOCH_3$ | F | 3-F | H | $CH_2SOCH_3$ |
| Cl | H | 2-Br | $CH_2SOCH_3$ | I | H | H | $CH_2SC_2H_5$ |
| Cl | H | 3-Br | $CH_2SOCH_3$ | I | H | H | $CH_2SCF_3$ |
| Cl | H | 3-$CH_3$ | $CH_2SOCH_3$ | I | H | H | $CH_2SCH_2CF_3$ |
| Cl | H | 2-$CH_3$ | $CH_2SOCH_3$ | I | H | H | $CH_2SCH_2CH_2F$ |
| Cl | H | H | $CH_2SOCHF_2$ | I | H | H | $CH_2SCH_2CHF_2$ |
| Cl | 2-Cl | H | $CH_2SC_2H_5$ | I | H | H | $CH_2SCH_3$ |

TABLE 5-continued

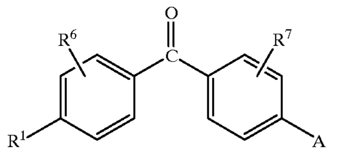

| $R^1$ | $R^6$ | $R^7$ | A | $R^1$ | $R^6$ | $R^7$ | A |
|---|---|---|---|---|---|---|---|
| Cl | 2-F | H | $CH_2SC_2H_5$ | I | H | H | $CH_2SCHF_2$ |
| Cl | 3-F | H | $CH_2SC_2H_5$ | I | H | H | $CH_2SO_2C_2H_5$ |
| Cl | 2-Cl | H | $CH_2SCH_3$ | I | H | H | $CH_2SO_2CH_3$ |
| Cl | 2-F | H | $CH_2SCH_3$ | I | H | H | $CH_2SOC_2H_5$ |
| I | H | H | $CH_2SOCH_3$ | | | | |
| Cl | H | H | $CH_2SOCH_3$ | | | | |
| Cl | H | H | $CH_2SCN$ | | | | |
| Cl | H | H | $CH_2SCSOCH_3$ | | | | |
| Cl | H | H | $CH_2CSOC_2H_5$ | | | | |
| Cl | H | H | $CH_2SCH_2Si(CH_3)_3$ | | | | |
| Cl | H | H | $CH_2SOCH_2Si(CH_3)_3$ | | | | |
| Cl | H | H | $CH_2SO_2CH_2Si(CH_3)_3$ | | | | |
| Br | H | H | $CH_2SCH_2Si(CH_3)_3$ | | | | |
| Br | H | H | $CH_2SOCH_2Si(CH_3)_3$ | | | | |
| Br | H | H | $CH_2SO_2CH_2Si(CH_3)_3$ | | | | |

In the process (g), the starting materials of the formula (XI) are in part known, for example, 4-chloro-4'-chloromethylbenzophenone is described in Japanese Patent Kokoku Publication Sho 46-10164 together with production method thereof, or the staring materials of the formula (I) can be obtained by halogenating benzophenones of the formula (XXV)

(XXV)

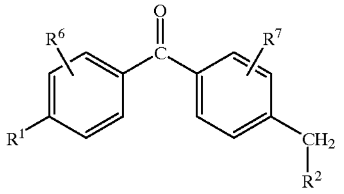

wherein, $R^1$, $R^2$, $R^6$ and $R^7$ have the same meanings as mentioned above, according to conventional methods, using, for example, N-bromosuccinimide or N-cheorosuccin imide as halogenating agent.

The compounds of the formula (XXV) can be obtained by a Friedel-Crafts reaction wherein substituted benzoyl halides and alkyl-substituted benzenes are used as starting materials, and aluminum chloride is used as a catalyst.

The compounds of the formula (XI) may be exemplified as follows:

4-chloro-4'-chloromethylbenzophenone, 4-chloromethyl-4'-fluorobenzophenone, 4-bromo-4'-chloromethylbenzophenone, 4-bromomethyl-4'-chlorobenzophenone, 4-bromomethyl-4'-fluorobenzophenone, 4-bromo-4'-bromomethylbenzophenone, 4-(1-bromoethyl)-4'-chlorobenzophenone, 4-(1-bromopropyl)-4'-chlorobenzophenone, and the like.

In the above process (g), the compounds of the formula (XII) are well known in the field of organic chemistry and, for example, there may be mentioned:

methylmercaptan and salts thereof, ethylmercaptan and salts thereof, and the like.

In the above process (h), the compounds of the formula (XIII) are novel and such compounds can be synthesized by, for instance, reacting benzophenones of the above formula (XI) with thiourea. This reaction is well known per se in the field of organic chemistry and can be carried out by the method analogous to that described in "Jikken Kagaku Koza (Experimental Chemistry Course)" fourth edition, edited by Japanese Chemical Society, Vol. 25, page 336, 1992, published by Maruzen.

Examples of the compounds of the formula (XIII) are are shown in following Table 6.

TABLE 6

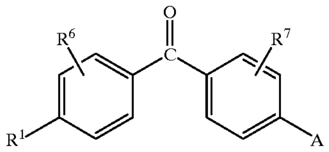

| $R^1$ | $R^6$ | $R^7$ | A |
|---|---|---|---|
| Br | H | H | $CH_2SC(=NH)NH_2.HBr$ |
| Cl | H | H | $CH(C_2H_5)SC(=NH)NH_2.HBr$ |
| Cl | H | H | $CH(CH_3)SC(=NH)NH_2.HBr$ |
| Cl | H | H | $CH(n\text{-}C3H_7)SC(=NH)NH_2.HBr$ |
| Cl | H | H | $CH_2SC(=NH)NH_2.HBr$ |
| Cl | H | 2-$CH_3$ | $CH_2SC(=NH)NH_2.HBr$ |
| Cl | H | 3-$CH_3$ | $CH_2SC(=NH)NH_2.HBr$ |
| Cl | H | 2-F | $CH_2SC(=NH)NH_2.HBr$ |
| Cl | H | 3-F | $CH_2SC(=NH)NH_2.HBr$ |
| Cl | H | 2-Cl | $CH_2SC(=NH)NH_2.HBr$ |
| Cl | H | 3-Cl | $CH_2SC(=NH)NH_2.HBr$ |
| Cl | H | 2-Br | $CH_2SC(=NH)NH_2.HBr$ |
| Cl | H | 3-Br | $CH_2SC(=NH)NH_2.HBr$ |
| Cl | 2-Cl | H | $CH_2SC(=NH)NH_2.HBr$ |
| Cl | 2-F | H | $CH_2SC(=NH)NH_2.HBr$ |
| Cl | 3-F | H | $CH_2SC(=NH)NH_2.HBr$ |
| Cl | 3-Cl | H | $CH_2SC(=NH)NH_2.HBr$ |
| F | H | H | $CH_2SC(=NH)NH_2.HBr$ |
| F | 3-F | H | $CH_2SC(=NH)NH_2.HBr$ |
| I | H | H | $CH_2SC(=NH)NH_2.HBr$ |

In the process (h), the compounds of the formula (XIV) are known in the field of organic chemistry and, for example, there may be mentioned:

methyl iodide, ethyl iodide, methyl bromide, ethyl bromide, boromodifluoromethane, iodotrifluoromethane, 1-bromo-2-fluoroethane, 1-bromo-2-chloroethane, 2,2,2-trifluoro-1-iodoethane, 1-bromo-2,2-difluoroethane, and the like.

In the process (j), the compounds of the formula (XV) can be obtained when compounds of the formula (XXVI)

(XXVI)

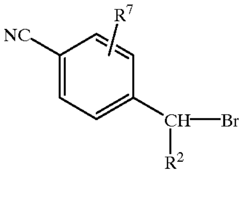

wherein $R^2$ and $R^7$ are defined as above, are reacted with the compound of the formula (XII), in the presence of an acid binder, and, if appropriate, in the presence of an inert solvent, under the same reaction conditions as described for process (g).

The compounds of the formula (XXVI) are well known and include the following:

4-cyanobenzyl bromide, 4-cyanobenzyl chloride, and the like.

In the process (j), the compounds of the formula (XV) are well known and exemplified by the following compounds:

4-methylmercaptobenzonitril, and the like.

In the process (j), the compounds of the formula (XVI) are obtained by metalation of compounds of the formula (XXVII)

(XXVII)

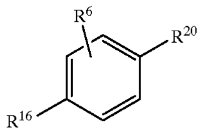

wherein $R^6$ and $R^{16}$ have same meaning as mentioned above, and $R^{20}$ is bromine or iodine, with alkyllithium or magnesium, in the presence of an inert solvent, and, if appropriate, in the presence of a catalyst.

The following compounds of the formula (XXVII) may be mentioned:

4-fluorobromobenzen, 4-fluoroiodobenzen, 4-chloroiodobenzen, 4-chlorobromobenzene, 2-fluoro-4-chlorobromobenzen, 3-fluoro-4-chlorobromobenzen, and the like.

In the process (k), the compounds of the formula (XVII) are obtained by metalation of compounds of the formula (XXVIII)

(XXVIII)

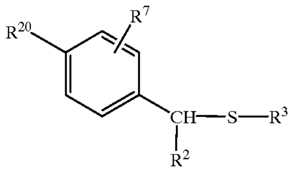

wherein, $R^2$, $R^3$, $R^7$ and $R^{20}$ have same meaning mentined above, with alkyllithium or magnesium, in the presence of an inert solvent, and, if appropriate, in the presence of a catalyst.

The compounds of the formula (XXVIII) are well known and include the following:

4-methylthiomethylbromobenzene, 4-methylthiomethyliodobenzene, 4-ethylthiomethylbromobenzene, 4-ethylthiomethyliodobenzene, and the like.

In the process (m), the compounds of the formula (XIX) are well known compounds in the field of organic chemistry, and include the following:

4-(4-chlorobenzoyl)benzylthiocyanate, and the like.

In the process (m), the compounds of the formula (XX) are well known compounds in the field of organic chemistry, and include the following:

iodotrifluoromethane, iodopentafluoroethane, and the like.

The reaction in the process (m) can be conducted by a method analogous to that described in Journal of Fluorine Chemistry Vol.43, 27–24 (1989).

In the process (n), the compounds of the formula (XXI) are synthesized by the above processes (g) to (m) and include the following:

4-fluoro-4'-methylmercaptomethylbenzophenone,
4-chloro-4'-methylmercaptomethylbenzophenone,
4-bromo-4'-methylmercaptomethylbenzophenone,
4-iodo-4'-methylmercaptomethylbenzophenone,
4-fluoro-4'-ethylmercaptomethylbenzophenone,
4-chloro-4'-ethylmercaptomethylbenzophenone,
4-bromo-4'-ethylmercaptomethylbenzophenone, and the like.

In the process (n), the compounds of the formula (XXII) are known in the field of organic chemistry and include the following:

methyl iodide, ethyl iodide, methyl bromide, ethyl bromide, and the like.

The process (n) is well known per se in the field of organic chemistry and can be carried out by, for example, the method similar to that described in "Jikken Kagaku Koza (Experimental Chemistry Course)" fourth edition, edited by Japanese Chemical Society, Vol. 25, page 329, 1992, published by Maruzen.

In the process (n), the compounds of the formula (XXII) are synthesized by the above processes (g) to (n). As examples thereof, the following compounds in addition to those exemplified as the compounds of the above formula (XXI) may be mentioned:

4-bromo-4'-(1-methylmercaptoethyl)benzophenone,
4-chloro-4'-(1-methylmercaptoethyl)benzophenone,
4-chloro-4'-(1-methylmercaptopropyl)benzophenone,
4-chloro-4'-(1-methylmercaptobutyl)benzophenone, and the like.

As the oxidizing agents used in the above process (p), there may be mentioned, for example, aqueous hydrogen peroxide, peracetic acid, m-chloroperbenzoic acid, OXONE™, sodium periodate, t-butylhydroperoxide and N-bromosuccinimide.

The oxidation reaction in the above production methods (p) and (q) can be carried out by, for example, the method similar to that described in "Jikken Kagaku Koza (Experimental Chemistry Course)" fourth edition, edited by Japanese Chemical Society, Vol. 24, page 350 or 365, 1992, published by Maruzen.

In the above process (q), the compounds of the formula (XXIV) are synthesized by the above production methods (g) to (p). As examples thereof, the following compounds in addition to those exemplified as the compounds of the above formulae (XXI) and (XXIII) may be mentioned:

4-fluoro-4'-methylsulfinylmethylbenzophenone, 4-chloro-4'-methylsulfinylmethylbenzophenone, 4-chloro-4'-difluoromethylsulfinylmethylbenzophenone, 4-bromo-4'-methylsulfinylmethylbenzophenone, 4-iodo-4'-methylsulfinylmethylbenzophenone, 4-ethylsulfinylmethyl-4'-fluorobenzophenone, 4-chloro-4'-ethylsulfinylmethylbenzophenone, 4-bromo-4'-ethylsulfinylmethylbenzophenone, 4-bromo-4'-(1-methylsulfinylethyl)benzophenone, 4-chloro-4'-(1-methylsulfinylethyl)benzophenone, 4-chloro-4'-(1-methylsulfinylpropyl)benzophenone, 4-chloro-4'-(1-methylsulfinylbutyl)benzophenone, and the like.

As the oxidizing agents which can be used in the above production method (q), there may be mentioned, for example, potassium permanganate, sodium perborate in addition to the oxidizing agents described in connection with the above production method (p).

In the process (a), starting compounds of the formula (III) mean compounds based on the above definition of $R^4$, preferably compounds based on the above preferred definition.

In the process (a), the compounds of the formula (III) are well known in the field of organic chemistry, and include the following:

hydrazine hydrate, methyl carbazate, ethyl carbazate, n-propyl carbazate, isopropyl carbazate, n-butyl carbazate, isobutyl carbazate, tert-butylhydrazine, acetohydrazide, benzohydrazide, semicarbazide, thiosemicarbazide, formic hydrazide, and the like.

In the processes (b) and (c), starting compounds of the formula (IV) mean compounds based on the above definition of $R^1$, $R^2$, $R^3$, $R^6$, $R^7$ and n, preferably compounds based on the above preferred definitions.

The compounds of the formula (IV) are synthesized by the above processes (a), (d), (e) and (f). Specific examples of the compounds of the formula (IV) include the following compounds:

4-fluoro-4'-methylmercaptomethylbenzophenone hydrazone, 4-chloro-4'-methylmercaptomethylbenzophenone hydrazone, 4-chloro-4'-difluoromethylmercaptomethylbenzophenone hydrazone, 4-chloro-4'-trifluoromethylmercaptomethylbenzophenone hydrazone, 4-bromo-4'-methylmercaptomethylbenzophenone hydrazone, 4-ethylmercaptomethyl-4'-fluorobenzophenone hydrazone, 4-chloro-4'-methylsulfinylmethylbenzophenone hydrazone, 4-ethylsulfinylmethyl-4'-bromobenzophenone hydrazone, 4-bromo-4'-methylsulfonylmethylbenzophenone hydrazone, 4-chloro-4'-methylsulfonylmethylbenzophenone hydrazone, and the like.

In the process (b), the compounds of the formula (V), as the starting material, are well known in the field of organic chemistry. Examples thereof which may be mentioned are as follows:

4-trifluoromethoxyphenylisocyanate, phenylisocyanate, and the like.

In the process (c), the compounds of the formula (VI) as the starting material are well known in the field of organic chemistry. Examples thereof which may be mentioned are as follows:

methyl chlorocarbonate, ethyl chlorocarbonate, propyl chlorocarbonate, isopropyl chlorocarbonate, butyl chlorocarbonate, isobutyl chlorocarbonate, tert-butyl chlorocarbonate, methyl bromocarbonate, ethyl bromocarbonate, propyl bromocarbonate, isopropyl bromocarbonate, butyl bromocarbonate, isobutyl bromocarbonate, tert-butyl bromocarbonate, allyl bromocarbonate, acetyl chloride, acetyl bromide, propionyl chloride, butyryl chloride, isobutyryl chloride, valeryl chloride, isovaleryl chloride, pivaloyl chloride, and the like.

In the processes (d), the compounds of the formula (VII) are synthesized by the above processes (a), (b), (c) and (f). Examples thereof include the following compounds:

4-fluoro-4'-methylmercaptomethylbenzophenone hydrazone, 4-bromo-4'-methylmercaptomethylbenzophenone hydrazone, 4-iodo-4'-methylmercaptomethylbenzophenone hydrazone, 4-chloro-4'-ethylmercaptomethylbenzophenone hydrazone, 4-bromo-4'-methylmercaptomethylbenzophenone ethoxycarbonylhydrazone, 4-chloro-4'-methylmercaptomethylbenzophenone ethoxycarbonylhydrazone, 4-chloro-4'-ethylmercaptomethylbenzophenone ethoxycarbonylhydrazone, 4-chloro-4'-(1-methylmercaptoethyl)benzophenone ethoxycarbonylhydrazone, and the like.

In the process (d), the compounds of the formula (VIII) as the starting material are those which are well known in the field of organic chemistry. Examples thereof which may be mentioned are as follows:

methyl iodide, ethyl iodide, propyl iodide, chloromethyl methyl ether, chloromethyl ethyl ether, chloromethyl methyl sulfide, acetyl chloride, benzoyl chloride, cinnamoyl chloride, methylchloroformate, methyl chlorocarbonate, ethyl chlorocarbonate, propyl chlorocarbonate, isopropyl chlorocarbonate, butyl chlorocarbonate, isobutyl chlorocarbonate, tert-butyl chlorocarbonate, methyl bromocarbonate, ethyl bromocarbonate, propyl bromocarbonate, isopropyl bromocarbonate, butyl bromocarbonate, isobutyl bromocarbonate, tert-butyl bromocarbonate, allyl bromocarbonate, and the like.

In the process (e), the compounds of the formula (IX) are obtained by the processes (a) to (d). Examples thereof include the following compounds, in addition to those exemplified as the compounds of formulae (IV) and (VII).

As the oxidizing agents which are used in the above processes (e) and (f), there may be mentioned the oxidizing agents described in connection with the process (n).

In the process (f), the compounds of the formula (X) are the compounds according to the invention, which are synthesized by the above processes (a) to (e). As example thereof, the following compounds in addition to those exemplified as the compounds of the above formulae (IV) and (VII) may be mentioned:

4-fluoro-4'-methylsulfinylmethylbenzophenone hydrazone, 4-bromo-4'-methylsulfinylmethylbenzophenone hydrazone, 4-iodo-4'-methylsulfinylmethylbenzophenone hydrazone, 4-chloro-4'-ethylsulfinylmethylbenzophenone hydrazone, 4-chloro-4'-methylsulfinylmethylbenzophenone ethoxycarbonylhydrazone, and 4-bromo-4'-ethylsulfinylmethylbenzophenone ethoxycarbonylhydrazone.

As are mentioned hereinabove, the compounds of the formulae (II), (XIII), (XIX), (XXI), (XXIII), and (XXIV) which are employed as starting materials or intermediates in the preparation of the compounds of the formula (I) are novel, and then those compounds can be represented by the following formula (XXIX):

(XXIX)

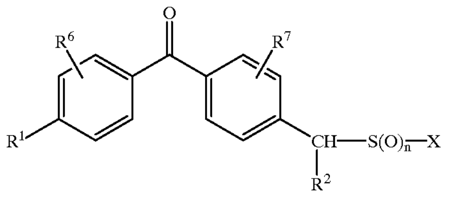

wherein $R^1$ is halogen, $R^2$ is hydrogen or $C_{1-4}$ alky, $R^6$ is hydrogen or halogen, $R^7$ is hydrogen, halogen or $C_{1-2}$ alkyl, n is 0, 1 or 2, X is cyano, optionally substituted $C_{1-4}$ alky, $C_{2-4}$ alkenyl, $C_{3-4}$ alkynyl, $C_{1-4}$ alkyl-carbonyl, $C_{1-4}$ alkoxy-thiocarbonyl or carboxamidine and their salts, provided that when X is cyano, $C_{1-4}$ alkyl-carbonyl $C_{1-4}$ alkoxy-thiocarbonyl or carboxamidine and their salts then n is 0.

The reaction of the above production method (a) can be carried out in an appropriate diluent. As such diluents, there may be mentioned optional inert organic solvents, for example, aliphatic, alicyclic or aromatic hydrocarbons (which may be optionally chlorinated), such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); nitrites such as acetonitrile, propionitrile and acrylonitrile; alcohols, with the proviso that $R^3$ is not monohalogenomethyl, such as methanol, ethanol, isopropanol, butanol and ethylene glycol; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (HMPA); and sulfones and sulfoxides such as dimethyl sulfoxide (DMSO) and sulfolan.

The reaction in the above production method (a), can be carried out in the presence of an acid cataylst. Examples of usable acid catalysts may be mentioned: mineral acids such as hydrochloric acid, sulfuric acid, phosphoric acid, hydrobromic acid, organic acids such as formic acid, acetic acid, trifluoroacetic acid, and propionic acid, methanesulfonic acid, benzenesulfonyl acid and p-toluenesulfonic acid: and organic amine hydrochlorides auch as pyridine hydrochloride and triethylamine hydrochloride and the like.

The reaction of the production method (a) can be conducted at a temperature within a substantially broad range, but it is generally possible to employ a reaction temperature of about −20 to about 200° C., preferably about 20 to about 150° C. Further, the reaction should preferably be conducted under normal pressure but it may optionally be operated under an elevated or reduced pressure.

For carrying out the production method (a), for instance, 1 mole of the compound of the formula (II) can be reacted with 1 to 10 moles of the compound of the formula (III) in a diluent such as ethanol and in the presence of an acid catalyst such as acetic acid to thereby obtain the object compound of the formula (I).

In carrying out the process (b) mentioned above, use may be made, as suitable diluent, of any inert solvent.

Examples of such diluents are aliphatic, cycloaliphatic and aromatic, optionally chlorinated, hydrocarbons such as pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like; ethers such as diethyl ether, methyl ethyl ether, diisopropyl ether, dibutyl ether, dioxane, dimethoxyethane(DME), tetrahydrofurane (THF), dimethylene glycol dimethyl ether and the like; ketones such as acetone, methylethyl ketone (MEK), methyl-isopropyl ketone, methyl-isobutyl ketone (MIBK) and the like; nitriles such as acetonitrile, propionitrile and the like; esters such as ethyl acetate, amyl acetate and the like, acid amides such as dimethyl formamide (DMF), dimethyl acetamide (DMA), N-methylpyrrolidone, 1,3-dimethyl-2-imidazolidinone, hexamethylphosphoric traimide (HWA) and the like; sulfones and sulfoxides such as dimethyl sulfoxide (DMSO), sulfolane and the like; and base such as pyridine.

In the above mentioned process (b), the reaction temperature can be varied within a substantially wide range. In general, the reaction is carried out at a temperature of from about −120° C. to about 200° C., preferably from 20° C. to about 100° C.

Further, the reaction is carried out under normal pressure, although it is also possible to employ a higher or reduced pressure.

When the above mentioned process (b) according to the present invention is carried out, use is made, for example, of about 1 to 3 moles of the compound of the formula (V) in a diluent such as acetonitrile per 1 mole of the compounds represented by the general formula (IV) to obtain the desired compounds.

The reaction of the above production method (c) can be carried out in an appropriate diluent, for example, an optional inert organic solvent. Examples of such organic solvents are: aliphatic, alicyclic or aromatic hydrocarbons (which may be optionally chlorinated), such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); ketones such as acetone, methyl ethyl ketone (MEK), methyl-isopropyl ketone and methyl isobutyl ketone (MIBK); nitriles such as acetonitrile, propionitrile and acrylonitrile; esters such as ethyl acetate and amyl acetate; acid amides such as dimethylformamide (DMF), dimethylacetamide (DMA), N-methylpyrrolidone, 1,3-dimethyl-2-imidazolidinone and hexamethylphosphoric triamide (HMPA); and sulfones and sulfoxides such as dimethyl sulfoxide (DMSO) and sulfolan.

The production method (c) can also be carried out in the presence of an acid binding agent. Examples of usable acid binding agents are as follows: inorganic bases, for example, hydroxides, carbonates and bicarbonates of alkali metals or alkaline earth metals, such as sodium hydrogencarbonate, potassium hydrogencarbonate, sodium carbonate, potassium carbonate, lithium hydroxide, sodium hydroxide, potassium hydroxide and calcium hydroxide; organic bases, for example, tertiary amines, N,N-dialkylanilines and pyridines, such as triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo [5,4,0]undec-6-ene (DBU).

The reaction of the production method (c) can be conducted at a temperature within a substantially broad range, but it is generally possible to employ a reaction temperature of about −70 to about 150° C., preferably about −10 to about 80° C. Further, the reaction should preferably be conducted under normal pressure but it may optionally be operated under an elevated or reduced pressure.

For carrying out the production method (c), for instance, 1 mole of the compound of the formula (IV) can be reacted with 1 to 3 moles of the compound of the formula (VI) in a diluent such as dichloromethane and in the presence of a base such as 4-(N,N-dimethylamino)pyridine to thereby obtain the object compound of the formula (I).

In carrying out the process (d) mentioned above, use may be made, as suitable diluent, of any inert solvent.

Examples of such diluents are aliphatic, cycloaliphatic and aromatic, optionally chlorinated, hydrocarbons such as pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like; ethers such as diethyl ether, methyl ethyl ether, diisopropyl ether, dibutyl ether, dioxane, dimethoxyethane(DME), tetrahydrofurane (THF) dimethylene glycol dimethyl ether and the like; ketones such as acetone, methylethyl ketone (MEK), methyl-isopropyl ketone, methyl-isobutyl ketone (MIBK) and the like; nitriles such as acetonitrile, propionitrile and the like; esters such as ethyl acetate, amyl acetate and the like, acid amides such as dimethyl formamide (DMF), dimethyl acetamide (DMA), N-methylpyrrolidone, 1,3-dimethyl-2-imidazolidinone, hexamethylphosphoric traimide (HMPA) and the like; sulfones and sulfoxides such as dimethyl sulfoxide (DMSO), sulfolane and the like; and base such as pyridine.

The process (d) according to the invention is carried out preferably in the presence of an acid binder. As example of such acid binder may be mentioned: inorganic bases including hydroxide, carbonate, bicarbonate of alkali metals and alkali earth metals such as, for example, sodium hydrogencarbonate, potassium hydrogencarbonate, sodium carbonate, potassium carbonate, and the like, inorganic alkali metal amide including lithium amide, sodium amide, potassium amide, and the like, organic bases including alkorate, tertiary amines, N,N-dialkylanilines, and pyridines such as, for example, triethylamine, tributylamine, 1,1,4,4-tetramethylenediamine (TMEDA), N,N-dimethylaniline, N,N-diethlaniline, pyridine, 4-dimethylaminopyridine (DMAP), 1,4-diaza-bicyclo-[2,2,2]octane (DABCO), 1,8-diazabicyclo[5,4,0]-undec-7-ene (DBU) and the like.

In the above mentioned process (d), the reaction temperature can be varied within a substantially wide range. In general, the reaction is carried out at a temperature of from about −70° C. about 150° C., preferably from −10° C. to about 100° C. Further, the reaction is carried out under normal pressure, although it is also possible to employ a higher or reduced pressure.

When the above mentioned process (d) according to the present invention is carried out, use is made, for example, about 1 to 5 moles of the compound of the formula (VIII), in diluent such as tetrahydrofurane and in the presence of an acid binder, such as sodium hydrogencarbonate, per 1 mole of the compounds represented by the general formula (VII) to obtain the desired compounds.

The reaction of the above production methods (e) and (f) can be carried out in an appropriate diluent. As such diluents, there may be mentioned water and optional inert organic solvents, for example, aliphatic, alicyclic or aromatic hydrocarbons (which may be optionally chlorinated) such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers such as ethyl ether, methyl ethyl ether, isopropyl ether, butyl ether, dioxane, dimethoxyethane (DME), tetrahydrofuran (THF) and diethylene glycol dimethyl ether (DGM); nitriles such as acetonitrile, propionitrile and acrylonitrile; and alcohols such as methanol, ethanol, isopropanol, butanol and ethylene glycol.

The reaction of the production method (e) can be conducted at a temperature within a substantially broad range, but it is generally possible to employ a reaction temperature of about −30° C. to about 150° C., preferably about −20° C. to about 100° C. Furthermore, the reaction should preferably be conducted under normal pressure but it may optionally be operated under an elevated or reduced pressure.

For carrying out the production method (e), for instance, 1 mole of the compound of the formula (IX) can be reacted with 1 to 10 moles of an oxidizing agent in a diluent such as methanol to thereby obtain the object compound of the formula (I).

The production method (f) can be conducted at a temperature within a substantially broad range, but it is generally possible to employ a reaction temperature of about −70° C. to about 150° C., preferably about −10° C. to about 100° C. Further, the reaction should preferably be conducted under normal pressure but it may optionally be operated under an elevated or reduced pressure.

For carrying out the production method (f), for instance, 1 mole of the compound of the formula (X) can be reacted with 1 to 3 moles of an oxidizing agent in a diluent such as dichloromethane to thereby obtain the object compound of the formula (I).

Further, the compounds of the formula (I), according to the invention can be used for combating a broad range of various pests, particularly injurious sucking insects, biting insects and other plantparasitic pests as well as pests of stored cereals and hygiene pests, and can be used as insecticides for combating them.

Examples of such pests are as follows:

As insects, there may be mentioned pests from the order of the Coleoptera, for example, *Callosobruchus chinensis, Sitophilus zeamais, Tribolium castaneum, Epilachna vigintioctomaculata, Agriotes fuscicollis, Anomala rufocuprea, Leptinotrarsa decemlineata*, Diabrotica spp., *Monochamus alternatus, Lissorhoptrus oryzophilus* and *Lyctus bruneus;* pests from the order of the Lepidoptera, for example, *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella xylostella, Heliothis virescens* and *Phyllocnistis citrella;* pests from the order of the Hemiptera, for example, *Nephotettix cincticeps, Nilaparvata lugens, Pseudococcus comstocki, Unaspis yanonensis, Myzus persicase, Aphis pomi, Aphis gossypii, Lipaphis erysimi, Stephanitis nashi*, Nezara spp., *Cimex lectularius, Trialeurodes vaporariorum* and Psylla spp.;

pests from the order of the Orthoptera, for example, *Blattela germanica, Periplaneta americana, Gryllotralpa africana* and *Locusta migratoria migratoriodes;* pests from the order of the Isoptera, for example, *Deucotermes speratus* and *Coptotermes formosanus*; and pests from the order of the Diptera, for example, *Musca domestica, Aedes aegypti, Hylemia platura, Culex pipiens, Anopheles sinensis* and *Culex tritaeniorhynchus.*

As mites, there may be mentioned, for example, *Tetranychus kanzawai, Tetranychus urticae, panonychus citri, Aculops pelekassi* and Tarsonemus spp.

As nematodes, there may be mentioned, for example, *Meloidogyne incognita, Bursaphelenchus xylophilus, Aphelenchoides besseyi, Heterodera glycines* and Pratylenchus spp.

Further, in the pharmaceutical field of veterinary medicine, the novel compounds according to the invention are effective against various injurious animal parasites (endoparasites and ectoparasites), such as insects and helminths. Examples of such animal parasites include the following pests:

As insects, there may be mentioned, for example, Gastrophilus spp., Stomoxys spp., Trichodectes spp., Rhodnius spp. and Ctenocephalides spp.

As mites, there may be mentioned, for example, Ornithodoros spp., Ixodes spp. and Boophilus spp.

In this specification, the "insecticide(s)" is a generic term for substances having combating action against all the pests as mentioned above.

In the case of the use as insecticides, the active compounds of the formula (I) can be converted into customary formulations, such as solutions, wettable powders, suspensions, powders, foams, pastes, tablets, granules, aerosols, natural and synthetic materials impregnated with active compounds, very fine capsules in polymeric substances and in coating compositions for seed, furthermore in formulations used with buring equipment, such as fumigating cartridges, fumigating cans and fumigating coils and the like, as well as ULV cold- and warm-mist formulations.

These formulations are produced in the manner known per se, for example, by mixing the active compounds with extenders, that is liquid solvents, liquefied gases under pressure and/or solid carriers, optionally with the use of surface-active agents, that is emulsifying agents and/or dispersing agents and/or foam-forming agents. Use of a surface-active agent is preferred.

As liquid solvents or carriers, there are suitable in the main: aromatic hydrocarbons, such as xylene, toluene or alkyl naphthalenes; chlorinated aromatic hydrocarbons and chlorinated aliphatic hydrocarbons, such as chlorobenzenes, chloroethylenes or methylene chloride; aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone; strongly polar solvents, such as dimethyl-formamide and dimethylsulfoxide; as well as water. In the case of the use of water as an liquid solvent or carrier, organic solvents can be used as auxiliary solvents.

By liquefied gaseous diluents or carriers there are meant liquids which are gaseous at normal temperature and under atmospheric pressure, for example aerosol propellants, such as butane, propane, nitrogen, carbon dioxide and halogenohydrocarbons.

As solid diluents or carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates.

As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there are suitable: for example non-ionic and anionic emulsifiers, such as polyoxy-ethylene-fatty acid esters, polyoxyethylene-fatty alcohol ethers, for example alkylaryl polyglycol ethers, alkylsulfonates, alkyl-sulfates, arylsulfonates as well as albumin hydrolysation products.

As dispersing agents there are suitable: for example lignin-sulphite waste liquors and methylcellulose.

Adhesives may also be used in formulations such as powders, granules and emulsions, and the followings are to be mentioned as examples of usable adhesives: for example carboxymethylcellulose and natural and synthetic polymers such as gum arabic, polyvinyl alcohol and polyvinyl acetate.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of metals, for example iron, manganese, boron, copper, cobalt, molybdenum and zinc.

The formulations in general can contain between 0.1 and 95 per cent by weight, preferably between 0.5 and 90% by weight of the above active compound.

The active compounds of the formula (I), according to the invention, can be present in their commercially available formulations and the use forms prepared with these formulations as a mixture with other active compounds, such as insecticides, attractants, sterilants, miticides, nematocides, fungicides, growth-regulating substances or herbicides. The above insecticides include, for example, organic phosphate, carbamates, carboxylates, chlorinated hydrocarbons and insecticidal substances produced by microorganisms.

The active compounds of the formula (I), according to the invention, can further be present as a mixture with synergistic agents. Synergistic agents are compounds which increase the action of the active compounds, without it being necessary for the synergistiec agent added to be active itself.

The content of the active compounds of the formula (I), according to the invention, in their use form can be varied within wide limits. The concentration of the active compounds of the formula (I) according to the invention in their use form can generally be from 0.0000001 to 100 per cent by weight, preferably between 0.00001 and 1 per cent by weight.

The compounds of the formula (I), according to the invention, can be employed in a customary manner appropriate for the use forms, for example, by spraying and by scattering. The ompounds of formula (I) can be applied for the treatment of soil and of leaves. They also show activity after systemic translocation. Further, the active compounds according to the invention have a good stability to alkali on limed substances and excellent residual action on wood and soil. Thus, they are extremely effective for combating hygiene pests and pests of stored cereals.

Then, the following Examples illustrates the invention, but they should not be regarded as limiting the scope of the invention.

SYNTHESIS EXAMPLE 1

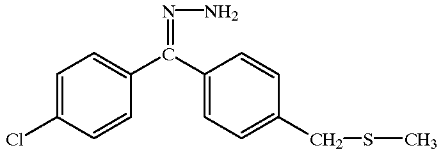

An ethanol solution (50 ml) of 4-chloro-4'-methylmercaptomethylbenzophenone (9.3 g), hydrazine hydrate (6 ml) and acetic acid (3 ml) was heated for 20 hours with refluxing. The solvent was distilled off under reduced pressure, and then the obtained oily substance was diluted with dichloromethane and washed successively with an aqueous 5% sodium hydroxide solution, water and an aqueous saturated a sodium chloride solution, followed by drying over anhydrous magnesium sulfate. The solvent was then distilled off to obtain 4-chloro-4'-methylmercaptomethylbenzophenone hydrazone (7.1 g) as an isomer mixture (syn form/anti form=about 1:1).

$n_D^{20}$ 1.6350

SYNTHESIS EXAMPLE 2

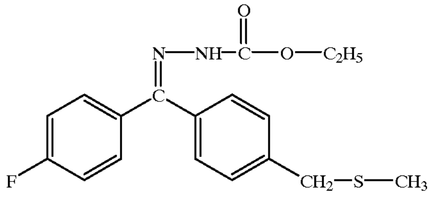

An ethanol solution (100 ml) of 4-fluoro-4'-methylmercaptomethylbenzophenone (7.8 g), ethyl carbazate (9.4 g) and acetic acid (9 ml) was heated for 20 hours with refluxing. The solvent was distilled off under reduced pressure, and then the obtained oily substance was diluted with dichloromethane, and washed successively with an aqueous 5% sodium hydroxide solution, water and an aqueous saturated sodium chloride solution, followed by drying over anhydrous magnesium sulfate. The solvent was then distilled off to obtain 4-fluoro-4'-methylmercaptomethylbenzophenone ethoxycarbonylhydrazone (6.4 g) as an isomer mixture.

$n_D^{20}$ 1.6040

SYNTHESIS EXAMPLE 3

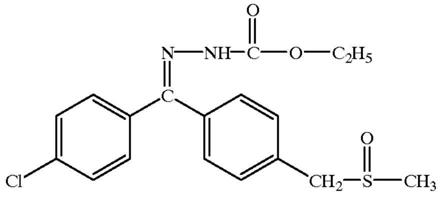

An ethanol solution (100 ml) of 4-chloro-4'-methylsulfinylmethyl benzophenone (5.8 g), ethyl carbazate (6.3 g) and pyridinium p-toluenesulfonate (0.1 g) was heated for 6 hours with refluxing. After cooling to a room temperature, the reaction mixture was poured into ice-water, and the precipitated crystals were collected by filtration, and washed successively with an aqueous sodium bicarbonate solution and water. After air-drying, 4-chloro-4'-methylsulfinylmethylbenzophenone ethoxycarbonylhydrazone (6.4 g) was obtained as an isomer mixture.

melting point: 65–70° C.

A reaction was conducted in the same manner as in Synthesis Example 3 except that 4-chloro-4'-methylsulfonylmethylbenzophenone (6.2 g) was used instead of 4-chloro-4'-methylsulfinylmethylbenzophenone to thereby obtain 4-chloro-4'-methylsulfonylmethylbenzophenone ethoxycarbonylhydrazone (6.7 g) as an isomer mixture.

melting point: 166–169° C.

SYNTHESIS EXAMPLE 4

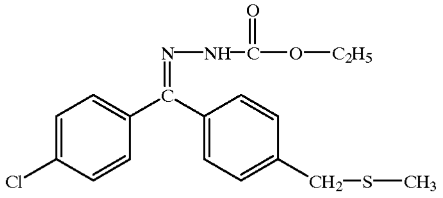

An ethanol solution (100 ml) of 4-chloro-4'-methylmercaptomethylbenzophenone (8.3 g), ethyl carbazate (10 g) and pyridinium p-toluenesulfonate (0.1 g) was heated for 16 hours with refluxing. After cooling to a room temperature, the reaction mixture was poured into ice water, and then the precipitated crystals were collected by filtration, and washed with water. After air-drying, 4-chloro-4'-methylmercaptomethylbenzophenone ethoxycarbonylhydrazone (9.4 g) was obtained as an isomer mixture.

melting point: 105–109° C.

This mixture (1.0 g) was purified by silica gel column chromatography (developing solvent: n-hexane:ethyl acetate=9:1) to obtain 0.24 g of Isomer A having a melting point of 106–107° C. from the first eluate portion and 0.56 g of Isomer B having a melting point of 117–120° C. from the second eluate portion.

SYNTHESIS EXAMPLE 5

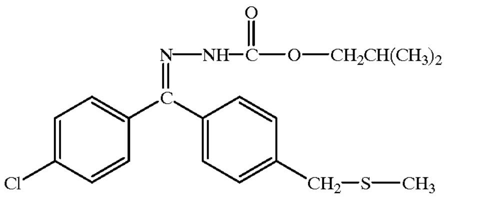

To a dichloromethane solution (30 ml) of 4-chloro-4'-methylmercaptomethylbenzophenone hydrazone (1.5 g) and 4-(N,N-dimethylamino)pyridine (1.2 g), isobutyl chlorocarbonate (0.8 g) was dropwise added under cooling with ice and subsequently stirred at a room temperature for 20 hours. The reaction mixture was then successively washed with 2N hydrochloric acid, water and an aqueous saturated sodium chloride solution, and dried over anhydrous magnesium sulfate. After distilling off the solvent, the crude product was purified by silica gel column chromatography (developing solvent: ethyl acetate:n-hexane=1:4) to obtain 4-chloro-4'-methylmercaptomethylbenzophenone isobutoxycarbonyl hydrazone (0.5 g) as an isomer mixture.

$n_D^{20}$ 1.6103

SYNTHESIS EXAMPLE 6

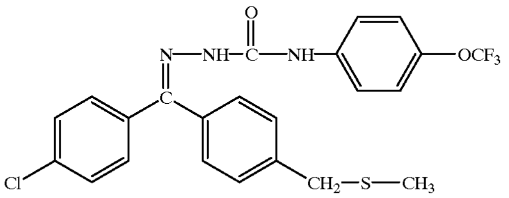

To a acetonitrile solution (10 ml) of 4-chloro-4'-methylmercaptomethylbenzophenone (0.5 g), 4-trifluoromethoxyphenyl isocyanate (0.3 g) was added and stirred at a room temperature for 10 hours. After the soluvent was distilled off under reduced pressure, the resdue was recrystallized from ethanol to obtain 4-chloro-4'-methylmercaptomethylbenzophenone4-(4-trifluoromethoxyphenyl)-semicarbazone (0.5 g).

melting point: 179–183° C.

SYNTHESIS EXAMPLE 7

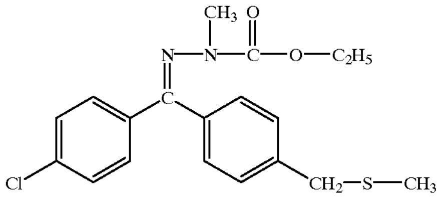

To a dimethylformamide solution (10 ml) of 4-chloro-4'-methylmercaptomethylbenzophenone ethoxycarbonylhydrazone (3.6 g), sodiumuhydride-60% oil suspension (0.4 g) was added under an argon atmosphere and stirred at a room temperature untill the evolution of hydrogen gas ceased.

And then methyl iodide (3 g) was added and stirred at room temperature for 16 hours. After the reaction mixture was poured into ice-water, ethyl acetate was added thereto. Then the organic layer was separated, and washed successively with an aqueous 2 N hydrochloric acid solution, water and aqueous saturated sodium chloride solution, followed by drying over anhydrous sodium sulfate. After distilling off the solvent, the obtained crude product was purified by silca gel colum chromatography (developing solvent n-hexane:ethyl acetate=5:1) to obtain 4-chloro-4'-methylmercaptomethylbenzophenone N'-ethoxycarbonyl-N'-methylhydrazone (1.5 g).

$n_D^{20}$ 1.6039

The following Table 7 shows the compounds synthesized in the above Synthesis Examples 1 to 7 together with the compounds synthesized in the same manner as those in the Synthesis Examples 1 to 7. Compounds of Nos. 1 to 30, and 33 to 216 are isomer mixtures (anti form/syn form). Compound Nos. 31 and 32 are pure isomers.

TABLE 7

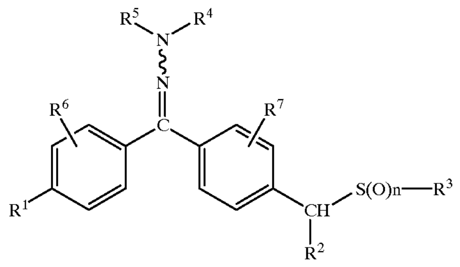

| Compound No. | $R^1$ | $R^2$ | $R^3$ | n | $R^4$ | $R^5$ | $R^6$ | $R^7$ | melting point or refractive index |
|---|---|---|---|---|---|---|---|---|---|
| 1 | Br | H | $CH_3$ | 0 | H | H | H | H | $n_D^{20}$ = 1.6890 |
| 2 | Cl | H | $CH_3$ | 0 | H | H | H | H | $n_D^{20}$ = 1.6350 |
| 3 | Cl | H | $CH_3$ | 1 | H | H | H | H | 45–51° C. |
| 4 | Cl | H | $CH_3$ | 2 | H | H | H | H | 124–130° C. |
| 5 | Br | H | $CH_3$ | 0 | $CO_2C_2H_5$ | $CH_2OCH_3$ | H | H | $n_D^{20}$ = 1.5972 |
| 6 | Br | H | $CH_3$ | 0 | $CO_2C_2H_5$ | $CH_2SCH_3$ | H | H | $n_D^{20}$ = 1.6032 |
| 7 | Br | H | $CH_3$ | 0 | $CO_2C_2H_5$ | $CH_3$ | H | H | $n_D^{20}$ = 1.6186 |
| 8 | Br | H | $CH_3$ | 0 | $CO_2C_2H_5$ | H | H | H | 98–103° C. |
| 9 | Br | H | $CH_3$ | 0 | $CO_2CH_3$ | $CH_2OCH_3$ | H | H | $n_D^{20}$ = 1.5984 |
| 10 | Br | H | $CH_3$ | 0 | $CO_2CH_3$ | H | H | H | 125–135° C. |
| 11 | Br | H | $C_2H_5$ | 0 | $CO_2CH_3$ | H | H | H | $n_D^{20}$ = 1.6267 |
| 12 | Br | H | $CH_2CF_3$ | 0 | $CO_2C_2H_5$ | H | H | H | $n_D^{20}$ = 1.5824 |
| 13 | Br | H | $CH_2CHF_2$ | 0 | $CO_2C_2H_5$ | H | H | H | $n_D^{20}$ = 1.5941 |
| 14 | Br | H | $CH_3$ | 1 | $CO_2CH_3$ | H | H | H | 58–63° C. |
| 15 | Br | H | $CH_3$ | 2 | $CO_2CH_3$ | H | H | H | 179–183° C. |
| 16 | Cl | H | $CH_3$ | 0 | $CO_2C_2H_5$ | $CH_2CO_2C_2H_5$ | H | H | $n_D^{20}$ = 1.5763 |
| 17 | Cl | H | $CH_3$ | 0 | $CO_2C_2H_5$ | $CH_2OC_2H_5$ | H | H | $n_D^{20}$ = 1.5773 |
| 18 | Cl | H | $CH_3$ | 0 | $CO_2C_2H_5$ | $CH_2OCH_3$ | H | H | $n_D^{20}$ = 1.5903 |
| 19 | Cl | H | $CH_3$ | 0 | $CO_2C_2H_5$ | $CH_2SCH_3$ | H | H | $n_D^{20}$ = 1.6088 |
| 20 | Cl | H | $CH_3$ | 0 | $CO_2C_2H_5$ | $CH_3$ | H | H | $n_D^{20}$ = 1.6039 |
| 21 | Cl | H | $CH_3$ | 0 | $CO_2C_2H_5$ | $CHF_2$ | H | H | $n_D^{20}$ = 1.5824 |
| 22 | Cl | H | $CH_3$ | 0 | $CO_2C_2H_5$ | 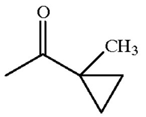 | H | H | $n_D^{20}$ = 1.5872 |
| 23 | Cl | H | $CH_3$ | 0 | $CO_2C_2H_5$ | $COC_3H_7$-iso | H | H | $n_D^{20}$ = 1.5740 |
| 24 | Cl | H | $CH_3$ | 0 | $CO_2C_2H_5$ | $COC_3H_7$-n | H | H | $n_D^{20}$ = 1.5830 |

TABLE 7-continued

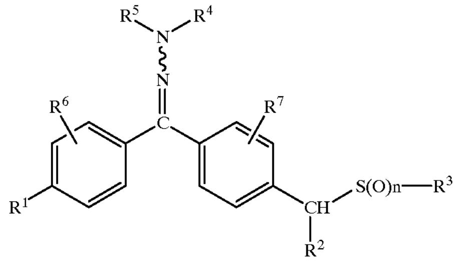

| Compound No. | $R^1$ | $R^2$ | $R^3$ | n | $R^4$ | $R^5$ | $R^6$ | $R^7$ | melting point or refractive index |
|---|---|---|---|---|---|---|---|---|---|
| 25 | Cl | H | $CH_3$ | 0 | $CO_2C_2H_5$ | 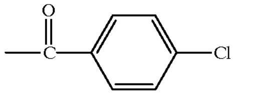 | H | H | $n_D^{20}$ = 1.5996 |
| 26 | Cl | H | $CH_3$ | 0 | $CO_2C_2H_5$ | 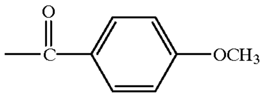 | H | H | $n_D^{20}$ = 1.6036 |
| 27 | Cl | H | $CH_3$ | 0 | $CO_2C_2H_5$ | $COC_6H_5$ | H | H | $n_D^{20}$ = 1.6175 |
| 28 | Cl | H | $CH_3$ | 0 | $CO_2C_2H_5$ | $COCH{=}CHC_6H_5$ | H | H | $n_D^{20}$ = 1.6318 |
| 29 | Cl | H | $CH_3$ | 0 | $CO_2C_2H_5$ | $COCH_3$ | H | H | $n_D^{20}$ = 1.6015 |
| 30 | Cl | H | $CH_3$ | 0 | $CO_2C_2H_5$ | H | H | H | 105–109° C. |
| 31 | Cl | H | $CH_3$ | 0 | $CO_2C_2H_5$ | H | H | H | 106–107° C. |
| 32 | Cl | H | $CH_3$ | 0 | $CO_2C_2H_5$ | H | H | H | 117–120° C. |
| 33 | Cl | H | $CH_2CN$ | 0 | $CO_2C_2H_5$ | H | H | H | 105–106.5° C. |
| 34 | Cl | H | $CH_3$ | 0 | $CO_2C_2H_5$ | n-$C_3H_7$ | H | H | $n_D^{20}$ = 1.5872 |
| 35 | Cl | H | $CH_3$ | 0 | $CO_2CH_2CF_3$ | H | H | H | $n_D^{20}$ = 1.5954 |
| 36 | Cl | H | $CH_3$ | 0 | $CO_2CH_2CH{=}CH_2$ | H | H | H | $n_D^{20}$ = 1.6229 |
| 37 | Cl | H | $CH_3$ | 0 | $CO_2CH_2CH_2Cl$ | H | H | H | 98–101° C. |
| 38 | Cl | H | $CH_3$ | 0 | $CO_2CH_3$ | $CH_2OCH_3$ | H | H | $n_D^{20}$ = 1.6029 |
| 39 | Cl | H | $CH_3$ | 0 | $CO_2CH_3$ | H | H | H | 136–140° C. |
| 40 | Cl | H | $CH_2CN$ | 0 | $CO_29H_3$ | H | H | H | 38.5–147.5° C. |
| 41 | Cl | H | $CH_3$ | 0 | $CO_2C_3H_7$-iso | H | H | H | 115–119° C. |
| 42 | Cl | H | $CH_3$ | 0 | $CO_2C_4H_9$-iso | H | H | H | $n_D^{20}$ = 1.6103 |
| 43 | Cl | H | $CH_3$ | 0 | $CO_2C_3H_7$-n | H | H | H | 94–98° C. |
| 44 | Cl | H | $CH_3$ | 0 | $CO_2C_4H_9$-n | H | H | H | 79–83° C. |
| 45 | Cl | H | $CH_3$ | 0 | $CO_2C_5H_{11}$-n | H | H | H | 86–89° C. |
| 46 | Cl | H | $CH_3$ | 0 | $CO_2C_6H_{13}$-n | H | H | H | 63.5–66.5° C. |
| 47 | Cl | H | $CH_3$ | 0 | $CO_2C_4H_9$-tert | H | H | H | 52–55° C. |
| 48 | Cl | H | $CH_3$ | 0 | $CO_2C_2H_5$ | H | H | 3-Br | 124–125° C. |
| 49 | Cl | H | $CH_3$ | 0 | $CO_2C_2H_5$ | H | H | 3-$CH_3$ | $n_D^{20}$ = 1.6147 |
| 50 | Cl | H | $C_2H_5$ | 0 | $CO_2C_2H_5$ | H | H | H | 77–78.5° C. |

TABLE 7-continued

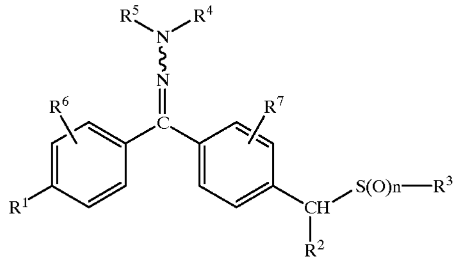

| Compound No. | $R^1$ | $R^2$ | $R^3$ | n | $R^4$ | $R^5$ | $R^6$ | $R^7$ | melting point or refractive index |
|---|---|---|---|---|---|---|---|---|---|
| 51 | Cl | H | $C_2H_5$ | 0 | $CO_2CH_2CF_3$ | H | H | H | $n_D^{20}$ = 1.5732 |
| 52 | Cl | H | $C_2H_5$ | 0 | $CO_2CH_3$ | H | H | H | 87–92° C. |
| 53 | Cl | H | $C_3H_7$-iso | 0 | $CO_2C_2H_5$ | H | H | H | 125–127° C. |
| 54 | Cl | H | $C_3H_7$-iso | 0 | $CO_2CH_3$ | H | H | H | $n_D^{20}$ = 1.6267 |
| 55 | Cl | H | $C_3H_7$-n | 0 | $CO_2C_2H_5$ | H | H | H | 70–71° C. |
| 56 | Cl | H | $C_3H_7$-n | 0 | $CO_2CH_3$ | H | H | H | 98–101° C. |
| 57 | Cl | H | $C_4H_9$-n | 0 | $CO_2C_2H_5$ | H | H | H | $n_D^{20}$ = 1.5908 |
| 58 | Cl | H | $CF_3$ | 0 | $CO_2C_2H_5$ | H | H | H | $n_D^{20}$ = 1.5772 |
| 59 | Cl | H | $CH_2C{\equiv}CH$ | 0 | $CO_2C_2H_5$ | H | H | H | 118–124° C. |
| 60 | Cl | H | $CH_2C{\equiv}CH$ | 0 | $CO_2CH_3$ | H | H | H | 127–137° C. |
| 61 | Cl | H | $CH_2CF_3$ | 0 | $CO_2C_2H_5$ | H | H | H | $n_D^{20}$ = 1.5838 |
| 62 | Cl | H | $CH_2CF_3$ | 0 | $CO_2CH_3$ | H | H | H | $n_D^{20}$ = 1.5603 |
| 63 | Cl | H | $CH_2CH_2CH_2Cl$ | 0 | $CO_2C_2H_5$ | H | H | H | 77–79° C. |
| 64 | Cl | H | $CH_2CH_2F$ | 0 | $CO_2C_2H_5$ | H | H | H | 75.5–77.5° C. |
| 65 | Cl | H | $CH_2CH_2F$ | 0 | $CO_2CH_3$ | H | H | H | 78–82° C. |
| 66 | Cl | H | $CH_2CH{=}CH_2$ | 0 | $CO_2C_2H_5$ | H | H | H | 67–81° C. |
| 67 | Cl | H | $CH_2CHF_2$ | 0 | $CO_2C_2H_5$ | H | H | H | $n_D^{20}$ = 1.5762 |
| 68 | Cl | H | $CH_2CHF_2$ | 0 | $CO_2CH_3$ | H | H | H | $n_D^{20}$ = 1.5838 |
| 69 | Cl | H | $CHF_2$ | 0 | $CO_2C_2H_5$ | H | H | H | 85–88.5° C. |
| 70 | Cl | H | $CHF_2$ | 0 | $CO_2CH_3$ | H | H | H | 85–88° C. |
| 71 | Cl | H | $CH_3$ | 1 | $CO_2C_2H_5$ | H | H | H | 65–70° C. |
| 72 | Cl | H | $CH_3$ | 1 | $CO_2CH_3$ | H | H | H | 60–75° C. |
| 73 | Cl | H | $C_2H_5$ | 1 | $CO_2C_2H_5$ | H | H | H | $n_D^{20}$ = 1.5835 |
| 74 | Cl | H | $C_3H_7$-n | 1 | $CO_2CH_3$ | H | H | H | 69.5–72° C. |
| 75 | Cl | H | $CH_2CF_3$ | 1 | $CO_2C_2H_5$ | H | H | H | 64.5–72° C. |
| 76 | Cl | H | $CHF_2$ | 1 | $CO_2C_2H_5$ | H | H | H | 57–69° C. |
| 77 | Cl | H | $CHF_2$ | 1 | $CO_2CH_3$ | H | H | H | amorphous |
| 78 | Cl | H | $CH_3$ | 2 | $CO_2C_2H_5$ | H | H | H | 166–169° C. |
| 79 | Cl | H | $CH_3$ | 2 | $CO_2CH_3$ | H | H | H | 205–208° C. |
| 80 | Cl | H | $CH_3$ | 2 | $CO_2C_4H_9$-tert | H | H | H | 190–193° C. |
| 81 | Cl | H | $C_2H_5$ | 2 | $CO_2CH_5$ | H | H | H | 93–95° C. |
| 82 | Cl | H | $C_2H_5$ | 2 | $CO_2CH_3$ | H | H | H | 70–78° C. |
| 83 | Cl | H | $C_3H_7$-iso | 2 | $CO_2CH_3$ | H | H | H | $n_D^{20}$ = 1.5930 |
| 84 | Cl | H | $C_3H_7$-n | 2 | $CO_2CH_3$ | H | H | H | 131–138° C. |
| 85 | Cl | H | $CH_2CHF_2$ | 2 | $CO_2C_2H_5$ | H | H | H | 147–149° C. |

TABLE 7-continued

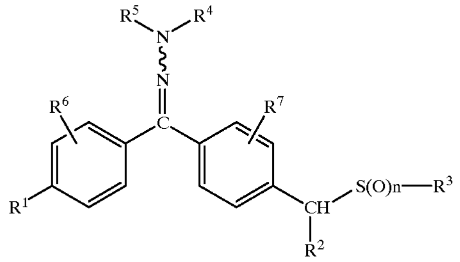

| Compound No. | $R^1$ | $R^2$ | $R^3$ | n | $R^4$ | $R^5$ | $R^6$ | $R^7$ | melting point or refractive index |
|---|---|---|---|---|---|---|---|---|---|
| 86 | Cl | $CH_3$ | $CH_3$ | 0 | $CO_2C_2H_5$ | H | H | H | $n_D^{20}$ = 1.6205 |
| 87 | Cl | $CH_3$ | $CH_3$ | 0 | $CO_2CH_3$ | H | H | H | $n_D^{20}$ = 1.6032 |
| 88 | Cl | $CH_3$ | $CH_3$ | 1 | $CO_2C_2H_5$ | H | H | H | 48–53° C. |
| 89 | Cl | $CH_3$ | $CH_3$ | 2 | $CO_2C_2H_5$ | H | H | H | 115–117° C. |
| 90 | Cl | $C_2H_5$ | $CH_3$ | 0 | $CO_2C_2H_5$ | H | H | H | $n_D^{20}$ = 1.6052 |
| 91 | Cl | n-$C_3H_7$ | $CH_3$ | 0 | $CO_2C_2H_5$ | H | H | H | $n_D^{20}$ = 1.5995 |
| 92 | Cl | H | $CH_3$ | 0 | $CO_2C_2H_5$ | H | 2-Cl | H | 52–55° C. |
| 93 | Cl | H | $CH_3$ | 0 | $CO_2CH_3$ | H | 2-Cl | H | 61–64° C. |
| 94 | Cl | H | $CH_3$ | 0 | $CO_2C_2H_5$ | H | 3-Cl | H | 135–143° C. |
| 95 | F | H | $CH_3$ | 0 | $CO_2C_2H_5$ | H | H | H | $n_D^{20}$ = 1.6040 |
| 96 | F | H | $CH_3$ | 0 | $CO_2C_2H_5$ | H | 3-F | H | $n_D^{20}$ = 1.5803 |
| 97 | I | H | $CH_3$ | 0 | $CO_2C_2H_5$ | H | H | H | 128–130° C. |
| 98 | Cl | H | $CH_3$ | 0 | $COCH_3$ | H | H | H | 124–128° C. |
| 99 | Cl | H | $CH_3$ | 0 | $COC_2H_5$ | H | H | H | 103–113° C. |
| 100 | Cl | H | $CH_3$ | 0 | $COC_3H_7$-n | H | H | H | 100–104° C. |
| 101 | Cl | H | $CH_3$ | 0 | $COC_4H_9$-n | H | H | H | 50–55° C. |
| 102 | Cl | H | $CH_3$ | 0 | $COC_4H_9$-tert | H | H | H | 88–94° C. |
| 103 | Cl | H | $CH_3$ | 0 | 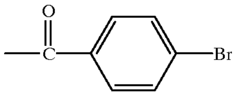 | H | H | H | 122–124° C. |
| 104 | Cl | H | $CH_3$ | 0 | 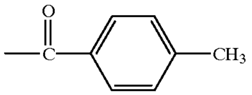 | H | H | H | 114–116° C. |
| 105 | Cl | H | $CH_3$ | 0 | 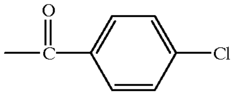 | H | H | H | 144–145° C. |

TABLE 7-continued

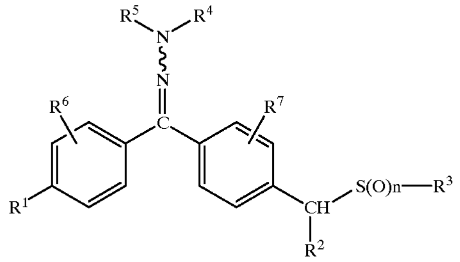

| Compound No. | $R^1$ | $R^2$ | $R^3$ | n | $R^4$ | $R^5$ | $R^6$ | $R^7$ | melting point or refractive index |
|---|---|---|---|---|---|---|---|---|---|
| 106 | Cl | H | $CH_3$ | 0 | $COC_6H_5$ | H | H | H | 126–130° C. |
| 107 | Cl | H | $CH_3$ | 0 | $COCH_2CH_2CH_2CH_2Cl$ | H | H | H | 100–103° C. |
| 108 | Cl | H | $CH_3$ | 0 | $COCH_2CH_2CH_2Cl$ | H | H | H | 83–88° C. |
| 109 | Cl | H | $CH_3$ | 0 | $COCH_2CH_2Cl$ | H | H | H | 98–101° C. |
| 110 | Cl | H | $CH_3$ | 1 | $COC_3H_7$-n | H | H | H | 140–145° C. |
| 111 | Cl | H | $CH_3$ | 2 | $COC_3H_7$-n | H | H | H | 121–131° C. |
| 112 | Cl | H | $CH_3$ | 0 | 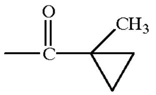 | H | H | H | 145–148° C. |
| 113 | Cl | H | $CH_3$ | 0 | $CONH_2$ | H | H | H | 167–176° C. |
| 114 | Cl | H | $CH_3$ | 0 | $CONHC_2H_5$ | H | H | H | $n_D^{20}$ = 1.6080 |
| 115 | Cl | H | $CH_3$ | 0 | 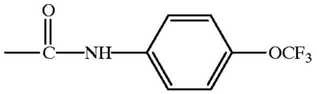 | H | H | H | 179–183° C. |
| 116 | Cl | H | $CH_3$ | 0 | $CONHCH_2CH_2Cl$ | H | H | H | 126–135° C. |
| 117 | Cl | H | $CH_3$ | 0 | $CSNH_2$ | H | H | H | 169–172° C. |
| 118 | Cl | H | $CH_3$ | 0 | 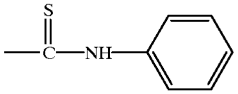 | H | H | H | $n_D^{20}$ = 1.6824 |
| 119 | Cl | H | $CH_3$ | 2 | $CONHC_2H_5$ | H | H | H | 186–189° C. |
| 120 | Cl | H | sec-$C_4H_9$ | 0 | $CO_2C_2H_5$ | H | H | H | mixture of crystal and oily substance |

TABLE 7-continued

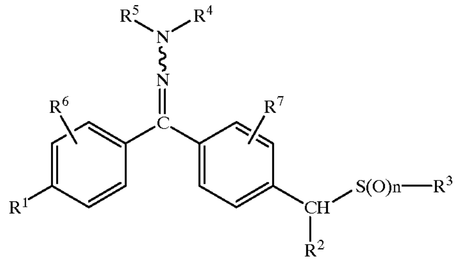

| Compound No. | $R^1$ | $R^2$ | $R^3$ | n | $R^4$ | $R^5$ | $R^6$ | $R^7$ | melting point or refractive index |
|---|---|---|---|---|---|---|---|---|---|
| 121 | Cl | H | $CH_3$ | 0 | 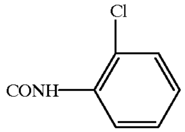 | H | H | H | 121–122.5° C. |
| 122 | Cl | H | $CH_3$ | 0 | 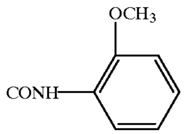 | H | H | H | $n_D^{20}$ = 1.6543 |
| 123 | Cl | H | $CH_3$ | 0 | $COCH_2CO_2C_2H_5$ | H | H | H | $n_D^{20}$ = 1.6148 |
| 124 | Cl | H | $CH_3$ | 0 | $CO_2C_2H_5$ | iso-$C_3H_7$ | H | H | $n_D^{20}$ = 1.5799 |
| 125 | Cl | H | $CH_3$ | 0 | 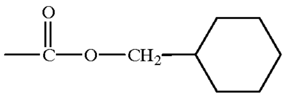 | H | H | H | $n_D^{20}$ = 1.6081 |
| 126 | Cl | H | $CH_3$ | 0 | $CO_2C_5H_{11}$-neo | H | H | H | 144–146° C. |
| 127 | Cl | H | $CH_3$ | 0 | $CO_2CH_2CH(CH_3)C_2H_5$ | H | H | H | $n_D^{20}$ = 1.6061 |
| 128 | Cl | H | $CH_3$ | 0 | $CO_2CH_2C(CH_3){=}CH_2$ | H | H | H | $n_D^{20}$ = 1.6195 |
| 129 | Cl | H | $CH_3$ | 0 | $CO_2C_2H_5$ | H | 3-F | H | $n_D^{20}$ = 1.6084 |
| 130 | Cl | H | $CH_3$ | 0 | $CO_2C_2H_5$ | H | 2-F | H | 73–76° C. |
| 131 | Cl | H | $CH_3$ | 0 | $CO_2C_2H_5$ | $CH_2C_6H_5$ | H | H | $n_D^{20}$ = 1.6250 |
| 132 | Cl | H | $CH_3$ | 0 | $CO_2C_2H_5$ | H | H | H | $n_D^{20}$ = 1.5939 |
| 133 | Cl | H | $CH_3$ | 0 | $COC_3H_7$-n | $CH_3$ | H | H | $n_D^{20}$ = 1.6139 |
| 134 | Cl | H | $(CH_2)_3F$ | 0 | $CO_2C_2H_5$ | H | H | H | 69.5–77.5° C. |
| 135 | Cl | H | $CH_2CF_3$ | 2 | $CO_2C_2H_5$ | H | H | H | 147.5–154.5° C. |
| 136 | Cl | H | $CH{=}CH_2$ | 0 | $CO_2C_2H_5$ | H | H | H | $n_D^{20}$ = 1.6233 |

TABLE 7-continued

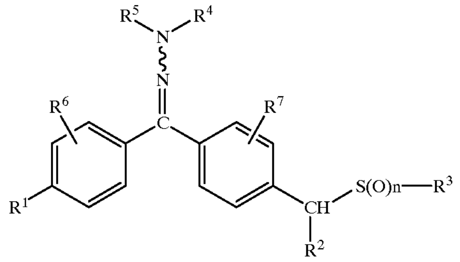

| Compound No. | $R^1$ | $R^2$ | $R^3$ | n | $R^4$ | $R^5$ | $R^6$ | $R^7$ | melting point or refractive index |
|---|---|---|---|---|---|---|---|---|---|
| 137 | Cl | H | $CH_2Cl$ | 0 | $CO_2C_2H_5$ | H | H | H | 102–103° C. |
| 138 | Cl | H | $CH_3$ | 0 | tert-$C_4H_9$ | H | H | H | $n_D^{20}$ = 1.5935 |
| 139 | Cl | H | $CH_3$ | 0 | $CO_2CH_3$ | $COC_3H_7$-n | H | H | $n_D^{20}$ = 1.5773 |
| 140 | Cl | H | $C_2H_5$ | 0 | $CO_2C_3H_7$-n | H | H | H | $n_D^{20}$ = 1.5927 |
| 141 | Cl | H | $C_2H_5$ | 0 | $CO_2C_3H_7$-iso | H | H | H | 93.5–101° C. |
| 142 | Cl | H | $CH_3$ | 0 | $COCH_2CN$ | H | H | H | 118–125.5° C. |
| 143 | Br | H | $CH_3$ | 2 | $CO_2C_2H_5$ | H | H | H | 159–161° C. |
| 144 | Cl | H | $CH_3$ | 2 | $CH_3$ | H | H | H | amorphous |
| 145 | Cl | H | $CH_3$ | 2 | $CH_3$ | $CH_3$ | H | H | 133.5–136° C. |
| 146 | Cl | H | $CH_3$ | 2 | $C_6H_5$ | H | H | H | 172.5–180.5° C. |
| 147 | Br | H | $C_2H_5$ | 0 | $CO_2C_3H_7$-n | H | H | H | $n_D^{20}$ = 1.6162 |
| 148 | Cl | H | $C_2H_5$ | 0 | $CO_2C_4H_9$-sec | H | H | H | $n_D^{20}$ = 1.5944 |
| 149 | Cl | H | $C_2H_5$ | 0 | $COCH_2OCH_3$ | H | H | H | 86–95° C. |
| 150 | Cl | H | $CH{=}CH_2$ | 0 | $CO_2CH_3$ | H | H | H | $n_D^{20}$ = 1.6282 |
| 151 | Cl | H | $C_2H_5$ | 0 | $CO_2C_4H_9$-iso | H | H | H | $n_D^{20}$ = 1.5914 |
| 152 | Cl | H | $C_2H_5$ | 0 | 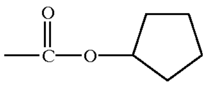 | H | H | H | $n_D^{20}$ = 1.5878 |
| 153 | Cl | H | $CH_3$ | 2 | $C_6H_5$ | $CH_3$ | H | H | 63–66.5° C. |
| 154 | Cl | H | $C_2H_5$ | 0 | 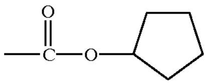 | H | H | H | $n_D^{20}$ = 1.5843 |
| 155 | Cl | H | $CH_3$ | 0 | $CO_2C_2H_5$ | $COC_2H_5$ | H | H | $n_D^{20}$ = 1.5756 |
| 156 | Cl | H | $C_2H_5$ | 0 | $CO_2C_3H_7$-n | $COC_3H_7$-n | H | H | $n_D^{20}$ = 1.5681 |
| 157 | Cl | H | $CH_2F$ | 0 | $CO_2C_2H_5$ | H | H | H | $n_D^{20}$ = 1.6051 |
| 158 | Cl | H | $CH_3$ | 0 | $CO_2C_2H_5$ | $C_2H_5$ | H | H | $n_D^{20}$ = 1.5931 |
| 159 | Cl | H | $C_2H_5$ | 0 | $CO_2C_2H_5$ | $C_3H_5$-iso | H | H | $n_D^{20}$ = 1.5694 |
| 160 | Br | H | $CH_3$ | 0 | $CO_2C_2H_5$ | $C_3H_5$-iso | H | H | $n_D^{20}$ = 1.5956 |
| 161 | Cl | H | $CH_3$ | 0 | $COCH_2OCH_3$ | $CO_2C_2H_5$ | H | H | $n_D^{20}$ = 1.5850 |

TABLE 7-continued

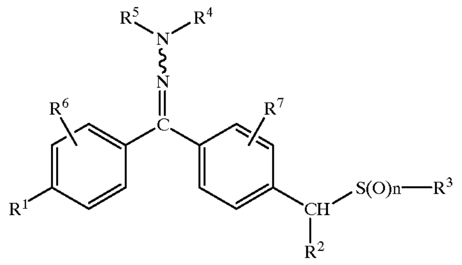

| Compound No. | $R^1$ | $R^2$ | $R^3$ | n | $R^4$ | $R^5$ | $R^6$ | $R^7$ | melting point or refractive index |
|---|---|---|---|---|---|---|---|---|---|
| 162 | Cl | H | $CH_3$ | 0 | 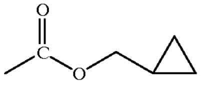 | H | H | H | 109–114.5° C. |
| 163 | Cl | H | $CH_3$ | 0 | $CO_2C_4H_9$-sec | H | H | H | $n_D^{20}$ = 1.5901 |
| 164 | Br | H | $C_2H_5$ | 0 | $CO_2C_2H_5$ | H | H | H | $n_D^{20}$ = 1.6231 |
| 165 | Cl | H | $C_2H_5$ | 0 | $CO_2CH_2Si(CH_3)_3$ | H | H | H | $n_D^{20}$ = 1.5811 |
| 166 | Cl | H | $CH_2OC_2H_5$ | 0 | $CO_2C_2H_5$ | H | H | H | 70–72° C. |
| 167 | Cl | H | $CH_2OCH_3$ | 0 | $CO_2CH_3$ | H | H | H | $n_D^{20}$ = 1.6141 |
| 168 | Cl | H | $CH_2Si(CH_3)_3$ | 0 | $CO_2C_2H_5$ | H | H | H | 74–75° C. |
| 169 | Cl | H | $CH_3$ | 0 | $CO_2CH_2CH_2OCH_3$ | H | H | H | $n_D^{20}$ = 1.6336 |
| 170 | Cl | H | $CH_3$ | 0 | H | $CO_2CH_2Si(CH_3)_3$ | H | H | $n_D^{20}$ = 1.5702 |
| 171 | Cl | H | $CH_3$ | 0 | H | 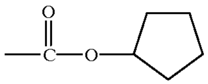 | H | H | $n_D^{20}$ = 1.6133 |
| 172 | Cl | H | n-$C_3H_7$ | 0 | H | —$CO_2C_3H_7$-n | H | H | $n_D^{20}$ = 1.6018 |
| 173 | Cl | H | $C_2H_5$ | 1 | H | $CO_2CH_3$ | H | H | 156.5–169° C. |
| 174 | Cl | H | $C_2H_5$ | 1 | H | $CO_2CH_2CF_3$ | H | H | 101.5–107° C. |
| 175 | Cl | H | n-$C_3H_7$ | 1 | H | $CO_2C_3H_7$-n | H | H | $n_D^{20}$ = 1.5681 |
| 176 | Br | H | $C_2H_5$ | 1 | H | $CO_2CH_3$ | H | H | 163–168.5° C. |
| 177 | Br | H | $C_2H_5$ | 1 | H | $CO_2C_2H_5$ | H | H | 131–135° C. |
| 178 | Cl | H | $CH_3$ | 0 | H | $CO(CH_2)5Br$ | H | H | $n_D^{20}$ = 1.6021 |
| 179 | Cl | H | $CH_3$ | 0 | H | 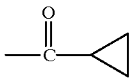 | H | H | 117–120.5° C. |
| 180 | Cl | H | $CH_3$ | 0 | n-$C_4H_9$ | $CO_2C_2H_5$ | H | H | $n_D^{20}$ = 1.5528 |
| 181 | Cl | H | $CH_3$ | 0 | $COC_4H_9$-n | $CO_2C_2H_5$ | H | H | $n_D^{20}$ = 1.5770 |

TABLE 7-continued

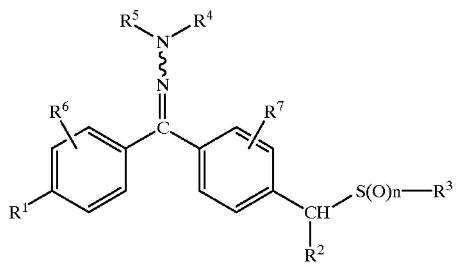

| Compound No. | $R^1$ | $R^2$ | $R^3$ | n | $R^4$ | $R^5$ | $R^6$ | $R^7$ | melting point or refractive index |
|---|---|---|---|---|---|---|---|---|---|
| 182 | Cl | H | $C_2H_5$ | 0 | $C_2H_5$ | $CO_2C_2H_5$ | H | H | $n_D^{20}$ = 1.5822 |
| 183 | Br | H | $C_2H_5$ | 0 | $C_2H_5$ | $CO_2C_3H_7$-n | H | H | $n_D^{20}$ = 1.5870 |
| 184 | Cl | H | $CH_3$ | 1 | $C_2H_5$ | $CO_2C_2H_5$ | H | H | $n_D^{20}$ = 1.5834 |
| 185 | Cl | H | $CH_3$ | 0 | H | $COCO_2C_2H_5$ | H | H | 118–123° C. |
| 186 | Cl | H | $CH_3$ | 0 | $CO_2C_2H_5$ | $CH_2CH{=}CH_2$ | H | H | $n_D^{20}$ = 1.5962 |
| 187 | Cl | H | $CH_3$ | 0 | $CO_2C_2H_5$ | $CH_2C{\equiv}CH$ | H | H | $n_D^{20}$ = 1.5944 |
| 188 | Cl | H | $CH_3$ | 0 | $CO_2C_2H_5$ | $CH_2CH_2F$ | H | H | $n_D^{20}$ = 1.5837 |
| 189 | Cl | H | $CH_3$ | 0 | $CO_2C_2H_5$ | $C_2H_5$ | H | H | 30–38° C. |
| 190 | Cl | H | $C_2H_5$ | 0 | $CO_2C_2H_5$ | $CH_3$ | H | H | $n_D^{20}$ = 1.6021 |
| 191 | Cl | H | $C_2H_5$ | 0 | $CO_2C_2H_5$ | $C_2H_5$ | H | H | $n_D^{20}$ = 1.5922 |
| 192 | Cl | H | $C_2H_5$ | 1 | $CO_2C_2H_5$ | $CH_3$ | H | H | $n_D^{20}$ = 1.5930 |
| 193 | Cl | H | $C_2H_5$ | 2 | $CO_2C_2H_5$ | $CH_3$ | H | H | $n_D^{20}$ = 1.5622 |
| 194 | Cl | H | $C_2H_5$ | 1 | $CO_2C_2H_5$ | $C_2H_5$ | H | H | $n_D^{20}$ = 1.5852 |
| 195 | Cl | H | $C_2H_5$ | 2 | $CO_2C_2H_5$ | $C_2H_5$ | H | H | $n_D^{20}$ = 1.5854 |
| 196 | Cl | H | $C_2H_5$ | 1 | $CO_2CH_3$ | $CH_3$ | H | H | $n_D^{20}$ = 1.6182 |
| 197 | Cl | H | $C_2H_5$ | 2 | $CO_2CH_3$ | $CH_3$ | H | H | 58–62° C. |
| 198 | Br | H | $CH_3$ | 0 | $CO_2C_2H_5$ | $C_2H_5$ | H | H | $n_D^{20}$ = 1.6020 |
| 199 | Br | H | $CH_3$ | 1 | $CO_2C_2H_5$ | $C_2H_5$ | H | H | $n_D^{20}$ = 1.5950 |
| 200 | Br | H | $CH_3$ | 2 | $C_2H_5$ | $CO_2C_2H_5$ | H | H | $n_D^{20}$ = 1.5880 |
| 201 | Cl | H | $CH_3$ | 0 | $CO_2C_2H_5$ | $CO_2CH_3$ | H | H | $n_D^{20}$ = 1.5852 |
| 202 | Cl | H | $CH_3$ | 1 | $CO_2CH_3$ | $CO_2C_2H_5$ | H | H | $n_D^{20}$ = 1.5858 |
| 203 | Cl | H | $CH_3$ | 0 | $CO_2C_2H_5$ | $CO_2C_2H_5$ | H | H | $n_D^{20}$ = 1.5728 |
| 204 | Cl | H | $CH_3$ | 0 | $CO_2C_4H_9$-iso | $C_2H_5$ | H | H | $n_D^{20}$ = 1.5783 |
| 205 | Cl | H | $CH_3$ | 0 | $CO_2C_2H_5$ | $(CH_2)5CH_3$ | H | H | $n_D^{20}$ = 1.5749 |
| 206 | Cl | H | $CH_3$ | 0 | $CO_2CH_2CF_3$ | $C_2H_5$ | H | H | amorphous |
| 207 | Cl | H | $CH_3$ | 0 | $COC_3H_7$-iso | H | H | H | $n_D^{20}$ = 1.6528 |
| 208 | Cl | H | $CH_3$ | 1 | $CO_2C_4H_9$-n | H | H | H | $n_D^{20}$ = 1.5944 |
| 209 | Cl | H | $C_2H_5$ | 1 | $CO_2C_4H_9$-iso | H | H | H | $n_D^{20}$ = 1.5763 |
| 210 | Cl | H | $CH_3$ | 0 | $CO_2C_2H_5$ | $CH_2CN$ | H | H | $n_D^{20}$ = 1.5977 |
| 211 | Cl | H | $C_2H_5$ | 0 | $CO_2C_2H_5$ | $COC_6H_5$ | H | H | $n_D^{20}$ = 1.5990 |
| 212 | Cl | H | $C_2H_5$ | 1 | $CO_2C_2H_5$ | $COC_6H_5$ | H | H | $n_D^{20}$ = 1.5890 |

TABLE 7-continued
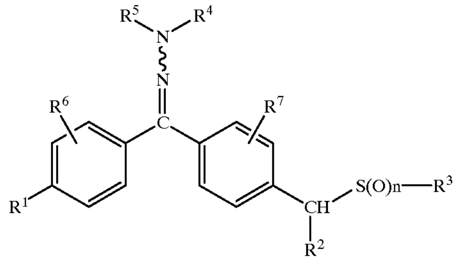
| Compound No. | $R^1$ | $R^2$ | $R^3$ | n | $R^4$ | $R^5$ | $R^6$ | $R^7$ | melting point or refractive index |
|---|---|---|---|---|---|---|---|---|---|
| 213 | Cl | H | $C_2H_5$ | 2 | $CO_2C_2H_5$ | $COC_6H_5$ | H | H | $n_D^{20}$ = 1.5980 |
| 214 | Cl | H | $CH_3$ | 0 | $COCH_3$ | $C_2H_5$ | H | H | $n_D^{20}$ = 1.6140 |
| 215 | Cl | H | $C_2H_5$ | 2 | $COC_3H_7$-n | $C_2H_5$ | H | H | $n_D^{20}$ = 1.5808 |
| 216 | Cl | H | $CH_3$ | 0 | $COC_6H_5$ | $COCH_3$ | H | H | $n_D^{20}$ = 1.6308 |

SYNTHESIS OF INTERMEDIATES

SYNTHESIS EXAMPLE 8

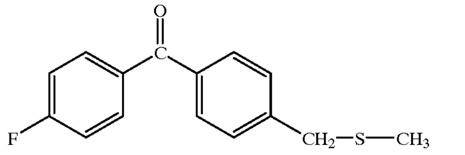

To an acetonitrile solution (200 ml) of 4-bromomethyl-4'-fluorobenzophenone (20 g), an aqueous 15% sodium methylmercaptan solution (60 ml) was added and the mixture was heated for 6 hours with refluxing. After the reaction mixture was restored to room temperature, water (500 ml) and toluene (300 ml) were added. The organic layer was separated, which was then successively washed with an aqueous 2N sodium hydroxide solution and water, and dried over anhydrous magnesium sulfate. After distilling off the solvent, the crude product was purified by silica gel column chromatography (developing solvent n-hexane:ethyl acetate=9:1) to obtain 4-fluoro-4'-methylmercaptomethylbenzophenone (17 g).

$n_D^{20}$ 1.6375

SYNTHESIS EXAMPLE 9

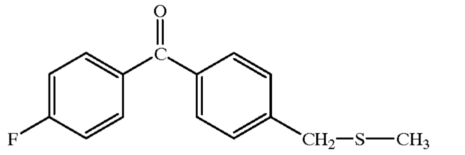

To an ether solution (30 ml) of 4-bromoflurorobenzene (1.75 g), 1.6 M n-butyllithium hexane solution (6.3 ml) was added at −78° C., and the mixture was stirred for an hour at the same temperature. An ether solution (10 ml) of 4-methylmercaptomethylbenzonitrile (1.63 g) was dropwise added thereto at −78 ° C., and the mixture was stirred for 16 hours while restoring the mixture gradually to room temperature. To the reaction mixture, an aqueous 6 N hydrochloric acid was added and stirred for an hour at room temperature, and ether (20 ml) was added. Then the organic layer was separated, and washed with water, followed by drying over anhydrous magnesium sulfate. After distilling off the solvent, the obtained crude product was purified by silica gel column chromatography (developing solvent, n-hexane:ethyl acetate 9:1) to obtain 4-fluoro-4'-methylmercaptomethylbenzophenone (1.12 g).

$n_D^{20}$ 1.6375

SYNTHESIS EXAMPLE 10

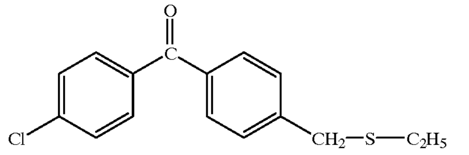

S-(4-(4-chlorobenzoyl)benzyl)thiouronium bromide (3.3 g) and potassium carbonate (1.5 g) were dissolved in dimethylformnamide (20 ml). A methanol solution (10 ml) of potassium hydroxide (1.0 g) was added and stirred at room temperature for 30 minutes. To the reaction mixture, water (100 ml) and toluene (100 ml) were added. The organic layer was separated, and washed with water and an aqueous saturated sodium chloride solution, followed by drying over anhydrous magnesium sulfate. After distilling off the solvent, the crude product was purified by silica gel column chromatography (developing solvent: ethyl acetaten:hexane=1:9) to obtain 4-chloro-4'-ethylmercaptomethylbenzophenone (1.3 g).

melting point: 34–35° C.

4-chloro-4'-difluoromethylmercaptomethylbenzophenone (0.8 g) was obtained in the same manner as in Synthesis Example 10 by using bromodifluoromethane (3.9 g) instead of ethyl iodide.

melting point: 60–62° C.

4-chloro-4'-rifluoromethylmercaptomethylbenzophenone (0.4 g) was obtained in the same manner as in Synthesis Example 10 by using trifluoromethyl iodide (5.9 g) instead of ethyl iodide.

melting point: 78–79° C.

SYNTHESIS EXAMPLE 11

(Synthesis of starting material for Synthesis Example 10)

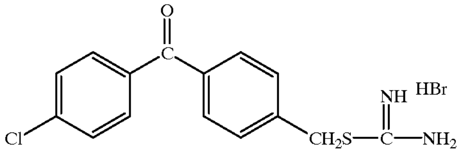

An acetone solution (500 ml) of 4-bromomethyl-4'-chlorobenzophenone (31 g) and thiourea (10 g) was heated for 30 minutes with refluxing. The precipitated crystals were then collected by filtration and washed with acetone to obtain S-(4-(4-chlorobenzoyl)benzyl)thiouronium bromide (33 g).

melting point: 76–78° C.

SYNTHESIS EXAMPLE 12

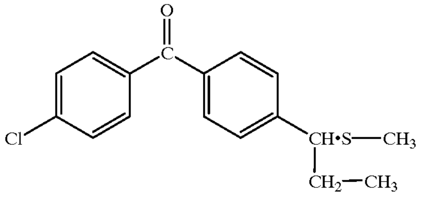

To a tetrahydrofuran solution (30 ml) of lithium diisopropylamide which was prepared from a 1.6 M n-butyllithium hexane solution (12.5 ml) and diisopropylamine (2.1 g), a tetrahydrofuran solution (10 ml) of 4-chloro-4'-methylmercaptomethylbenzophenone (2.8 g) was added at −78° C., and the mixture was stirred for 30 minutes at the same temperature. Ethyl iodide (3.0 g) was subsequently added thereto at −78° C., and the mixture was stirred for 6 hours while restoring the mixture gradually to room temperature. After completing the reaction, the reaction mixture was washed with aqueous 5% ammonium chloride solution and aqueous saturated sodium chloride solution, and dried over anhydrous magnesium sulfate. After distilling off the solvent, the obtained crude product was purified by silica gel column chromatography (developing solvent: n-hexane:ethyl acetate=4:1) to obtain 4-chloro-4'-(1-methylmercaptopropyl)benzophenone (0.3 g) as oily substance.

$^1$H-NMR (90 MHz, $CDCl_3$) (0.93 3H t) (1.88 3H s) (1.96 2H m); (3.63 1H t) (7.27–7.80 8H m)

SYNTHESIS EXAMPLE 13

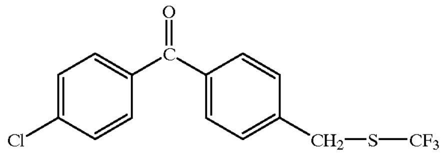

To a pyridine solution (30 ml) of 4-(4-chlorobenzolyl) benzylthiocyanate (1.5 g) and benzylthiocyanate (1.5 g), zinc powder (0.4 g) was added and stirred at room temperature for 24 hours under trifluoromethyl iodide atmosphere. Then toluene (50 ml) was added and zink powder was filtered off. The filtrate was washed with 2N HCl aq. (30 ml tree times) and dried over anhydrous magnesium sulfate. After the solvent was evaporated the residue was purified by means of column chromatography (n-hexane:ethylacetate=6:1). Then 4-chloro-4'-trifluoromethylmercaptobenzophenone (0.5 g) was obtained.

melting point: 78–79° C.

SYNTHESIS EXAMPLE 14

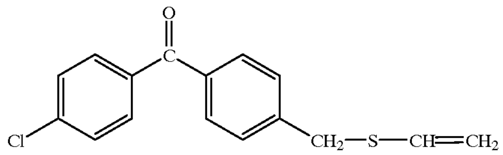

A mixture of 4-chloro-4'-(2-chloroethylmercaptomethyl) benzophenone (4.9 g) and 1,8-diaza-bicyclo[5.4.0]undec-7-ene (4.3 g) in 100 ml of toluene was stirred for 3 hours at 80° C. After that, the mixture was washed with aqueous 2N hydrochloric acid solution and water, followed by drying over anhydrous sodium sulfate. The solvent was distilled off under reduced pressure to obtain 4-chloro-4'-vinylmercaptomethylbenzophenone (4.3 g).

$n_D^{20}$ 1.6363

SYNTHESIS EXAMPLE 15

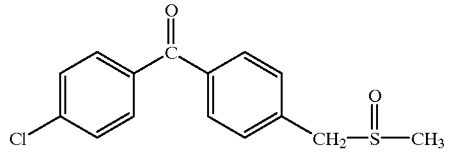

To an acetic acid solution (30 ml) of 4-chloro-4'-methylmercaptomethylbenzophenone (8.3 g), aqueous 30% hydrogen peroxide solution (3.5 ml) was added, and the mixture was stirred for 2 hours while keeping at 10° C. To the reaction solution, water (200 ml) and toluene (200 ml) were added, and then the organic layer was separated, and washed successively with water, an aqueous sodium bicarbonate solution and an aqueous saturated sodium chloride solution, followed by drying over anhydrous magnesium sulfate. After distilling off the solvent, the crude product was purified by silicagel column chromatography (developing solvent: acetone:n-hexane=50:50) to obtain 4-chloro-4'-methylsulfinylmethylbenzophenone (5.3 g).

melting point: 125–128° C.

SYNTHESIS EXAMPLE 16

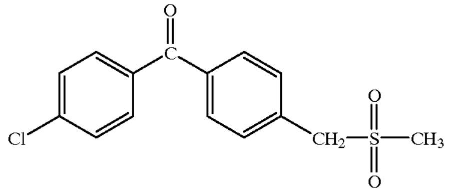

4-Chloro-4'-methylsulfinylmethylbenzophenone (2.9 g) and m-chloroperbenzoic acid (2.5 g) were dissolved in dichloromethane, and the mixture was stirred for 12 hours at 0° C. After the precipitated crystals were filtered off, the filtrate was successively washed with aquous sodium bicarbonate solution, aqueous 5% sodium thiosulfate solution and water, and dried over anhydrous magnesium sulfate. After distilling off the solvent, the crude product was purified by silica gel column chromatography (developing solvent: ethyl acetate:n-hexane=1:5) to obtain 4-chloro-4'-methylsulfonylmethylbenzophenone (1.8 g).

melting point: 173–174° C.

SYNTHESIS EXAMPLE 17

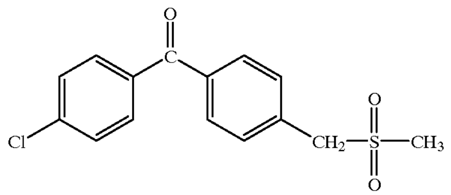

To an acetic acid solution (70 ml) of 4-chloro-4'-methylmercaptomethylbenzophenone (8.3 g), aqueous 30% hydrogen peroxide solution (7 ml) was added at room temperature, and the mixture was stirred for 6 hours at 70° C. The reaction mixture was poured into ice-water, and the precipitated crystals was collected by filtration, and washed with an aqueous sodium bicarbonate solution and water. The crystals was then air-dried to obtain 4-chloro-4'-methylsulfonylmethylbenzophenone (4.3 g).

melting point: 173–174° C.

REFERENCE EXAMPLE 1 (Synthesis of starting materials for Synthesis Example 8)

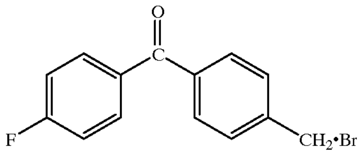

A carbon tetrachloride solution (200 ml) of 4-fluoro-4'-methylbenzophenone (16 g), N-bromosuccinimide (14.2 g) and 2,2'-azodi-isobutyronitrile (0.1 g) was heated for 16 hours with refluxing. After the mixture was cooled to a room temperature, the precipitates were collected by filtration, and the solvent was distilled off to obtain 4-bromomethyl-4'-fluorobenzophenone (20 g).

melting point: 73–75° C.

REFERENCE EXAMPLE 2 (Synthesis of starting material for Reference Example 1)

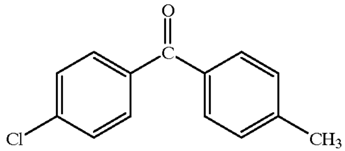

Into a toluene suspension (200 ml) of aluminum chloride (26 g), a toluene solution (50 ml) of p-fluorobenzoyl chloride (16 g) was dropwise added at a room temperature. Subsequently, the mixture was stirred for 20 hours at a room temperature, and then carefully poured into ice-water. Toluene (200 ml) was added thereto, and then the organic layer was separated, and washed successively with aqueous 2N hydrochloric acid solution, water and aqueous saturated sodium chloride solution, followed by drying over anhydrous sodium sulfate. The solvent was distilled off under reduced pressure to obtain 4-fluoro-4'-methylbenzophenone (16 g).

melting point: 97–98° C.

REFERENCE EXAMPLE 3 (Synthesis of starting material for Synthesis Example 9)

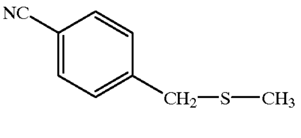

To an acetonitrile solution (500 ml) of 4-cyanobenzyl bromide (50 g), 15% methyl mercaptan sodium salt (120 ml) was added at a room temperature and heated for 6 hours with refluxing. After cooling to a room temperature, water (1 l) and toluene (1 l) was added thereto. The organic layer was separated and washed successively with an aqueous 2N sodium hydroxide solution sulfate. After distilling off the solvent, 4-methylmercaptomethylbenzonitrile (38 g) was obtained.

$n_D^{20}$ 1.5821

The following Table 8 shows the compounds synthesized in the above Synthesis Examples 8 to 17 together with compounds synthesized in the same manner as those in the Synthesis Examples 8 to 17.

TABLE 8

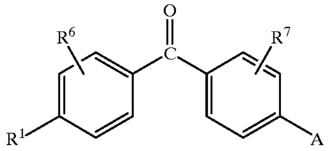

| $R^1$ | $R^6$ | $R^7$ | A | Melting Point or Refrective Index |
|---|---|---|---|---|
| Br | H | H | $CH_2SC(=NH)NH_2.HBr$ | 225–231° C. |
| Cl | H | H | $CH(CH_3)SC(=NH)NH_2.HBr$ | 158–159° C. |
| Cl | H | H | $CH_2SC(=NH)NH_2.HBr$ | 76–78° C. |
| Cl | H | 2-Cl | $CH_2SC(=NH)NH_2.HBr$ | 110–114° C. |
| Cl | H | 3-Cl | $CH_2SC(=NH)NH_2.HBr$ | 198–201° C. |
| I | H | H | $CH_2SC(=NH)NH_2.HBr$ | 196–210° C. |
| Cl | H | H | $CH_2SCN$ | 149–150° C. |
| Cl | H | H | $CH_2S(CS)OC_2H_5$ | 62–68° C. |
| Cl | H | H | $CH_2S(CO)CH_3$ | 98–99° C. |
| Br | H | H | $CH_2SC_2H_5$ | 46–48° C. |
| Cl | H | H | $CH(CH_3)SCH_3$ | $n_D^{20}$ 1.6198 |
| Cl | H | H | $CH_2SC_2H_5$ | 34–35° C. |
| Cl | H | H | $CH_2SC_3H_7$-iso | $n_D^{20}$ 1.6320 |
| Cl | H | H | $CH_2SC_3H_7$-n | $n_D^{20}$ 1.6211 |
| Cl | H | H | $CH_2SCF_3$ | 78–79° C. |
| Cl | H | H | $CH_2SCH_2C{\equiv}CH$ | 80–81° C. |
| Cl | H | H | $CH_2SCH_2CF_3$ | 77–78° C. |
| Cl | H | H | CH2SCH═CH2 | $n_D^{20}$ 1.6363 |
| Cl | H | H | $CH_2SCH_2CH=CH_2$ | $n_D^{20}$ 1.6368 |
| Cl | H | H | $CH_2SCH_2CH_2Cl$ | 65–67° C. |
| Cl | H | H | $CH_2SCH_2CH_2F$ | 44–45° C. |
| Cl | H | 3-Br | $CH_2SCH_3$ | $n_D^{20}$ 1.6502 |
| Cl | H | 3-$CH_3$ | $CH_2SCH_3$ | $n_D^{20}$ 1.6345 |
| Cl | H | 2-$CH_3$ | $CH_2SCH_3$ | $n_D^{20}$ = 1.6324 |
| Cl | H | H | $CH_2SCHF$ | $n_D^{20}$ 1.6237 |
| Cl | H | H | $CH_2SCHF_2$ | 60–62° C. |
| Cl | H | H | $CH_2(SO_2)CH_3$ | 173–174° C. |
| Cl | H | H | $CH_2(SO)CH_3$ | 125–128° C. |
| Cl | 2-Cl | H | $CH_2SCH_3$ | $n_D^{20}$ 1.6369 |
| Cl | 3-Cl | H | $CH_2SCH_3$ | 66–67° C. |
| F | H | H | $CH_2SCH_3$ | $n_D^{20}$ 1.6375 |
| F | 3-F | H | $CH_2SCH_3$ | $n_D^{20}$ 1.6306 |
| I | H | H | $CH_2SCH_3$ | 89–91° C. |
| Cl | H | H | $CH_2SCH_2CN$ | 87.5–88° C. |
| Cl | H | H | $CH_2SCH_2CHF_2$ | 59–60.5° C. |
| Cl | H | H | $CH_2SCH_2CH_2CH_2Cl$ | $n_D^{20}$ 1.6113 |
| Br | H | H | $CH_2SCH_2CF_3$ | 79.5–81.5° C. |
| Br | H | H | $CH_2SCH_2CHF_2$ | 62–64° C. |
| Cl | H | H | $CH_2SCH_2CH_2CH_2F$ | 39–40.5° C. |
| Cl | H | H | $CH_2SCH_2Si(CH_3)_3$ | 95–100° C. |

BIOLOGICAL TEST EXAMPLES

Preparation of Test Solutions

Solvent: 3 parts by weight of xylol

Emulsifier: 1 part by weight of polyoxyethylene alkyl phenyl ether

To produce a suitable preparation of active compound, 1 part by weight of active compound was mixed with the stated amount of solvent containing the stated amount of emulsifier, and the mixture was diluted with water to the prescribed concentration to prepare test solutions.

Test Example 1 (Test against *Spodoptera litura* larvae)

Testing Procedure

Leaves of cabbage (Brassica oleracea) were dipped into the solution of the active compound at the prescribed concentration. After air-drying the solution, the treated leaves were placed in a petridish, and ten third-instar larvae of common cutworm (*Spodoptera litura*) were released. The dish was then placed at an incubation chamber of 25° C.

After 7 days, the number of dead larvae was examined to calculate mortality in %. The test was conducted with 2 replications, and the mortality in % is shown in their average.

Results

Compound Nos. 8, 12, 16, 34, 37, 43, 48, 50, 54, 57, 60, 63, 74, 83, 92, 106, 171, 121, 125, 132, 139, 140, 141, 142, 147, 148, 149, 151, 152, 155, 157, 158, 159, 160, 161, 162, 163, 164, 165, 168, 170, 171, 172, 173, 174, 175 and 176 exhibited 100% of mortality at the concentration of 200 ppm, and compound Nos. 1, 5, 22, 29, 33, 40, 47, 49, 68, 75, 79, 87, 100, 111, 113, 116, 123, 130, 133, 135, 136, 137, 143, 144, 145, 150, 154, 156 and 169 exhibited 100% of mortality at the concentration of 100 ppm.

Test Example 2 (Test against *Aulacophora femoralis*)

Testing Procedure

Leaves of cucumber (*Cucumis sativus*) were dipped into the solution of the active compound at the prescribed concentration. After air-drying the solution, the treated leaves were placed in a Petridish, and ten second-instar larvae of cucurbit leaf beetle (*Aulacophora femoralis*) were released. The dish was then placed at an incubation chamber of 25° C. After 7 days, the number of dead larvae was examined to calculate mortality in %. The test was conducted with 2 replications, and the mortality in % is shown in their average.

Results

Compound Nos. 3, 7, 15, 18, 23, 25, 31, 36, 39, 44, 51, 58, 59, 61, 65, 73, 77, 78, 84, 85, 91, 93, 96, 98, 101, 103, 109, 114, 115, 119, 120, 126, 129, 131, 133, 135, 136, 140, 145, 148, 150, 152, 154, 156, 163, 167, 169, 170 and 172 exhibited 100% of mortality at the concentration of 200 ppm.

Test Example 3 (Test against *Plutella xylostella* larvae resistant to benzoylureas)

Testing Procedure

Leaves of cabbage (*Brassica oleracea*) were dipped into the solution of the active compound at the prescribed concentration. After air-drying the solution, the treated leaves were placed in a petridish, and ten second-instar larvae of diamondback moth (*Plutella xylostella*) resistant to benzoylureas were released. The dish was then placed at an incubation chamber of 25° C. After 7 days, the number of dead larvae was examined to calculate mortality in %. The test was conducted with 2 replications, and the mortality in % is shown in their average.

Results

Compound Nos. 2, 11, 15, 17, 20, 26, 28, 30, 35, 41, 45, 53, 56, 62, 69, 71, 81, 86, 88, 90, 97, 99, 102, 104, 107, 127, 134, 139, 142, 147, 149, 152, 154, 156, 159, 167 and 168 exhibited 100% of mortality at the concentration of 200 ppm.

Test Example 4 (Test against *Cnaphalocrocis medinalis*)

Testing Procedure

The solution of the active compound at the prescribed concentration were spread on 3.5-leaf stage of rice. After air-drying the solution, the treated leaves were cut and were placed in a Petridish, and ten third-instar larvae of rice leafroller (*Cnaphalocrocis medinalis*) were released. The dish was then placed at an incubation chamber of 25° C. After 7 days, the number of dead larvae was examined to calculate mortality in %. The test was conducted with 2 replications, and the mortality in % is shown in their average.

Results

Compound Nos. 4, 9, 10, 13, 24, 27, 32, 42, 46, 52, 55, 64, 67, 70, 72, 76, 82, 89, 94, 95, 105, 108, 110, 112, 124, 128, 140, 148, 151, 160, 163 and 165 exhibited 100% of mortality at the concentration of 50 ppm.

Test Example 5 (Test against *Diabrotica balteata*)

Preparation of Test Formulation carrier: 7 parts by weight of Kaolin emulsifier: 1 part by weight of detergent For the seed treatment a certain amount of active ingredient is solved acetone and mixed into a the stated amount of carrier containing the stated amount of emulsifier.

For seed coating 200 mg of the formulation are dispersed with 0.2 ml of water within a plastic pot. 10 g of maize are added to the dispersion and mixed thoroughly on rotary shaker for 2 minutes.

Testing Procedure

After drying of the seed coating five treated/untreated seedcernels were added into 300 ml of standardized wet soil and kept at a temperature of 20° C. Two replications are prepared for each preparation.

After two days each pot is infested with 20 second-instar-larvae of *Diabrotica balteata*, seven days after infestation the number of emerged plants per pot is counted.

The efficacy is calculated to 100% Abbot, if all plants emerged and to 0% Abbot, if no plant emerged.

Results Compound Nos. 8, 39, 70 and 95 exhibited 100% of mortality at the 0.1 g of the active ingredient per 10 g seedcernels.

We claim:

1. A compound of the formula:

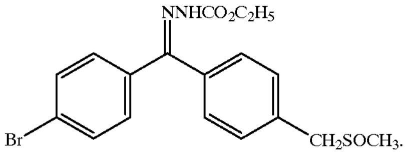

2. A method of treating seeds to prevent pesticidal infestation which comprises applying an effective amount of a compound (I)

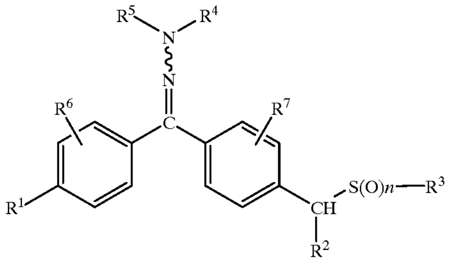

wherein $R^1$ is Br or Cl, $R^2$ is H, $R^3$ is $Ch_3$ or $C_2H_5$, n is 1 or 2, $R^4$ is $CO_2H_5$, $R^5$ is H, $R^6$ is H and $R^7$ is H.

according to claim 1 to said seeds.

3. A composition for treating seeds to prevent pesticidal infestation which comprises an effective amount of a compound according to claim 1 and an inert carrier.

* * * * *